United States Patent [19]

Hanagan et al.

[11] Patent Number: 4,699,650

[45] Date of Patent: Oct. 13, 1987

[54] HERBICIDAL ORTHO-ALKYL-AND ORTHO-ALKENYL SUBSTITUTED BENZENESULFONAMIDES

[75] Inventors: Mary A. Hanagan, Blue Bell, Pa.; Mark E. Thompson, Wilmington, Del.

[73] Assignee: E. I. Du Pont de Nemours and Company, Wilmington, Del.

[21] Appl. No.: 818,395

[22] Filed: Jan. 13, 1986

Related U.S. Application Data

[63] Continuation of Ser. No. 516,078, Jul. 25, 1983, abandoned, which is a continuation-in-part of Ser. No. 416,563, Sep. 10, 1982, abandoned.

[51] Int. Cl.$^4$ .................... C07D 239/47; A01N 47/36
[52] U.S. Cl. ............................................ 71/92; 71/93; 544/208; 544/211; 544/321; 544/323; 544/332
[58] Field of Search ............... 544/321, 332, 323, 208, 544/211; 71/92

[56] References Cited

U.S. PATENT DOCUMENTS

| | | | |
|---|---|---|---|
| 4,332,611 | 6/1982 | Peteron | 71/92 |
| 4,348,219 | 9/1982 | Levitt | 71/92 |
| 4,348,220 | 9/1982 | Schwing | 71/92 |
| 4,486,589 | 12/1984 | Farnham | 544/321 |

FOREIGN PATENT DOCUMENTS

| | | |
|---|---|---|
| 836449 | 7/1983 | South Africa . |
| 834956 | 1/1984 | South Africa . |
| 8427225 | 10/1984 | South Africa . |

OTHER PUBLICATIONS

Hermanus L. Ploeg "Declaration", Mar. 14, 1985.
Henry Kuratle, III, "Declaration", Mar. 14, 1985.

*Primary Examiner*—Robert Gerstl

[57] ABSTRACT

A class of ortho-alkyl- and ortho-alkenyl-substituted benzenesulfonamides are useful as general or selective pre-emergent or post-emergent herbicides and as plant growth regulants.

27 Claims, No Drawings

HERBICIDAL ORTHO-ALKYL- AND ORTHO-ALKENYL SUBSTITUTED BENZENESULFONAMIDES

CROSS-REFERENCE TO RELATED APPLICATION

This application is a file wrapper continuation of copending application U.S. Ser. No. 516,078 filed July 25, 1983, now abandoned, which is a continuation-in-part of copending application U.S. Ser. No. 416,563 filed Sept. 10, 1982, now abandoned.

BACKGROUND OF THE INVENTION

The present invention relates to a class of ortho-alkyl- and ortho-alkenyl-substituted benzenesulfonamides which are useful as general or selective pre-emergent or post-emergent herbicides and plant growth regulants.

U.S. Pat. No. 4,368,069 discloses and claims a class of herbicidal sulfonamides including compounds of the following structure:

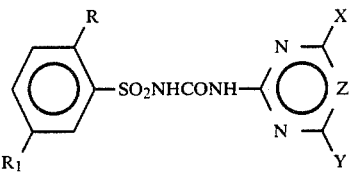

wherein
R is

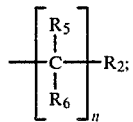

$R_2$ can be $C_2-C_5$ alkenyl;
n is 0 or 1;
$R_1$ can be H;
X and Y can be various substituents including $CH_3$ or $OCH_3$; and
Z can be CH or N.

European Patent Application No. 81303176.2 (Publication Number 0 044 209) discloses and claims a large number of o-benzyl-substituted sulfonamides including the following:

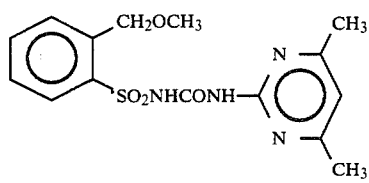

These compounds are useful as plant growth regulants and as herbicides.

SUMMARY OF THE INVENTION

This invention relates to novel compounds of Formula I, suitable agricultural compositions containing them and their method-of-use as general or selective pre-emergent or post-emergent herbicides and plant growth regulants.

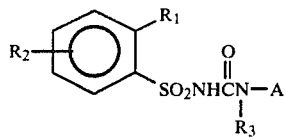

wherein
$R_1$ is $(CH_2)_nCH_2CHR_4R_5$,

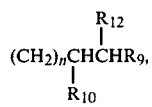

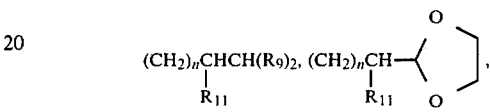

$CHClCH_2Cl$, $CHClCHCl_2$, $CH=CBr_2$, $CH=CHR_9$, $CH=CHCO_2CH_3$ or $CH=CF_2$;
$R_2$ is H, F, Cl, $CH_3$, $OCH_3$ or $CF_3$;
$R_3$ is H or $CH_3$;
$R_4$ is H, F, Cl, Br or $CH_3$;
$R_5$ is F, Cl, Br, $OC(O)R_6$, $OC(O)CF_3$, OH, $OCH_2\phi$, $OSO_2R_6$, $OSO_2CF_3$, $OSO_2C_6H_5R_7$, $S(O)_mR_6$, $OSO_2N(CH_3)_2$ or $CO_2R_8$;
$R_6$ is $C_1-C_3$ alkyl;
$R_7$ is H, F, Cl, Br, $CH_3$, $OCH_3$ or $CF_3$;
$R_8$ is $C_1-C_3$ alkyl, $CH_2CH=CH_2$, $CH_2CH_2OCH_3$ or $CH_2CH_2Cl$;
$R_9$ is $OCH_3$ or $OCH_2CH_3$;
$R_{10}$ is H, $OCH_3$ or $OCH_2CH_3$;
$R_{11}$ is H, Cl or $OCH_3$;
$R_{12}$ is H or $CH_3$;
n is 0 or 1;
m is 0, 1 or 2;
A is

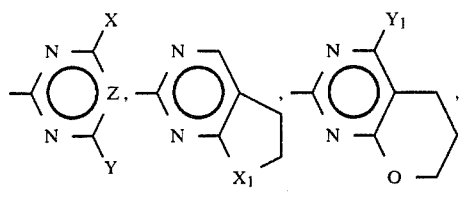

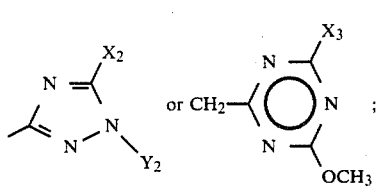

X is $CH_3$, $OCH_3$, Cl, F, Br, $CH_2CH_3$, $OCH_2CH_3$ or $OCF_2H$;

Y is H, $NH_2$, $NHCH_3$, $N(CH_3)_2$, $C_1-C_4$ alkyl, $C_1-C_4$ alkyl substituted with 1-3 atoms of (a) F, (b) Cl or (c) Br, $CH_2OCH_3$, $CH_2OCH_2CH_3$, $C_1-C_4$ alkoxy, $C_1-C_2$ alkylthio, $C_3-C_4$ alkenyloxy, $C_3-C_4$ alkynyloxy, $OCH_2CH_2OCH_3$, $CH(OCH_3)_2$, $CH(OCH_2CH_3)_2$,

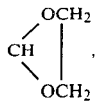

$OCH_2CF_3$, $OCH_2CH_2F$, $OCH_2CH_2Cl$, $OCH_2CH_2Br$ or $GCF_2T$; wherein G is O or S and T is H, CHClF, CHBrF, $CF_2H$ or $CHFCF_3$;

Z is CH, N, $CCH_3$, CBr, CCl, CF or $CCH_2CH_3$;
$X_1$ is O or $CH_2$;
$Y_1$ is H, $CH_3$, $OCH_3$ or Cl;
$X_2$ is $CH_3$, $OCH_3$ or $SCH_3$;
$Y_2$ is $CH_3$, $CH_2CH_3$ or $CH_2CF_3$; and
$X_3$ is $CH_3$ or $OCH_3$;

and their argiculturally suitable salts; provided that
(a) when $R_4$ is halogen, $R_5$ is the same halogen;
(b) when $R_5$ is halogen, $R_4$ is either hydrogen or the same halogen;
(c) when n is 1, $R_{11}$ is hydrogen;
(d) when $R_{12}$ is $CH_3$ and $R_{10}$ is alkoxy, $R_9$ is the same alkoxy; and
(e) when X is Cl, then Z is CH and Y is $NH_2$, $NHCH_3$, $N(CH_3)_2$, $CH_3$, $OCH_3$, or $OCF_2H$.

Preferred for reasons of their higher herbicidal activity, greater plant growth regulant activity and/or more favorable ease of synthesis are:
(1) Compounds of generic Formula I wherein $R_2$ is H and $R_1$ is $(CH_2)_nCH_2CHR_4R_5$,

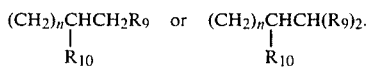

(2) Compounds of Preferred 1 wherein
A is A-1; Z is CH or N; X is $CH_3$, $OCH_3$, Cl or $OCF_2H$ and Y is $CH_3$, $CH_2CH_3$, $OCH_3$, $OCH_2CH_3$, $OCF_2H$, $SCF_2H$, $CH_2OCH_3$ or $CF_3$.
(3) Compounds of Preferred 2 wherein
$R_1$ is $CH_2CH_2Cl$, $CH_2CH_2OH$, $CH(OCH_3)CH_2OCH_3$ or

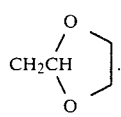

(4) Compounds of Preferred 3 wherein $R_3$ is H.

Spefically preferred for reasons of their highest herbicidal activity, greatest plant growth regulant activity and/or most favorable ease of synthesis are:
N-[(4,6-dimethoxy-1,3,5-triazin-2-yl)aminocarbonyl-]aminosulfonyl-2-(2-methoxyethyl)benzenesulfonamide;
N-[(4-methoxy-6-methylpyrimidin-2-yl)aminocarbonyl-]aminosulfonyl-2-(2-methoxyethyl)benzenesulfonamide;
N-[(4,6-dimethoxypyrimidin-2-yl)aminocarbonyl-]aminosulfonyl-2-(2-p-toluenesulfonyloxyethyl)benzenesulfonamide;
N-[(4-methoxy-6-methylpyrimidin-2-yl)aminocarbonyl-]aminosulfonyl-2-(2-p-toluenesulfonyloxyethyl)benzenesulfonamide;
N-[(4-methoxy-6-methyl-1,3,5-triazin-2-yl)aminocarbonyl]aminosulfonyl-2-(2-p-toluenesulfonyloxyethyl)benzenesulfonamide;
N-[(4-methoxy-6-methylpyrimidin-2-yl)aminocarbonyl-]aminosulfonyl-2-(2-chloroethyl)benzenesulfonamide;
N-[(4,6-dimethoxypyrimidin-2-yl)aminocarbonyl-]aminosulfonyl-2-(2-chloroethyl)benzenesulfonamide; and
N-[(4,6-dimethoxy-1,3,5-triazin-2-yl)aminocarbonyl-]aminosulfonyl-2-(2-chloroethyl)benzenesulfonamide.

SYNTHESIS

The compounds of Formula I may be prepared as shown below in Equation 1 by the reaction of an appropriate aryl sulfonyl isocyanate, II, with an appropriate amino heterocycle, III.

Equation 1

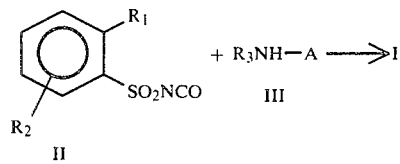

wherein $R_1$, $R_2$, $R_3$ and A are as previously defined except that $R_5$ is not OH.

The reaction of Equation 1 is best carried out in an inert aprotic solvent such as methylene chloride, tetrahydrofuran or acetonitrile at a temperature between 20° C. and 80° C. A catalytic amount of 1,4-diazabicyclo[2,2,2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, diethyl ether, or methanol, and filtration.

The aryl sulfonyl isocyanates of Formula II may be prepared as shown in Equation 2, by phosgenation of the sulfonamides of Formula IV in the presence of butyl isocyanate.

Equation 2

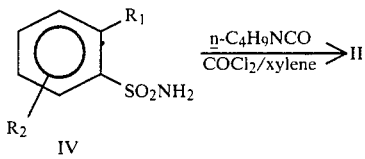

wherein $R_1$ and $R_2$ are as previously defined except that $R_5$ is not OH.

The above reaction is carried out by heating a mixture of the appropriate sulfonamide IV, an alkyl isocyanate such as butyl isocyanate, and a catalytic amount of a tertiary amine such as 1,4-diazabicyclo[2,2,2]octane (DABCO) in xylene, or other inert solvent of boiling point ≧135° C., to approximately 135° C. Phosgene is then added to the mixture over a 1-6 hour period at 125°-135° C. until an excess is present as indicated by a permanent drop in the boiling point to less than 130° C. The mixture is cooled and filtered to remove a small amount of insoluble by-products. The solvent and the alkyl isocyanate are distilled off in vacuo leaving a residue of the crude sulfonyl isocyanate II, which can be used without further purification.

Sulfonyl isocyanates of Formula II may also be prepared as shown in Equation 3, by phosgenation of the appropriate butylureas of Formula V.

Equation 3

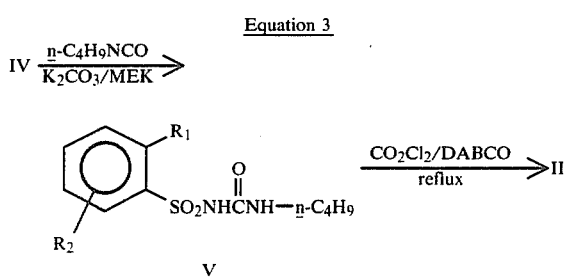

wherein $R_1$ and $R_2$ are as previously defined except that $R_5$ is not OH.

The compounds of Formula V are conveniently prepared by stirring a mixture of the sulfonamides, IV, anhydrous potassium carbonate, and n-butyl isocyanate in acetone or methyl ethyl ketone at 25°-80° C. until all of the isocyanate has reacted. The products are isolated by quenching in dilute mineral acid and recrystallizing the solid product. The compounds V are treated with phosgene and a catalytic amount of DABCO in refluxing xylene or chlorobenzene in a manner analogous to that described in Equation 2.

Sulfonyl isocyanates of Formula II may also be prepared by the two-step procedure shown below in Equation 4 starting from the appropriate sulfonamides.

Equation 4

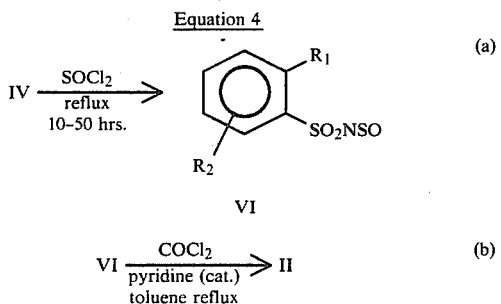

wherein $R_1$ and $R_2$ are as previously defined except that $R_5$ is not OH.

The reactions of Equation 4 (a) and (b) are best carried out according to the procedure of Ulrich et al. in *J. Org. Chem.*, 34, 3200 (1969). The sulfonamide is boiled under reflux with an excess of thionyl chloride which functions as both a reactant and solvent. When the sulfonamide protons are no longer detectable by proton NMR (15-20 hrs. on the average), the thionyl chloride is removed under reduced pressure and the residue is dissolved in an inert solvent such as toluene, benzene, xylenes, etc. A catalytic amount of pyridine is added. The mixture is treated with at least one equivalent of phosgene and heated to 60°-140° C. with 80°-100° C. preferred. Conversion to the isocyanate is substantially complete within about ¼ to 3 hours. The mixture containing the sulfonyl isocyanate can be used directly or the sulfonyl isocyanate can be isolated in pure form by filtration and evaporation of the filtrate followed by vacuum distillation if necessary.

Compounds of Formula Ia are conveniently prepared by mild hydrolysis of the corresponding trifluoroacetates using mild base followed by an appropriate acid such as dilute hydrochloric acid, as shown in Equation 5.

Equation 5

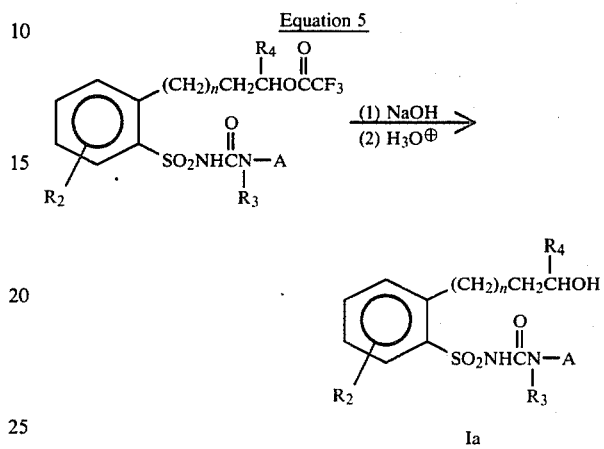

wherein
$R_2$, $R_3$, n, and A are as defined in the Summary of the Invention; and
$R_4$ is H or $CH_3$.

Alternatively, compounds of Formula I may be prepared as shown in Equation 6 by the reaction of an appropriate carbamate, VII, with an appropriate amino heterocycle, III.

Equation 6

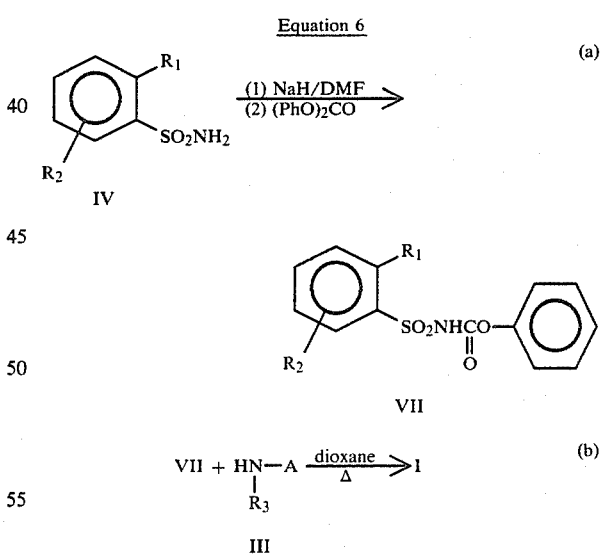

wherein $R_1$, $R_2$, $R_3$, and A are as previously defined except that $R_5$ is not OH.

The reactions of Equation 6 are best carried out according to the methods taught in EPO Publication No. 44,807.

Compounds of Formula Ib can be prepared by the reaction of an appropriately substituted sulfonamide, IV, with the methyl carbamate of the appropriate amino heterocycle, VIII, in the presence of one equivalent of trimethylaluminum as shown in Equation 7.

Equation 7

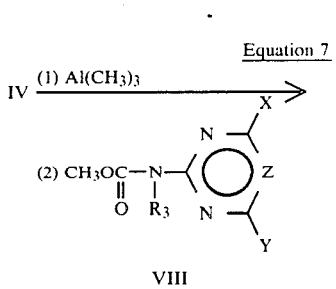

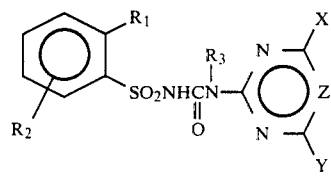

wherein $R_1$, $R_2$, $R_3$, X, Y and Z are as previously defined.

The reaction of Equation 7 is best carried out according to the procedure described in EPO Publication No. 44,210, Jan. 10, 1982.

Benzenesulfonamides of Formula IVa and IVb may be prepared as shown in Equation 8.

Equation 8

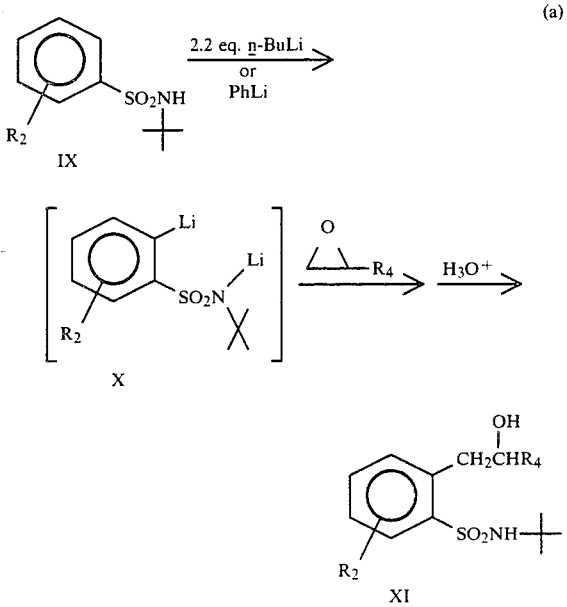

wherein
$R_2$ is H, 3-, 4- or 6-F, Cl, $OCH_3$ or $CF_3$; and
$R_4$ is H or $CH_3$.

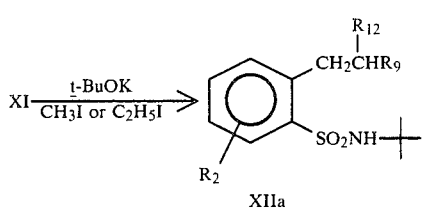

wherein $R_2$ is H, F, Cl, $CH_3$, $OCH_3$ or $CF_3$;
$R_9$ is $OCH_3$ or $OC_2H_5$; and
$R_{12}$ is H or $CH_3$.

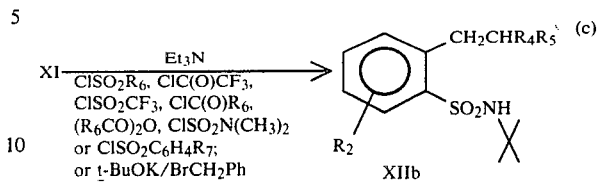

wherein
$R_2$ is H, F, Cl, $CH_3$, $OCH_3$ or $CF_3$;
$R_4$ is H or $CH_3$;
$R_5$ is $OC(O)R_6$, $OC(O)CF_3$, $OSO_2R_6$, $OSO_2CF_3$, $OSO_2C_6H_4R_7$, $OCH_2Ph$ or $OSO_2N(CH_3)_2$; and
$R_6$ and $R_7$ are as previously defined.

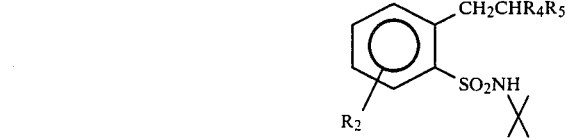

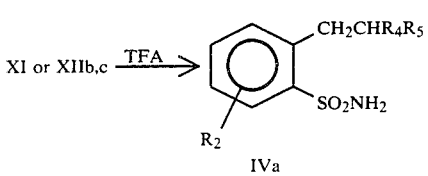

wherein
$R_2$ is H, F, Cl, $CH_3$, $OCH_3$ or $CF_3$;
$R_4$ is H or $CH_3$; and
$R_5$ is F, Cl or Br.

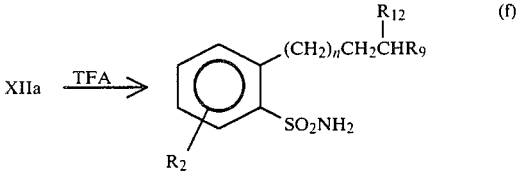

wherein
$R_2$ is as previously defined;
$R_4$ is H or $CH_3$;
$R_5$ is OH, F, Cl, Br, $OC(O)R_6$, $OC(O)CF_3$, $OSO_2R_6$, $OSO_2CF_3$, $OSO_2C_6H_4R_7$, $OCH_2Ph$ or $OSO_2N(CH_3)_2$; and
$R_6$ and $R_7$ are as previously defined.

wherein $R_2$, $R_9$, $R_{12}$, and n are as defined in the Summary of the Invention.

REACTION STEP 8(a)

Reaction Step 8(a) is best carried out under nitrogen in an anhydrous aprotic solvent such as tetrahydrofuran, diethyl ether or hexane at temperatures between −45° C. and 40° C. according to the method of J. G. Lombardino [*J. Org. Chem.*, 36, 1843 (1971)].

The preferred mode of addition is to add the n-butyllithium to a cold solution of the sulfonamide in tetrahydrofuran. An exothermic reaction occurs accompanied by a color change and, in some cases, a precipitate. The appropriate electrophile (ethylene oxide or propylene oxide) is then added and the mixture is stirred at ambient to reflux temperatures for 6 to 20 hours. The addition of dilute acetic acid or ammonium chloride removes inorganic salts from the product contained in the organic phase. Evaporation of the solvent yields the crude product, which can be used without further purification or can be chromatographed.

When $R_2$ is in the 3- or 6-position, lithiation occurs at the 2-position. The lithiation of aromatic sulfones and sulfonamides is described in the following references:

W. E. Truce and M. F. Amos, *J. Am. Chem. Soc.*, 73, 3013 (1951)

S. J. Shafer and W. D. Clossen, *J. Org. Chem.*, 40, 889 (1975)

D. Hellwinkel and M. Supp. *Tetrahedron Lett.*, 1499 (1975)

H. W. Gschwend and H. R. Rodriquez, *Organic Reactions*, 26, 1 (1979).

REACTION STEP 8(b)

Compounds of Formula XIIa are conveniently prepared from the appropriate alcohols, XI. The reaction is best carried out by adding the alcohol to a suspension of at least two equivalents of potassium t-butoxide in tetrahydrofuran at temperatures between −78° C. and 0° C. An alkyl halide is then added and the mixture stirred at −78° C. to ambient temperature for 15 minutes to 6 hours. The addition of a dilute acid such as hydrochloric acid removes the salts from the product in the organic phase. Evaporation of the solvent in vacuo yields the crude product which can be used without further purification.

REACTION STEP 8(c)

Reaction Step 8(c) is best carried out by stirring a solution of the appropriate alcohol, XI, with triethylamine and the appropriate electrophile (alkanesulfonyl chloride, aryl sulfonyl chloride, trifluoromethanesulfonyl chloride, trifluoroacetyl chloride, acyl chloride or the corresponding anhydride or sulfamoyl chloride) in methylene chloride at ambient to reflux temperatures for 2 to 18 hours. The salts are washed out of the solvent with dilute hydrochloric acid and the product isolated by evaporation. The products can be triturated with solvents such as diethyl ether or 1-chlorobutane or purified by column chromatography.

Benzyl ethers of Formula XIIb, in which $R_5$ is $OCH_2Ph$, can be most conveniently prepared by treatment of the appropriate alcohols, XI, first with potassium tert-butoxide in a suitable solvent such as tetrahydrofuran. The resulting alkoxide is then quenched with benzyl bromide and the product isolated as described above.

REACTION STEP 8(d)

The conversion of methanesulfonate esters such as XIII to the corresponding alkyl halides XIIc (wherein $R_5$=F, Cl, or Br) via nucleophilic displacement is well-precedented in the chemical literature. For example, alkyl bromides of Formula XIIc ($R_5$=Br) are best prepared according to the procedure described by Cason and Correia (*J. Org. Chem.*, 26, 3645 (1961)). A mixture of the methanesulfonate ester XIII and excess sodium bromide in a suitable solvent such as dimethylformamide, dimethyl sulfoxide, acetone, or methyl ethyl ketone is stirred rapidly under an inert atmosphere at temperatures between 25° C. and 100° C. Reaction process is conveniently followed by thin-layer chromatography and is complete when little or no starting material can be detected. The solution is then filtered to separate insoluble salts, and the filtrate concentrated to give the desired product which can be purified by crystallization or column chromatography. Alternatively, the reaction solution is diluted with water and the product extracted with a suitable solvent such as diethyl ether, dichloromethane or ethyl acetate. Evaporation of the solvent from the organic layer then affords the product which can be further purified if necessary.

Alkyl chlorides of Formula XIIc ($R_5$=Cl) can be synthesized in an analogous fashion as described by Buck and Foster (*J. Am. Chem. Soc.*, 85, 2217 (1963)) via reaction of the methansulfonate esters, XIII, with lithium chloride in dimethylformamide or ethanol.

Alkyl fluorides of Formula XIIc ($R_5$=F) may be prepared according to the method of Kissman and Weiss (*J. Am. Chem. Soc.*, 80, 5559 (1958)), in which the methanesulfonate esters XIII are treated with potassium fluoride monohydrate in methanol heated under pressure, or by the procedure of Taylor and Kent (*J. Chem. Soc.*, 872 (1958)) using anhydrous potassium fluoride in glycol solvent. Alkyl fluorides can also be prepared from the corresponding chlorides or bromides. The methods for effecting this transformation have been reviewed by A. L. Henne (*Org. Reactions*, 2, 49 (1944)).

REACTION STEPS 8(e) AND 8(f)

Reaction Steps 8(e) and 8(f) are best carried out in trifluoroacetic acid or ethanolic hydrogen chloride between ambient and reflux temperatures for 18 to 48 hours according to the method of J. G. Lombardino [*J. Org. Chem.*, 36, 1843 (1971)].

The deprotection appears to be concentration-dependent. The yield of the sulfonamides, IVa and IVb, can usually be increased by using a large excess of the acid as a solvent, or by stripping off the volatile by-products after 18 hours, redissolving or resuspending the residue in the acid of choice, and stirring an additional 20 to 30 hours. The solvent is distilled off in vacuo and the residue treated with aqueous sodium bicarbonate and ether or methylene chloride. The products can be extracted from the organic phase with dilute aqueous sodium hydroxide and precipitated with aqueous hydrochloric acid. The products can be purified by recrystallization from solvents such as hexane/n-butyl chloride or hexane/chloroform.

The sulfonamides of Formula XIa can be prepared from compounds of Formula IXa as shown in Equation 9.

Equation 9

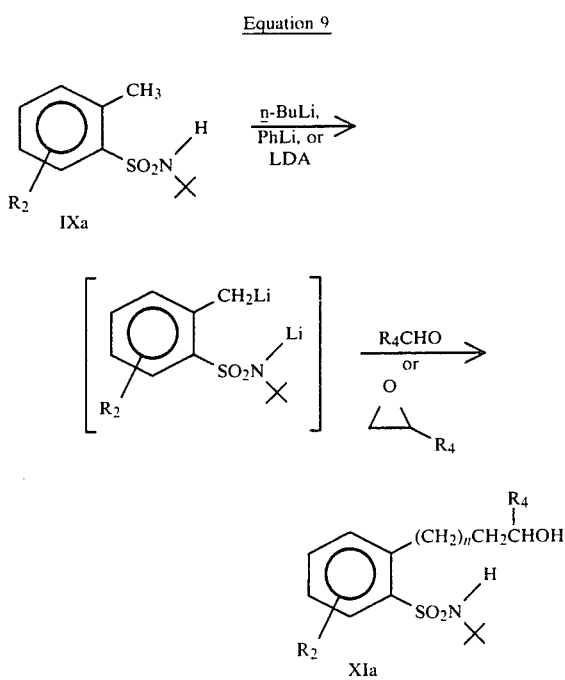

wherein
$R_2$ is as defined in the Summary of the Invention;
$R_4$ is H or $CH_3$; and
n is 0 or 1.

The above reaction is best carried out under the conditions described for Equation 8(a). The lithiation of o-toluenesulfonamide and its subsequent reaction with ketones is described by H. Watanabe and C. R. Hauser (*J. Org. Chem.*, 33, 4278 (1968)).

Compounds of Formula XIa can be elaborated and deprotected as described in Equation 8(a-f).

The sulfonamides of Formulas IX and IXa preferably are prepared from the appropriate sulfonyl chlorides XIV or XIVa and t-butylamine according to the method of J. G. Lombardino (*J. Org. Chem.*, 36, 1843 (1971)), as shown in Equation 10.

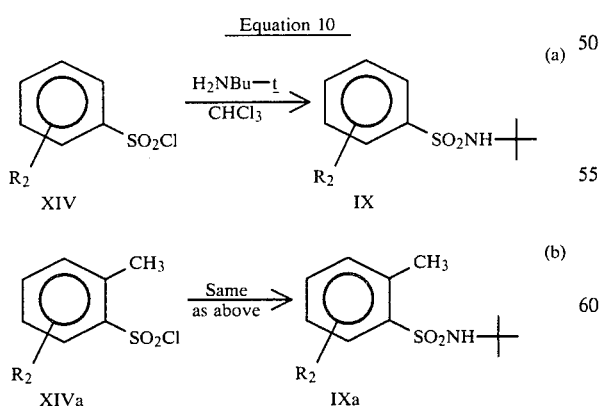

wherein $R_2$ is as previously defined.

The sulfonyl chlorides of Formula XIVa can be prepared as shown in Equation 11.

Equation 11

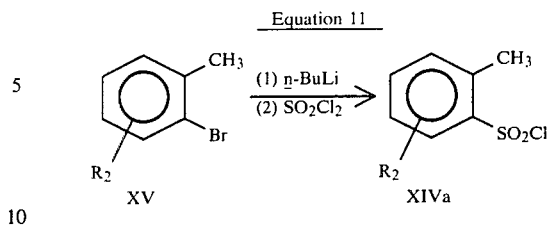

wherein $R_2$ is as previously defined.

The reaction in Equation 11 is best carried out under nitrogen in an anhydrous, aprotic solvent such as tetrahydrofuran or diethyl ether with at least one equivalent of the alkyllithium at temperatures between $-110°$ C. and $-45°$ C. for 15 minutes to two hours. Sulfuryl chloride is then added and the mixture allowed to warm to ambient temperature over 1 to 4 hours. The reaction is often accompanied by several color changes. An aqueous wash removes inorganic salts, and the product is obtained after evaporation of the solvent in vacuo. The crude sulfonyl chlorides can be used without further purification. The reaction of sulfuryl chloride and phenyllithium is described by S. N. Bhattacharya et al. (*J. Chem. Soc., C*, 1265 (1968)).

Certain sulfonyl chlorides are best prepared by chlorosulfonation of a substituted benzene according to the teaching of H. T. Clarke et al., *Org. Synth.* Coll. Vol. 1, 2nd Ed., 1941, p. 85. Other benzenesulfonyl chlorides are best prepared by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.*, 25, 1824 (1960). In addition, the oxidative chlorination of mercaptans to prepare sulfonyl chlorides is widely reported in the literature, e.g., Gilbert, *Sulfonation and Related Reactions*, pp. 202–214, Interscience Publishers, New York, 1965.

Benzenesulfonamides of Formula IVc can best be prepared via the two-step sequence shown in Equation 12 from the appropriate aryl bromides of Formula XVI.

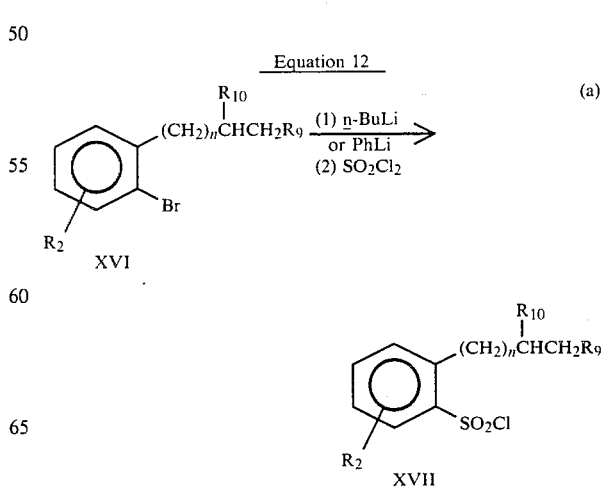

-continued
Equation 12

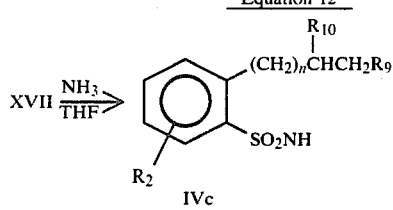
XVII $\xrightarrow{\text{NH}_3}{\text{THF}}$ IVc (b)

wherein $R_2$, $R_9$, and n are as previously defined; and $R_{10}$ is $OCH_3$ or $OC_2H_5$.

The reaction of Equation 12(a) is best effected according to the procedure of Bhattacharya et al. (J. Chem. Soc., C. 1265 (1968)), as described above for Equation 11.

The reaction of Equation 12(b) is preferably carried out by treatment of a solution of the sulfonyl chlorides XVII in a suitable solvent such as tetrahydrofuran or methylene chloride at $-30°$ C. to $10°$ C. with excess anhydrous ammonia gass or concentrated ammonium hydroxide. The reaction mixture is the stirred at ambient temperature for 0.5–3 hours. If ammonium chloride has precipitated, the solution is filtered and the filtrate concentrated in vacuo; otherwise the solvent is simply evaporated. The pure sulfonamides can be obtained by trituration or column chormatography.

Aryl bromides of Formula XVI can be prepared as shown in Equation 13 starting from the appropriate α-alkoxy ketone of Formula XVIII.

Equation 13

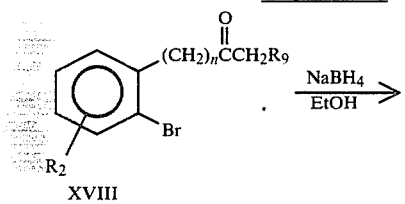

wherein
$R_2$, $R_9$, and n are as previously defined; and
$R_{10}$ is $OCH_3$ or $OC_2H_5$.

The reduction of carbonyl compounds, particularly ketones, to the corresponding alcohols with sodium borohydride is well precedented in the chemical literature. For many pertinent examples see H. O. House, "Modern Synthetic Reactions," 2nd Ed., W. A. Benjamin, Inc., California, 1972, pp. 45–70.

The alkylation of alcohols of Formula XIX as shown in Equation 13(b) is best carried out as described for Equation 8(b) above.

α-Alkoxy ketones of Formula XVIII can be synthesized according to the procedures described by Wissner (Tetrahedron Lett., 2749 (1967) and J. Org. Chem., 44, 4617 (1979)). This process, which involves the reaction of an appropriate acid chloride of Formula XX with a suitable bis-trimethylsilyl ketone acetal of Formula XXI and subsequent mild acid hydrolysis, is summarized in Equation 14.

Equation 14

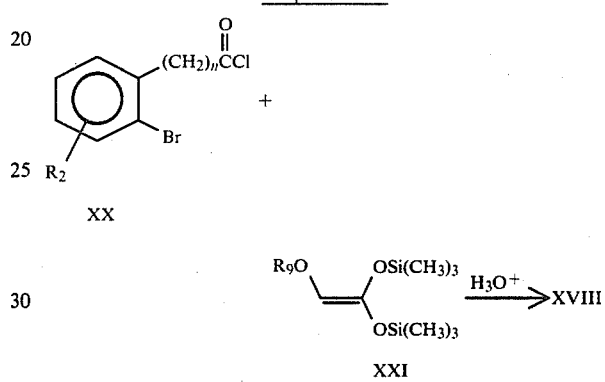

wherein $R_2$, $R_9$, and n are as previously defined.

The preparation and use of ketone acetals of Formula XXI is discussed in the above references by Wissner.

Benzenesulfonamides of Formula IVd also may be prepared as shown in Equation 15 by the procedure of Bhattacharya as described above in Equations 11 and 12.

Equation 15

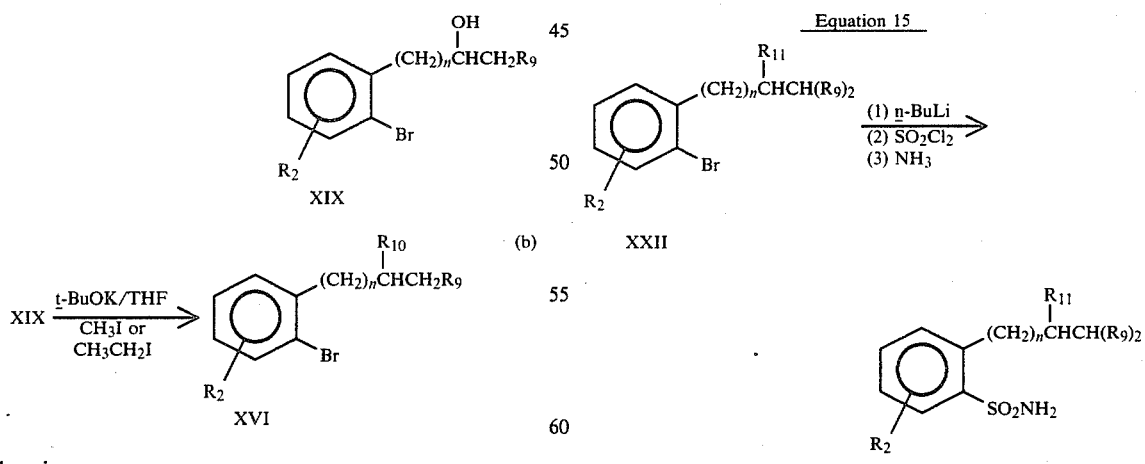

wherein $R_2$, $R_9$, and $R_{11}$ are as previously defined.

The aryl bromides, XXIIa, (wherein $R_{11}=H$) can be prepared via acetalization of the appropriate aldehydes of Formula XXIII as shown in Equation 16.

Equation 16

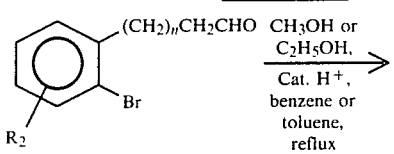

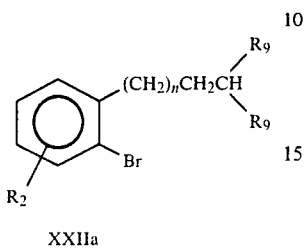

XXIIa wherein $R_2$, $R_9$, and n as previously defined.

The reaction of Equation 16 is best carried out by heating a mixture of the appropriate aldehyde XXIII and at least one equivalent of an appropriate alcohol (methanol or ethanol) with a catalytic amount of acid catalyst such as p-toluensulfonic or camphorsulfonic acid at reflux temperatures in a suitable solvent such as benzene, toluene, or xylene. Water given off during the reaction is most conveniently removed by use of a Dean-Stark water separator. When reaction is complete as evidenced by thin-layer chromatography or IR spectral analysis (typically 1–6 hours), inorganic and acidic materials are washed out of the organic layer with water and saturated sodium bicarbonate solution. Removal of the solvent in vacuo affords the aryl bromide acetals XXIIa, which can be purified by distillation or colun chromatography if necessary.

The aryl bromides of Formula XXIIb, wherein $R_{11}=Cl$ and $n=0$, may be prepared from the corresponding acetals XXIIa ($n=0$, $R_{11}=H$) by benzylic chlorination as shown in Equation 17.

Equation 17

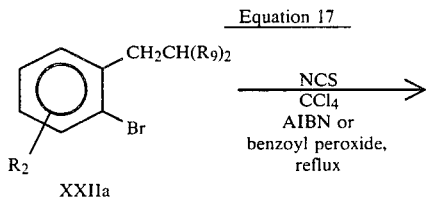

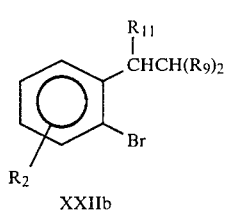

XXIIb wherein
$R_2$ and $R_9$ are as previously defined, and
$R_{11}$ is Cl.

The chlorination reaction of Equation 17 preferably is carried out by heating a mixture of the appropriate acetal XXIIa and one equivalent of N-chlorosuccinimide (NCS) at reflux temperature in carbon tetrachloride solvent; a free-radical initiator such as 2,2′-azobisisobutyronitrile (AIBN) or benzoyl peroxide generally is employed in catalytic amount. When reaction is complete, as judged by proton NMR, the products may be isolated by simple filtration to remove insoluble by-products and evaporation of the filtrate in vacuo.

Aryl bromides of Formula XXIIc, wherein $R_{11}=OCH_3$ and $n=0$, may be most conveniently synthesized by the procedure summarized in Equation 18.

Equation 18

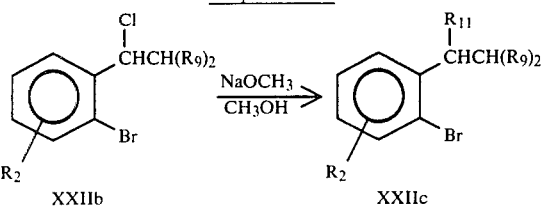

wherein
$R_2$ and $R_9$ are as previously defined; and
$R_{11}$ is $OCH_3$.

The reaction of Equation 18 is well known in the chemical literature as the Williamson ether synthesis. For relevant examples, see A. I. Vogel, *J. Chem. Soc.*, 616 (1948).

Benzenesulfonamides of Formulas IVe, IVf, and IVg also may be prepared by the method of Bhattacharya as described above for Equations 11 and 12. The synthesis of sulfonamides IVe, IVf, and IVg is summarized in Equations 19a, 19b and 19c, respectively.

Equation 19

(a)

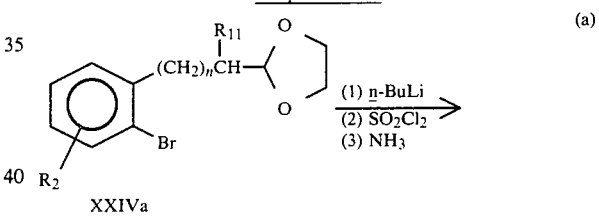

XXIVa

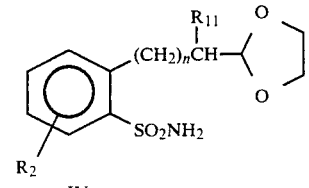

IVe (b)

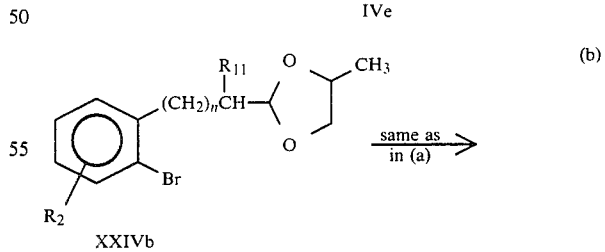

XXIVb

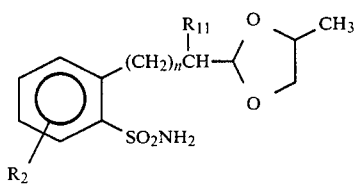

IVf

-continued
Equation 19

(c) XXIVc: benzene ring with (CH$_2$)$_n$CH(R$_{11}$)- attached to 1,3-dioxane (six-membered acetal), Br at ortho position, R$_2$ on ring. → same as in (a) →

IVg: benzene ring with (CH$_2$)$_n$CH(R$_{11}$)- attached to 1,3-dioxane, SO$_2$NH$_2$ at ortho position, R$_2$ on ring.

wherein R$_2$, R$_{11}$, and n are as previously defined.

The aryl bromides XXIVa, XXIVb and XXIVc, wherein R$_{11}$ is H, can most conveniently be prepared via acetalization of the appropriate aldehydes of Formula XXIII as shown in Equation 20(a–c).

Equation 20

(a) XXIII: benzene with (CH$_2$)$_n$CH$_2$CHO, Br, R$_2$ + HOCH$_2$CH$_2$CH$_2$OH (1,3-propanediol equivalent written HO—OH), Cat. H$^+$, benzene or toluene, reflux → XXIVa (b) XXIII + HOCH(CH$_3$)CH$_2$OH (propylene glycol), Cat. H$^+$, benzene or toluene reflux → XXIVb (c) XXIII + HOCH$_2$CH$_2$CH$_2$CH$_2$OH, Cat. H$^+$, benzene or toluene reflux → XXIVc wherein R$_2$ and n are as previously defined.

The reactions of Equation 20(a–c) are best carried out in a manner analogous to that described above for Equation 16 except that the appropriate glycol is used in lieu of methanol or ethanol to effect acetal formation.

Aryl bromides of Formula XIVd, XXIVe, and XXIVf, wherein R$_{11}$=Cl and n=0, may be obtained via benzylic chlorination of the corresponding acetals XXIVa, XXIVb, and XXIVc, as shown in Equation 21(a–c).

Equation 21

(a) XXIVa → NCS, CCl$_4$, AIBN or benzoyl peroxide, reflux → XXIVd: benzene with —CHCl— linked to dioxolane-type acetal (R$_{11}$=Cl shown as CHCH group to 1,3-dioxolane), Br, R$_2$.

-continued
Equation 21

(b) XXIVb → Same as in (a) → XXIVe: benzene with CH(R$_{11}$)CH- to 5-membered acetal with CH$_3$ substituent, Br, R$_2$.

(c) XXIVc → Same as in (a) → XXIVf: benzene with CH(R$_{11}$)CH- to 6-membered 1,3-dioxane, Br, R$_2$.

wherein
R$_2$ is as previously defined; and
R$_{11}$ is Cl.

The reactions shown in Equation 21(a–c) are best carried out as described for Equation 17 above.

Aryl bromides of Formula XXIVg, XXIVh, and XXIVi, wherein R$_{11}$=OCH$_3$ and n=0, can be most conveniently prepared by a Williamson ether synthesis, as shown in Equation 22(a–c), starting from the appropriate acetals of Formula XXIVd, XXIVe, or XXIVf.

Equation 22

(a) XXIVd → NaOCH$_3$/CH$_3$OH → XXIVg: benzene with CH(R$_{11}$)- to 1,3-dioxolane, Br, R$_2$.

(b) XXIVe → Same as in (a) → XXIVh: benzene with CH(R$_{11}$)- to acetal with CH$_3$ substituent, Br, R$_2$.

(c) XXIVf → Same as in (a) → XXIVi: benzene with CH(R$_{11}$)- to 1,3-dioxane, Br, R$_2$.

wherein
R$_2$ is as previously defined; and
R$_{11}$ is OCH$_3$.

The aldehydes of Formula XXIIIa, wherein n=0, and R$_{11}$=H, may be prepared from the corresponding alcohols XXV by oxidation with pyridinium chlorochromate (PCC), as shown in Equation 23.

Equation 23

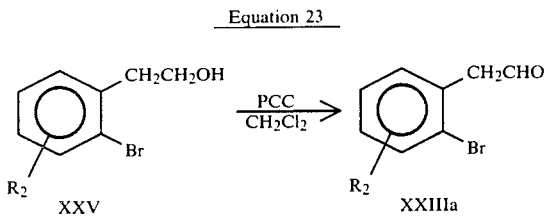

wherein $R_2$ is as previously defined.

The oxidation of Equation 23 is best carried out according to the procedure of E. J. Corey, *Tetrahedron Lett.*, 2644 (1975). Thus, a solution of pyridinium chlorochromate in methylene chloride is added to a stirred solution of the alcohol XXV in methylene chloride at room temperature; sodium acetate may be added to serve as a buffer. When the reaction is complete, as determined most conveniently by thin-layer chromatography, the reaction mixture is diluted with diethyl ether and filtered through a pad of Celite. The filtrate is then further purified by passage through a short column of silica gel or Florisil. Removal of the solvents in vacuo affords the aldehyde XXIIIa which generally can be used without additional purification.

Alcohols of Formula XXV may be prepared by reduction of the corresponding carboxylic acid esters, XXVI, as shown in Equation 24.

Equation 24

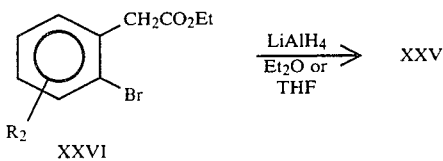

wherein $R_2$ is as previously defined.

The reaction of Equation 24 is conveniently carried out by adding a solution of the ester XXVI in a suitable solvent such as diethyl ether or tetrahydrofuran to a suspension of lithium aluminum hydride (LiAlH4) in the same solvent at ambient to reflux temperatures. After being heated at reflux temperature for 1 to 8 hours, the reaction mixture is cooled to 0° C., and excess hydride reagent destroyed by either the dropwise addition of saturated sodium sulfate (ether solvent) or by the procedure of Fieser (*Reagents for Organic Synthesis*, Vol. 1, John Wiley and Sons, Inc., New York, 1967, pp. 583–584). The suspension is filtered to remove insoluble aluminum salts and the filtrate is dried and concentrated to give the alcohol XXV, which can be used directly or purified by chromatography.

The carboxylic acid esters, XXVI, are preferably prepared by hydrolysis of the corresponding nitriles of Formula XXVII as shown in Equation 25.

Equation 25

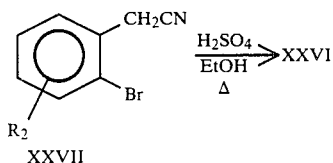

wherein $R_2$ is as previously defined.

The reaction of Equation 25 is carried out by heating a solution of the appropriate nitrile of Formula XXVII in ethanolic sulfuric acid at reflux temperature for 1 to 6 hours. The entire solution is then poured into ice water and the desired ester XXVI extracted with a suitable solvent such as diethyl ether or methylene chloride. Drying and evaporation of the organic layers yield the pure product.

Many nitriles of Formula XXVII are known in the literature. These compounds may be prepared by reaction of the appropriate benzyl bromides, XXVIII, with sodium or potassium cyanide, as shown in Equation 26.

Equation 26

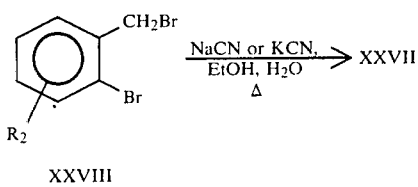

wherein $R_2$ is as previously defined.

The displacement reaction of Equation 26 can best be effected according to the procedure of F. Bickelhaupt et al., *Chem. Ber.*, 685 (1965). Thus, a solution of the bromide XXVIII in a suitable solvent such an ethanol is added dropwise to a room temperature solution of sodium or potassium cyanide in aqueous ethanol. The resultant mixture is then heated to reflux temperature for about 30 minutes. Removal of the solvent in vacuo affords a residue which is washed thoroughly with diethyl ether and filtered to remove NaBr. The filtrate is then washed with several small portions of water, dried, and evaporated in vacuo to give the crude nitrile of Formula XXVII which can most conveniently be purified by either vacuum distillation or column chromatography.

The aldehydes of Formula XXIIIb, wherein n=1 and $R_{11}$=H, can be prepared in a straightforward manner from the appropriate alcohols of Formula XXV via a classical five-step homologation sequence as shown in Equation 27(a–e).

Equation 27

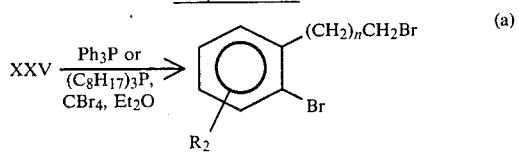

(a)

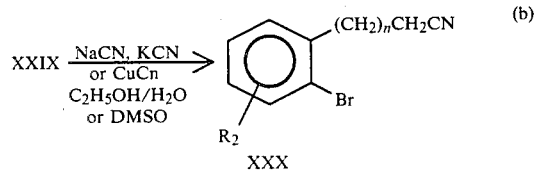

(b)

-continued
Equation 27

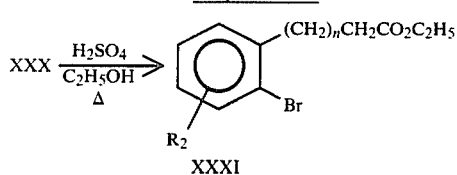
(c)

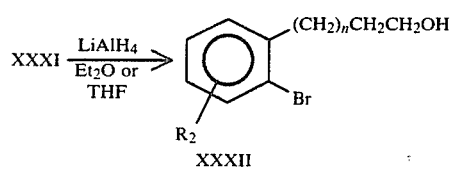
(d)

(e)

wherein
R$_2$ is as previously defined; and
n is 1.

The conversion of alcohols such as XXV to the corresponding bromides, XXIX, as shown in Equation 27(a), is well precedented in the literature and can be effected according to the procedure described by I. M. Downie, et al., *Chem. Ind. (London)*, 900 (1966).

The displacement reaction of Equation 27(b), whereby bromides, XXIX, are converted to the corresponding nitriles of Formula XXX, has been discussed above for Equation 26. For relevant procedures, see L. Friedman and H. Schechter, *J. Org. Chem.*, 25, 877 (1960); also, R. A. Smiley and C. Arnold, ibid. 25, 257 (1960).

The hydrolysis reaction of Equation 27(c) is preferably carried out as described above for Equation 25.

Reduction of carboxylic acid esters of Formula XXXI to the corresponding alcohols, XXXII, as shown in Equation 27(d), can be accomplished by use of lithium aluminum hydride as described for Equation 24.

The desired aldehydes, XXIIIb, can be obtained as shown in Equation 27(e) via oxidation of the appropriate alcohols of Formula XXXII with pyridinium chlorochromate (PCC) according to the method of Corey, *Tetrahedron Lett.*, 2644 (1975).

Benzenesulfonamides of Formula IVh may be prepared as illustrated in Equation 28.

Equation 28

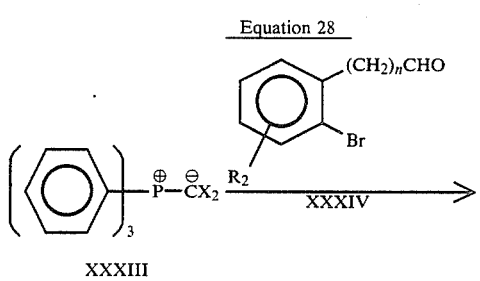
(a)

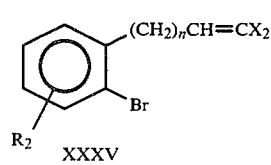

-continued
Equation 28

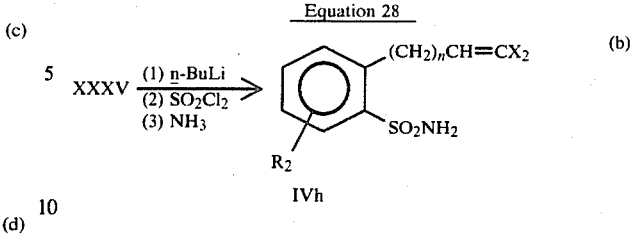
(b)

wherein
X is F, Br, or Cl; and
R$_2$ and n are as previously defined.

REACTION STEP 28(a)

Reaction step 28(a) is conveniently carried out following the method of R. H. Smithers, *J. Org. Chem.*, 43, 2833 (1978).

The synthesis of the appropriate Wittig reagents, XXXIII, is taught in the following references:

Ph$_3$P$^\oplus$—O$^\ominus$Cl$_2$/B. A. Clement and R. L. Soulen, *J. Org. Chem.*, 41, 556 (1976).

Ph$_3$P$^\oplus$—O$^\ominus$Br$_2$/E. J. Corey and P. L. Fuchs, *Tetrahedron Lett.*, 3769 (1972).

Ph$_3$P$^\oplus$—O$^\ominus$F$_2$/D. G. Naae and D. J. Burton, *Fluorine Chem.*, 1, 123 (1971); *Synth. Comm.*, 3, 197 (1973).

REACTION STEP 28(b)

The reaction shown in Equation 28(b) is best effected according to the procedure of S. N. Bhattacharya et al., *J. Chem. Soc.*, (C) 1265 (1968). This procedure is discussed under Equation 11 above. Step 3 of Equation 28(b) is carried out in a manner analogous to that described for Equation 12 above.

Benzenesulfonamides of Formula IVi and IVj can also be synthesized by use of the appropriate Wittig or phosphonate reagents, XXXIIIa or XXXIIIb, respectively. The intermediate aryl bromides XXXVII and XXXVIII can then be treated according to the procedure of Bhattacharya as described above. These reactions are summarized in Equation 29.

Equation 29

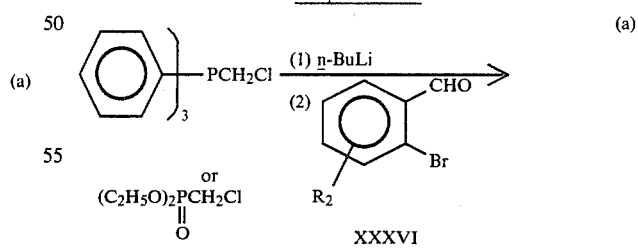
(a)

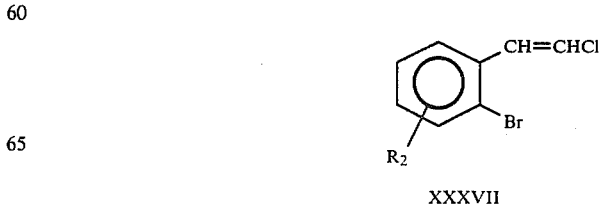

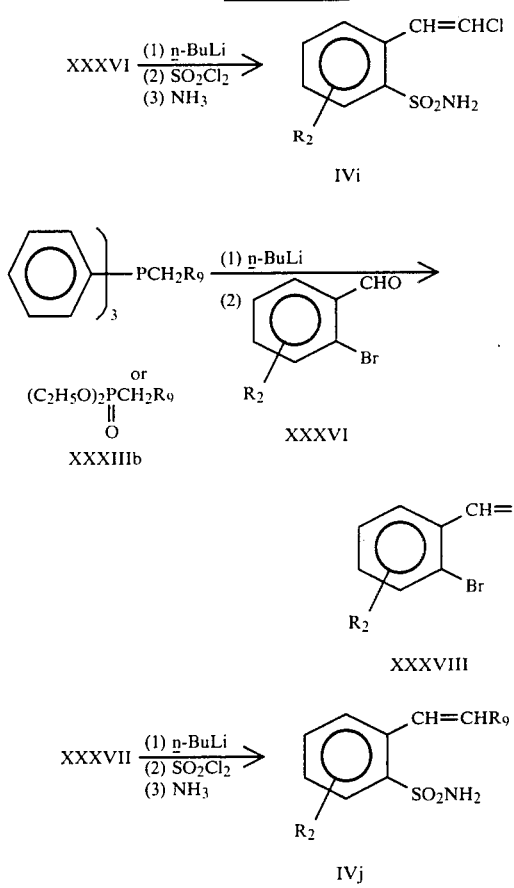

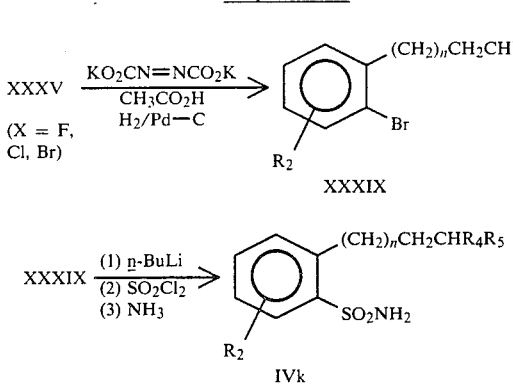

wherein
$R_2$ and n are as previously defined; and
$R_4 = R_5 = F$, Cl, or Br.

The reduction step of Equation 30(a) can be accomplished by following the procedure of J. W. Hamersma and E. I. Snyder, *J. Org. Chem.*, 30, 3985 (1965).

There are numerous ways of preparing alkyl thioethers such as XLII. One of the best-known methods starts with the corresponding alkyl bromides, XIb, as shown in Equation 31.

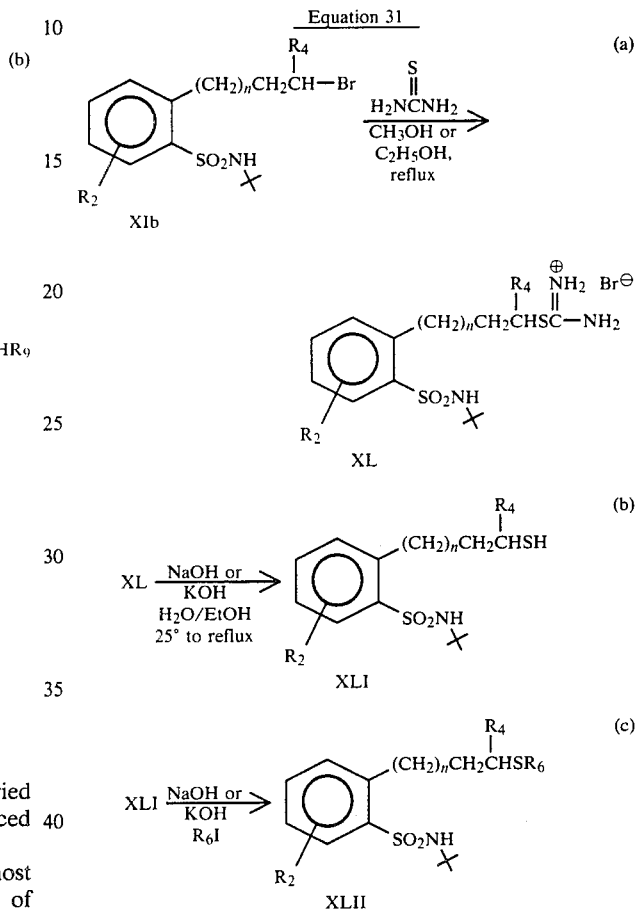

wherein
$R_2$, $R_6$, and n are as previously defined; and
$R_4$ is H or $CH_3$.

The displacement of alkyl bromides with thiourea to generate thiouronium bromide salts, XL, is well known in the literature. This reaction can best be carried out according to the methods of T. B. Johnson and J. M. Sprague, *J. Am. Chem. Soc.*, 58, 1348 (1936); 59, 1837, 2439 (1937); 61, 176 (1939).

The reaction of Equation 31(b), in which the thiouronium salts of Formula XL are hydrolyzed to the corresponding thiols, XLI, is most conveniently carried out by the procedure described by B. C. Cossar et al., *J. Org. Chem.*, 27, 93 (1962).

The third step shown in Equation 31 involves alkylation of the sodium or potassium salts of thiols XLI with the appropriate $C_1$–$C_3$ alkyl iodide to give the desired alkyl thioesters of Formula XLII. Mercaptide alkylations of this kind can be effected by a wide variety of methods. For reviews, see Reid, "Organic Chemistry of Bivalent Sulfur", Vol. 2, pp. 16–21, 24–49; Vol. 3, pp. 11–14 (1960); also, Patai, "The Chemistry of the Thiol Group", pt. 2, pp. 721–735, and references cited therein.

The t-butyl sulfonamides of Formula XLII can be deprotected as described above in Equation 8(e) and elaborated further as in Equations 2, 3, 4, 6, or 7.

Alternatively, the alkyl thio ethers of Formula XLII may be oxidized as represented in Equation 32 to give the corresponding sulfoxides (XLIII, m=1) or sulfones (XLIII, m=2).

Equation 32

$$XLII \xrightarrow[\text{CH}_2\text{Cl}_2 \text{ or } \text{CHCl}_3]{\text{m-CPBA}}$$

[structure with $(CH_2)_nCH_2CHS(O)_mR_6$, $R_4$, $R_2$, $SO_2NH$-t-Bu, labeled XLIII]

wherein
$R_2$, $R_6$, n, and m are as previously defined; and
$R_4$ is H or $CH_3$.

The oxidation of Equation 32 may be accomplished using a variety of literature procedures with m-chloroperoxybenzoic acid (m-CPBA); for example, see C. R. Johnson, et al., *Tetrahedron*, 25, 5649 (1969).

The t-butyl sulfonamides of Formula XLII can be deprotected as described above in Equation 8(e) and elaborated further as in Equations 2, 3, 4, 6, or 7.

Bromides of Formula XIb can be easily prepared from the corresponding alcohols, XIa, by treatment with triphenyl or trioctyl phosphine and carbon tetrabromide as shown above for XXV in Equation 27(a). For a detailed procedure, see I. M. Downie, et al., *Chem. Ind. (London)*, 900 (1966).

Benzenesulfonamides of Formula IVm may be obtained as shown in Equation 33 via chlorination of the appropriate vinyl chlorides XXXVII.

Equation 33

[structure: phenyl with CH=CHCl and Br, $R_2$, labeled XXXVII] 
$\xrightarrow[\text{SO}_2\text{Cl}_2]{\substack{(1)\ \text{Cl}_2 \\ (2)\ \underline{n}\text{-BuLi} \\ \text{THF}}}$
(3) $NH_3$
[structure: phenyl with $CHCHCl_2$ bearing Cl, and $Br$, $R_2$, labeled IVm]

wherein $R_2$ is as previously defined.

The addition of chlorine to olefins is a well known reaction and can be accomplished by a variety of methods. For pertinent examples, see Houben-Weyl, *Methoden der Organischen Chemie*, Georg Thieme Verlag, Stuttgart, 4th Ed., Vol. 5, Pt. 3, p. 529.

The intermediates obtained in reaction step 1 of Equation 33 can be converted to the appropriate sulfonamides of Formula IVm according to the procedure of Bhattacharya as described previously.

Benzenesulfonamides of Formula IVn may also be prepared via chlorination of suitable olefins of Formula XLIV as shown below in Equation 34.

Equation 34

[structure: phenyl with $CH=CH_2$, $SO_2NH_2$, $R_2$, labeled XLIV] $\xrightarrow{Cl_2}$ [structure: phenyl with $CHCH_2Cl$ bearing Cl, $SO_2NH_2$, $R_2$, labeled IVn]

wherein $R_2$ is as previously defined.

The transformation shown above is best effected using the procedure referenced for Equation 33. The sulfonamides, IVn, may then be converted to the sulfonylureas by methods taught earlier.

Olefins of general structure XLIV can most conveniently be prepared according to methods taught in U.S. Pat. No. 4,368,069, issued Jan. 11, 1982.

Sulfonylureas of Formula Id, wherein $R_5$ is $CO_2R_8$ and $R_8$ is $C_2$-$C_3$ alkyl, $CH_2CH=CH_2$, $CH_2CH_2OCH_3$, or $CH_2CH_2Cl$, can most conveniently be prepared by a transesterification reaction of the corresponding compounds of Formula Ic, wherein $R_5=CO_2R_8$ and $R_8$ is $CH_3$. This is summarized in Equation 35.

Equation 35

[structure: phenyl with $(CH_2)_nCH_2CHCO_2CH_3$, $R_4$, $SO_2NH-C(=O)-N(R_3)-A$, $R_2$, labeled Ic]
$\xrightarrow[\text{R}_8\text{OH}]{\text{Al(CH}_3)_3 \text{ or Ti(OPr)}_4}$
[structure: phenyl with $(CH_2)_nCH_2CHCO_2R_8$, $R_4$, $SO_2NH-C(=O)-N(R_3)-A$, $R_2$, labeled Id]

wherein
$R_2$, $R_3$, n, and A are as previously defined;
$R_4$ is H or $CH_3$; and
$R_8$ is $C_2$-$C_3$ alkyl, $CH_2CH=CH_2$, $CH_2CH_2OCH_3$ or $CH_2CH_2Cl$.

The reaction of Equation 35 is most conveniently carried out by adding a slight excess of trimethylaluminum (as a standardized toluene solution) to a solution of the appropriate alcohol of Formula $R_8OH$ in a dry suitable solvent such as benzene or toluene at temperatures of $-5°$ C. to $5°$ C. After being stirred at ambient temperature for about 30 minutes, the reaction mixture is treated with the appropriate sulfonylurea (Ic) and the solution is heated to reflux temperature (80°–110° C.) until most or all of the methyl ester has been converted to the desired product Id. The solution is then cooled to room temperature and acidified by the addition of 10% HCl. The desired product often separates from solution and may be isolated by filtration. If no precipitate forms, then extraction into a suitable solvent such as methylene chloride or ethyl acetate followed by drying and evaporation of the solvent in vacuo affords the product which may be purified by recrystallization or column chromatography if necessary.

For examples of titanate-mediated transesterifications, refer to D. Seebach, *Synthesis,* 138 (1982).

Sulfonylureas of Formula Ic are best prepared by methods described earlier starting from the appropriate benzenesulfonamides of Formula IVo. These sulfonamides, IVo, are most conveniently synthesized by the reduction of the corresponding α,3-unsaturated carboxylic acid esters of Formula XLV as shown in Equation 36.

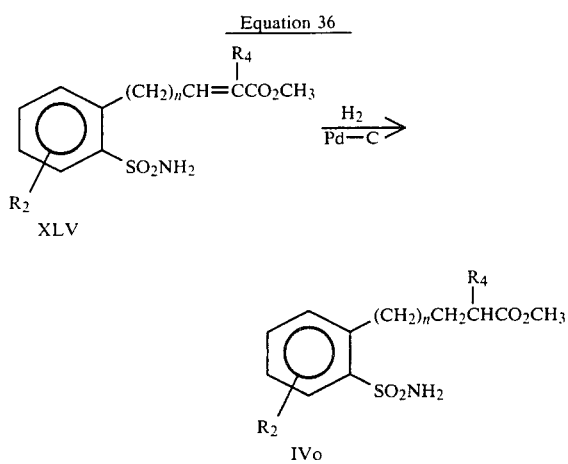

wherein
$R_2$ and n are as previously defined; and
$R_4$ is H or $CH_3$.

The reaction of Equation 36 may be carried out in an inert solvent such as methanol or acetic acid using a suitable catalyst such as palladium-on-carbon and one to five atmospheres of hydrogen. When hydrogen uptake has ceased, the reaction mixture is filtered through a pad of Celite to remove the catalyst. Evaporation of the solvent in vacuo typically affords the pure sulfonamides IVo.

Benzenesulfonamides of Formula XLV are best prepared by the two-step procedure shown in Equation 37.

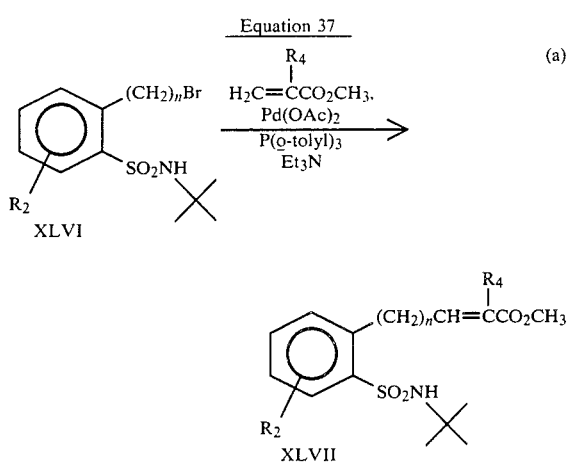

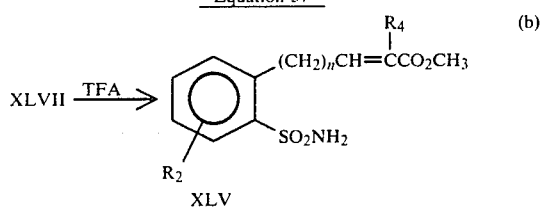

wherein
$R_2$ and n are as previously defined; and
$R_4$ is H or $CH_3$.

Reaction step (a) of Equation 37 is best carried out as follows: the appropriate acrylate ester and bromide XLVI are mixed together and heated to 100° C. in the presence of catalytic amounts of palladium acetate and tris-(o-tolyl)phosphine and excess triethylamine for a period of from 1 to 10 hours. The reaction preferably is performed in a sealed vessel. The mixture is allowed to cool and is poured into ammonium chloride solution. Extraction with a suitable solvent such as diethyl ether or methylene chloride followed by drying and evaporation of the organic layers gives the α,β-unsaturated esters XLVII. Purification may be achieved by column chromatography if necessary.

Removal of the t-butyl protecting group from compounds XLVII can be accomplished using trifluoroacetic acid as described above in Equation 8(e and f).

The t-butyl sulfonamides of Formula XLVIa, where n=0, can be conveniently prepared as described above in Equation 10. Sulfonamides of Formula XLVIb, where n=1, can be obtained by benzylic bromination of the appropriate compounds IXa as shown in Equation 38.

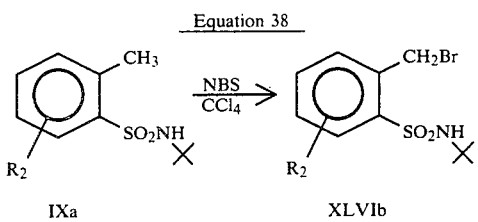

wherein $R_2$ is as previously defined.

The bromination of Equation 38 is best carried out according to methods taught by L. Horner and E. H. Winkelmann, *Angew. Chem.,* 71, 349 (1959) and references cited therein.

The heterocyclic amines of Formula III in Equation 1 are also important intermediates for the preparation of the compounds of this invention and can be prepared by the following methods.

The pyrimidines and triazines of Formula IIIa to IIIc below, wherein $R_3$=H, are either known or can be prepared by obvious methods by one skilled in the art. For instance, the synthesis of pyrimidines and triazines of the general formula VIIa has been reviewed in *The Chemistry of Heterocyclic Compounds,* a series published by Interscience Publishers, Inc., New York and London. 2-Aminopyrimidines are described by D. J. Brown in *The Pyrimidines,* Vol. 16 of this series. 2-Amino-1,3,5-triazines and reviewed by E. M. Smolin and L. Rapaport in *s-Triazines and Derivatives,* Vol. 13 of the same series. The synthesis of triazines is also described by F.

C. Schaefer, U.S. Pat. No. 3,154,547 and by K. R. Huffman and F. C. Schaefer, *J. Org. Chem.*, 28, 1812 (1963). The syntheses of the bicyclic amines IIIb and IIIc are described in EPO Publication No. 15,683.

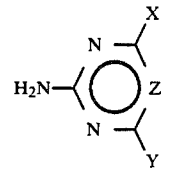    IIIa

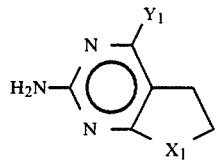    IIIb

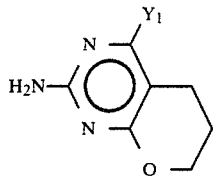    IIIc wherein X, Y, Z, X₁, and Y₁ are as previously defined, except that Y is not CH(OCH₃)₂, CH(OCH₂CH₃)₂, or

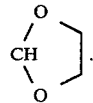

Pyrimidines below of Formula IIId, where Y is CH(OC₂H₅)₂, are described by W. Braker et al., *J. Am. Chem. Soc.*, 69, 3072 (1947), the disclosure of which is herein incorporated by reference. Using techniques taught by Braker, or suitable modifications that would be obvious to one skilled in the art, the pyrimidines IIId can be prepared.

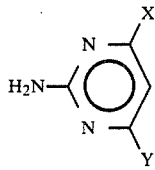    IIId wherein
X is CH₃, OCH₃, or Cl; and
Y is CH(OCH₃)₂ or

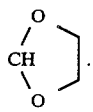

Triazines of Formula IIIe may be prepared according to the methods outlined in Equations 39 and 40.

Equation 39

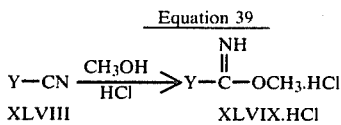    (a)

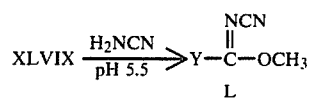    (b)

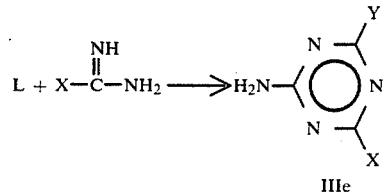    (c)

wherein
X is CH₃ or OCH₃; and
Y is CH(OCH₃)₂ or

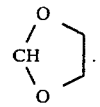

Equation 40

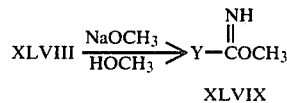    (a)

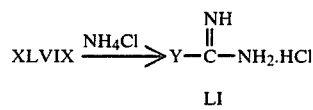    (b)

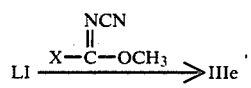    (c)

wherein X and Y are as defined in Equation 39.

The reaction of Equation 39a is carried out according to the teachings of J. M. McElvain and R. L. Clarke, *J. Am. Chem. Soc.*, 69, 2657 (1947), in which the preparation of ethyl diethoxyiminoacetate is described. The intermediate N-cyanoimidate of Formula L may be prepared according to the teaching of D. Lwowski in *Synthesis*, 1971, 263, by reacting XLVIX with cyanamide at pH 5.5, and this may be condensed according to reaction 39(c) with either acetamidine or O-methyl isourea in an alcoholic solvent at 25° C. to 80° C. to provide the appropriate triazines. Alternatively, the reaction of Equation 40(a), described for substituted acetonitriles by F. C. Schaefer and G. A. Peters in *J. Org. Chem.*, 26, 412 (1961), may be used to convert nitriles of Formula XLVIII to the corresponding iminoesters. The free bases may be carried on through reactions 40(b) and 40(c), or, alternatively, converted to the amidinium hydrochloride salts LI as described in the aforementioned reference, and condensed with either methyl N-cyanoacetimidate or with dimethyl N-cyano imidocarbonate in the presence of one equivalent of sodium methoxide to provide the triazines of Formula IIIe.

Cyclic acetals of Formula IIIg also may be prepared from compounds of Formula IIIf according to Equation 41 by acetal exchange.

Equation 41

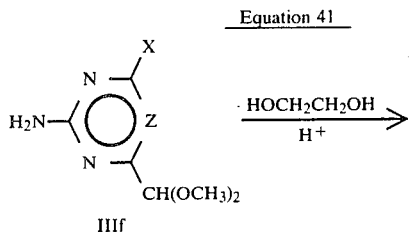
IIIf

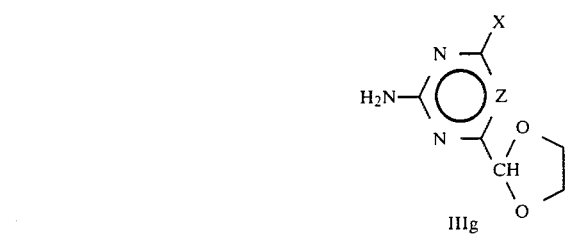
IIIg wherein
X is CH₃ or OCH₃; and
Z is CH or N.

The reaction of Equation 41 is carried out by heating the acyclic acetal in an inert solvent in the presence of one equivalent of ethylene glycol and slightly more than one equivalent of a strong acid, such as p-toluenesulfonic acid, with removal of the methanol or ethanol formed in the reaction by distillation. The product is isolated by treatment with aqueous base and extraction with an organic solvent, and purified by crystallization or column chromatography.

Preparations of 3-amino-1,2,4-triazoles of Formula III in Equation 1 are known in the art and 1,2,4-triazoles are reviewed in *The Chemistry of Heterocyclic Compounds,* "Triazoles 1,2,4" (John Wiley and Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature syntheses are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); *Chem. Ber.,* 96, 1064 (1963).

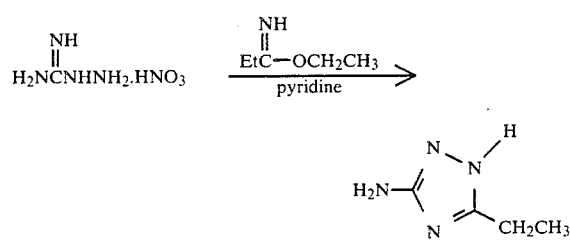

Condensation of hydrazine with ethyl N-cyanoacetimidate yields 3-amino-5-methyltriazole; *J. Org. Chem.,* 28, 1816 (1963).

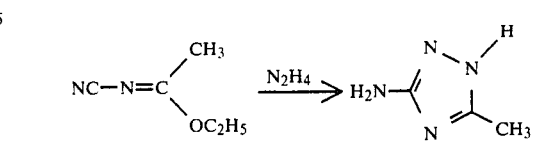

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

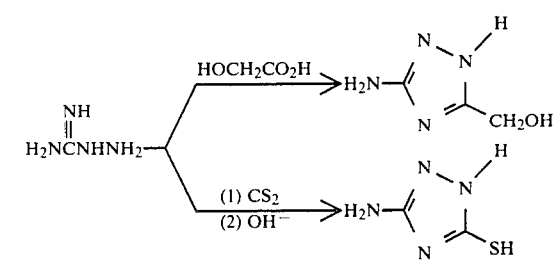

Condensing hydrazine with dimethyl cyanodithioimidocarbonate in acetonitrile gives 3-amino-5-methylthio-1,2,4-triazole, while reaction of hydrazine with dimethyl N-cyanoimidocarbonate produces 3-amino-5-methoxy-1,2,4-triazole; *J. Org. Chem.,* 39, 1522 (1974).

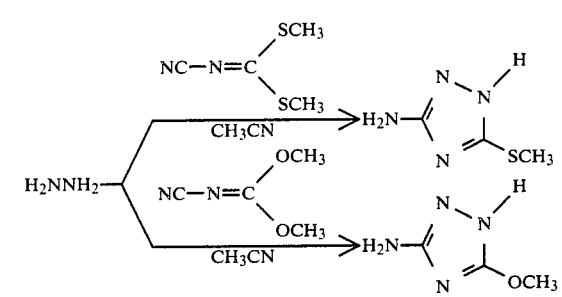

Reaction of substituted hydrazines with N-cyanothioimidocarbonates (prepared according to the procedure given in D. M. Wieland, Ph.D. Thesis, 1971, pp. 123-124) yields disubstituted aminotriazoles as shown below.

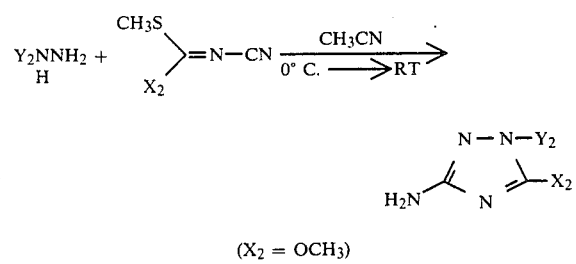

($X_2 = OCH_3$)

Many of the aminoheterocyclic intermediates of Formula III where $R_3$ is methyl may be prepared by a two-step procedure as described for IIIh in Equation 42.

Equation 42

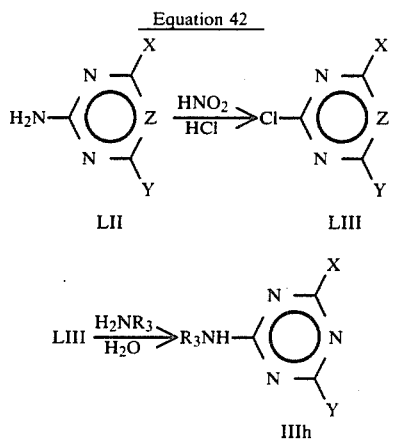

wherein
X, Y, and Z are as originally defined; and
$R_3$ is $CH_3$.

A solution of the amine LII in concentrated hydrochloric acid is treated with sodium nitrite solution and the chloro compound LIII is isolated in the usual manner by filtration of the acidic solution. A representative procedure is described by Bee and Rose in *J. Chem. Soc.*, C, 2031 (1966), for the case in which $Z=CH$, and $X=Y=OCH_3$. Displacement of the chlorine of LIII may be accomplished by heating with an excess of methylamine in water to obtain the methylamino heterocycle IIIh.

Equation 43 below illustrates the preparation of the required methyl pyrimidinyl carbamates and methyl triazinyl carbamates of Formula VIII in Equation 7. By suitable modifications, other methyl carbamates of Formula VIII may be prepared by this method by one skilled in the art.

Equation 43

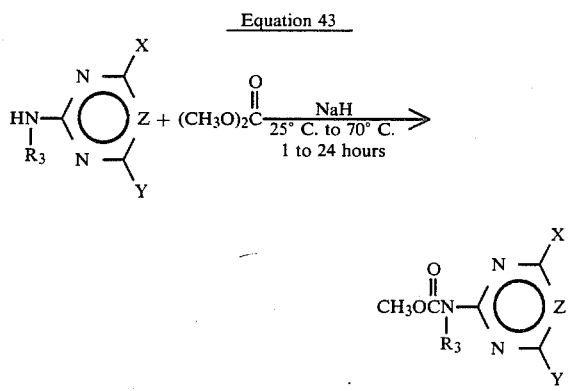

wherein X, Y, Z, and $R_3$ are as originally defined.

According to Equation 43, a heterocyclic amine is reacted with two equivalents of sodium hydride and excess dimethyl carbonate to form VIII. The reaction is run in an inert solvent such as tetrahydrofuran at 25° C. to reflux for 1 to 24 hours. The product is isolated by (a) adding about two equivalents of concentrated hydrochloric acid under nitrogen at 0° C. to 30° C.; (b) filtering; and (c) separating out the organic phase, then drying (sodium sulfate and/or magnesium sulfate) and concentrating to dryness in vacuo. The product VIII may be purified further by recrystallization or chromatography procedures.

The aminomethyl triazines of Formula IIIi can most conveniently be prepared via a three-step sequence as shown in Equation 44.

Equation 44

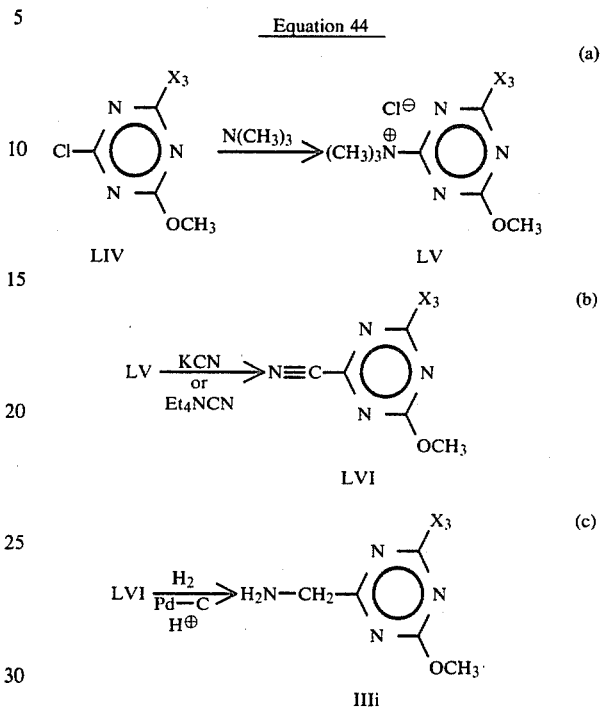

wherein $X_3$ is $CH_3$ or $OCH_3$.

REACTION STEP 44(a)

The displacement reaction shown in Equation 44(a) above is preferably carried out by adding at least one equivalent of liquid trimethylamine to a cooled (0° C.) solution of the appropriate 2-chlorotriazine LIV in a suitable solvent such as acetone or tetrahydrofuran. The reaction solution is stirred at ambient temperature for 1-24 hours, during which time the product LV typically precipitates. Filtration and drying in vacuo affords the pure salts of Formula LV.

REACTION STEP 44(b)

The reaction of Equation 44(b) can best be accomplished by adding excess potassium cyanide to a warm (80°-100° C.) mixture of the salts of Formula LV and molten acetamide; the evolution of trimethylamine is immediately apparent. Following the addition, the solution is heated at temperatures of 80°-100° C. for 1 to 4 hours. Addition of water, extraction of the aqueous layer with a suitable solvent such as diethyl ether, and evaporation of the organic layer yields the nitriles, LVI, which are usually of sufficient purity to carry on to the next step.

Alternatively, the salts LV may be treated with tetrabutyl ammonium cyanide according to the procedure of K. Hermann and G. Simchen, *Ann.*, 1981 333.

REACTION STEP 44(c)

The heterocyclic nitriles of Formula LVI may be hydrogenated in a suitable solvent such as methanol using a palladium-on-carbon catalyst and in the presence of one equivalent of concentrated hydrochloric acid; a hydrogen atmosphere of 40-50 p.s.i. is optimal. When hydrogen uptake has ceased, the solution is filtered through Celite to remove the catalyst, and the volatiles are distilled off in vacuo. The residue is taken up in water and sodium hydroxide is added until the aqueous layer is pH 10-12. In some cases, the amines IIIi precipitates from solution and may be obtained by filtration. If this does not occur, extraction with a suitable solvent (e.g., methylene chloride) followed by drying and evaporation of the organic layer affords the desired amines of Formula IIIi.

The requisite 2-chloro-1,3,5-triazines of Formula LIV are known compounds. See J. Kobe et al., *Monatsh.* 101, 724 (1970), for the synthesis of triazines, IIIi, wherein $X_3=CH_3$; and for the preparation of triazines, IIIi, wherein $X_3=OCH_3$.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts useful in this invention can be obtained by reacting a compound of Formula I with a suitable acid, e.g., p-toluenesulfonic acid, trichloroacetic acid, or the like.

The compounds of this invention and their preparation are further illustrated by the following examples wherein temperatures are given in degrees centigrade and all parts are by weight unless otherwise indicated.

EXAMPLE 1

2-(2-Hydroxyethyl)-N-(1,1-dimethylethyl)benzenesulfonamide

A solution of N-(1,1-dimethylbenzenesulfonamide (40.0 g) in 550 ml dry tetrahydrofuran was cooled to 0° and 250 ml of 1.6M n-butyllithium added dropwise at 0°. After the addition of one equivalent of base, the solution turned yellow. After stirring for 2 hours at room temperature, the resulting suspension was cooled to 0° and 13 ml of ethylene oxide added dropwise. After stirring of 3.5 hours at room temperature, the homogeneous yellow solution was poured into water. The product was extracted with ether and dried (Na2SO4). Concentration gave a yellow oil which was purified by column chromatography [400 g silica gel, ether/hexane (1:1) followed by ethyl acetate]. Pure 2-(2-hydroxyethyl)-N-(1,1-dimethylethyl)benzenesulfonamide was obtained as a colorless oil which solidified after several days; m.p. 43°-45°.

NMR (CDCl3)δ: 8.09 (1H, d); 7.19-7.68 (3H, m); 5.55 (1H, s); 3.98 (2H, m); 3.31 (2H, t, J=7 Hz); 3.01 (1H, t, OH); and 1.25 (9H, s, C(CH3)3).

IR (neat) 3400, 3200, 1300, 1140, cm−1.

EXAMPLE 2

2-(2-Methoxyethyl)-N-(1,1-dimethylethyl)benzenesulfonamide

A suspension of 37.0 g of potassium t-butoxide in 400 ml dry tetrahydrofuran was cooled to 0° and a solution of 39.2 g of the product from Example 1 in 300 ml tetrahydrofuran was added dropwise. After the addition was complete, the reaction mixture was stirred at room temperature for 1 hour. After cooling to 0°, 9.3 ml of methyl iodide was added dropwise and the mixture stirred for 15 minutes at 0°. The solution was diluted with ether, washed with water and dried (Na2SO4). Concentration gave a viscous brown oil which was used in the following example, without further purification.

NMR (CDCl3): δ3.32 (3H, s, OCH3); and 1.23 (9H, s, C(CH3)3).

EXAMPLE 3

2-(2-Methoxyethyl)benzenesulfonamide

A solution of the crude ether from Example 2 (35.0 g) and 80 ml trifluoroacetic acid was stirred at room temperature for 16 hours. The trifluoroacetic acid was removed in vacuo and methylene chloride added to the residue. The organic phase was washed twice with cold saturated sodium bicarbonate, once with water and dried (Na2SO4). Concentration gave a viscous brown oil which was triturated with hexane. The resulting sticky solid was recrystallized from chloroform/hexane (1:1) to provide 11.0 g of pure 2-(2-methoxyethyl)benzenesulfonamide as a white solid; m.p. 79-81.

NMR (CDCl3+DMSO-d6): δ7.93-8.12 (1H, m); 7.18-7.63 (3H, m); 6.19 (2H, broad s, NH2); 3.60-3.82 (2H, m); and 3.18-3.49 (5H, m).

IR (Nujol) 3420 and 3320 (NH2) cm−1.

EXAMPLE 4

N-(4,6-dimethoxypyrimidin-2-yl)aminocarbonyl)-2-(2-methoxyethyl)benzenesulfonamide To a solution of the product from Example 3 (2.0 g) in 100 ml methylene chloride was added 4.7 ml of 2M trimethylaluminum in toluene via syringe. Gas evolution was observed. After 30 minutes, 1.98 g N-(4,6-dimethyoxypyrimidin-2-yl)methylcarbamate was added and the reaction mixture heated at reflux for 16 hours. The mixture was poured into cold 10% hydrochloric acid and diluted with methylene chloride. The organic phase was washed with water and dried (Na2SO4). Concentration gave a white solid which was stirred with 100 ml acetone and collected by filtration to provide 1.1 g of N-[(4-6)dimethoxypyrimidin-2-yl)aminocarbonyl]-2-(2-methoxyethyl)benzenesulfonamide; m.p. 178°-181° C.

NMR (DMSO-d6): 12.80 (1H, broad s, NH); 10.55 (1H, s, NH); 8.01-8.20 (1H, m); 7.39-7.83 (3H, m); 6.00 (1H, s); 3.92 (6H, s, OCH3); 3.12-3.65 (4H, m); and 3.10 (3H, s, OCH3).

IR (Nujol) 1700 (C=O) cm−1.

EXAMPLE 5

2-[2-(Acetyloxy)ethyl]-N-(1,1-dimethylethyl)benzenesulfonamide

A solution of 29.0 g of the product from Example 1 and 24 ml triethylamine in 290 ml of dichloromethane was cooled to 0° C. and treated with 13 ml acetic anhydride. The reaction mixture was stirred at room temperature for 22 hours. Dichloromethane (200 ml) was added and the organic layer washed with three 50 ml portions of water and one portion of brine. Drying the organic layer over magnesium sulfate followed by concentrating in vacuo gave the crude product. Purification by silica gel chromatography (elution with hexanes-ethyl acetate, 70:30) afforded 19.5 g of pure 2-[2-(acetyloxy)ethyl]-N-(1,1-dimethylethyl)benzenesulfonamide as a colorless oil.

NMR (CDCl$_3$): $\delta$8.1–8.3 (1H, m); 7.3–7.5 (3H, m); 5.3 (1H, brs, NH); 4.4 (2H, t, J=7 Hz, —CH$_2$OAc); 3.4 (2H, t, J=7 Hz, —CH$_2$—); 2.1 (3H, s, COCH$_3$); and 1.3 (9H, s, t-Bu).

IR (neat): 3290 (NH stretch), 1730 (C=O stretch) cm$^{-1}$.

EXAMPLE 6

2-[2-(Acetyloxy)ethyl]benzenesulfonamide

The product from Example 5 (13.8 g) was added in portions to 75 ml of trifluoroacetic acid at room temperature and the resulting solution was stirred for 21 hours. Removal of the trifluoroacetic acid in vacuo gave a light orange oil which crystallized upon addition of diethyl ether. Filtration and air drying yielded 9.18 g of pure 2-[2-(acetyloxy)ethyl]benzenesulfonamide as a white powder, m.p. 116°–117.5° C.

NMR (CDCl$_3$+DMSO-d$_6$): $\delta$8.0 (1H, m); 7.3–7.5 (3H, m); 7.1 (2H, brs, NH$_2$); 4.3 (2H, t, J=7 Hz, —CH$_2$—), 3.4 (2H, t, J=7 Hz, —CH$_2$OAc); and 2.0 (3H, s, —COCH$_3$).

EXAMPLE 7

2-[2-(Acetyloxy)ethyl]benzenesulfonyl isocyanate

A solution of 9.18 g of the sulfonamide from Example 6 in 125 ml thionyl chloride was heated at reflux temperature for 46 hours; an aliquot withdrawn showed the complete absence of starting material by $^1$H NMR. Excess thionyl chloride was removed in vacuo and the resulting yellow oil was treated with 74.0 g of a 10% (wt/wt) phosgene/toluene solution and a catalytic amount (ca. 20 drops) of pyridine. The resulting reaction mixture was heated at reflux temperature for 4 hours. After being allowed to cool, the solution was filtered under a stream of nitrogen and all volatiles were removed in vacuo to afford 11.0 g of 2-[2-(acetyloxy)ethyl]benzenesulfonyl isocyanate as a viscous orange oil.

NMR (CDCl$_3$): 8.1–8.2 (1H, m); 7.4–7.7 (3H, m); 4.4 (2H, t, J=7 Hz, —CH$_2$OAc); 3.4 (2H, t, J=7 Hz, —CH$_2$—; and 2.0 (3H, s, COCH$_3$).

EXAMPLE 8

2-[2-(Acetyloxy)ethyl]-N-[(4,6-dimethoxypyrimidin-2-yl)aminocarbonyl]benzenesulfonamide To a stirred solution of 2.3 g of the sulfonyl isocyanate from Example 7 in 25 ml dry acetonitrile was added 1.2 g of 2-amino-4,6-dimethoxypyrimidine. The reaction mixture was warmed to 50° C. for 1¼ hour and then stirred at room temperature for 2 days. Filtration of the insoluble solids and washing with 1-chlorobutane followed by drying afforded 1.8 g of 2-[2-(acetyloxy)ethyl]-N-[(4,6-dimethoxypyrimidin-2-yl)aminocarbonyl]benzenesulfonamide as a light yellow solid, m.p. 160°–162° C.

NMR (CDCl$_3$+DMSO-d$_6$): $\delta$12.9 (1H, brs, NH); 10.5 (1H, s, NH); 8.2 (1H, m); 7.4–7.7 (3H, m); 5.9 (1H, s, heterocyclic H); 4.3 (2H, t, J=6 Hz, —CH$_2$—); 4.0 (6H, s, OCH$_3$'s); 3.4 (2H, t, J=6 Hz, —CH$_2$OAc); and 2.0 (3H, s, —COCH$_3$).

EXAMPLE 9

2-[2-(Methylsulfonyloxy)ethyl]-N-(2,2-dimethylethyl)-benzenesulfonamide

The alcohol from Example 1 (33.1 g) and 20 ml of triethylamine were dissolved in 350 ml of dichloromethane, cooled to 0° C., and treated with 11 ml methanesulfonyl chloride. After being stirred at room temperature for about 20 hours, the reaction mixture was diluted with dichloromethane (100 ml) and the organic layer was washed with three 50-ml portions of water and one of brine. Drying and concentration in vacuo gave the crude product which gradually crystallized upon standing. The solid was washed with diethyl ether, filtered, and dried to yield 12.0 g of 2-[2-(methylsulfonyloxy)ethyl]-N-(2,2-dimethylethyl)benzenesulfonamide as a white powder, m.p. 106°–108° C.

NMR (CDCl$_3$ DMSO-d$_6$): $\delta$8.0 (1H, m); 7.5 (3H, m,); 7.2 (1H, brs, NH); 4.5 (2H, t, J=7 Hz, —CH$_2$OMs); 3.5 (2H, t, J=7 Hz, —CH$_2$—); 2.9 (3H, s, J=6 Hz, —CH$_2$—); 4.0 (6H, s, OCH$_3$'s); 3.4 (2H, t, J=6 Hz, —CH$_2$OAc); and 2.0 (3H, s, —COCH$_3$).

EXAMPLE 10

2-(2-Bromoethyl)-N-(1,1-dimethylethyl)benzenesulfonamide

A mixture of 8.0 g of the product from Example 9, 4.9 g sodium bromide and 1.0 g potassium bromide in methyl ethyl ketone was heated at reflux temperature for approximately 24 hours. The reaction solution was allowed to cool to room temperature and was filtered to remove the insoluble salts. Evaporation of the filtrate under reduced pressure gave the crude bromide as a yellow oil. Purification by silica gel chromatography (elution with hexanes-ethyl acetate, 60:40) afforded 6.4 g of pure 2-(2-bromoethyl)-N-(1,1-dimethylethyl)benzenesulfonamide as a viscous, colorless oil.

NMR (CDCl$_3$): $\delta$8.0–8.2 (1H, m); 7.3–7.6 (3H, m); 5.0 (1H, brs, NH); 3.6 (4H, brt, —CH$_2$CH$_2$—); and 1.2 (9H, s, t-Bu).

EXAMPLE 11

2-(2-Bromoethyl)benzenesulfonamide

A solution of 6.3 g of the product from Example 10 in 30 ml trifluoroacetic acid was stirred at room temperature for one hour. The desired product was insoluble in the reaction mixture and was isolated by filtration. Washing with diethyl ether and drying gave 4.5 g of 2-(2-bromoethyl)benzenesulfonamide as a white solid, m.p. 169°–171° C. (dec.).

NMR (CDCl$_3$): $\delta$8.0–8.1 (1H, m); 7.3–7.5 (3H, m); 6.9 (2H, brs, NH$_2$); and 3.6–3.7 (4H, m, —CH$_2$CH$_2$—).

EXAMPLE 12

2-(2-Bromoethyl)benzenesulfonyl isocyanate

A solution of 4.0 g of the product from Example 11 in 45 ml thionyl chloride was heated at reflux temperature for 19 hours at which time no starting material could be detected by $^1$H NMR. The solution was concentrated in vacuo and the resulting solid was taken up in 30 g of a 10% (wt/wt) phosgene/toluene mixture. A catalytic amount of pyridine was added (ca. 6 drops) and the reaction solution was heted to reflux for 4 hours. Insoluble material was removed by filtration under nitrogen and the filtrate was concentrated in vacuo to yield 4.5 g of the sulfonyl isocyanate as an orange oil.

IR (neat): 2240 cm$^{-1}$ (isocyanate stretch)

EXAMPLE 13

2-(2-Bromoethyl)-N-[(4,6-dimethoxypyrimidin-2-yl)-aminocarbonyl]benzenesulfonamide To a stirred solution of 2.2 g of the sulfonyl isocyanate from Example 12 in 15 ml dry acetonitrile was added 1.0 g of 2-amino-4,6-dimethoxypyrimidine and the mixture was warmed to 45° C. for 45 minutes. Upon cooling, the solution yielded the desired product which was collected by filtration, washed with 1-chlorobutane, and dried. The yield of 2-(2-bromoethyl)-N-[(4,6-dimethoxypyrimidin-2-yl)aminocarbonyl]benzenesulfonamide was 1.6 g light yellow powder, m.p. 163°-166° C.

NMR (CDCl$_3$+DMSO-d$_6$): δ13.0 (1H, s, NH); 10.3 (1H, s, NH); 8.2 (1H, m); 7.4-7.7 (3H, m); 5.8 (1H, s, heterocyclic H); 4.0 (6H, s, OCH$_3$'s); and 3.6 (4H, m, —CH$_2$CH$_2$—).

IR (KBr): 1710 cm$^{-1}$ (C=O stretch).

EXAMPLE 14

2-(2-Chloroethyl)-N-(1,1-dimethylethyl)benzenesulfonamide

A solution of 32.5 g of the alcohol from Example 1 and 32.5 g triphenylphosphine in 244 ml of carbon tetrachloride was stirred at room temperature and under an atmosphere of nitrogen for 72 hours. Excess carbon tetrachloride was removed in vacuo to give 83 g of a crude yellow oil. Purification by silica gel chromatography (hexanes-20% ethyl acetate) afforded a colorless viscous oil which crystallized on standing. The product was isolated by trituration with hexanes, filtration, and drying. The yield of pure 2-(2-chloroethyl)-N-(1,1-dimethylethyl)benzenesulfonamide, m.p. 64°-65° C., was 15.9 g.

NMR (CDCl$_3$): δ8.0-8.2 (1H, mult); 7.4-7.6 (3H, mult); 5.7 (1H, br s, NH); 3.9 (2H, br t, —CH$_2$Cl); 3.5 (2H, br t, ArCH$_2$—); and 1.2 (9H, s).

EXAMPLE 15

2-(2-Chloroethyl)benzenesulfonamide

The product from Example 14 (15.8 g) was added to 96 ml of trifluoroacetic acid at room temperature. After being stirred for 30 inutes, the reaction mixture yielded white crystals which were collected by filtration, washed well with diethyl ether, and dried to afford 10.9 g of the title compound, m.p. 168°-171° C.

NMR (CDCl$_3$+DMSO-d$_6$): δ8.0-8.1 (1H, mult); 7.4-7.6 (3H, mult); 7.0 (2H, s, NH$_2$'s); 3.9 (2H, t, J=7 Hz, —CH$_2$Cl); and 3.5 (2H, t, J=7 Hz, ArCH$_2$—).

IR(KBr): 3360 and 3260 cm$^{-1}$.

EXAMPLE 16

2-(2-Chloroethyl)benzenesulfonyl isocyanate

A solution of 10.1 g of the product from Example 15 in 140 ml thionyl chloride was heated at reflux temperature for 19 hours. The reaction mixture was then allowed to cool, 2 ml of dry toluene was added, and all volatile materials were removed in vacuo. To the resulting residue was added 91 g of a 10% (by weight) solution of phosgene in toluene and 25 drops of pyridine. The mixture was heated to gentle reflux for 4 hours and was then allowed to cool to room temperature. Filtration under a stream of dry nitrogen followed by concentration in vacuo gave the desired sulfonyl isocyanate as a yellow oil. The infrared spectrum of the product displayed a characteristic isocyanate stretching absorption at 2240 cm$^{-1}$.

EXAMPLE 17

2-(2-Chloroethyl)-N-[(4,6-dimethoxypyrimidin-2-yl)-aminocarbonyl]benzenesulfonamide The sulfonyl isocyanate (1.9 g) from Example 16 in 17 ml dry acetonitrile was treated with 1.2 g of 2-amino-4,6-dimethoxypyrimidine at room temperature. Within 10 minutes, a precipiate formed. The reaction mixture was warmed to 40°-45° C. for one hour and then stirred at room temperature for several days. The solids were filtered, washed with 1-chlorobutane, and dried in vacuo to give 1.7 g of 2-(2-chloroethyl)-N-[(4,6-dimethoxypyrimidin-2-yl)aminocarbonyl]benzenesulfonamide as a white powder, m.p. 169°-171° C.

NMR (CDCl$_3$+DMSO-d$_6$): δ13.0 (1H, br s, NH); 9.2 (1H, br s, NH); 8.2 (1H, mult); 7.5 (3H, mult); 5.8 (1H, s, pyrimidine H); 4.0 (6H, s, OCH$_3$'s); 3.8 (2H, t, J=7 Hz, —CH$_2$Cl); and 3.5 (2H, t, J=7 Hz, ArCH$_2$—).

IR (KBr): 1710, 1360, 1200 and 1170 cm$^{-1}$.

MS m/e (rel. intensity): 403 (M$^+$ +2, 3), 401 (M$^+$, 8), 156 (100).

Using the procedures and examples described above and choosing the appropriate aminoheterocycle and sulfonamide or sulfonyl isocyanate, the compounds described in Tables I-XXXVII may be prepared.

TABLE I

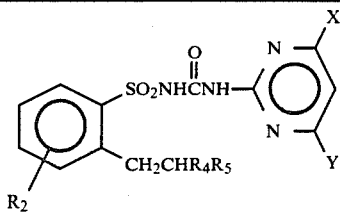

| R$_2$ | R$_4$ | R$_5$ | X | Y | m.p.(°C.) |
|---|---|---|---|---|---|
| H | H | F | CH$_3$ | CH$_3$ | |
| H | H | F | OCH$_3$ | CH$_3$ | |
| H | H | F | OCH$_3$ | OCH$_3$ | |
| H | H | F | Cl | OCH$_3$ | |
| 3-CH$_3$ | H | F | OCH$_3$ | CH$_3$ | |
| 3-OCH$_3$ | H | F | OCH$_3$ | OCH$_3$ | |
| 6-Cl | H | F | OCH$_3$ | CH$_3$ | |
| H | F | F | OCH$_3$ | CH$_3$ | |
| H | F | F | OCH$_3$ | OCH$_3$ | |
| H | H | Cl | CH$_3$ | CH$_3$ | 179–181° d |
| H | H | Cl | OCH$_3$ | CH$_3$ | 162–163° d |
| H | H | Cl | OCH$_3$ | OCH$_3$ | 167–169° |
| 6-Cl | H | Cl | OCH$_3$ | CH$_3$ | |
| 6-CH$_3$ | H | Cl | OCH$_3$ | OCH$_3$ | |
| 6-OCH$_3$ | H | Cl | CH$_3$ | CH$_3$ | |
| 3-CF$_3$ | H | Cl | OCH$_3$ | CH$_3$ | |
| 4-F | H | Cl | OCH$_3$ | OCH$_3$ | |
| 5-CH$_3$ | H | Cl | OCH$_3$ | CH$_3$ | |
| H | Cl | Cl | OCH$_3$ | CH$_3$ | |
| H | Cl | Cl | OCH$_3$ | OCH$_3$ | |
| H | H | Br | CH$_3$ | CH$_3$ | |
| H | H | Br | OCH$_3$ | CH$_3$ | |
| H | H | Br | OCH$_3$ | OCH$_3$ | 163–166° |
| H | Br | Br | OCH$_3$ | CH$_3$ | |
| H | Br | Br | OCH$_3$ | OCH$_3$ | |
| H | H | OC(O)CH$_3$ | CH$_3$ | CH$_3$ | |
| H | H | OC(O)CH$_3$ | OCH$_3$ | CH$_3$ | 143–145° |
| H | H | OC(O)CH$_3$ | OCH$_3$ | OCH$_3$ | 160–162° |
| H | CH$_3$ | OC(O)CH$_3$ | OCH$_3$ | CH$_3$ | |
| H | H | OC(O)CH$_2$CH$_3$ | OCH$_3$ | CH$_3$ | |
| H | H | OC(O)CH$_2$CH$_2$CH$_3$ | OCH$_3$ | OCH$_3$ | |
| H | H | OC(O)CF$_3$ | CH$_3$ | CH$_3$ | 154–157° |
| H | H | OC(O)CF$_3$ | OCH$_3$ | CH$_3$ | 152–157° |
| H | H | OC(O)CF$_3$ | OCH$_3$ | OCH$_3$ | 154–164° (d) |
| H | H | OC(O)CF$_3$ | Cl | OCH$_3$ | |
| H | H | OC(O)CF$_3$ | OCH$_2$CH$_3$ | CH$_3$ | 136–142° |
| H | H | OC(O)CF$_3$ | CH$_3$ | CH(OCH$_3$)$_2$ | 152–155° |
| 6-CH$_3$ | H | OC(O)CF$_3$ | OCH$_3$ | CH$_3$ | |
| 6-Cl | H | OC(O)CF$_3$ | OCH$_3$ | OCH$_3$ | |
| 3-OCH$_3$ | H | OC(O)CF$_3$ | OCH$_3$ | CH$_3$ | |
| H | CH$_3$ | OC(O)CF$_3$ | OCH$_3$ | CH$_3$ | |
| H | H | OH | CH$_3$ | CH$_3$ | 129–134° (d) |
| H | H | OH | OCH$_3$ | CH$_3$ | 126–132° |
| H | H | OH | OCH$_3$ | OCH$_3$ | 136–139° |
| H | H | OH | Cl | OCH$_3$ | 139–143° (d) |
| H | H | OH | OCH$_2$CH$_3$ | CH$_3$ | 134–136° |
| H | H | OH | CH$_3$ | CH(OCH$_3$)$_2$ | |
| 6-Cl | H | OH | OCH$_3$ | CH$_3$ | |
| 6-OCH$_3$ | H | OH | OCH$_3$ | OCH$_3$ | |
| 3-CF$_3$ | H | OH | OCH$_3$ | CH$_3$ | |
| H | CH$_3$ | OH | OCH$_3$ | CH$_3$ | |
| H | CH$_3$ | OH | OCH$_3$ | OCH$_3$ | |
| H | CH$_3$ | OH | Cl | OCH$_3$ | |
| H | H | OCH$_2$C$_6$H$_5$ | CH$_3$ | CH$_3$ | 148–152° |
| H | H | OCH$_2$C$_6$H$_5$ | OCH$_3$ | CH$_3$ | 163–165° |
| H | H | OCH$_2$C$_6$H$_5$ | OCH$_3$ | OCH$_3$ | 137–143° |
| H | CH$_3$ | OCH$_2$C$_6$H$_5$ | OCH$_3$ | CH$_3$ | |
| H | H | OSO$_2$CH$_3$ | CH$_3$ | CH$_3$ | |
| H | H | OSO$_2$CH$_3$ | OCH$_3$ | CH$_3$ | 148–149° |
| H | H | OSO$_2$CH$_3$ | OCH$_3$ | OCH$_3$ | 152–154° |
| 6-Cl | H | OSO$_2$CH$_3$ | OCH$_3$ | CH$_3$ | |
| 3-OCH$_3$ | H | OSO$_2$CH$_3$ | OCH$_3$ | OCH$_3$ | |
| 5-Cl | H | OSO$_2$CH$_3$ | OCH$_3$ | CH$_3$ | |
| H | H | OSO$_2$CH$_2$CH$_3$ | OCH$_3$ | CH$_3$ | |
| H | H | OSO$_2$CH$_2$CH$_2$CH$_3$ | OCH$_3$ | OCH$_3$ | |
| H | CH$_3$ | OSO$_2$CH$_3$ | OCH$_3$ | CH$_3$ | |
| H | H | OSO$_2$CF$_3$ | CH$_3$ | CH$_3$ | |
| H | H | OSO$_2$CF$_3$ | OCH$_3$ | CH$_3$ | |
| H | H | OSO$_2$CF$_3$ | OCH$_3$ | OCH$_3$ | |
| H | CH$_3$ | OSO$_2$CF$_3$ | OCH$_3$ | CH$_3$ | |

TABLE I-continued

[Structure: phenyl ring with R2 substituent and CH2CHR4R5 group, attached via SO2NHC(O)NH to a pyrimidine ring with X and Y substituents]

| R2 | R4 | R5 | X | Y | m.p.(°C.) |
|---|---|---|---|---|---|
| H | H | OSO2C6H5 | OCH3 | CH3 | |
| H | H | 2'-OSO2C6H4F | CH3 | CH3 | |
| H | H | 3'-OSO2C6H4Cl | OCH3 | CH3 | |
| H | H | 4'-OSO2C6H4Br | OCH3 | OCH3 | |
| H | H | 4'-OSO2C6H4CH3 | CH3 | CH3 | |
| H | H | 4'-OSO2C6H4CH3 | OCH3 | CH3 | 141–143° |
| H | H | 4'-OSO2C6H4CH3 | OCH3 | OCH3 | 122–124° |
| H | H | 5'-OSO2C6H4CH3 | CH3 | CH3 | |
| H | H | 6'-OSO2C6H4OCH3 | OCH3 | CH3 | |
| H | H | 2'-OSO2C6H4CF3 | OCH3 | OCH3 | |
| H | H | SCH3 | CH3 | CH3 | |
| H | H | SCH3 | OCH3 | CH3 | |
| H | H | SCH3 | OCH3 | OCH3 | |
| H | CH3 | SCH3 | OCH3 | CH3 | |
| H | H | S(O)CH3 | OCH3 | CH3 | |
| H | H | S(O)CH3 | OCH3 | OCH3 | |
| H | H | S(O)2CH3 | CH3 | CH3 | |
| H | H | S(O)2CH3 | OCH3 | CH3 | |
| H | H | S(O)2CH3 | OCH3 | OCH3 | |
| H | CH3 | S(O)2CH3 | OCH3 | CH3 | |
| H | H | SCH2CH3 | OCH3 | CH3 | |
| H | H | S(O)CH2CH3 | OCH3 | CH3 | |
| H | H | S(O)2CH2CH3 | OCH3 | OCH3 | |
| H | H | SCH2CH2CH3 | OCH3 | OCH3 | |
| H | H | S(O)CH2CH2CH3 | OCH3 | CH3 | |
| H | H | S(O)2CH2CH2CH3 | OCH3 | CH3 | |
| H | H | S(O)2CH2CH2CH3 | OCH3 | OCH3 | |
| H | H | OSO2N(CH3)2 | CH3 | CH3 | |
| H | H | OSO2N(CH3)2 | OCH3 | CH3 | |
| H | H | OSO2N(CH3)2 | OCH3 | OCH3 | |
| 6-Cl | H | OSO2N(CH3)2 | OCH3 | CH3 | |
| 3-OCH3 | H | OSO2N(CH3)2 | OCH3 | OCH3 | |
| H | CH3 | OSO2N(CH3)2 | OCH3 | CH3 | |
| H | CH3 | OSO2N(CH3)2 | OCH3 | OCH3 | |
| H | H | CO2CH3 | OCH3 | CH3 | 176–181° (d) |
| H | H | CO2CH3 | OCH3 | OCH3 | |
| H | CH3 | CO2CH3 | OCH3 | CH3 | |
| H | H | CO2CH2CH3 | OCH3 | CH3 | |
| H | H | CO2CH2CH2CH3 | OCH3 | OCH3 | |
| H | H | CO2CH2CH=CH2 | OCH3 | CH3 | |
| H | H | CO2CH2CH2OCH3 | OCH3 | OCH3 | |
| H | H | CO2CH2CH2Cl | OCH3 | CH3 | |

TABLE II

[Structure: phenyl ring with R2 substituent and CH2CHR4R5 group, attached via SO2NHC(O)NH to a triazine ring with X and Y substituents]

| R2 | R4 | R5 | X | Y | m.p.(°C.) |
|---|---|---|---|---|---|
| H | H | F | CH3 | CH3 | |
| H | H | F | OCH3 | CH3 | |
| H | H | F | OCH3 | OCH3 | |
| 3-CH3 | H | F | OCH3 | CH3 | |
| 3-OCH3 | H | F | OCH3 | OCH3 | |
| 6-Cl | H | F | OCH3 | CH3 | |
| H | F | F | OCH3 | CH3 | |
| H | F | F | OCH3 | OCH3 | |
| H | H | Cl | CH3 | CH3 | |
| H | H | Cl | OCH3 | CH3 | 170–172° d |
| H | H | Cl | OCH3 | OCH3 | 186–188° |

TABLE II-continued

| R₂ | R₄ | R₅ | X | Y | m.p.(°C.) |
|---|---|---|---|---|---|
| 6-Cl | H | Cl | OCH₃ | CH₃ | |
| 6-CH₃ | H | Cl | OCH₃ | OCH₃ | |
| 6-OCH₃ | H | Cl | CH₃ | CH₃ | |
| 3-CF₃ | H | Cl | OCH₃ | CH₃ | |
| 4-F | H | Cl | OCH₃ | OCH₃ | |
| 5-CH₃ | H | Cl | OCH₃ | CH₃ | |
| H | Cl | Cl | OCH₃ | CH₃ | |
| H | Cl | Cl | OCH₃ | OCH₃ | |
| H | H | Br | CH₃ | CH₃ | |
| H | H | Br | OCH₃ | CH₃ | 168–170° |
| H | H | Br | OCH₃ | OCH₃ | |
| H | Br | Br | OCH₃ | CH₃ | |
| H | Br | Br | OCH₃ | OCH₃ | |
| H | H | OC(O)CH₃ | CH₃ | CH₃ | |
| H | H | OC(O)CH₃ | OCH₃ | CH₃ | 123–127° |
| H | H | OC(O)CH₃ | OCH₃ | OCH₃ | 124–126° |
| H | CH₃ | OC(O)CH₃ | OCH₃ | CH₃ | |
| H | H | OC(O)CH₂CH₃ | OCH₃ | CH₃ | |
| H | H | OC(O)CH₂CH₂CH₃ | OCH₃ | OCH₃ | |
| H | H | OC(O)CF₃ | CH₃ | CH₃ | 145–150° |
| H | H | OC(O)CF₃ | OCH₃ | CH₃ | 142–145° (d) |
| H | H | OC(O)CF₃ | OCH₃ | OCH₃ | 156–162° |
| H | H | OC(O)CF₃ | OCH₂CH₃ | CH₃ | |
| H | H | OC(O)CF₃ | CH₃ | CH(OCH₃)₂ | |
| 6-CH₃ | H | OC(O)CF₃ | OCH₃ | CH₃ | |
| 6-Cl | H | OC(O)CF₃ | OCH₃ | OCH₃ | |
| 3-OCH₃ | H | OC(O)CF₃ | OCH₃ | CH₃ | |
| H | CH₃ | OC(O)CF₃ | OCH₃ | CH₃ | |
| H | H | OH | CH₃ | CH₃ | 118–123° (d) |
| H | H | OH | OCH₃ | CH₃ | 141–145° (d) |
| H | H | OH | OCH₃ | OCH₃ | 134–138° |
| H | H | OH | OCH₂CH₃ | CH₃ | |
| H | H | OH | CH₃ | CH(OCH₃)₂ | |
| 6-Cl | H | OH | OCH₃ | CH₃ | |
| 6-OCH₃ | H | OH | OCH₃ | OCH₃ | |
| 3-CF₃ | H | OH | OCH₃ | CH₃ | |
| H | CH₃ | OH | OCH₃ | CH₃ | |
| H | CH₃ | OH | OCH₃ | OCH₃ | |
| H | H | OCH₂C₆H₅ | CH₃ | CH₃ | 141–144° |
| H | H | OCH₂C₆H₅ | OCH₃ | CH₃ | 158–162° |
| H | H | OCH₂C₆H₅ | OCH₃ | OCH₃ | 152–157° |
| H | CH₃ | OCH₂C₆H₅ | OCH₃ | CH₃ | |
| H | H | OSO₂CH₃ | CH₃ | CH₃ | |
| H | H | OSO₂CH₃ | OCH₃ | CH₃ | 159–164° |
| H | H | OSO₂CH₃ | OCH₃ | OCH₃ | |
| 6-Cl | H | OSO₂CH₃ | OCH₃ | CH₃ | |
| 3-OCH₃ | H | OSO₂CH₃ | OCH₃ | OCH₃ | |
| 5-Cl | H | OSO₂CH₃ | OCH₃ | CH₃ | |
| H | H | OSO₂CH₂CH₃ | OCH₃ | CH₃ | |
| H | H | OSO₂CH₂CH₂CH₃ | OCH₃ | OCH₃ | |
| H | CH₃ | OSO₂CH₃ | OCH₃ | CH₃ | |
| H | H | OSO₂CF₃ | CH₃ | CH₃ | |
| H | H | OSO₂CF₃ | OCH₃ | CH₃ | |
| H | H | OSO₂CF₃ | OCH₃ | OCH₃ | |
| H | CH₃ | OSO₂CF₃ | OCH₃ | CH₃ | |
| H | H | OSO₂C₆H₅ | OCH₃ | CH₃ | |
| H | H | 2'-OSO₂C₆H₄F | CH₃ | CH₃ | |
| H | H | 3'-OSO₂C₆H₄Cl | OCH₃ | CH₃ | |
| H | H | 4'-OSO₂C₆H₄Br | OCH₃ | OCH₃ | |
| H | H | 4'-OSO₂C₆H₄CH₃ | CH₃ | CH₃ | 132–136° d |
| H | H | 4'-OSO₂C₆H₄CH₃ | OCH₃ | CH₃ | |
| H | H | 4'-OSO₂C₆H₄CH₃ | OCH₃ | OCH₃ | |
| H | H | 5'-OSO₂C₆H₄CH₃ | CH₃ | CH₃ | |
| H | H | 6'-OSO₂C₆H₄OCH₃ | OCH₃ | CH₃ | |
| H | H | 2'-OSO₂C₆H₄CF₃ | OCH₃ | OCH₃ | |
| H | H | SCH₃ | CH₃ | CH₃ | |
| H | H | SCH₃ | OCH₃ | CH₃ | |
| H | H | SCH₃ | OCH₃ | OCH₃ | |
| H | CH₃ | SCH₃ | OCH₃ | CH₃ | |
| H | H | S(O)CH₃ | OCH₃ | CH₃ | |

TABLE II-continued

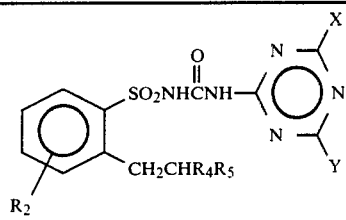

| R2 | R4 | R5 | X | Y | m.p.(°C.) |
|---|---|---|---|---|---|
| H | H | S(O)CH3 | OCH3 | OCH3 | |
| H | H | S(O)2CH3 | CH3 | CH3 | |
| H | H | S(O)2CH3 | OCH3 | CH3 | |
| H | H | S(O)2CH3 | OCH3 | OCH3 | |
| H | CH3 | S(O)2CH3 | OCH3 | CH3 | |
| H | H | SCH2CH3 | OCH3 | CH3 | |
| H | H | S(O)CH2CH3 | OCH3 | CH3 | |
| H | H | S(O)2CH2CH3 | OCH3 | OCH3 | |
| H | H | SCH2CH2CH3 | OCH3 | OCH3 | |
| H | H | S(O)CH2CH2CH3 | OCH3 | CH3 | |
| H | H | S(O)2CH2CH2CH3 | OCH3 | CH3 | |
| H | H | S(O)2CH2CH2CH3 | OCH3 | OCH3 | |
| H | H | OSO2N(CH3)2 | CH3 | CH3 | |
| H | H | OSO2N(CH3)2 | OCH3 | CH3 | |
| H | H | OSO2N(CH3)2 | OCH3 | OCH3 | |
| 6-Cl | H | OSO2N(CH3)2 | OCH3 | CH3 | |
| 3-OCH3 | H | OSO2N(CH3)2 | OCH3 | OCH3 | |
| H | CH3 | OSO2N(CH3)2 | OCH3 | CH3 | |
| H | CH3 | OSO2N(CH3)2 | OCH3 | OCH3 | |
| H | H | CO2CH3 | OCH3 | CH3 | |
| H | H | CO2CH3 | OCH3 | OCH3 | |
| H | CH3 | CO2CH3 | OCH3 | CH3 | |
| H | H | CO2CH2CH3 | OCH3 | CH3 | |
| H | H | CO2CH2CH2CH3 | OCH3 | OCH3 | |
| H | H | CO2CH2CH=CH2 | OCH3 | CH3 | |
| H | H | CO2CH2CH2OCH3 | OCH3 | OCH3 | |
| H | H | CO2CH2CH2Cl | OCH3 | CH3 | |

TABLE III

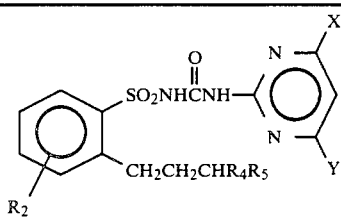

| R2 | R4 | R3 | X | Y | m.p.(°C.) |
|---|---|---|---|---|---|
| H | H | F | CH3 | CH3 | |
| H | H | F | OCH3 | CH3 | |
| H | H | F | OCH3 | OCH3 | |
| H | H | F | Cl | OCH3 | |
| 3-CH3 | H | F | OCH3 | CH3 | |
| 3-OCH3 | H | F | OCH3 | OCH3 | |
| 6-Cl | H | F | OCH3 | CH3 | |
| H | F | F | OCH3 | CH3 | |
| H | F | F | OCH3 | OCH3 | |
| H | H | Cl | CH3 | CH3 | |
| H | H | Cl | OCH3 | CH3 | |
| H | H | Cl | OCH3 | OCH3 | |
| 6-Cl | H | Cl | OCH3 | CH3 | |
| 6-CH3 | H | Cl | OCH3 | OCH3 | |
| 6-OCH3 | H | Cl | CH3 | CH3 | |
| 3-CF3 | H | Cl | OCH3 | CH3 | |
| 4-F | H | Cl | OCH3 | OCH3 | |
| 5-CH3 | H | Cl | OCH3 | CH3 | |
| H | Cl | Cl | OCH3 | CH3 | |
| H | Cl | Cl | OCH3 | OCH3 | |
| H | H | Br | CH3 | CH3 | |
| H | H | Br | OCH3 | CH3 | |
| H | H | Br | OCH3 | OCH3 | |
| H | Br | Br | OCH3 | CH3 | |
| H | Br | Br | OCH3 | OCH3 | |
| H | H | OC(O)CH3 | CH3 | CH3 | |

TABLE III-continued

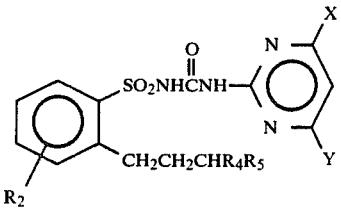

| R₂ | R₄ | R₃ | X | Y | m.p.(°C.) |
|---|---|---|---|---|---|
| H | H | OC(O)CH₃ | OCH₃ | CH₃ | |
| H | H | OC(O)CH₃ | OCH₃ | OCH₃ | |
| H | CH₃ | OC(O)CH₃ | OCH₃ | CH₃ | |
| H | H | OC(O)CH₂CH₃ | OCH₃ | CH₃ | |
| H | H | OC(O)CH₂CH₂CH₃ | OCH₃ | OCH₃ | |
| H | H | OC(O)CF₃ | CH₃ | CH₃ | |
| H | H | OC(O)CF₃ | OCH₃ | CH₃ | |
| H | H | OC(O)CF₃ | OCH₃ | OCH₃ | |
| H | H | OC(O)CF₃ | Cl | OCH₃ | |
| H | H | OC(O)CF₃ | OCH₂CH₃ | CH₃ | |
| H | H | OC(O)CF₃ | CH₃ | CH(OCH₃)₂ | |
| 6-CH₃ | H | OC(O)CF₃ | OCH₃ | CH₃ | |
| 6-Cl | H | OC(O)CF₃ | OCH₃ | OCH₃ | |
| 3-OCH₃ | H | OC(O)CF₃ | OCH₃ | CH₃ | |
| H | CH₃ | OC(O)CF₃ | OCH₃ | CH₃ | |
| H | H | OH | CH₃ | CH₃ | |
| H | H | OH | OCH₃ | CH₃ | |
| H | H | OH | OCH₃ | OCH₃ | |
| H | H | OH | Cl | OCH₃ | |
| H | H | OH | OCH₂CH₃ | CH₃ | |
| H | H | OH | CH₃ | CH(OCH₃)₂ | |
| 6-Cl | H | OH | OCH₃ | CH₃ | |
| 6-OCH₃ | H | OH | OCH₃ | OCH₃ | |
| 3-CF₃ | H | OH | OCH₃ | CH₃ | |
| H | CH₃ | OH | OCH₃ | CH₃ | |
| H | CH₃ | OH | OCH₃ | OCH₃ | |
| H | CH₃ | OH | Cl | OCH₃ | |
| H | H | OCH₂C₆H₅ | CH₃ | CH₃ | |
| H | H | OCH₂C₆H₅ | OCH₃ | CH₃ | |
| H | H | OCH₂C₆H₅ | OCH₃ | OCH₃ | |
| H | CH₃ | OCH₂C₆H₅ | OCH₃ | CH₃ | |
| H | H | OSO₂CH₃ | CH₃ | CH₃ | |
| H | H | OSO₂CH₃ | OCH₃ | CH₃ | |
| H | H | OSO₂CH₃ | OCH₃ | OCH₃ | |
| 6-Cl | H | OSO₂CH₃ | OCH₃ | CH₃ | |
| 3-OCH₃ | H | OSO₂CH₃ | OCH₃ | OCH₃ | |
| 5-Cl | H | OSO₂CH₃ | OCH₃ | CH₃ | |
| H | H | OSO₂CH₂CH₃ | OCH₃ | CH₃ | |
| H | H | OSO₂CH₂CH₂CH₃ | OCH₃ | OCH₃ | |
| H | CH₃ | OSO₂CH₃ | OCH₃ | CH₃ | |
| H | H | OSO₂CF₃ | CH₃ | CH₃ | |
| H | H | OSO₂CF₃ | OCH₃ | CH₃ | |
| H | H | OSO₂CF₃ | OCH₃ | OCH₃ | |
| H | CH₃ | OSO₂CF₃ | OCH₃ | CH₃ | |
| H | H | OSO₂C₆H₅ | OCH₃ | CH₃ | |
| H | H | 2'-OSO₂C₆H₄F | CH₃ | CH₃ | |
| H | H | 3'-OSO₂C₆H₄Cl | OCH₃ | CH₃ | |
| H | H | 4'-OSO₂C₆H₄Br | OCH₃ | OCH₃ | |
| H | H | 4'-OSO₂C₆H₄CH₃ | CH₃ | CH₃ | |
| H | H | 4'-OSO₂C₆H₄CH₃ | OCH₃ | CH₃ | |
| H | H | 4'-OSO₂C₆H₄CH₃ | OCH₃ | OCH₃ | |
| H | H | 5'-OSO₂C₆H₄CH₃ | CH₃ | CH₃ | |
| H | H | 6'-OSO₂C₆H₄OCH₃ | OCH₃ | CH₃ | |
| H | H | 2'-OSO₂C₆H₄CF₃ | OCH₃ | OCH₃ | |
| H | H | SCH₃ | CH₃ | CH₃ | |
| H | H | SCH₃ | OCH₃ | CH₃ | |
| H | H | SCH₃ | OCH₃ | OCH₃ | |
| H | CH₃ | SCH₃ | OCH₃ | CH₃ | |
| H | H | S(O)CH₃ | OCH₃ | CH₃ | |
| H | H | S(O)CH₃ | OCH₃ | OCH₃ | |
| H | H | S(O)₂CH₃ | CH₃ | CH₃ | |
| H | H | S(O)₂CH₃ | OCH₃ | CH₃ | |
| H | H | S(O)₂CH₃ | OCH₃ | OCH₃ | |
| H | CH₃ | S(O)₂CH₃ | OCH₃ | CH₃ | |
| H | H | SCH₂CH₃ | OCH₃ | CH₃ | |
| H | H | S(O)CH₂CH₃ | OCH₃ | CH₃ | |
| H | H | S(O)₂CH₂CH₃ | OCH₃ | OCH₃ | |
| H | H | SCH₂CH₂CH₃ | OCH₃ | OCH₃ | |
| H | H | S(O)CH₂CH₂CH₃ | OCH₃ | CH₃ | |
| H | H | S(O)₂CH₂CH₂CH₃ | OCH₃ | CH₃ | |

TABLE III-continued

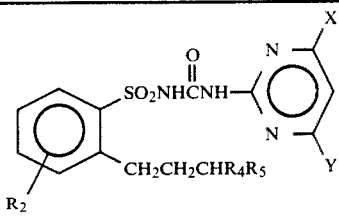

| R$_2$ | R$_4$ | R$_3$ | X | Y | m.p.(°C.) |
|---|---|---|---|---|---|
| H | H | S(O)$_2$CH$_2$CH$_2$CH$_3$ | OCH$_3$ | OCH$_3$ | |
| H | H | OSO$_2$N(CH$_3$)$_2$ | CH$_3$ | CH$_3$ | |
| H | H | OSO$_2$N(CH$_3$)$_2$ | OCH$_3$ | CH$_3$ | |
| H | H | OSO$_2$N(CH$_3$)$_2$ | OCH$_3$ | OCH$_3$ | |
| 6-Cl | H | OSO$_2$N(CH$_3$)$_2$ | OCH$_3$ | CH$_3$ | |
| 3-OCH$_3$ | H | OSO$_2$N(CH$_3$)$_2$ | OCH$_3$ | CH$_3$ | |
| H | CH$_3$ | OSO$_2$N(CH$_3$)$_2$ | OCH$_3$ | CH$_3$ | |
| H | CH$_3$ | OSO$_2$N(CH$_3$)$_2$ | OCH$_3$ | OCH$_3$ | |
| H | H | CO$_2$CH$_3$ | OCH$_3$ | CH$_3$ | |
| H | H | CO$_2$CH$_3$ | OCH$_3$ | OCH$_3$ | |
| H | CH$_3$ | CO$_2$CH$_3$ | OCH$_3$ | CH$_3$ | |
| H | H | CO$_2$CH$_2$CH$_3$ | OCH$_3$ | CH$_3$ | |
| H | H | CO$_2$CH$_2$CH$_2$CH$_3$ | OCH$_3$ | OCH$_3$ | |
| H | H | CO$_2$CH$_2$CH=CH$_2$ | OCH$_3$ | CH$_3$ | |
| H | H | CO$_2$CH$_2$CH$_2$OCH$_3$ | OCH$_3$ | OCH$_3$ | |
| H | H | CO$_2$CH$_2$CH$_2$Cl | OCH$_3$ | CH$_3$ | |

TABLE IV

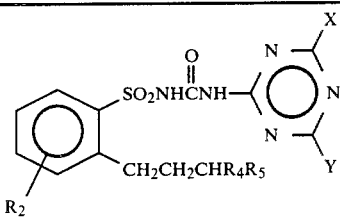

| R$_2$ | R$_4$ | R$_5$ | X | Y | m.p.(°C.) |
|---|---|---|---|---|---|
| H | H | F | CH$_3$ | CH$_3$ | |
| H | H | F | OCH$_3$ | CH$_3$ | |
| H | H | F | OCH$_3$ | OCH$_3$ | |
| 3-CH$_3$ | H | F | OCH$_3$ | CH$_3$ | |
| 3-OCH$_3$ | H | F | OCH$_3$ | OCH$_3$ | |
| 6-Cl | H | F | OCH$_3$ | CH$_3$ | |
| H | F | F | OCH$_3$ | CH$_3$ | |
| H | F | F | OCH$_3$ | OCH$_3$ | |
| H | H | Cl | CH$_3$ | CH$_3$ | |
| H | H | Cl | OCH$_3$ | CH$_3$ | |
| H | H | Cl | OCH$_3$ | OCH$_3$ | |
| 6-Cl | H | Cl | OCH$_3$ | CH$_3$ | |
| 6-CH$_3$ | H | Cl | OCH$_3$ | OCH$_3$ | |
| 6-OCH$_3$ | H | Cl | CH$_3$ | CH$_3$ | |
| 3-CF$_3$ | H | Cl | OCH$_3$ | CH$_3$ | |
| 4-F | H | Cl | OCH$_3$ | OCH$_3$ | |
| 5-CH$_3$ | H | Cl | OCH$_3$ | CH$_3$ | |
| H | Cl | Cl | OCH$_3$ | CH$_3$ | |
| H | Cl | Cl | OCH$_3$ | OCH$_3$ | |
| H | H | Br | CH$_3$ | CH$_3$ | |
| H | H | Br | OCH$_3$ | CH$_3$ | |
| H | H | Br | OCH$_3$ | OCH$_3$ | |
| H | Br | Br | OCH$_3$ | CH$_3$ | |
| H | Br | Br | OCH$_3$ | OCH$_3$ | |
| H | H | O(CO)CH$_3$ | CH$_3$ | CH$_3$ | |
| H | H | OC(O)CH$_3$ | OCH$_3$ | CH$_3$ | |
| H | H | OC(O)CH$_3$ | OCH$_3$ | OCH$_3$ | |
| H | CH$_3$ | OC(O)CH$_3$ | OCH$_3$ | CH$_3$ | |
| H | H | OC(O)CH$_2$CH$_3$ | OCH$_3$ | CH$_3$ | |
| H | H | OC(O)CH$_2$CH$_2$CH$_3$ | OCH$_3$ | OCH$_3$ | |
| H | H | OC(O)CF$_3$ | CH$_3$ | CH$_3$ | |
| H | H | OC(O)CF$_3$ | OCH$_3$ | CH$_3$ | |
| H | H | OC(O)CF$_3$ | OCH$_3$ | OCH$_3$ | |
| H | H | OC(O)CF$_3$ | OCH$_2$CH$_3$ | CH$_3$ | |
| H | H | OC(O)CF$_3$ | CH$_3$ | CH(OCH$_3$)$_2$ | |
| 6-CH$_3$ | H | OC(O)CF$_3$ | OCH$_3$ | CH$_3$ | |
| 6-Cl | H | OC(O)CF$_3$ | OCH$_3$ | OCH$_3$ | |

TABLE IV-continued

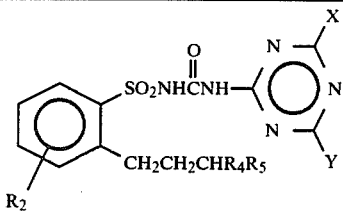

| R$_2$ | R$_4$ | R$_5$ | X | Y | m.p.(°C.) |
|---|---|---|---|---|---|
| 3-OCH$_3$ | H | OC(O)CF$_3$ | OCH$_3$ | CH$_3$ | |
| H | CH$_3$ | OC(O)CF$_3$ | OCH$_3$ | CH$_3$ | |
| H | H | OH | CH$_3$ | CH$_3$ | |
| H | H | OH | OCH$_3$ | CH$_3$ | |
| H | H | OH | OCH$_3$ | OCH$_3$ | |
| H | H | OH | OCH$_2$CH$_3$ | CH$_3$ | |
| H | H | OH | CH$_3$ | CH(OCH$_3$)$_2$ | |
| 6-Cl | H | OH | OCH$_3$ | CH$_3$ | |
| 6-OCH$_3$ | H | OH | OCH$_3$ | OCH$_3$ | |
| 3-CF$_3$ | H | OH | OCH$_3$ | CH$_3$ | |
| H | CH$_3$ | OH | OCH$_3$ | CH$_3$ | |
| H | CH$_3$ | OH | OCH$_3$ | OCH$_3$ | |
| H | H | OCH$_2$C$_6$H$_5$ | CH$_3$ | CH$_3$ | |
| H | H | OCH$_2$C$_6$H$_5$ | OCH$_3$ | CH$_3$ | |
| H | H | OCH$_2$C$_6$H$_5$ | OCH$_3$ | OCH$_3$ | |
| H | CH$_3$ | OCH$_2$C$_6$H$_5$ | OCH$_3$ | CH$_3$ | |
| H | H | OSO$_2$CH$_3$ | CH$_3$ | CH$_3$ | |
| H | H | OSO$_2$CH$_3$ | OCH$_3$ | CH$_3$ | |
| H | H | OSO$_2$CH$_3$ | OCH$_3$ | OCH$_3$ | |
| 6-Cl | H | OSO$_2$CH$_3$ | OCH$_3$ | CH$_3$ | |
| 3-OCH$_3$ | H | OSO$_2$CH$_3$ | OCH$_3$ | OCH$_3$ | |
| 5-Cl | H | OSO$_2$CH$_3$ | OCH$_3$ | CH$_3$ | |
| H | H | OSO$_2$CH$_2$CH$_3$ | OCH$_3$ | CH$_3$ | |
| H | H | OSO$_2$CH$_2$CH$_2$CH$_3$ | OCH$_3$ | OCH$_3$ | |
| H | CH$_3$ | OSO$_2$CH$_3$ | OCH$_3$ | CH$_3$ | |
| H | H | OSO$_2$CF$_3$ | CH$_3$ | CH$_3$ | |
| H | H | OSO$_2$CF$_3$ | OCH$_3$ | CH$_3$ | |
| H | H | OSO$_2$CF$_3$ | OCH$_3$ | OCH$_3$ | |
| H | CH$_3$ | OSO$_2$CF$_3$ | OCH$_3$ | CH$_3$ | |
| H | H | OSO$_2$C$_6$H$_5$ | OCH$_3$ | CH$_3$ | |
| H | H | 2'-OSO$_2$C$_6$H$_4$F | CH$_3$ | CH$_3$ | |
| H | H | 3'-OSO$_2$C$_6$H$_4$Cl | OCH$_3$ | CH$_3$ | |
| H | H | 4-OSO$_2$C$_6$H$_4$Br | OCH$_3$ | OCH$_3$ | |
| H | H | 4'-OSO$_2$C$_6$H$_4$CH$_3$ | CH$_3$ | CH$_3$ | |
| H | H | 4'-OSO$_2$C$_6$H$_4$CH$_3$ | OCH$_3$ | CH$_3$ | |
| H | H | 4'-OSO$_2$C$_6$H$_4$CH$_3$ | OCH$_3$ | OCH$_3$ | |
| H | H | 5'-OSO$_2$C$_6$H$_4$CH$_3$ | CH$_3$ | CH$_3$ | |
| H | H | 6'-OSO$_2$C$_6$H$_4$OCH$_3$ | OCH$_3$ | CH$_3$ | |
| H | H | 2'-OSO$_2$C$_6$H$_4$CF$_3$ | OCH$_3$ | OCH$_3$ | |
| H | H | SCH$_3$ | CH$_3$ | CH$_3$ | |
| H | H | SCH$_3$ | OCH$_3$ | CH$_3$ | |
| H | H | SCH$_3$ | OCH$_3$ | OCH$_3$ | |
| H | CH$_3$ | SCH$_3$ | OCH$_3$ | CH$_3$ | |
| H | H | S(O)CH$_3$ | OCH$_3$ | CH$_3$ | |
| H | H | S(O)CH$_3$ | OCH$_3$ | OCH$_3$ | |
| H | H | S(O)$_2$CH$_3$ | CH$_3$ | CH$_3$ | |
| H | H | S(O)$_2$CH$_3$ | OCH$_3$ | CH$_3$ | |
| H | H | S(O)$_2$CH$_3$ | OCH$_3$ | OCH$_3$ | |
| H | CH$_3$ | S(O)$_2$CH$_3$ | OCH$_3$ | CH$_3$ | |
| H | H | SCH$_2$CH$_3$ | OCH$_3$ | CH$_3$ | |
| H | H | S(O)CH$_2$CH$_3$ | OCH$_3$ | CH$_3$ | |
| H | H | S(O)$_2$CH$_2$CH$_3$ | OCH$_3$ | OCH$_3$ | |
| H | H | SCH$_2$CH$_2$CH$_3$ | OCH$_3$ | OCH$_3$ | |
| H | H | S(O)CH$_2$CH$_2$CH$_3$ | OCH$_3$ | CH$_3$ | |
| H | H | S(O)$_2$CH$_2$CH$_2$CH$_3$ | OCH$_3$ | CH$_3$ | |
| H | H | S(O)$_2$CH$_2$CH$_2$CH$_3$ | OCH$_3$ | OCH$_3$ | |
| H | H | OSO$_2$N(CH$_3$)$_2$ | CH$_3$ | CH$_3$ | |
| H | H | OSO$_2$N(CH$_3$)$_2$ | OCH$_3$ | CH$_3$ | |
| H | H | OSO$_2$N(CH$_3$)$_2$ | OCH$_3$ | OCH$_3$ | |
| 6-Cl | H | OSO$_2$N(CH$_3$)$_2$ | OCH$_3$ | CH$_3$ | |
| 3-OCH$_3$ | H | OSO$_2$N(CH$_3$)$_2$ | OCH$_3$ | OCH$_3$ | |
| H | CH$_3$ | OSO$_2$N(CH$_3$)$_2$ | OCH$_3$ | CH$_3$ | |
| H | CH$_3$ | OSO$_2$N(CH$_3$)$_2$ | OCH$_3$ | OCH$_3$ | |
| H | H | CO$_2$CH$_3$ | OCH$_3$ | CH$_3$ | |
| H | H | CO$_2$CH$_3$ | OCH$_3$ | OCH$_3$ | |
| H | CH$_3$ | CO$_2$CH$_3$ | OCH$_3$ | CH$_3$ | |
| H | H | CO$_2$CH$_2$CH$_3$ | OCH$_3$ | CH$_3$ | |
| H | H | CO$_2$CH$_2$CH$_2$CH$_3$ | OCH$_3$ | OCH$_3$ | |
| H | H | CO$_2$CH$_2$CH=CH$_2$ | OCH$_3$ | CH$_3$ | |
| H | H | CO$_2$CH$_2$CH$_2$OCH$_3$ | OCH$_3$ | OCH$_3$ | |

TABLE IV-continued

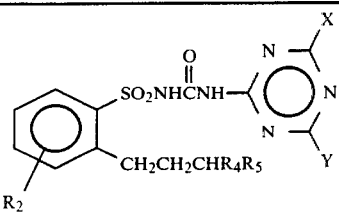

| R2 | R4 | R5 | X | Y | m.p.(°C.) |
|---|---|---|---|---|---|
| H | H | CO2CH2CH2Cl | OCH3 | CH3 | |

TABLE V

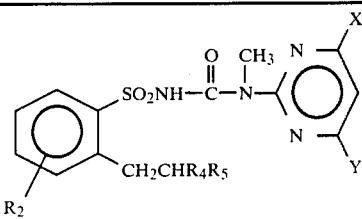

| R2 | R4 | R5 | X | Y | m.p. (°C.) |
|---|---|---|---|---|---|
| H | H | F | CH3 | CH3 | |
| H | H | F | OCH3 | CH3 | |
| H | H | F | OCH3 | OCH3 | |
| H | H | F | Cl | OCH3 | |
| 3-CH3 | H | F | OCH3 | CH3 | |
| 3-OCH3 | H | F | OCH3 | OCH3 | |
| 6-Cl | H | F | OCH3 | CH3 | |
| H | F | F | OCH3 | CH3 | |
| H | F | F | OCH3 | OCH3 | |
| H | H | Cl | CH3 | CH3 | |
| H | H | Cl | OCH3 | CH3 | |
| H | H | Cl | OCH3 | OCH3 | |
| 6-Cl | H | Cl | OCH3 | CH3 | |
| 6-CH3 | H | Cl | OCH3 | OCH3 | |
| 6-OCH3 | H | Cl | OCH3 | CH3 | |
| 3-CF3 | H | Cl | OCH3 | CH3 | |
| 4-F | H | Cl | OCH3 | OCH3 | |
| 5-CH3 | H | Cl | OCH3 | CH3 | |
| H | Cl | Cl | OCH3 | CH3 | |
| H | Cl | Cl | OCH3 | OCH3 | |
| H | H | Br | CH3 | CH3 | |
| H | H | Br | OCH3 | CH3 | |
| H | H | Br | OCH3 | OCH3 | |
| H | Br | Br | OCH3 | CH3 | |
| H | Br | Br | OCH3 | OCH3 | |
| H | H | OC(O)CH3 | CH3 | CH3 | |
| H | H | OC(O)CH3 | OCH3 | CH3 | |
| H | H | OC(O)CH3 | OCH3 | OCH3 | |
| H | CH3 | OC(O)CH3 | OCH3 | CH3 | |
| H | H | OC(O)CH2CH3 | OCH3 | CH3 | |
| H | H | OC(O)CH2CH2CH3 | OCH3 | OCH3 | |
| H | H | OC(O)CF3 | CH3 | CH3 | |
| H | H | OC(O)CF3 | OCH3 | CH3 | |
| H | H | OC(O)CF3 | OCH3 | OCH3 | |
| H | H | OC(O)CF3 | Cl | OCH3 | |
| H | H | OC(O)CF3 | OCH2CH3 | CH3 | |
| H | H | OC(O)CF3 | CH3 | CH(OCH3)2 | |
| 6-CH3 | H | OC(O)CF3 | OCH3 | CH3 | |
| 6-Cl | H | OC(O)CF3 | OCH3 | OCH3 | |
| 3-OCH3 | H | OC(O)CF3 | OCH3 | CH3 | |
| H | CH3 | OC(O)CF3 | OCH3 | CH3 | |
| H | H | OH | CH3 | CH3 | |
| H | H | OH | OCH3 | CH3 | |
| H | H | OH | OCH3 | OCH3 | |
| H | H | OH | Cl | OCH3 | |
| H | H | OH | OCH2CH3 | CH3 | |
| H | H | OH | CH3 | CH(OCH3)2 | |
| 6-Cl | H | OH | OCH3 | CH3 | |
| 6-OCH3 | H | OH | OCH3 | OCH3 | |
| 3-CF3 | H | OH | OCH3 | CH3 | |
| H | CH3 | OH | OCH3 | CH3 | |
| H | CH3 | OH | OCH3 | OCH3 | |

TABLE V-continued

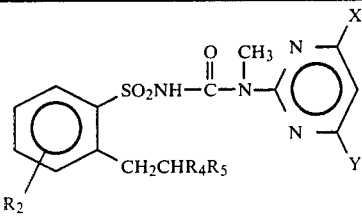

| R2 | R4 | R5 | X | Y | m.p. (°C.) |
|---|---|---|---|---|---|
| H | CH3 | OH | Cl | OCH3 | |
| H | H | OCH2C6H5 | CH3 | CH3 | |
| H | H | OCH2C6H5 | OCH3 | CH3 | |
| H | H | OCH2C6H5 | OCH3 | OCH3 | |
| H | CH3 | OCH2C6H5 | OCH3 | CH3 | |
| H | H | OSO2CH3 | CH3 | CH3 | |
| H | H | OSO2CH3 | OCH3 | CH3 | |
| H | H | OSO2CH3 | OCH3 | OCH3 | |
| 6-Cl | H | OSO2CH3 | OCH3 | CH3 | |
| 3-OCH3 | H | OSO2CH3 | OCH3 | OCH3 | |
| 5-Cl | H | OSO2CH3 | OCH3 | OCH3 | |
| H | H | OSO2CH2CH3 | OCH3 | CH3 | |
| H | H | OSO2CH2CH2CH3 | OCH3 | OCH3 | |
| H | CH3 | OSO2CH3 | OCH3 | CH3 | |
| H | H | OSO2CF3 | CH3 | CH3 | |
| H | H | OSO2CF3 | OCH3 | CH3 | |
| H | H | OSO2CF3 | OCH3 | OCH3 | |
| H | CH3 | OSO2CF3 | OCH3 | CH3 | |
| H | H | OSO2C6H5 | OCH3 | CH3 | |
| H | H | 2'-OSO2C6H4F | CH3 | CH3 | |
| H | H | 3'-OSO2C6H4Cl | OCH3 | CH3 | |
| H | H | 4'-OSO2C6H4Br | OCH3 | OCH3 | |
| H | H | 4'-OSO2C6H4CH3 | CH3 | CH3 | |
| H | H | 4'-OSO2C6H4CH3 | OCH3 | CH3 | |
| H | H | 4'-OSO2C6H4CH3 | OCH3 | OCH3 | |
| H | H | 5'-OSO2C6H4CH3 | OCH3 | CH3 | |
| H | H | 6'-OSO2C6H4OCH3 | OCH3 | CH3 | |
| H | H | 2'-OSO2C6H4CF3 | OCH3 | OCH3 | |
| H | H | SCH3 | CH3 | CH3 | |
| H | H | SCH3 | OCH3 | CH3 | |
| H | H | SCH3 | OCH3 | OCH3 | |
| H | CH3 | SCH3 | OCH3 | CH3 | |
| H | H | S(O)CH3 | OCH3 | CH3 | |
| H | H | S(O)CH3 | OCH3 | OCH3 | |
| H | H | S(O)2CH3 | CH3 | CH3 | |
| H | H | S(O)2CH3 | OCH3 | CH3 | |
| H | H | S(O)2CH3 | OCH3 | OCH3 | |
| H | CH3 | S(O)2CH3 | OCH3 | CH3 | |
| H | H | SCH2CH3 | OCH3 | CH3 | |
| H | H | S(O)CH2CH3 | OCH3 | CH3 | |
| H | H | S(O)2CH2CH3 | OCH3 | OCH3 | |
| H | H | SCH2CH2CH3 | OCH3 | OCH3 | |
| H | H | S(O)CH2CH2CH3 | OCH3 | CH3 | |
| H | H | S(O)2CH2CH2CH3 | OCH3 | OCH3 | |
| H | H | OSO2N(CH3)2 | CH3 | CH3 | |
| H | H | OSO2N(CH3)2 | OCH3 | CH3 | |
| H | H | OSO2N(CH3)2 | OCH3 | OCH3 | |
| 6-Cl | H | OSO2N(CH3)2 | OCH3 | CH3 | |
| 3-OCH3 | H | OSO2N(CH3)2 | OCH3 | OCH3 | |
| H | CH3 | OSO2N(CH3)2 | OCH3 | CH3 | |
| H | CH3 | OSO2N(CH3)2 | OCH3 | OCH3 | |

TABLE V-continued

Structure: benzene ring with SO$_2$NH-C(=O)-N(CH$_3$)- attached to pyrimidine ring having X and Y substituents; benzene also bears CH$_2$CHR$_4$R$_5$ and R$_2$.

| R$_2$ | R$_4$ | R$_5$ | X | Y | m.p. (°C.) |
|---|---|---|---|---|---|
| H | H | CO$_2$CH$_3$ | OCH$_3$ | CH$_3$ | |
| H | H | CO$_2$CH$_3$ | OCH$_3$ | OCH$_3$ | |
| H | CH$_3$ | CO$_2$CH$_3$ | OCH$_3$ | CH$_3$ | |
| H | H | CO$_2$CH$_2$CH$_3$ | OCH$_3$ | CH$_3$ | |
| H | H | CO$_2$CH$_2$CH$_2$CH$_3$ | OCH$_3$ | OCH$_3$ | |
| H | H | CO$_2$CH$_2$CH=CH$_2$ | OCH$_3$ | CH$_3$ | |
| H | H | CO$_2$CH$_2$CH$_2$OCH$_3$ | OCH$_3$ | OCH$_3$ | |
| H | H | CO$_2$CH$_2$CH$_2$Cl | OCH$_3$ | CH$_3$ | |

TABLE VI

Structure: benzene ring with SO$_2$NH-C(=O)-N(CH$_3$)- attached to triazine ring having X and Y substituents; benzene also bears CH$_2$CHR$_4$R$_5$ and R$_2$.

| R$_2$ | R$_4$ | R$_5$ | X | Y | m.p. (°C.) |
|---|---|---|---|---|---|
| H | H | F | CH$_3$ | CH$_3$ | |
| H | H | F | OCH$_3$ | CH$_3$ | |
| H | H | F | OCH$_3$ | OCH$_3$ | |
| 3-CH$_3$ | H | F | OCH$_3$ | CH$_3$ | |
| 3-OCH$_3$ | H | F | OCH$_3$ | OCH$_3$ | |
| 6-Cl | H | F | OCH$_3$ | CH$_3$ | |
| H | F | F | OCH$_3$ | CH$_3$ | |
| H | F | F | OCH$_3$ | OCH$_3$ | |
| H | H | Cl | CH$_3$ | CH$_3$ | |
| H | H | Cl | OCH$_3$ | CH$_3$ | |
| H | H | Cl | OCH$_3$ | OCH$_3$ | |
| 6-Cl | H | Cl | OCH$_3$ | CH$_3$ | |
| 6-CH$_3$ | H | Cl | OCH$_3$ | OCH$_3$ | |
| 6-OCH$_3$ | H | Cl | CH$_3$ | CH$_3$ | |
| 3-CF$_3$ | H | Cl | OCH$_3$ | CH$_3$ | |
| 4-F | H | Cl | OCH$_3$ | OCH$_3$ | |
| 5-CH$_3$ | H | Cl | OCH$_3$ | CH$_3$ | |
| H | Cl | Cl | OCH$_3$ | CH$_3$ | |
| H | Cl | Cl | OCH$_3$ | OCH$_3$ | |
| H | H | Br | CH$_3$ | CH$_3$ | |
| H | H | Br | OCH$_3$ | CH$_3$ | |
| H | H | Br | OCH$_3$ | OCH$_3$ | |
| H | Br | Br | OCH$_3$ | CH$_3$ | |
| H | Br | Br | OCH$_3$ | OCH$_3$ | |
| H | H | OC(O)CH$_3$ | CH$_3$ | CH$_3$ | |
| H | H | OC(O)CH$_3$ | OCH$_3$ | CH$_3$ | |
| H | H | OC(O)CH$_3$ | OCH$_3$ | OCH$_3$ | |
| H | CH$_3$ | OC(O)CH$_3$ | OCH$_3$ | CH$_3$ | |
| H | H | OC(O)CH$_2$CH$_3$ | OCH$_3$ | CH$_3$ | |
| H | H | OC(O)CH$_2$CH$_2$CH$_3$ | OCH$_3$ | OCH$_3$ | |
| H | H | OC(O)CF$_3$ | CH$_3$ | CH$_3$ | |
| H | H | OC(O)CF$_3$ | OCH$_3$ | CH$_3$ | |
| H | H | OC(O)CF$_3$ | OCH$_3$ | OCH$_3$ | |
| H | H | OC(O)CF$_3$ | OCH$_2$CH$_3$ | CH$_3$ | |
| H | H | OC(O)CF$_3$ | CH$_3$ | CH(OCH$_3$)$_2$ | |
| 6-CH$_3$ | H | OC(O)CF$_3$ | OCH$_3$ | CH$_3$ | |
| 6-Cl | H | OC(O)CF$_3$ | OCH$_3$ | OCH$_3$ | |
| 3-OCH$_3$ | H | OC(O)CF$_3$ | OCH$_3$ | CH$_3$ | |
| H | CH$_3$ | OC(O)CF$_3$ | OCH$_3$ | CH$_3$ | |
| H | H | OH | CH$_3$ | CH$_3$ | |
| H | H | OH | OCH$_3$ | CH$_3$ | |
| H | H | OH | OCH$_3$ | OCH$_3$ | |
| H | H | OH | OCH$_2$CH$_3$ | CH$_3$ | |
| H | H | OH | CH$_3$ | CH(OCH$_3$)$_2$ | |
| 6-Cl | H | OH | OCH$_3$ | CH$_3$ | |

TABLE VI-continued

| R$_2$ | R$_4$ | R$_5$ | X | Y | m.p. (°C.) |
|---|---|---|---|---|---|
| 6-OCH$_3$ | H | OH | OCH$_3$ | OCH$_3$ | |
| 3-CF$_3$ | H | OH | OCH$_3$ | CH$_3$ | |
| H | CH$_3$ | OH | OCH$_3$ | CH$_3$ | |
| H | CH$_3$ | OH | OCH$_3$ | OCH$_3$ | |
| H | H | OCH$_2$C$_6$H$_5$ | CH$_3$ | CH$_3$ | |
| H | H | OCH$_2$C$_6$H$_5$ | OCH$_3$ | CH$_3$ | |
| H | H | OCH$_2$C$_6$H$_5$ | OCH$_3$ | OCH$_3$ | |
| H | CH$_3$ | OCH$_2$C$_6$H$_5$ | OCH$_3$ | CH$_3$ | |
| H | H | OSO$_2$CH$_3$ | CH$_3$ | CH$_3$ | |
| H | H | OSO$_2$CH$_3$ | OCH$_3$ | CH$_3$ | |
| H | H | OSO$_2$CH$_3$ | OCH$_3$ | OCH$_3$ | |
| 6-Cl | H | OSO$_2$CH$_3$ | OCH$_3$ | CH$_3$ | |
| 3-OCH$_3$ | H | OSO$_2$CH$_3$ | OCH$_3$ | OCH$_3$ | |
| 5-Cl | H | OSO$_2$CH$_3$ | OCH$_3$ | CH$_3$ | |
| H | H | OSO$_2$CH$_2$CH$_3$ | OCH$_3$ | CH$_3$ | |
| H | H | OSO$_2$CH$_2$CH$_2$CH$_3$ | OCH$_3$ | OCH$_3$ | |
| H | CH$_3$ | OSO$_2$CH$_3$ | OCH$_3$ | CH$_3$ | |
| H | H | OSO$_2$CF$_3$ | CH$_3$ | CH$_3$ | |
| H | H | OSO$_2$CF$_3$ | OCH$_3$ | CH$_3$ | |
| H | H | OSO$_2$CF$_3$ | OCH$_3$ | OCH$_3$ | |
| H | CH$_3$ | OSO$_2$CF$_3$ | OCH$_3$ | CH$_3$ | |
| H | H | OSO$_2$C$_6$H$_5$ | OCH$_3$ | CH$_3$ | |
| H | H | 2'-OSO$_2$C$_6$H$_4$F | CH$_3$ | CH$_3$ | |
| H | H | 3'-OSO$_2$C$_6$H$_4$Cl | OCH$_3$ | CH$_3$ | |
| H | H | 4'-OSO$_2$C$_6$H$_4$Br | OCH$_3$ | OCH$_3$ | |
| H | H | 4'-OSO$_2$C$_6$H$_4$CH$_3$ | CH$_3$ | CH$_3$ | |
| H | H | 4'-OSO$_2$C$_6$H$_4$CH$_3$ | OCH$_3$ | CH$_3$ | |
| H | H | 4'-OSO$_2$C$_6$H$_4$CH$_3$ | OCH$_3$ | OCH$_3$ | |
| H | H | 5'-OSO$_2$C$_6$H$_4$CH$_3$ | CH$_3$ | CH$_3$ | |
| H | H | 6'-OSO$_2$C$_6$H$_4$OCH$_3$ | OCH$_3$ | CH$_3$ | |
| H | H | 2'-OSO$_2$C$_6$H$_4$CF$_3$ | OCH$_3$ | OCH$_3$ | |
| H | H | SCH$_3$ | CH$_3$ | CH$_3$ | |
| H | H | SCH$_3$ | OCH$_3$ | CH$_3$ | |
| H | H | SCH$_3$ | OCH$_3$ | OCH$_3$ | |
| H | CH$_3$ | SCH$_3$ | OCH$_3$ | CH$_3$ | |
| H | H | S(O)CH$_3$ | CH$_3$ | CH$_3$ | |
| H | H | S(O)CH$_3$ | OCH$_3$ | CH$_3$ | |
| H | H | S(O)$_2$CH$_3$ | CH$_3$ | CH$_3$ | |
| H | H | S(O)$_2$CH$_3$ | OCH$_3$ | CH$_3$ | |
| H | H | S(O)$_2$CH$_3$ | OCH$_3$ | OCH$_3$ | |
| H | CH$_3$ | S(O)$_2$CH$_3$ | OCH$_3$ | CH$_3$ | |
| H | H | SCH$_2$CH$_3$ | OCH$_3$ | CH$_3$ | |
| H | H | S(O)CH$_2$CH$_3$ | OCH$_3$ | CH$_3$ | |
| H | H | S(O)$_2$CH$_2$CH$_3$ | OCH$_3$ | CH$_3$ | |
| H | H | SCH$_2$CH$_3$ | OCH$_3$ | OCH$_3$ | |
| H | H | SCH$_2$CH$_2$CH$_3$ | OCH$_3$ | CH$_3$ | |
| H | H | S(O)CH$_2$CH$_2$CH$_3$ | OCH$_3$ | CH$_3$ | |
| H | H | S(O)$_2$CH$_2$CH$_2$CH$_3$ | OCH$_3$ | CH$_3$ | |
| H | H | S(O)$_2$CH$_2$CH$_2$CH$_3$ | OCH$_3$ | OCH$_3$ | |
| H | H | OSO$_2$N(CH$_3$)$_2$ | CH$_3$ | CH$_3$ | |
| H | H | OSO$_2$N(CH$_3$)$_2$ | OCH$_3$ | CH$_3$ | |
| H | H | OSO$_2$N(CH$_3$)$_2$ | OCH$_3$ | OCH$_3$ | |
| 6-Cl | H | OSO$_2$N(CH$_3$)$_2$ | OCH$_3$ | CH$_3$ | |
| 3-OCH$_3$ | H | OSO$_2$N(CH$_3$)$_2$ | OCH$_3$ | OCH$_3$ | |
| H | CH$_3$ | OSO$_2$N(CH$_3$)$_2$ | OCH$_3$ | CH$_3$ | |
| H | CH$_3$ | OSO$_2$N(CH$_3$)$_2$ | OCH$_3$ | OCH$_3$ | |
| H | H | CO$_2$CH$_3$ | OCH$_3$ | CH$_3$ | |
| H | H | CO$_2$CH$_3$ | OCH$_3$ | OCH$_3$ | |
| H | CH$_3$ | CO$_2$CH$_3$ | OCH$_3$ | CH$_3$ | |
| H | H | CO$_2$CH$_2$CH$_3$ | OCH$_3$ | CH$_3$ | |
| H | H | CO$_2$CH$_2$CH$_2$CH$_3$ | OCH$_3$ | OCH$_3$ | |
| H | H | CO$_2$CH$_2$CH=CH$_2$ | OCH$_3$ | CH$_3$ | |
| H | H | CO$_2$CH$_2$CH$_2$OCH$_3$ | OCH$_3$ | OCH$_3$ | |
| H | H | CO$_2$CH$_2$CH$_2$Cl | OCH$_3$ | CH$_3$ | |

TABLE VII

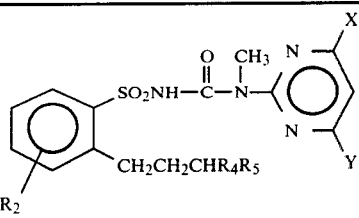

| R2 | R4 | R5 | X | Y | m.p. (°C.) |
|---|---|---|---|---|---|
| H | H | F | CH3 | CH3 | |
| H | H | F | OCH3 | CH3 | |
| H | H | F | OCH3 | OCH3 | |
| H | H | F | Cl | OCH3 | |
| 3-CH3 | H | F | OCH3 | CH3 | |
| 3-OCH3 | H | F | OCH3 | OCH3 | |
| 6-Cl | H | F | OCH3 | CH3 | |
| H | F | F | OCH3 | CH3 | |
| H | F | F | OCH3 | OCH3 | |
| H | H | Cl | CH3 | CH3 | |
| H | H | Cl | OCH3 | CH3 | |
| H | H | Cl | OCH3 | OCH3 | |
| 6-Cl | H | Cl | OCH3 | CH3 | |
| 6-CH3 | H | Cl | OCH3 | OCH3 | |
| 6-OCH3 | H | Cl | CH3 | CH3 | |
| 3-CF3 | H | Cl | OCH3 | CH3 | |
| 4-F | H | Cl | OCH3 | OCH3 | |
| 5-CH3 | H | Cl | OCH3 | OCH3 | |
| H | Cl | Cl | OCH3 | CH3 | |
| H | Cl | Cl | OCH3 | OCH3 | |
| H | H | Br | CH3 | CH3 | |
| H | H | Br | OCH3 | CH3 | |
| H | H | Br | OCH3 | OCH3 | |
| H | Br | Br | OCH3 | CH3 | |
| H | Br | Br | OCH3 | OCH3 | |
| H | H | OC(O)CH3 | CH3 | CH3 | |
| H | H | OC(O)CH3 | OCH3 | CH3 | |
| H | H | OC(O)CH3 | OCH3 | OCH3 | |
| H | CH3 | OC(O)CH3 | OCH3 | CH3 | |
| H | H | OC(O)CH2CH3 | OCH3 | CH3 | |
| H | H | OC(O)CH2CH2CH3 | OCH3 | OCH3 | |
| H | H | OC(O)CF3 | CH3 | CH3 | |
| H | H | OC(O)CF3 | OCH3 | CH3 | |
| H | H | OC(O)CF3 | OCH3 | OCH3 | |
| H | H | OC(O)CF3 | Cl | OCH3 | |
| H | H | OC(O)CF3 | OCH2CH3 | CH3 | |
| H | H | OC(O)CF3 | CH3 | CH(OCH3)2 | |
| 6-CH3 | H | OC(O)CF3 | OCH3 | CH3 | |
| 6-Cl | H | OC(O)CF3 | OCH3 | OCH3 | |
| 3-OCH3 | H | OC(O)CF3 | OCH3 | CH3 | |
| H | CH3 | OC(O)CF3 | OCH3 | CH3 | |
| H | H | OH | CH3 | CH3 | |
| H | H | OH | OCH3 | CH3 | |
| H | H | OH | OCH3 | OCH3 | |
| H | H | OH | Cl | OCH3 | |
| H | H | OH | OCH2CH3 | CH3 | |
| H | H | OH | CH3 | CH(OCH3)2 | |
| 6-Cl | H | OH | OCH3 | CH3 | |
| 6-OCH3 | H | OH | OCH3 | OCH3 | |
| 3-CF3 | H | OH | OCH3 | CH3 | |
| H | CH3 | OH | OCH3 | CH3 | |
| H | CH3 | OH | OCH3 | OCH3 | |
| H | CH3 | OH | Cl | OCH3 | |
| H | H | OCH2C6H5 | CH3 | CH3 | |
| H | H | OCH2C6H5 | OCH3 | CH3 | |
| H | H | OCH2C6H5 | OCH3 | OCH3 | |
| H | CH3 | OCH2C6H5 | OCH3 | CH3 | |
| H | H | OSO2CH3 | CH3 | CH3 | |
| H | H | OSO2CH3 | OCH3 | CH3 | |
| H | H | OSO2CH3 | OCH3 | OCH3 | |
| 6-Cl | H | OSO2CH3 | OCH3 | CH3 | |
| 3-OCH3 | H | OSO2CH3 | OCH3 | CH3 | |
| 5-Cl | H | OSO2CH3 | OCH3 | OCH3 | |
| H | H | OSO2CH2CH3 | OCH3 | CH3 | |
| H | H | OSO2CH2CH2CH3 | OCH3 | CH3 | |
| H | CH3 | OSO2CH3 | OCH3 | CH3 | |
| H | H | OSO2CF3 | CH3 | CH3 | |
| H | H | OSO2CF3 | OCH3 | CH3 | |
| H | H | OSO2CF3 | OCH3 | OCH3 | |
| H | CH3 | OSO2CF3 | OCH3 | CH3 | |

TABLE VII-continued

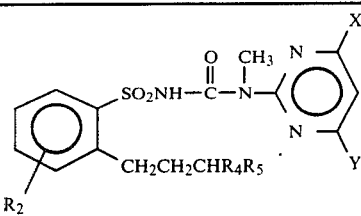

| R2 | R4 | R5 | X | Y | m.p. (°C.) |
|---|---|---|---|---|---|
| H | H | OSO2C6H5 | OCH3 | CH3 | |
| H | H | 2'-OSO2C6H4F | CH3 | CH3 | |
| H | H | 3'-OSO2C6H4Cl | OCH3 | CH3 | |
| H | H | 4'-OSO2C6H4Br | OCH3 | OCH3 | |
| H | H | 4'-OSO2C6H4CH3 | CH3 | CH3 | |
| H | H | 4'-OSO2C6H4CH3 | OCH3 | CH3 | |
| H | H | 4'-OSO2C6H4CH3 | OCH3 | OCH3 | |
| H | H | 5'-OSO2C6H4CH3 | OCH3 | CH3 | |
| H | H | 6'-OSO2C6H4OCH3 | OCH3 | CH3 | |
| H | H | 2'-OSO2C6H4CF3 | OCH3 | OCH3 | |
| H | H | SCH3 | CH3 | CH3 | |
| H | H | SCH3 | OCH3 | CH3 | |
| H | H | SCH3 | OCH3 | OCH3 | |
| H | CH3 | SCH3 | OCH3 | CH3 | |
| H | H | S(O)CH3 | OCH3 | CH3 | |
| H | H | S(O)CH3 | OCH3 | OCH3 | |
| H | H | S(O)2CH3 | CH3 | CH3 | |
| H | H | S(O)2CH3 | OCH3 | CH3 | |
| H | H | S(O)2CH3 | OCH3 | OCH3 | |
| H | CH3 | S(O)2CH3 | OCH3 | CH3 | |
| H | H | SCH2CH3 | OCH3 | CH3 | |
| H | H | S(O)CH2CH3 | OCH3 | CH3 | |
| H | H | S(O)2CH2CH3 | OCH3 | CH3 | |
| H | H | SCH2CH2CH3 | OCH3 | CH3 | |
| H | H | S(O)CH2CH2CH3 | OCH3 | CH3 | |
| H | H | S(O)2CH2CH2CH3 | OCH3 | CH3 | |
| H | H | S(O)2CH2CH2CH3 | OCH3 | OCH3 | |
| H | H | OSO2N(CH3)2 | CH3 | CH3 | |
| H | H | OSO2N(CH3)2 | OCH3 | CH3 | |
| H | H | OSO2N(CH3)2 | OCH3 | OCH3 | |
| 6-Cl | H | OSO2N(CH3)2 | OCH3 | CH3 | |
| 3-OCH3 | H | OSO2N(CH3)2 | OCH3 | CH3 | |
| H | CH3 | OSO2N(CH3)2 | OCH3 | CH3 | |
| H | CH3 | OSO2N(CH3)2 | OCH3 | OCH3 | |
| H | H | CO2CH3 | OCH3 | CH3 | |
| H | H | CO2CH3 | OCH3 | OCH3 | |
| H | CH3 | CO2CH3 | OCH3 | CH3 | |
| H | H | CO2CH2CH3 | OCH3 | CH3 | |
| H | H | CO2CH2CH2CH3 | OCH3 | CH3 | |
| H | H | CO2CH2CH=CH2 | OCH3 | CH3 | |
| H | H | CO2CH2CH2OCH3 | OCH3 | CH3 | |
| H | H | CO2CH2CH2Cl | OCH3 | CH3 | |

TABLE VIII

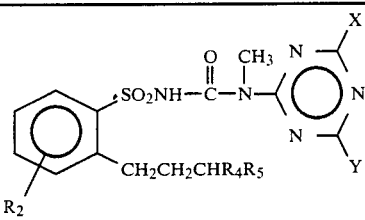

| R2 | R4 | R5 | X | Y | m.p. (°C.) |
|---|---|---|---|---|---|
| H | H | F | CH3 | CH3 | |
| H | H | F | OCH3 | CH3 | |
| H | H | F | OCH3 | OCH3 | |
| 3-CH3 | H | F | OCH3 | CH3 | |
| 3-OCH3 | H | F | OCH3 | OCH3 | |
| 6-Cl | H | F | OCH3 | CH3 | |
| H | F | F | OCH3 | CH3 | |
| H | F | F | OCH3 | OCH3 | |
| H | H | Cl | CH3 | CH3 | |
| H | H | Cl | OCH3 | OCH3 | |

TABLE VIII-continued

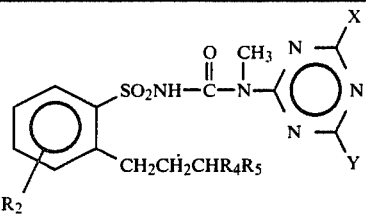

| R2 | R4 | R5 | X | Y | m.p. (°C.) |
|---|---|---|---|---|---|
| 6-Cl | H | Cl | OCH3 | CH3 | |
| 6-CH3 | H | Cl | OCH3 | OCH3 | |
| 6-OCH3 | H | Cl | CH3 | CH3 | |
| 3-CF3 | H | Cl | OCH3 | CH3 | |
| 4-F | H | Cl | OCH3 | OCH3 | |
| 5-CH3 | H | Cl | OCH3 | CH3 | |
| H | Cl | Cl | OCH3 | CH3 | |
| H | Cl | Cl | OCH3 | OCH3 | |
| H | H | Br | CH3 | CH3 | |
| H | H | Br | OCH3 | CH3 | |
| H | H | Br | OCH3 | OCH3 | |
| H | Br | Br | OCH3 | CH3 | |
| H | Br | Br | OCH3 | OCH3 | |
| H | H | OC(O)CH3 | CH3 | CH3 | |
| H | H | OC(O)CH3 | OCH3 | CH3 | |
| H | H | OC(O)CH3 | OCH3 | OCH3 | |
| H | CH3 | OC(O)CH3 | OCH3 | CH3 | |
| H | H | OC(O)CH2CH3 | OCH3 | CH3 | |
| H | H | OC(O)CH2CH2CH3 | OCH3 | OCH3 | |
| H | H | OC(O)CF3 | CH3 | CH3 | |
| H | H | OC(O)CF3 | OCH3 | CH3 | |
| H | H | OC(O)CF3 | OCH3 | OCH3 | |
| H | H | OC(O)CF3 | OCH2CH3 | CH3 | |
| H | H | OC(O)CF3 | CH3 | CH(OCH3)2 | |
| 6-CH3 | H | OC(O)CF3 | OCH3 | CH3 | |
| 6-Cl | H | OC(O)CF3 | OCH3 | OCH3 | |
| 3-OCH3 | H | OC(O)CF3 | OCH3 | CH3 | |
| H | CH3 | OC(O)CF3 | OCH3 | CH3 | |
| H | H | OH | CH3 | CH3 | |
| H | H | OH | OCH3 | CH3 | |
| H | H | OH | OCH3 | OCH3 | |
| H | H | OH | OCH2CH3 | CH3 | |
| H | H | OH | CH3 | CH(OCH3)2 | |
| 6-Cl | H | OH | OCH3 | CH3 | |
| 6-OCH3 | H | OH | OCH3 | OCH3 | |
| 3-CF3 | H | OH | OCH3 | CH3 | |
| H | CH3 | OH | OCH3 | CH3 | |
| H | CH3 | OH | OCH3 | OCH3 | |
| H | H | OCH2C6H5 | CH3 | CH3 | |
| H | H | OCH2C6H5 | OCH3 | CH3 | |
| H | H | OCH2C6H5 | OCH3 | OCH3 | |
| H | CH3 | OCH2C6H5 | OCH3 | CH3 | |
| H | H | OSO2CH3 | CH3 | CH3 | |
| H | H | OSO2CH3 | OCH3 | CH3 | |
| 6-Cl | H | OSO2CH3 | OCH3 | CH3 | |
| 3-OCH3 | H | OSO2CH3 | OCH3 | OCH3 | |
| 5-Cl | H | OSO2CH3 | OCH3 | CH3 | |
| H | H | OSO2CH2CH3 | OCH3 | CH3 | |

TABLE VIII-continued

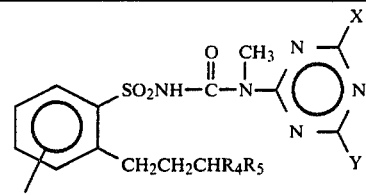

| R2 | R4 | R5 | X | Y | m.p. (°C.) |
|---|---|---|---|---|---|
| H | H | OSO2CH2CH2CH3 | OCH3 | OCH3 | |
| H | CH3 | OSO2CH3 | OCH3 | CH3 | |
| H | H | OSO2CF3 | CH3 | CH3 | |
| H | H | OSO2CF3 | OCH3 | CH3 | |
| H | H | OSO2CF3 | OCH3 | OCH3 | |
| H | CH3 | OSO2CF3 | OCH3 | CH3 | |
| H | H | OSO2C6H5 | OCH3 | CH3 | |
| H | H | 2'-OSO2C6H4F | CH3 | CH3 | |
| H | H | 3'-OSO2C6H4Cl | OCH3 | CH3 | |
| H | H | 4'-OSO2C6H4Br | OCH3 | OCH3 | |
| H | H | 4'-OSO2C6H4CH3 | CH3 | CH3 | |
| H | H | 4'-OSO2C6H4CH3 | OCH3 | CH3 | |
| H | H | 4'-OSO2C6H4CH3 | OCH3 | OCH3 | |
| H | H | 5'-OSO2C6H4CH3 | OCH3 | CH3 | |
| H | H | 6'-OSO2C6H4OCH3 | OCH3 | CH3 | |
| H | H | 2'-OSO2C6H4CF3 | OCH3 | OCH3 | |
| H | H | SCH3 | CH3 | CH3 | |
| H | H | SCH3 | OCH3 | CH3 | |
| H | CH3 | SCH3 | OCH3 | CH3 | |
| H | H | S(O)CH3 | OCH3 | OCH3 | |
| H | H | S(O)2CH3 | CH3 | CH3 | |
| H | H | S(O)2CH3 | OCH3 | CH3 | |
| H | H | S(O)2CH3 | OCH3 | OCH3 | |
| H | CH3 | S(O)2CH3 | OCH3 | CH3 | |
| H | H | SCH2CH3 | OCH3 | CH3 | |
| H | H | S(O)CH2CH3 | OCH3 | CH3 | |
| H | H | S(O)2CH2CH3 | OCH3 | OCH3 | |
| H | H | SCH2CH2CH3 | OCH3 | OCH3 | |
| H | H | S(O)CH2CH2CH3 | OCH3 | CH3 | |
| H | H | S(O)2CH2CH2CH3 | OCH3 | CH3 | |
| H | H | S(O)2CH2CH2CH3 | OCH3 | OCH3 | |
| H | H | OSO2N(CH3)2 | CH3 | CH3 | |
| H | H | OSO2N(CH3)2 | OCH3 | OCH3 | |
| 6-Cl | H | OSO2N(CH3)2 | OCH3 | CH3 | |
| 3-OCH3 | H | OSO2N(CH3)2 | OCH3 | OCH3 | |
| H | CH3 | OSO2N(CH3)2 | OCH3 | CH3 | |
| H | CH3 | OSO2N(CH3)2 | OCH3 | OCH3 | |
| H | H | CO2CH3 | OCH3 | CH3 | |
| H | H | CO2CH3 | OCH3 | OCH3 | |
| H | CH3 | CO2CH3 | OCH3 | CH3 | |
| H | H | CO2CH2CH3 | OCH3 | CH3 | |
| H | H | CO2CH2CH2CH3 | OCH3 | OCH3 | |
| H | H | CO2CH2CH=CH2 | OCH3 | CH3 | |
| H | H | CO2CH2CH2OCH3 | OCH3 | OCH3 | |
| H | H | CO2CH2CH2Cl | OCH3 | CH3 | |

TABLE IX

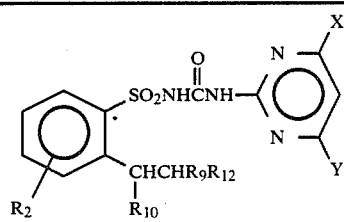

| R2 | R9 | R10 | R12 | X | Y | m.p. (°C.) |
|---|---|---|---|---|---|---|
| H | OCH3 | H | H | CH3 | CH3 | 173–178° |
| H | OCH3 | H | H | OCH3 | CH3 | 147–153° |
| H | OCH3 | H | H | OCH3 | OCH3 | 178–181° |
| H | OCH3 | H | H | OCH2CH3 | CH3 | |
| H | OCH3 | H | H | Cl | OCH3 | |

TABLE IX-continued

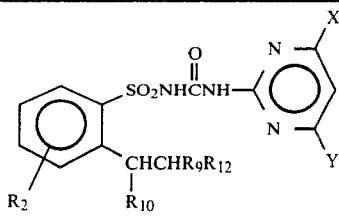

| R₂ | R₉ | R₁₀ | R₁₂ | X | Y | m.p. (°C.) |
|---|---|---|---|---|---|---|
| H | OCH₃ | H | H | OCF₂H | CH₃ | |
| 3-Cl | OCH₃ | H | H | OCH₃ | CH₃ | |
| 4-CH₃ | OCH₃ | H | H | OCH₃ | OCH₃ | |
| 5-CF₃ | OCH₃ | H | H | OCH₃ | CH₃ | |
| 6-OCH₃ | OCH₃ | H | H | OCH₃ | OCH₃ | |
| 6-Cl | OCH₃ | H | H | OCH₃ | CH₃ | |
| 3-F | OCH₃ | H | H | OCH₃ | OCH₃ | |
| H | OCH₃ | H | CH₃ | CH₃ | CH₃ | |
| H | OCH₃ | H | CH₃ | OCH₃ | CH₃ | |
| H | OCH₃ | H | CH₃ | OCH₃ | OCH₃ | |
| H | OCH₃ | H | CH₃ | Cl | OCH₃ | |
| H | OCH₃ | H | CH₃ | OCF₂H | CH₃ | |
| 6-Cl | OCH₃ | H | CH₃ | OCH₃ | CH₃ | |
| 6-OCH₃ | OCH₃ | H | CH₃ | OCH₃ | OCH₃ | |
| 3-CF₃ | OCH₃ | H | CH₃ | OCH₃ | CH₃ | |
| H | OCH₂CH₃ | H | H | CH₃ | CH₃ | |
| H | OCH₂CH₃ | H | H | OCH₃ | CH₃ | |
| H | OCH₂CH₃ | H | H | OCH₃ | OCH₃ | |
| H | OCH₂CH₃ | H | H | Cl | OCH₃ | |
| H | OCH₂CH₃ | H | H | OCF₂H | CH₃ | |
| 6-Cl | OCH₂CH₃ | H | H | OCH₃ | CH₃ | |
| 6-OCH₃ | OCH₂CH₃ | H | H | OCH₃ | OCH₃ | |
| 3-OCH₃ | OCH₂CH₃ | H | H | OCH₃ | CH₃ | |
| H | OCH₂CH₃ | H | CH₃ | OCH₃ | CH₃ | |
| H | OCH₂CH₃ | H | CH₃ | OCH₃ | OCH₃ | |
| 6-Cl | OCH₂CH₃ | H | CH₃ | OCH₃ | CH₃ | |
| H | OCH₃ | OCH₃ | H | CH₃ | CH₃ | |
| H | OCH₃ | OCH₃ | H | OCH₃ | CH₃ | |
| H | OCH₃ | OCH₃ | H | OCH₃ | OCH₃ | |
| H | OCH₃ | OCH₃ | CH₃ | OCH₃ | CH₃ | |
| H | OCH₃ | OCH₃ | CH₃ | OCH₃ | OCH₃ | |
| H | OCH₃ | OCH₂CH₃ | H | OCH₃ | CH₃ | |
| H | OCH₂CH₃ | OCH₃ | H | OCH₃ | OCH₃ | |
| H | OCH₂CH₃ | OCH₂CH₃ | H | OCH₃ | CH₃ | |
| H | OCH₂CH₃ | OCH₂CH₃ | H | OCH₃ | OCH₃ | |
| H | OCH₂CH₃ | OCH₂CH₃ | CH₃ | OCH₃ | CH₃ | |

TABLE X

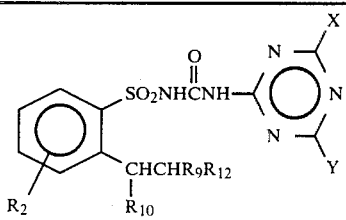

| R₂ | R₉ | R₁₀ | R₁₂ | X | Y | m.p. (°C.) |
|---|---|---|---|---|---|---|
| H | OCH₃ | H | H | CH₃ | CH₃ | 154–156° |
| H | OCH₃ | H | H | OCH₃ | CH₃ | 138–141° |
| H | OCH₃ | H | H | OCH₃ | OCH₃ | 140–147° |
| H | OCH₃ | H | H | OCH₂CH₃ | CH₃ | |
| H | OCH₃ | H | H | OCF₂H | CH₃ | |
| 3-Cl | OCH₃ | H | H | OCH₃ | CH₃ | |
| 4-CH₃ | OCH₃ | H | H | OCH₃ | OCH₃ | |
| 5-CF₃ | OCH₃ | H | H | OCH₃ | CH₃ | |
| 6-OCH₃ | OCH₃ | H | H | OCH₃ | OCH₃ | |
| 6-Cl | OCH₃ | H | H | OCH₃ | CH₃ | |
| 3-F | OCH₃ | H | H | OCH₃ | OCH₃ | |
| H | OCH₃ | H | CH₃ | CH₃ | CH₃ | |
| H | OCH₃ | H | CH₃ | OCH₃ | CH₃ | |
| H | OCH₃ | H | CH₃ | OCH₃ | OCH₃ | |
| H | OCH₃ | H | CH₃ | OCF₂H | CH₃ | |
| 6-Cl | OCH₃ | H | CH₃ | OCH₃ | CH₃ | |
| 6-OCH₃ | OCH₃ | H | CH₃ | OCH₃ | OCH₃ | |

TABLE X-continued

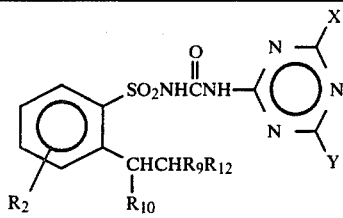

| R2 | R9 | R10 | R12 | X | Y | m.p. (°C.) |
|---|---|---|---|---|---|---|
| 3-CF3 | OCH3 | H | CH3 | OCH3 | CH3 | |
| H | OCH2CH3 | H | H | CH3 | CH3 | |
| H | OCH2CH3 | H | H | OCH3 | CH3 | |
| H | OCH2CH3 | H | H | OCH3 | OCH3 | |
| H | OCH2CH3 | H | H | OCF2H | CH3 | |
| 6-Cl | OCH2CH3 | H | H | OCH3 | CH3 | |
| 6-OCH3 | OCH2CH3 | H | H | OCH3 | OCH3 | |
| 3-OCH3 | OCH2CH3 | H | H | OCH3 | CH3 | |
| H | OCH2CH3 | H | CH3 | OCH3 | CH3 | |
| H | OCH2CH3 | H | CH3 | OCH3 | OCH3 | |
| 6-Cl | OCH2CH3 | H | CH3 | OCH3 | CH3 | |
| H | OCH3 | OCH3 | H | CH3 | CH3 | |
| H | OCH3 | OCH3 | H | OCH3 | CH3 | |
| H | OCH3 | OCH3 | H | OCH3 | OCH3 | |
| H | OCH3 | OCH3 | CH3 | OCH3 | CH3 | |
| H | OCH3 | OCH3 | CH3 | OCH3 | OCH3 | |
| H | OCH3 | OCH2CH3 | H | OCH3 | CH3 | |
| H | OCH2CH3 | OCH3 | H | OCH3 | OCH3 | |
| H | OCH2CH3 | OCH2CH3 | H | OCH3 | CH3 | |
| H | OCH2CH3 | OCH2CH3 | H | OCH3 | OCH3 | |
| H | OCH2CH3 | OCH2CH3 | CH3 | OCH3 | CH3 | |

TABLE XI

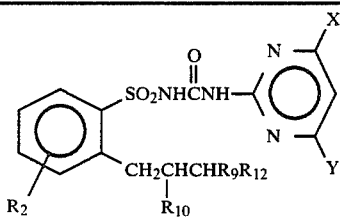

| R2 | R9 | R10 | R12 | X | Y | m.p. (°C.) |
|---|---|---|---|---|---|---|
| H | OCH3 | H | H | CH3 | CH3 | |
| H | OCH3 | H | H | OCH3 | CH3 | |
| H | OCH3 | H | H | OCH3 | OCH3 | |
| H | OCH3 | H | H | OCH2CH3 | CH3 | |
| H | OCH3 | H | H | Cl | OCH3 | |
| H | OCH3 | H | H | OCF2H | CH3 | |
| 3-Cl | OCH3 | H | H | OCH3 | CH3 | |
| 4-CH3 | OCH3 | H | H | OCH3 | OCH3 | |
| 5-CF3 | OCH3 | H | H | OCH3 | OCH3 | |
| 6-OCH3 | OCH3 | H | H | OCH3 | OCH3 | |
| 6-Cl | OCH3 | H | H | OCH3 | CH3 | |
| 3-F | OCH3 | H | H | OCH3 | OCH3 | |
| H | OCH3 | H | CH3 | CH3 | CH3 | |
| H | OCH3 | H | CH3 | OCH3 | CH3 | |
| H | OCH3 | H | CH3 | OCH3 | OCH3 | |
| H | OCH3 | H | CH3 | Cl | OCH3 | |
| H | OCH3 | H | CH3 | OCF2H | CH3 | |
| 6-Cl | OCH3 | H | CH3 | OCH3 | CH3 | |
| 6-OCH3 | OCH3 | H | CH3 | OCH3 | OCH3 | |
| 3-CF3 | OCH3 | H | CH3 | OCH3 | CH3 | |
| H | OCH2CH3 | H | H | CH3 | CH3 | |
| H | OCH2CH3 | H | H | OCH3 | CH3 | |
| H | OCH2CH3 | H | H | OCH3 | OCH3 | |
| H | OCH2CH3 | H | H | Cl | OCH3 | |
| H | OCH2CH3 | H | H | OCF2H | CH3 | |
| 6-Cl | OCH2CH3 | H | H | OCH3 | CH3 | |
| 6-OCH3 | OCH2CH3 | H | H | OCH3 | OCH3 | |
| 3-OCH3 | OCH2CH3 | H | H | OCH3 | CH3 | |
| H | OCH2CH3 | H | CH3 | OCH3 | CH3 | |
| 6-Cl | OCH2CH3 | H | CH3 | OCH3 | CH3 | |

TABLE XI-continued

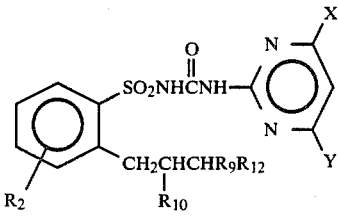

| R2 | R9 | R10 | R12 | X | Y | m.p. (°C.) |
|---|---|---|---|---|---|---|
| H | OCH3 | OCH3 | H | CH3 | CH3 | |
| H | OCH3 | OCH3 | H | OCH3 | CH3 | |
| H | OCH3 | OCH3 | H | OCH3 | OCH3 | |
| H | OCH3 | OCH3 | CH3 | OCH3 | CH3 | |
| H | OCH3 | OCH3 | CH3 | OCH3 | OCH3 | |
| H | OCH3 | OCH2CH3 | H | OCH3 | CH3 | |
| H | OCH2CH3 | OCH3 | H | OCH3 | OCH3 | |
| H | OCH2CH3 | OCH2CH3 | H | OCH3 | CH3 | |
| H | OCH2CH3 | OCH2CH3 | H | OCH3 | OCH3 | |
| H | OCH2CH3 | OCH2CH3 | CH3 | OCH3 | CH3 | |

TABLE XII

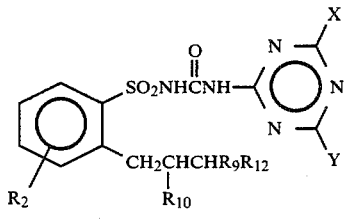

| R2 | R9 | R10 | R12 | X | Y | m.p. (°C.) |
|---|---|---|---|---|---|---|
| H | OCH3 | H | H | CH3 | CH3 | |
| H | OCH3 | H | H | OCH3 | CH3 | |
| H | OCH3 | H | H | OCH3 | OCH3 | |
| H | OCH3 | H | H | OCH2CH3 | CH3 | |

TABLE XII-continued

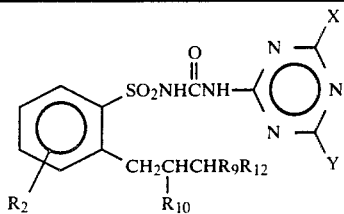

| R₂ | R₉ | R₁₀ | R₁₂ | X | Y | m.p. (°C.) |
|---|---|---|---|---|---|---|
| H | OCH₃ | H | H | OCF₂H | CH₃ | |
| 3-Cl | OCH₃ | H | H | OCH₃ | CH₃ | |
| 4-CH₃ | OCH₃ | H | H | OCH₃ | OCH₃ | |
| 5-CF₃ | OCH₃ | H | H | OCH₃ | CH₃ | |
| 6-OCH₃ | OCH₃ | H | H | OCH₃ | OCH₃ | |
| 6-Cl | OCH₃ | H | H | OCH₃ | CH₃ | |
| 3-F | OCH₃ | H | H | OCH₃ | OCH₃ | |
| H | OCH₃ | H | CH₃ | CH₃ | CH₃ | |
| H | OCH₃ | H | CH₃ | OCH₃ | CH₃ | |
| H | OCH₃ | H | CH₃ | OCH₃ | OCH₃ | |
| H | OCH₃ | H | CH₃ | OCF₂H | CH₃ | |
| 6-Cl | OCH₃ | H | CH₃ | OCH₃ | CH₃ | |
| 6-OCH₃ | OCH₃ | H | CH₃ | OCH₃ | OCH₃ | |
| 3-CF₃ | OCH₃ | H | CH₃ | OCH₃ | CH₃ | |
| H | OCH₂CH₃ | H | H | CH₃ | CH₃ | |
| H | OCH₂CH₃ | H | H | OCH₃ | CH₃ | |
| H | OCH₂CH₃ | H | H | OCH₃ | OCH₃ | |

TABLE XII-continued

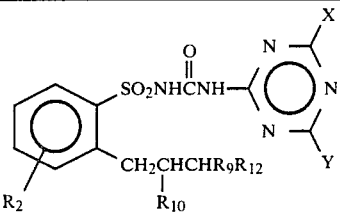

| R₂ | R₉ | R₁₀ | R₁₂ | X | Y | m.p. (°C.) |
|---|---|---|---|---|---|---|
| H | OCH₂CH₃ | H | H | OCF₂H | CH₃ | |
| 6-Cl | OCH₂CH₃ | H | H | OCH₃ | CH₃ | |
| 6-OCH₃ | OCH₂CH₃ | H | H | OCH₃ | OCH₃ | |
| 3-OCH₃ | OCH₂CH₃ | H | H | OCH₃ | CH₃ | |
| H | OCH₂CH₃ | H | CH₃ | OCH₃ | CH₃ | |
| H | OCH₂CH₃ | H | CH₃ | OCH₃ | OCH₃ | |
| 6-Cl | OCH₂CH₃ | H | CH₃ | OCH₃ | CH₃ | |
| H | OCH₃ | OCH₃ | H | CH₃ | CH₃ | |
| H | OCH₃ | OCH₃ | H | OCH₃ | OCH₃ | |
| H | OCH₃ | OCH₃ | CH₃ | OCH₃ | CH₃ | |
| H | OCH₃ | OCH₃ | CH₃ | OCH₃ | OCH₃ | |
| H | OCH₃ | OCH₂CH₃ | H | OCH₃ | CH₃ | |
| H | OCH₂CH₃ | OCH₃ | H | OCH₃ | CH₃ | |
| H | OCH₂CH₃ | OCH₂CH₃ | H | OCH₃ | CH₃ | |
| H | OCH₂CH₃ | OCH₂CH₃ | H | OCH₃ | OCH₃ | |
| H | OCH₂CH₃ | OCH₂CH₃ | CH₃ | OCH₃ | CH₃ | |

TABLE XIII

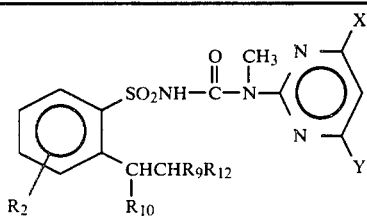

| R₂ | R₉ | R₁₀ | R₁₂ | X | Y | m.p. (°C.) |
|---|---|---|---|---|---|---|
| H | OCH₃ | H | H | CH₃ | CH₃ | |
| H | OCH₃ | H | H | OCH₃ | CH₃ | |
| H | OCH₃ | H | H | OCH₃ | OCH₃ | |
| H | OCH₃ | H | H | OCH₂CH₃ | CH₃ | |
| H | OCH₃ | H | H | Cl | OCH₃ | |
| H | OCH₃ | H | H | OCF₂H | CH₃ | |
| 3-Cl | OCH₃ | H | H | OCH₃ | CH₃ | |
| 4-CH₃ | OCH₃ | H | H | OCH₃ | OCH₃ | |
| 5-CF₃ | OCH₃ | H | H | OCH₃ | CH₃ | |
| 6-OCH₃ | OCH₃ | H | H | OCH₃ | OCH₃ | |
| 6-Cl | OCH₃ | H | H | OCH₃ | CH₃ | |
| 3-F | OCH₃ | H | H | OCH₃ | OCH₃ | |
| H | OCH₃ | H | CH₃ | CH₃ | CH₃ | |
| H | OCH₃ | H | CH₃ | OCH₃ | CH₃ | |
| H | OCH₃ | H | CH₃ | OCH₃ | OCH₃ | |
| H | OCH₃ | H | CH₃ | Cl | OCH₃ | |
| H | OCH₃ | H | CH₃ | OCF₂H | CH₃ | |
| 6-Cl | OCH₃ | H | CH₃ | OCH₃ | CH₃ | |
| 6-OCH₃ | OCH₃ | H | CH₃ | OCH₃ | OCH₃ | |
| 3-CF₃ | OCH₃ | H | CH₃ | OCH₃ | CH₃ | |
| H | OCH₂CH₃ | H | H | CH₃ | CH₃ | |
| H | OCH₂CH₃ | H | H | OCH₃ | CH₃ | |
| H | OCH₂CH₃ | H | H | OCH₃ | OCH₃ | |
| H | OCH₂CH₃ | H | H | Cl | OCH₃ | |
| H | OCH₂CH₃ | H | H | OCF₂H | CH₃ | |
| 6-Cl | OCH₂CH₃ | H | H | OCH₃ | CH₃ | |
| 6-OCH₃ | OCH₂CH₃ | H | H | OCH₃ | OCH₃ | |
| 3-OCH₃ | OCH₂CH₃ | H | H | OCH₃ | CH₃ | |
| H | OCH₂CH₃ | H | CH₃ | OCH₃ | CH₃ | |
| H | OCH₂CH₃ | H | CH₃ | OCH₃ | OCH₃ | |
| 6-Cl | OCH₂CH₃ | H | CH₃ | OCH₃ | CH₃ | |
| H | OCH₃ | OCH₃ | H | CH₃ | CH₃ | |
| H | OCH₃ | OCH₃ | H | OCH₃ | CH₃ | 175–176° |
| H | OCH₃ | OCH₃ | H | OCH₃ | OCH₃ | 204–206° |
| H | OCH₃ | OCH₃ | CH₃ | OCH₃ | CH₃ | |

TABLE XIII-continued

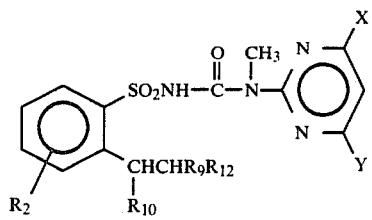

| R2 | R9 | R10 | R12 | X | Y | m.p. (°C.) |
|---|---|---|---|---|---|---|
| H | OCH3 | OCH3 | CH3 | OCH3 | OCH3 | |
| H | OCH3 | OCH2CH3 | H | OCH3 | CH3 | |
| H | OCH2CH3 | OCH3 | H | OCH3 | OCH3 | |
| H | OCH2CH3 | OCH2CH3 | H | OCH3 | CH3 | |
| H | OCH2CH3 | OCH2CH3 | H | OCH3 | OCH3 | |
| H | OCH2CH3 | OCH2CH3 | CH3 | OCH3 | CH3 | |

TABLE XIV

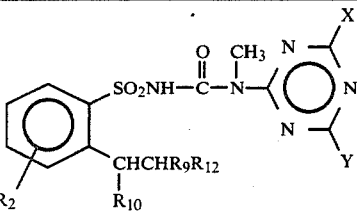

| R2 | R9 | R10 | R12 | X | Y | m.p. (°C.) |
|---|---|---|---|---|---|---|
| H | OCH3 | H | H | CH3 | CH3 | |
| H | OCH3 | H | H | OCH3 | CH3 | |
| H | OCH3 | H | H | OCH3 | OCH3 | |
| H | OCH3 | H | H | OCH2CH3 | CH3 | |
| H | OCH3 | H | H | OCF2H | CH3 | |
| 3-Cl | OCH3 | H | H | OCH3 | CH3 | |
| 4-CH3 | OCH3 | H | H | OCH3 | OCH3 | |
| 5-CF3 | OCH3 | H | H | OCH3 | CH3 | |
| 6-OCH3 | OCH3 | H | H | OCH3 | OCH3 | |
| 6-Cl | OCH3 | H | H | OCH3 | CH3 | |
| 3-F | OCH3 | H | H | OCH3 | OCH3 | |
| H | OCH3 | H | CH3 | CH3 | CH3 | |
| H | OCH3 | H | CH3 | OCH3 | CH3 | |
| H | OCH3 | H | CH3 | OCH3 | OCH3 | |
| H | OCH3 | H | CH3 | OCF2H | CH3 | |
| 6-Cl | OCH3 | H | CH3 | OCH3 | CH3 | |
| 6-OCH3 | OCH3 | H | CH3 | OCH3 | OCH3 | |
| 3-CF3 | OCH3 | H | CH3 | OCH3 | CH3 | |
| H | OCH2CH3 | H | H | CH3 | CH3 | |
| H | OCH2CH3 | H | H | OCH3 | CH3 | |
| H | OCH2CH3 | H | H | OCH3 | OCH3 | |
| H | OCH2CH3 | H | H | OCF2H | CH3 | |
| 6-Cl | OCH2CH3 | H | H | OCH3 | CH3 | |
| 6-OCH3 | OCH2CH3 | H | H | OCH3 | OCH3 | |
| 3-OCH3 | OCH2CH3 | H | H | OCH3 | CH3 | |
| H | OCH2CH3 | H | CH3 | OCH3 | CH3 | |
| H | OCH2CH3 | H | CH3 | OCH3 | OCH3 | |
| 6-Cl | OCH2CH3 | H | CH3 | OCH3 | CH3 | |
| H | OCH3 | OCH3 | H | CH3 | CH3 | |
| H | OCH3 | OCH3 | H | OCH3 | CH3 | |
| H | OCH3 | OCH3 | H | OCH3 | OCH3 | |
| H | OCH3 | OCH3 | CH3 | OCH3 | CH3 | |
| H | OCH3 | OCH3 | CH3 | OCH3 | OCH3 | |
| H | OCH3 | OCH2CH3 | H | OCH3 | CH3 | |
| H | OCH2CH3 | OCH3 | H | OCH3 | CH3 | |
| H | OCH2CH3 | OCH2CH3 | H | OCH3 | CH3 | |
| H | OCH2CH3 | OCH2CH3 | H | OCH3 | OCH3 | |
| H | OCH2CH3 | OCH2CH3 | CH3 | OCH3 | CH3 | |

TABLE XV

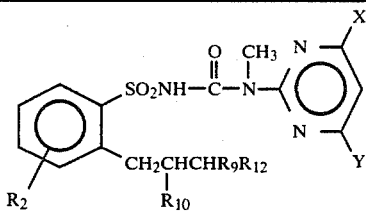

| R2 | R9 | R10 | R12 | X | Y | m.p. (°C.) |
|---|---|---|---|---|---|---|
| H | OCH3 | H | H | CH3 | CH3 | |
| H | OCH3 | H | H | OCH3 | CH3 | |
| H | OCH3 | H | H | OCH3 | OCH3 | |
| H | OCH3 | H | H | OCH2CH3 | CH3 | |
| H | OCH3 | H | H | Cl | OCH3 | |
| H | OCH3 | H | H | OCF2H | CH3 | |
| 3-Cl | OCH3 | H | H | OCH3 | CH3 | |
| 4-CH3 | OCH3 | H | H | OCH3 | OCH3 | |
| 5-CF3 | OCH3 | H | H | OCH3 | CH3 | |
| 6-OCH3 | OCH3 | H | H | OCH3 | OCH3 | |
| 6-Cl | OCH3 | H | H | OCH3 | CH3 | |
| 3-F | OCH3 | H | H | OCH3 | OCH3 | |
| H | OCH3 | H | CH3 | CH3 | CH3 | |
| H | OCH3 | H | CH3 | OCH3 | CH3 | |
| H | OCH3 | H | CH3 | Cl | CH3 | |
| H | OCH3 | H | CH3 | OCF2H | CH3 | |
| 6-Cl | OCH3 | H | CH3 | OCH3 | CH3 | |
| 6-OCH3 | OCH3 | H | CH3 | OCH3 | CH3 | |
| 3-CF3 | OCH3 | H | CH3 | OCH3 | CH3 | |
| H | OCH2CH3 | H | H | CH3 | CH3 | |
| H | OCH2CH3 | H | H | OCH3 | CH3 | |
| H | OCH2CH3 | H | H | OCH3 | OCH3 | |
| H | OCH2CH3 | H | H | Cl | CH3 | |
| H | OCH2CH3 | H | H | OCF2H | CH3 | |
| 6-Cl | OCH2CH3 | H | H | OCH3 | CH3 | |
| 6-OCH3 | OCH2CH3 | H | H | OCH3 | OCH3 | |
| 3-OCH3 | OCH2CH3 | H | H | OCH3 | CH3 | |
| H | OCH2CH3 | H | CH3 | OCH3 | CH3 | |
| H | OCH2CH3 | H | CH3 | OCH3 | OCH3 | |
| 6-Cl | OCH2CH3 | H | CH3 | OCH3 | CH3 | |
| H | OCH3 | OCH3 | H | CH3 | CH3 | |
| H | OCH3 | OCH3 | H | OCH3 | CH3 | |
| H | OCH3 | OCH3 | H | OCH3 | OCH3 | |
| H | OCH3 | OCH3 | CH3 | OCH3 | CH3 | |
| H | OCH3 | OCH3 | CH3 | OCH3 | OCH3 | |
| H | OCH3 | OCH2CH3 | H | OCH3 | CH3 | |
| H | OCH2CH3 | OCH3 | H | OCH3 | CH3 | |
| H | OCH2CH3 | OCH2CH3 | H | OCH3 | CH3 | |
| H | OCH2CH3 | OCH2CH3 | H | OCH3 | OCH3 | |
| H | OCH2CH3 | OCH2CH3 | CH3 | OCH3 | CH3 | |

TABLE XVI

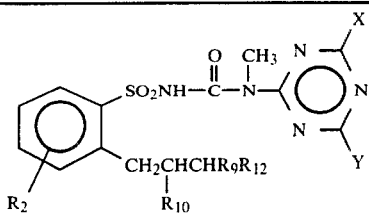

| R₂ | R₉ | R₁₀ | R₁₂ | X | Y | m.p. (°C.) |
|---|---|---|---|---|---|---|
| H | OCH₃ | H | H | CH₃ | CH₃ | |
| H | OCH₃ | H | H | OCH₃ | CH₃ | |
| H | OCH₃ | H | H | OCH₃ | OCH₃ | |
| H | OCH₃ | H | H | OCH₂CH₃ | CH₃ | |
| H | OCH₃ | H | H | OCF₂H | CH₃ | |
| 3-Cl | OCH₃ | H | H | OCH₃ | CH₃ | |
| 4-CH₃ | OCH₃ | H | H | OCH₃ | OCH₃ | |
| 5-CF₃ | OCH₃ | H | H | OCH₃ | CH₃ | |
| 6-OCH₃ | OCH₃ | H | H | OCH₃ | OCH₃ | |
| 6-Cl | OCH₃ | H | H | OCH₃ | CH₃ | |
| 3-F | OCH₃ | H | H | OCH₃ | OCH₃ | |
| H | OCH₃ | H | CH₃ | CH₃ | CH₃ | |
| H | OCH₃ | H | CH₃ | OCH₃ | CH₃ | |
| H | OCH₃ | H | CH₃ | OCH₃ | OCH₃ | |
| H | OCH₃ | H | CH₃ | OCF₂H | CH₃ | |
| 6-Cl | OCH₃ | H | CH₃ | OCH₃ | CH₃ | |
| 6-OCH₃ | OCH₃ | H | CH₃ | OCH₃ | CH₃ | |
| 3-CF₃ | OCH₃ | H | CH₃ | OCH₃ | CH₃ | |
| H | OCH₂CH₃ | H | H | CH₃ | CH₃ | |
| H | OCH₂CH₃ | H | H | OCH₃ | CH₃ | |
| H | OCH₂CH₃ | H | H | OCH₃ | OCH₃ | |
| H | OCH₂CH₃ | H | H | OCF₂H | CH₃ | |
| 6-Cl | OCH₂CH₃ | H | H | OCH₃ | CH₃ | |
| 6-OCH₃ | OCH₂CH₃ | H | H | OCH₃ | OCH₃ | |
| 3-OCH₃ | OCH₂CH₃ | H | H | OCH₃ | CH₃ | |
| H | OCH₂CH₃ | H | CH₃ | OCH₃ | CH₃ | |
| H | OCH₂CH₃ | H | CH₃ | OCH₃ | OCH₃ | |
| 6-Cl | OCH₂CH₃ | H | CH₃ | OCH₃ | CH₃ | |
| H | OCH₃ | OCH₃ | H | CH₃ | CH₃ | |
| H | OCH₃ | OCH₃ | H | OCH₃ | CH₃ | |
| H | OCH₃ | OCH₃ | H | OCH₃ | OCH₃ | |
| H | OCH₃ | OCH₃ | CH₃ | OCH₃ | CH₃ | |
| H | OCH₃ | OCH₃ | CH₃ | OCH₃ | OCH₃ | |
| H | OCH₃ | OCH₂CH₃ | H | OCH₃ | CH₃ | |
| H | OCH₃ | OCH₂CH₃ | H | OCH₃ | OCH₃ | |
| H | OCH₂CH₃ | OCH₂CH₃ | H | OCH₃ | CH₃ | |
| H | OCH₂CH₃ | OCH₂CH₃ | H | OCH₃ | OCH₃ | |
| H | OCH₂CH₃ | OCH₂CH₃ | CH₃ | OCH₃ | CH₃ | |

TABLE XVII

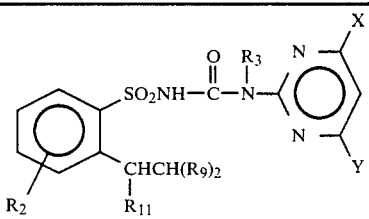

| R₂ | R₃ | R₉ | R₁₁ | X | Y | m.p. (°C.) |
|---|---|---|---|---|---|---|
| H | H | OCH₃ | H | CH₃ | CH₃ | |
| H | H | OCH₃ | H | OCH₃ | CH₃ | |
| H | H | OCH₃ | H | OCH₃ | OCH₃ | |
| H | H | OCH₃ | H | Cl | OCH₃ | |
| H | H | OCH₃ | H | OCF₂H | CH₃ | |
| H | CH₃ | OCH₃ | H | OCH₃ | CH₃ | |
| H | CH₃ | OCH₃ | H | OCH₃ | OCH₃ | |
| 6-OCH₃ | H | OCH₃ | H | OCH₃ | CH₃ | |
| 3-Cl | H | OCH₃ | H | OCH₃ | CH₃ | |
| 3-OCH₃ | CH₃ | OCH₃ | H | OCH₃ | CH₃ | |
| H | H | OCH₂CH₃ | H | CH₃ | CH₃ | |
| H | H | OCH₂CH₃ | H | OCH₃ | CH₃ | |
| H | H | OCH₂CH₃ | H | OCH₃ | OCH₃ | |

TABLE XVII-continued

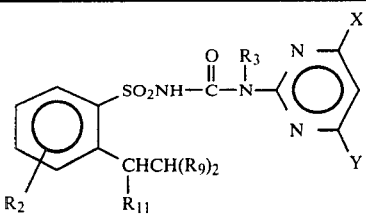

| R₂ | R₃ | R₉ | R₁₁ | X | Y | m.p. (°C.) |
|---|---|---|---|---|---|---|
| H | H | OCH₂CH₃ | H | Cl | OCH₃ | |
| H | CH₃ | OCH₂CH₃ | H | OCH₃ | CH₃ | |
| 6-OCH₃ | H | OCH₂CH₃ | H | OCH₃ | OCH₃ | |
| H | H | OCH₃ | Cl | OCH₃ | CH₃ | |
| H | H | OCH₃ | Cl | OCH₃ | OCH₃ | |
| 6-Cl | H | OCH₃ | Cl | OCH₃ | CH₃ | |
| H | H | OCH₃ | Cl | OCH₃ | OCH₃ | |
| H | H | OCH₂CH₃ | Cl | OCH₃ | CH₃ | |
| H | CH₃ | OCH₂CH₃ | Cl | OCH₃ | CH₃ | |
| H | H | OCH₃ | OCH₃ | CH₃ | CH₃ | |
| H | H | OCH₃ | OCH₃ | OCH₃ | CH₃ | |
| H | H | OCH₃ | OCH₃ | OCH₃ | OCH₃ | |
| H | CH₃ | OCH₃ | OCH₃ | OCH₃ | CH₃ | |
| 6-OCH₃ | H | OCH₃ | OCH₃ | OCH₃ | OCH₃ | |
| H | H | OCH₂CH₃ | OCH₃ | OCH₃ | CH₃ | |
| H | CH₃ | OCH₂CH₃ | OCH₃ | OCH₃ | OCH₃ | |

TABLE XVIII

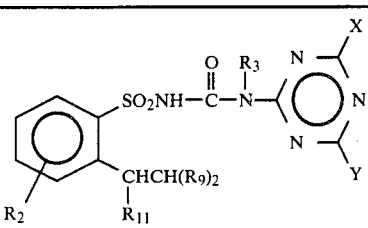

| R₂ | R₃ | R₉ | R₁₁ | X | Y | m.p. (°C.) |
|---|---|---|---|---|---|---|
| H | H | OCH₃ | H | CH₃ | CH₃ | |
| H | H | OCH₃ | H | OCH₃ | CH₃ | |
| H | H | OCH₃ | H | OCH₃ | OCH₃ | |
| H | H | OCH₃ | H | OCF₂H | CH₃ | |
| H | CH₃ | OCH₃ | H | OCH₃ | CH₃ | |
| H | CH₃ | OCH₃ | H | OCH₃ | OCH₃ | |
| 6-OCH₃ | H | OCH₃ | H | OCH₃ | CH₃ | |
| 3-Cl | H | OCH₃ | H | OCH₃ | OCH₃ | |
| 3-OCH₃ | CH₃ | OCH₃ | H | OCH₃ | CH₃ | |
| H | H | OCH₂CH₃ | H | CH₃ | CH₃ | |
| H | H | OCH₂CH₃ | H | OCH₃ | CH₃ | |
| H | H | OCH₂CH₃ | H | OCH₃ | OCH₃ | |
| H | CH₃ | OCH₂CH₃ | H | OCH₃ | CH₃ | |
| 6-OCH₃ | H | OCH₂CH₃ | H | OCH₃ | OCH₃ | |
| H | H | OCH₃ | Cl | OCH₃ | CH₃ | |
| H | H | OCH₃ | Cl | OCH₃ | OCH₃ | |
| 6-Cl | H | OCH₃ | Cl | OCH₃ | CH₃ | |
| H | CH₃ | OCH₃ | Cl | OCH₃ | CH₃ | |
| H | H | OCH₂CH₃ | Cl | OCH₃ | CH₃ | |
| H | CH₃ | OCH₂CH₃ | Cl | OCH₃ | CH₃ | |
| H | H | OCH₃ | OCH₃ | CH₃ | CH₃ | |
| H | H | OCH₃ | OCH₃ | OCH₃ | CH₃ | |
| H | H | OCH₃ | OCH₃ | OCH₃ | OCH₃ | |
| H | CH₃ | OCH₃ | OCH₃ | OCH₃ | CH₃ | |
| 6-OCH₃ | H | OCH₃ | OCH₃ | OCH₃ | OCH₃ | |
| H | H | OCH₂CH₃ | OCH₃ | OCH₃ | CH₃ | |
| H | CH₃ | OCH₂CH₃ | OCH₃ | OCH₃ | OCH₃ | |

TABLE XIX

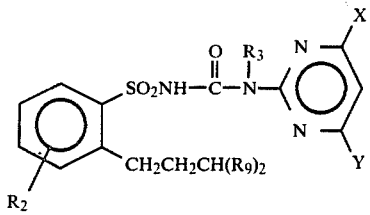

| R2 | R3 | R9 | X | Y | m.p. (°C.) |
|---|---|---|---|---|---|
| H | H | OCH3 | CH3 | CH3 | |
| H | H | OCH3 | OCH3 | CH3 | |
| H | H | OCH3 | OCH3 | OCH3 | |
| H | H | OCH3 | Cl | OCH3 | |
| H | H | OCH3 | OCF2H | CH3 | |
| H | CH3 | OCH3 | CH3 | CH3 | |
| H | CH3 | OCH3 | OCH3 | CH3 | |
| 6-OCH3 | H | OCH3 | OCH3 | CH3 | |
| 3-Cl | H | OCH3 | OCH3 | CH3 | |
| 3-OCH3 | CH3 | OCH3 | OCH3 | CH3 | |
| H | H | OCH2CH3 | CH3 | CH3 | |
| H | H | OCH2CH3 | OCH3 | CH3 | |
| H | H | OCH2CH3 | OCH3 | OCH3 | |
| H | H | OCH2CH3 | Cl | OCH3 | |
| H | CH3 | OCH2CH3 | OCH3 | CH3 | |
| 6-OCH3 | H | OCH2CH3 | OCH3 | OCH3 | |

TABLE XX

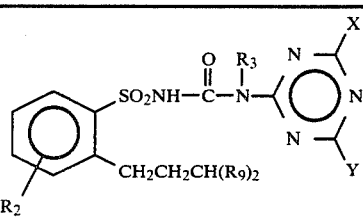

| R2 | R3 | R9 | X | Y | m.p. (°C.) |
|---|---|---|---|---|---|
| H | H | OCH3 | CH3 | CH3 | |
| H | H | OCH3 | OCH3 | CH3 | |
| H | H | OCH3 | OCH3 | OCH3 | |
| H | H | OCH3 | OCF2H | CH3 | |
| H | CH3 | OCH3 | OCH3 | CH3 | |
| H | CH3 | OCH3 | OCH3 | OCH3 | |
| 6-OCH3 | H | OCH3 | OCH3 | CH3 | |
| 3-Cl | H | OCH3 | OCH3 | CH3 | |
| 3-OCH3 | CH3 | OCH3 | OCH3 | CH3 | |
| H | H | OCH2CH3 | CH3 | CH3 | |
| H | H | OCH2CH3 | OCH3 | CH3 | |
| H | H | OCH2CH3 | OCH3 | OCH3 | |
| H | CH3 | OCH2CH3 | OCH3 | CH3 | |
| 6-OCH3 | H | OCH2CH3 | OCH3 | OCH3 | |

TABLE XXI

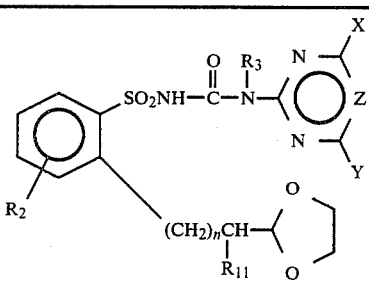

| R2 | R3 | n | R11 | X | Y | Z | m.p. (°C.) |
|---|---|---|---|---|---|---|---|
| H | H | 0 | H | CH3 | CH3 | CH | |
| H | H | 0 | H | OCH3 | CH3 | CH | 176–180° (d) |

TABLE XXI-continued

| R2 | R3 | n | R11 | X | Y | Z | m.p. (°C.) |
|---|---|---|---|---|---|---|---|
| H | H | 0 | H | OCH3 | OCH3 | CH | 176–177° |
| H | H | 0 | H | CH3 | CH3 | N | |
| H | H | 0 | H | OCH3 | CH3 | N | |
| H | H | 0 | H | OCH3 | OCH3 | N | |
| H | H | 0 | H | Cl | OCH3 | CH | |
| 6-Cl | H | 0 | H | OCH3 | CH3 | CH | |
| 6-OCH3 | H | 0 | H | OCH3 | OCH3 | N | |
| 3-CF3 | H | 0 | H | OCH3 | CH3 | N | |
| 4-CH3 | H | 0 | H | OCH3 | OCH3 | CH | |
| H | H | 0 | Cl | OCH3 | CH3 | CH | |
| H | H | 0 | OCH3 | OCH3 | OCH3 | CH | |
| H | H | 1 | H | CH3 | CH3 | N | |
| H | H | 1 | H | OCH3 | CH3 | CH | |
| H | H | 1 | H | OCH3 | OCH3 | CH | |
| H | H | 1 | H | Cl | OCH3 | CH | |
| H | H | 1 | H | OCF2H | CH3 | N | |
| H | H | 1 | H | OCH3 | CH3 | N | |
| 6-OCH3 | H | 1 | H | OCH3 | CH3 | N | |
| 6-F | H | 1 | H | OCH3 | OCH3 | N | |
| 3-Cl | H | 1 | H | OCH3 | CH3 | CH | |
| 3-OCH3 | H | 1 | H | OCH3 | CH3 | CH | |
| H | CH3 | 0 | H | OCH3 | OCH3 | CH | |
| 3-OCH3 | CH3 | 0 | H | Cl | OCH3 | CH | |
| H | CH3 | 1 | H | OCH3 | CH3 | N | |
| H | CH3 | 1 | H | OCH3 | OCH3 | CH | |
| 3-Cl | CH3 | 1 | H | OCF2H | CH3 | CH | |

TABLE XXII

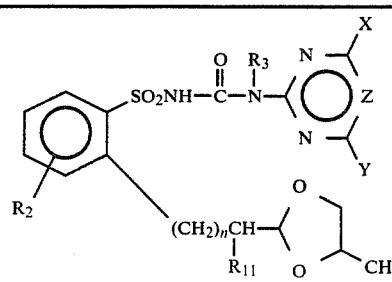

| R2 | R3 | n | R11 | X | Y | Z | m.p. (°C.) |
|---|---|---|---|---|---|---|---|
| H | H | 0 | H | CH3 | CH3 | CH | |
| H | H | 0 | H | OCH3 | CH3 | N | |
| H | H | 0 | H | OCH3 | OCH3 | N | |
| H | H | 0 | H | OCF2H | CH3 | CH | |
| 6-Cl | H | 0 | H | OCH3 | CH3 | CH | |
| 6-OCH3 | H | 0 | H | OCH3 | OCH3 | CH | |
| 3-CF3 | H | 0 | H | OCH3 | CH3 | N | |
| 4-CH3 | H | 0 | H | OCH3 | OCH3 | CH | |
| H | H | 0 | Cl | OCH3 | CH3 | CH | |
| H | H | 0 | CH3 | OCH3 | OCH3 | N | |
| H | H | 1 | H | CH3 | CH3 | CH | |
| H | H | 1 | H | OCH3 | CH3 | CH | |
| H | H | 1 | H | OCH3 | OCH3 | N | |
| H | H | 1 | H | OCF2H | CH3 | N | |
| 6-OCH3 | H | 1 | H | OCH3 | CH3 | N | |
| 6-F | H | 1 | H | OCH3 | OCH3 | N | |
| 3-Cl | H | 1 | H | OCH3 | CH3 | CH | |
| 3-OCH3 | H | 1 | H | OCH3 | CH3 | CH | |
| H | CH3 | 0 | H | OCH3 | OCH3 | N | |
| 3-OCH3 | CH3 | 0 | H | OCH3 | OCH3 | CH | |

TABLE XXII-continued

Structure: Ar-SO₂NH-C(O)-N(R₃)-[triazine with X, Y, Z]; phenyl has R₂ and (CH₂)ₙCH(R₁₁)-[1,3-dioxolane with CH₃]

| R₂ | R₃ | n | R₁₁ | X | Y | Z | m.p. (°C.) |
|---|---|---|---|---|---|---|---|
| H | CH₃ | 1 | H | OCH₃ | CH₃ | N | |
| H | CH₃ | 1 | H | OCH₃ | OCH₃ | N | |
| 3-Cl | CH₃ | 1 | H | OCF₂H | CH₃ | CH | |

TABLE XXIII

Structure: Ar-SO₂NH-C(O)-N(R₃)-[pyrimidine with X, Y]; phenyl has R₂ and (CH₂)ₙCH(R₁₁)-[1,3-dioxane]

| R₂ | R₃ | n | R₁₁ | X | Y | m.p. (°C.) |
|---|---|---|---|---|---|---|
| H | H | 0 | H | CH₃ | CH₃ | |
| H | H | 0 | H | OCH₃ | CH₃ | |
| H | H | 0 | H | Cl | OCH₃ | |
| H | H | 0 | H | OCF₂H | CH₃ | |
| 6-Cl | H | 0 | H | OCH₃ | CH₃ | |
| 6-OCH₃ | H | 0 | H | OCH₃ | CH₃ | |
| 3-CF₃ | H | 0 | H | OCH₃ | CH₃ | |
| 4-CH₃ | H | 0 | H | OCH₃ | OCH₃ | |
| H | H | 0 | H | OCH₃ | OCH₃ | |
| H | H | 0 | H | Cl | OCH₃ | |
| H | H | 0 | CH₃ | CH₃ | CH₃ | |
| H | H | 0 | Cl | OCH₃ | CH₃ | |
| H | H | 0 | CH₃ | OCH₃ | OCH₃ | |
| H | H | 0 | CH₃ | Cl | OCH₃ | |
| H | H | 0 | CH₃ | OCF₂H | CH₃ | |
| H | H | 0 | OCH₃ | OCH₃ | CH₃ | |
| H | H | 0 | CH₃ | OCH₃ | OCH₃ | |
| 6-OCH₃ | H | 0 | CH₃ | OCH₃ | CH₃ | |
| 6-Cl | H | 0 | CH₃ | OCH₃ | CH₃ | |
| 3-Cl | H | 0 | CH₃ | OCH₃ | CH₃ | |
| H | H | 1 | H | CH₃ | CH₃ | |
| H | H | 1 | H | OCH₃ | CH₃ | |
| H | H | 1 | H | OCH₃ | OCH₃ | |
| H | H | 1 | H | Cl | OCH₃ | |
| H | H | 1 | H | OCF₂H | CH₃ | |
| H | H | 1 | H | OCH₃ | OCH₃ | |
| H | H | 1 | H | OCH₃ | CH₃ | |
| 6-OCH₃ | H | 1 | H | OCH₃ | CH₃ | |
| 6-F | H | 1 | H | OCH₃ | OCH₃ | |
| 3-Cl | H | 1 | H | OCH₃ | CH₃ | |
| 3-OCH₃ | H | 1 | H | OCH₃ | CH₃ | |
| H | CH₃ | 0 | H | OCH₃ | CH₃ | |
| H | CH₃ | 0 | CH₃ | OCH₃ | CH₃ | |
| 3-OCH₃ | CH₃ | 0 | H | Cl | OCH₃ | |
| H | CH₃ | 1 | H | OCH₃ | CH₃ | |
| H | CH₃ | 1 | H | OCH₃ | OCH₃ | |
| 3-Cl | CH₃ | 1 | H | OCF₂H | CH₃ | |

TABLE XXIV

Structure: Ar-SO₂NH-C(O)-N(R₃)-[triazine with X, Y]; phenyl has R₂ and (CH₂)ₙCH(R₁₁)-[1,3-dioxane]

| R₂ | R₃ | n | R₁₁ | X | Y | m.p. (°C.) |
|---|---|---|---|---|---|---|
| H | H | 0 | H | CH₃ | CH₃ | |
| H | H | 0 | H | OCH₃ | CH₃ | |
| H | H | 0 | H | OCH₃ | OCH₃ | |
| H | H | 0 | H | OCF₂H | CH₃ | |
| 6-Cl | H | 0 | H | OCH₃ | CH₃ | |
| 6-OCH₃ | H | 0 | H | OCH₃ | OCH₃ | |
| 3-CF₃ | H | 0 | H | OCH₃ | CH₃ | |
| 4-CH₃ | H | 0 | H | OCH₃ | OCH₃ | |
| H | H | 0 | H | OCH₃ | CH₃ | |
| H | H | 0 | CH₃ | CH₃ | CH₃ | |
| H | H | 0 | Cl | OCH₃ | CH₃ | |
| H | H | 0 | CH₃ | OCH₃ | OCH₃ | |
| H | H | 0 | CH₃ | OCF₂H | CH₃ | |
| H | H | 0 | OCH₃ | OCH₃ | CH₃ | |
| H | H | 0 | CH₃ | OCH₃ | OCH₃ | |
| 6-OCH₃ | H | 0 | CH₃ | OCH₃ | CH₃ | |
| 6-Cl | H | 0 | CH₃ | OCH₃ | CH₃ | |
| 3-Cl | H | 0 | CH₃ | OCH₃ | CH₃ | |
| H | H | 1 | H | CH₃ | CH₃ | |
| H | H | 1 | H | OCH₃ | CH₃ | |
| H | H | 1 | H | OCF₂H | CH₃ | |
| H | H | 1 | H | OCH₃ | OCH₃ | |
| H | H | 1 | H | OCH₃ | CH₃ | |
| 6-OCH₃ | H | 1 | H | OCH₃ | CH₃ | |
| 6-F | H | 1 | H | OCH₃ | OCH₃ | |
| 3-Cl | H | 1 | H | OCH₃ | CH₃ | |
| 3-OCH₃ | H | 1 | H | OCH₃ | CH₃ | |
| H | CH₃ | 0 | H | OCH₃ | CH₃ | |
| H | CH₃ | 0 | CH₃ | OCH₃ | CH₃ | |
| H | CH₃ | 1 | H | OCH₃ | CH₃ | |
| H | CH₃ | 1 | H | OCH₃ | OCH₃ | |
| 3-Cl | CH₃ | 1 | H | OCF₂H | CH₃ | |

TABLE XXV

Structure: Ar-SO₂NH-C(O)-N(R₃)-[pyrimidine with X, Y]; phenyl has R₁ and R₂

| R₁ | R₂ | R₃ | X | Y | m.p. (°C.) |
|---|---|---|---|---|---|
| CHClCH₂Cl | H | H | OCH₃ | CH₃ | |
| CHClCH₂Cl | H | CH₃ | OCH₃ | OCH₃ | |
| CHClCH₂Cl | 6-Cl | H | OCH₃ | CH₃ | |
| CHClCHCl₂ | H | H | OCH₃ | CH₃ | |
| CHClCHCl₂ | H | H | OCH₃ | OCH₃ | |
| CHClCHCl₂ | H | CH₃ | OCH₃ | CH₃ | |
| CH=CBr₂ | H | H | OCH₃ | CH₃ | |
| CH=CBr₂ | H | H | OCH₃ | OCH₃ | |
| CH=CBr₂ | H | CH₃ | OCH₃ | CH₃ | |
| CH=CF₂ | H | H | OCH₃ | CH₃ | |
| CH=CF₂ | 6-OCH₃ | H | OCH₃ | OCH₃ | |
| CH=CF₂ | H | H | OCH₃ | OCH₃ | |
| CH=CHOCH₃ | H | H | OCH₃ | CH₃ | |
| CH=CHOCH₃ | H | H | OCH₃ | OCH₃ | |
| CH=CHOCH₃ | H | CH₃ | OCH₃ | CH₃ | |
| CH=CHOCH₂CH₃ | H | H | OCH₃ | CH₃ | |
| CH=CHOCH₂CH₃ | H | H | OCH₃ | OCH₃ | |

TABLE XXV-continued

Structure: benzene ring with R1, R2 substituents, SO2NHC(O)N(R3)- linked to pyrimidine with X, Y substituents

| R1 | R2 | R3 | X | Y | m.p. (°C.) |
|---|---|---|---|---|---|
| CH=CHCO2CH3 | H | H | OCH3 | CH3 | |
| CH=CHCO2CH3 | H | H | OCH3 | OCH3 | |
| CH=CHCO2CH3 | H | CH3 | OCH3 | CH3 | |

TABLE XXVI

| R1 | R2 | R3 | X | Y | m.p. (°C.) |
|---|---|---|---|---|---|
| CHClCH2Cl | H | H | OCH3 | CH3 | |
| CHClCH2Cl | H | CH3 | OCH3 | OCH3 | |
| CHClCH2Cl | 6-Cl | H | OCH3 | CH3 | |
| CHClCHCl2 | H | H | OCH3 | CH3 | |
| CHClCHCl2 | H | H | OCH3 | OCH3 | |
| CHClCHCl2 | H | CH3 | OCH3 | CH3 | |
| CH=CBr2 | H | H | OCH3 | CH3 | |
| CH=CBr2 | H | H | OCH3 | OCH3 | |
| CH=CBr2 | H | CH3 | OCH3 | CH3 | |
| CH=CF2 | H | H | OCH3 | CH3 | |
| CH=CF2 | 6-OCH3 | H | OCH3 | CH3 | |
| CH=CF2 | H | H | OCH3 | OCH3 | |
| CH=CHOCH3 | H | H | OCH3 | CH3 | |
| CH=CHOCH3 | H | H | OCH3 | OCH3 | |
| CH=CHOCH3 | H | CH3 | OCH3 | CH3 | |
| CH=CHOCH2CH3 | H | H | OCH3 | CH3 | |
| CH=CHOCH2CH3 | H | H | OCH3 | OCH3 | |
| CH=CHCO2CH3 | H | H | OCH3 | CH3 | |
| CH=CHCO2CH3 | H | H | OCH3 | OCH3 | |
| CH=CHCO2CH3 | H | CH3 | OCH3 | CH3 | |

TABLE XXVII

| R1 | R2 | R3 | X1 | Y1 | m.p. (°C.) |
|---|---|---|---|---|---|
| CH2CH2F | H | H | CH2 | H | |
| CH2CH2F | H | H | CH2 | CH3 | |
| CH2CH2F | H | H | CH2 | OCH3 | |
| CH2CH2F | H | H | CH2 | Cl | |
| CH2CH2Br | H | H | O | H | |
| CH2CH2Br | H | H | O | CH3 | |
| CH2CH2Cl | H | H | O | OCH3 | |
| CH2CH2Cl | H | H | O | Cl | |
| CH2CH2Cl | H | CH3 | O | OCH3 | |
| CH2CH2Cl | 6-Cl | H | O | CH3 | |
| CH2CH2Cl | 3-OCH3 | CH3 | O | CH3 | |

TABLE XXVII-continued

| R1 | R2 | R3 | X1 | Y1 | m.p. (°C.) |
|---|---|---|---|---|---|
| CH2CH2OC(O)CH3 | H | H | CH2 | Cl | |
| CH2CH2OC(O)CF3 | H | H | O | OCH3 | |
| CH2CH2OH | H | H | O | Cl | |
| CH2CH2OH | H | H | O | OCH3 | |
| CH2CH2OH | H | CH3 | CH2 | OCH3 | |
| CH2CH2OH | 6-OCH3 | H | O | Cl | |
| CH2CH2OCH2C6H5 | H | H | O | Cl | |
| CH2CH2OSO2CH3 | H | CH3 | CH2 | OCH3 | |
| CH2CH2OSO2—4-C6H4CH3 | H | H | O | OCH3 | |
| CH2CH2SCH3 | H | H | O | H | |
| CH2CH2S(O)2CH3 | H | H | O | OCH3 | |
| CH2CH2OSO2N(CH3)2 | H | H | CH2 | Cl | |
| CH2CH2CO2CH3 | H | H | O | OCH3 | |
| CH2CH2OCH3 | H | H | O | OCH3 | |
| CH2CH2OCH3 | H | H | O | Cl | |
| CH2CH2OCH3 | H | CH3 | O | OCH3 | |
| CH2CH2OCH3 | 6-Cl | H | O | CH3 | |
| CH2CH2OCH3 | 3-OCH3 | CH3 | O | Cl | |
| CH2CH2OCH2CH3 | H | H | O | OCH3 | |
| CH(OCH3)CH2(OCH3) | H | H | CH2 | OCH3 | |
| CH(OCH3)CH2(OCH3) | H | H | O | Cl | |
| CH(OCH3)CH2(OCH3) | H | CH3 | O | OCH3 | |
| CH(OCH3)CH2(OCH3) | 6-OCH3 | H | O | CH3 | |
| CH(OCH2CH3)CH2(OCH2CH3) | H | H | CH2 | Cl | |
| CH(OCH2CH3)CH2(OCH2CH3) | H | H | O | OCH3 | |
| CH2CH(OCH3)2 | H | H | O | CH3 | |
| CH2CH(OCH3)2 | H | H | O | Cl | |
| CH2CH(OCH3)2 | H | CH3 | O | OCH3 | |
| CH2CH(OCH3)2 | 6-CF3 | H | CH2 | H | |
| CH2CH(OCH2CH3)2 | H | H | O | Cl | |
| CH(OCH3)CH(OCH3)2 | H | H | O | OCH3 | |
| CH(OCH3)CH(OCH3)2 | H | CH3 | CH2 | Cl | |
| CH(OCH3)CH(OCH2CH3)2 | H | H | O | OCH3 | |
| CH(Cl)CH(OCH3)2 | H | H | O | OCH3 | |
| CH(Cl)CH(OCH3)2 | H | H | O | Cl | |
| CH(Cl)CH(OCH2CH3)2 | H | H | CH2 | OCH3 | |
| CH2—(1,3-dioxolan-2-yl) | H | H | O | OCH3 | |
| CH2—(1,3-dioxolan-2-yl) | H | H | CH2 | Cl | |
| CH(Cl)—(1,3-dioxolan-2-yl) | H | H | O | Cl | |
| CH(OCH3)—(1,3-dioxolan-2-yl) | H | H | O | OCH3 | |
| CH(Cl)—(1,3-dioxolan-2-yl) | H | H | O | CH3 | |

TABLE XXVII-continued

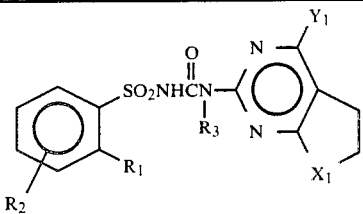

| R₁ | R₂ | R₃ | X₁ | Y₁ | m.p. (°C.) |
|---|---|---|---|---|---|
| CH₂-CH(O-CH(CH₃)-O) | H | H | CH₂ | OCH₃ | |
| CH(Cl)-CH(O-CH(CH₃)-O) | H | H | O | OCH₃ | |
| CH(OCH₃)-CH(O-CH(CH₃)-O) | H | H | O | CH₃ | |
| CH₂-CH(O-CH₂CH₂-O) (1,3-dioxane) | H | H | O | OCH₃ | |

TABLE XXVII-continued

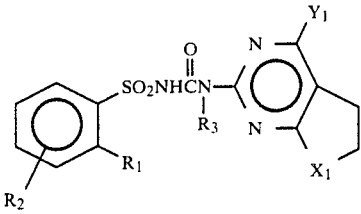

| R₁ | R₂ | R₃ | X₁ | Y₁ | m.p. (°C.) |
|---|---|---|---|---|---|
| CH(Cl)-CH(O-CH₂CH₂-O) (1,3-dioxane) | H | H | O | Cl | |
| CH(OCH₃)-CH(O-CH₂CH₂-O) (1,3-dioxane) | H | H | O | CH₃ | |
| CHClCH₂Cl | H | H | O | OCH₃ | |
| CHClCH₂Cl | H | H | O | Cl | |
| CHClCHCl₂ | H | H | CH₂ | Cl | |
| CHClCHCl₂ | H | H | O | OCH₃ | |
| CH=CBr₂ | H | H | CH₂ | OCH₃ | |
| CH=CF₂ | H | H | O | CH₃ | |
| CH=CH(OCH₃) | H | H | O | OCH₃ | |
| CH=CH(OCH₃) | H | H | O | Cl | |
| CH=CH(OCH₂CH₃) | H | H | CH₂ | OCH₃ | |
| CH=CHCO₂CH₃ | H | H | O | OCH₃ | |

TABLE XXVIII

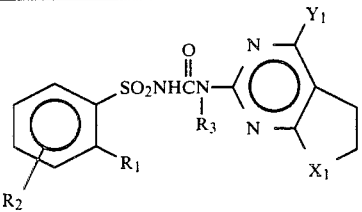

| R₁ | R₂ | R₃ | X₁ | Y₁ | m.p. (°C.) |
|---|---|---|---|---|---|
| CH₂CH₂CH₂F | H | H | CH₂ | H | |
| CH₂CH₂CH₂F | H | H | CH₂ | CH₃ | |
| CH₂CH₂CH₂F | H | H | CH₂ | OCH₃ | |
| CH₂CH₂CH₂F | H | H | CH₂ | Cl | |
| CH₂CH₂CH₂Br | H | H | O | H | |
| CH₂CH₂CH₂Br | H | H | O | CH₃ | |
| CH₂CH₂CH₂Cl | H | H | O | OCH₃ | |
| CH₂CH₂CH₂Cl | H | H | O | Cl | |
| CH₂CH₂CH₂Cl | H | CH₃ | O | OCH₃ | |
| CH₂CH₂CH₂Cl | 6-Cl | H | O | CH₃ | |
| CH₂CH₂CH₂Cl | 3-OCH₃ | CH₃ | O | CH₃ | |
| CH₂CH₂CH₂OC(O)CH₃ | H | H | CH₂ | Cl | |
| CH₂CH₂CH₂OC(O)CF₃ | H | H | O | OCH₃ | |
| CH₂CH₂CH₂OH | H | H | O | Cl | |
| CH₂CH₂CH₂OH | H | H | O | OCH₃ | |
| CH₂CH₂CH₂OH | H | CH₃ | CH₂ | OCH₃ | |
| CH₂CH₂CH₂OH | 6-OCH₃ | H | O | OCH₃ | |
| CH₂CH₂CH₂OCH₂C₆H₅ | H | H | O | Cl | |
| CH₂CH₂CH₂OSO₂CH₃ | H | CH₃ | CH₂ | OCH₃ | |
| CH₂CH₂CH₂OSO₂—4-C₆H₄CH₃ | H | H | O | OCH₃ | |
| CH₂CH₂CH₂SCH₃ | H | H | O | H | |
| CH₂CH₂CH₂S(O)₂CH₃ | H | H | O | OCH₃ | |
| CH₂CH₂CH₂OSO₂N(CH₃)₂ | H | H | CH₂ | Cl | |
| CH₂CH₂CH₂CO₂CH₃ | H | H | O | OCH₃ | |
| CH₂CH₂CH₂OCH₃ | H | H | O | OCH₃ | |
| CH₂CH₂CH₂OCH₃ | H | H | O | Cl | |
| CH₂CH₂CH₂OCH₃ | H | CH₃ | O | OCH₃ | |
| CH₂CH₂CH₂OCH₃ | 6-Cl | H | O | CH₃ | |
| CH₂CH₂CH₂OCH₃ | 3-OCH₃ | CH₃ | O | Cl | |

TABLE XXVIII-continued

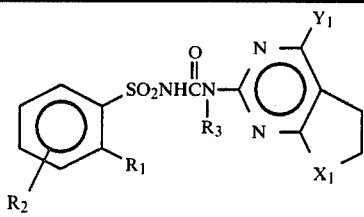

| R₁ | R₂ | R₃ | X₁ | Y₁ | m.p. (°C.) |
|---|---|---|---|---|---|
| CH₂CH₂CH₂OCH₂CH₃ | H | H | O | OCH₃ | |
| CH₂CH(OCH₃)CH₂(OCH₃) | H | H | CH₂ | OCH₃ | |
| CH₂CH(OCH₃)CH₂(OCH₃) | H | H | O | Cl | |
| CH₂CH(OCH₃)CH₂(OCH₃) | H | CH₃ | O | OCH₃ | |
| CH₂CH(OCH₃)CH₂(OCH₃) | 6-OCH₃ | H | O | CH₃ | |
| CH₂CH(OCH₂CH₃)CH₂(OCH₂CH₃) | H | H | CH₂ | Cl | |
| CH₂CH(OCH₂CH₃)CH₂(OCH₂CH₃) | H | H | O | OCH₃ | |
| CH₂CH₂CH(OCH₃)₂ | H | H | O | CH₃ | |
| CH₂CH₂CH(OCH₃)₂ | H | H | O | Cl | |
| CH₂CH₂CH(OCH₃)₂ | H | CH₃ | O | OCH₃ | |
| CH₂CH₂CH(OCH₃)₂ | 6-CF₃ | H | CH₂ | H | |
| CH₂CH₂CH(OCH₂CH₃)₂ | H | H | O | Cl | |
| CH₂CH₂-[1,3-dioxolan-2-yl] | H | H | O | OCH₃ | |
| CH₂CH₂-[1,3-dioxolan-2-yl] | H | H | CH₂ | Cl | |
| CH₂CH₂-[4-methyl-1,3-dioxolan-2-yl] | H | H | CH₂ | OCH₃ | |
| CH₂CH₂-[1,3-dioxan-2-yl] | H | H | O | OCH₃ | |

TABLE XXIX

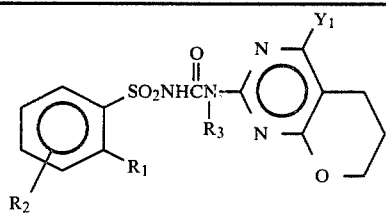

TABLE XXIX-continued

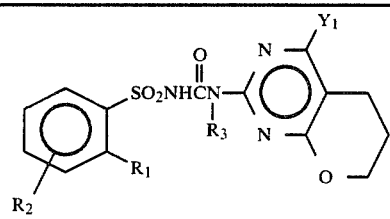

| R₁ | R₂ | R₃ | Y₁ | m.p. (°C.) | R₁ | R₂ | R₃ | Y₁ | m.p. (°C.) |
|---|---|---|---|---|---|---|---|---|---|
| CH₂CH₂F | H | H | H | | CH₂CH₂OH | H | CH₃ | OCH₃ | |
| CH₂CH₂F | H | H | CH₃ | | CH₂CH₂OH | 6-OCH₃ | H | OCH₃ | |
| CH₂CH₂F | H | H | OCH₃ | | CH₂CH₂OCH₂C₆H₅ | H | H | Cl | |
| CH₂CH₂F | H | H | Cl | | CH₂CH₂OSO₂CH₃ | H | CH₃ | OCH₃ | |
| CH₂CH₂Br | H | H | H | | CH₂CH₂OSO₂—4-C₆H₄CH₃ | H | H | OCH₃ | |
| CH₂CH₂Br | H | H | CH₃ | | CH₂CH₂SCH₃ | H | H | H | |
| CH₂CH₂Cl | H | H | OCH₃ | | CH₂CH₂S(O)₂CH₃ | H | H | OCH₃ | |
| CH₂CH₂Cl | H | H | Cl | | CH₂CH₂OSO₂N(CH₃)₂ | H | H | Cl | |
| CH₂CH₂Cl | H | CH₃ | OCH₃ | | CH₂CH₂CO₂CH₃ | H | H | OCH₃ | |
| CH₂CH₂Cl | 6-Cl | H | CH₃ | | CH₂CH₂OCH₃ | H | H | OCH₃ | |
| CH₂CH₂Cl | 3-OCH₃ | CH₃ | CH₃ | | CH₂CH₂OCH₃ | H | H | Cl | |
| CH₂CH₂OC(O)CH₃ | H | H | Cl | | CH₂CH₂OCH₃ | H | CH₃ | OCH₃ | |
| CH₂CH₂OC(O)CF₃ | H | H | OCH₃ | | CH₂CH₂OCH₃ | 6-Cl | H | CH₃ | |
| CH₂CH₂OH | H | H | Cl | | CH₂CH₂OCH₃ | 3-OCH₃ | CH₃ | Cl | |
| CH₂CH₂OH | H | H | OCH₃ | | CH₂CH₂OCH₂CH₃ | H | H | OCH₃ | |

TABLE XXIX-continued

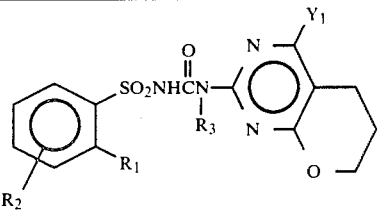

| $R_1$ | $R_2$ | $R_3$ | $Y_1$ | m.p. (°C.) |
|---|---|---|---|---|
| CH(OCH$_3$)CH$_2$(OCH$_3$) | H | H | OCH$_3$ | |
| CH(OCH$_3$)CH$_2$(OCH$_3$) | H | H | Cl | |
| CH(OCH$_3$)CH$_2$(OCH$_3$) | H | CH$_3$ | OCH$_3$ | |
| CH(OCH$_3$)CH$_2$(OCH$_3$) | 6-OCH$_3$ | H | CH$_3$ | |
| CH(OCH$_2$CH$_3$)CH$_2$(OCH$_2$CH$_3$) | H | H | Cl | |
| CH(OCH$_2$CH$_3$)CH$_2$(OCH$_2$CH$_3$) | H | H | OCH$_3$ | |
| CH$_2$CH(OCH$_3$)$_2$ | H | H | CH$_3$ | |
| CH$_2$CH(OCH$_3$)$_2$ | H | H | Cl | |
| CH$_2$CH(OCH$_3$)$_2$ | H | CH$_3$ | OCH$_3$ | |
| CH$_2$CH(OCH$_3$)$_2$ | 6-CF$_3$ | H | H | |
| CH$_2$CH(OCH$_2$CH$_3$)$_2$ | H | H | Cl | |
| CH(OCH$_3$)CH(OCH$_3$)$_2$ | H | H | OCH$_3$ | |
| CH(OCH$_3$)CH(OCH$_3$)$_2$ | H | CH$_3$ | Cl | |
| CH(OCH$_3$)CH(OCH$_2$CH$_3$)$_2$ | H | H | OCH$_3$ | |
| CH(Cl)CH(OCH$_3$)$_2$ | H | H | OCH$_3$ | |
| CH(Cl)CH(OCH$_3$)$_2$ | H | H | Cl | |
| CH(Cl)CH(OCH$_2$CH$_3$)$_2$ | H | H | OCH$_3$ | |
| CH$_2$-(1,3-dioxolan-2-yl) | H | H | OCH$_3$ | |
| CH$_2$-(1,3-dioxolan-2-yl) | H | H | Cl | |
| CH(Cl)-(1,3-dioxolan-2-yl) | H | H | Cl | |
| CH(OCH$_3$)-(1,3-dioxolan-2-yl) | H | H | OCH$_3$ | |
| CH$_2$-(4-methyl-1,3-dioxolan-2-yl) | H | H | OCH$_3$ | |
| CH(Cl)-(4-methyl-1,3-dioxolan-2-yl) | H | H | CH$_3$ | |
| CH(Cl)-(4-methyl-1,3-dioxolan-2-yl) | H | H | Cl | |
| CH(OCH$_3$)-(4-methyl-1,3-dioxolan-2-yl) | H | H | OCH$_3$ | |
| CH$_2$-(1,3-dioxan-2-yl) | H | H | OCH$_3$ | |
| CH(Cl)-(1,3-dioxan-2-yl) | H | H | Cl | |
| CH(OCH$_3$)-(1,3-dioxan-2-yl) | H | H | CH$_3$ | |
| CHClCH$_2$Cl | H | H | OCH$_3$ | |
| CHClCH$_2$Cl | H | H | Cl | |
| CHClCHCl$_2$ | H | H | Cl | |
| CHClCHCl$_2$ | H | H | OCH$_3$ | |
| CH=CBr$_2$ | H | H | OCH$_3$ | |
| CH=CF$_2$ | H | H | CH$_3$ | |
| CH=CH(OCH$_3$) | H | H | OCH$_3$ | |
| CH=CH(OCH$_3$) | H | H | Cl | |
| CH=CH(OCH$_2$CH$_3$) | H | H | OCH$_3$ | |
| CH=CHCO$_2$CH$_3$ | H | H | OCH$_3$ | |

TABLE XXX

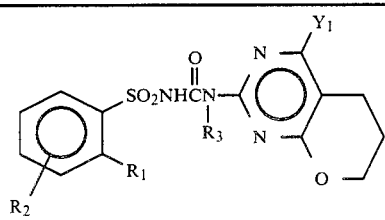

| $R_1$ | $R_2$ | $R_3$ | $Y_1$ | m.p. (°C.) |
|---|---|---|---|---|
| CH$_2$CH$_2$CH$_2$F | H | H | H | |
| CH$_2$CH$_2$CH$_2$F | H | H | CH$_3$ | |
| CH$_2$CH$_2$CH$_2$F | H | H | OCH$_3$ | |
| CH$_2$CH$_2$CH$_2$F | H | H | Cl | |
| CH$_2$CH$_2$CH$_2$Br | H | H | H | |
| CH$_2$CH$_2$CH$_2$Br | H | H | CH$_3$ | |

TABLE XXX-continued

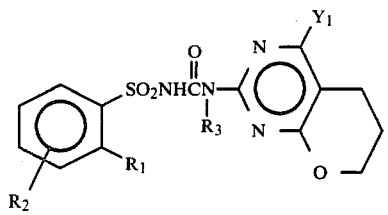

| R₁ | R₂ | R₃ | Y₁ | m.p. (°C.) |
|---|---|---|---|---|
| CH₂CH₂CH₂Cl | H | H | OCH₃ | |
| CH₂CH₂CH₂Cl | H | H | Cl | |
| CH₂CH₂CH₂Cl | H | CH₃ | OCH₃ | |
| CH₂CH₂CH₂Cl | 6-Cl | H | CH₃ | |
| CH₂CH₂CH₂Cl | 3-OCH₃ | CH₃ | CH₃ | |
| CH₂CH₂CH₂OC(O)CH₃ | H | H | Cl | |
| CH₂CH₂CH₂OC(O)CF₃ | H | H | OCH₃ | |
| CH₂CH₂CH₂OH | H | H | Cl | |
| CH₂CH₂CH₂OH | H | H | OCH₃ | |
| CH₂CH₂CH₂OH | H | CH₃ | OCH₃ | |
| CH₂CH₂CH₂OH | 6-OCH₃ | H | OCH₃ | |
| CH₂CH₂CH₂OCH₂C₆H₅ | H | H | Cl | |
| CH₂CH₂CH₂OSO₂CH₃ | H | CH₃ | OCH₃ | |
| CH₂CH₂CH₂OSO₂—4-C₆H₄CH₃ | H | H | OCH₃ | |
| CH₂CH₂CH₂SCH₃ | H | H | H | |
| CH₂CH₂CH₂S(O)₂CH₃ | H | H | OCH₃ | |
| CH₂CH₂CH₂OSO₂N(CH₃)₂ | H | H | Cl | |
| CH₂CH₂CH₂CO₂CH₃ | H | H | OCH₃ | |
| CH₂CH₂CH₂OCH₃ | H | H | OCH₃ | |
| CH₂CH₂CH₂OCH₃ | H | H | Cl | |
| CH₂CH₂CH₂OCH₃ | H | CH₃ | OCH₃ | |
| CH₂CH₂CH₂OCH₃ | 6-Cl | H | CH₃ | |
| CH₂CH₂CH₂OCH₃ | 3-OCH₃ | CH₃ | Cl | |
| CH₂CH₂CH₂OCH₂CH₃ | H | H | OCH₃ | |
| CH₂CH(OCH₃)CH₂(OCH₃) | H | H | OCH₃ | |
| CH₂CH(OCH₃)CH₂(OCH₃) | H | H | Cl | |
| CH₂CH(OCH₃)CH₂(OCH₃) | H | CH₃ | OCH₃ | |
| CH₂CH(OCH₃)CH₂(OCH₃) | 6-OCH₃ | H | CH₃ | |
| CH₂CH(OCH₂CH₃)CH₂(OCH₂CH₃) | H | H | Cl | |
| CH₂CH(OCH₂CH₃)CH₂(OCH₂CH₃) | H | H | OCH₃ | |
| CH₂CH₂CH(OCH₃)₂ | H | H | CH₃ | |
| CH₂CH₂CH(OCH₃)₂ | H | H | Cl | |
| CH₂CH₂CH(OCH₃)₂ | H | CH₃ | OCH₃ | |
| CH₂CH₂CH(OCH₃)₂ | 6-CF₃ | H | H | |
| CH₂CH₂CH(OCH₂CH₃)₂ | H | H | Cl | |
|  | H | H | OCH₃ | |
|  | H | H | Cl | |
| 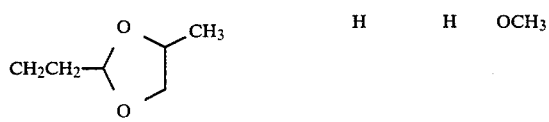 | H | H | OCH₃ | |
|  | H | H | OCH₃ | |

TABLE XXXI

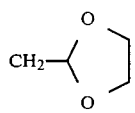

| R₁ | R₂ | R₃ | X₂ | Y₂ | m.p. (°C.) |
|---|---|---|---|---|---|
| CH₂CH₂F | H | H | CH₃ | CH₃ | |
| CH₂CH₂F | H | H | CH₃ | CH₂CH₃ | |
| CH₂CH₂F | H | H | CH₃ | CH₂CF₃ | |
| CH₂CH₂F | H | H | OCH₃ | CH₃ | |
| CH₂CH₂Br | H | H | OCH₃ | CH₂CH₃ | |
| CH₂CH₂Br | H | H | OCH₃ | CH₂CF₃ | |
| CH₂CH₂Cl | H | H | OCH₃ | CH₃ | |
| CH₂CH₂Cl | H | H | OCH₃ | CH₂CH₃ | |
| CH₂CH₂Cl | H | CH₃ | SCH₃ | CH₃ | |
| CH₂CH₂Cl | 6-Cl | H | SCH₃ | CH₂CH₃ | |
| CH₂CH₂Cl | 3-OCH₃ | CH₃ | SCH₃ | CH₂CF₃ | |
| CH₂CH₂OC(O)CH₃ | H | H | OCH₃ | CH₃ | |
| CH₂CH₂OC(O)CF₃ | H | H | SCH₃ | CH₃ | |
| CH₂CH₂OH | H | H | OCH₃ | CH₂CH₃ | |
| CH₂CH₂OH | H | H | OCH₃ | CH₂CF₃ | |
| CH₂CH₂OH | H | CH₃ | OCH₃ | CH₃ | |
| CH₂CH₂OH | 6-OCH₃ | H | CH₃ | CH₃ | |
| CH₂CH₂OCH₂C₆H₅ | H | H | CH₃ | CH₂CH₃ | |
| CH₂CH₂OSO₂CH₃ | H | CH₃ | CH₃ | CH₂CF₃ | |
| CH₂CH₂OSO₂—4-C₆H₄CH₃ | H | H | OCH₃ | CH₃ | |
| CH₂CH₂SCH₃ | H | H | SCH₃ | CH₃ | |
| CH₂CH₂S(O)₂CH₃ | H | H | CH₃ | CH₃ | |
| CH₂CH₂OSO₂N(CH₃)₂ | H | H | OCH₃ | CH₃ | |
| CH₂CH₂CO₂CH₃ | H | H | CH₃ | CH₃ | |
| CH₂CH₂OCH₃ | H | H | CH₃ | CH₃ | |
| CH₂CH₂OCH₃ | H | H | OCH₃ | CH₃ | |
| CH₂CH₂OCH₃ | H | CH₃ | SCH₃ | CH₃ | |
| CH₂CH₂OCH₃ | 6-Cl | H | CH₃ | CH₃ | |
| CH₂CH₂OCH₃ | 3-OCH₃ | CH₃ | OCH₃ | CH₃ | |
| CH₂CH₂OCH₂CH₃ | H | H | SCH₃ | CH₃ | |
| CH(OCH₃)CH₂(OCH₃) | H | H | CH₃ | CH₃ | |
| CH(OCH₃)CH₂(OCH₃) | H | H | OCH₃ | CH₃ | |
| CH(OCH₃)CH₂(OCH₃) | H | CH₃ | CH₃ | CH₂CF₃ | |
| CH(OCH₃)CH₂(OCH₃) | 6-OCH₃ | H | OCH₃ | CH₃ | |
| CH(OCH₂CH₃)CH₂(OCH₂CH₃) | H | H | SCH₃ | CH₂CH₃ | |
| CH(OCH₂CH₃)CH₂(OCH₂CH₃) | H | H | OCH₃ | CH₃ | |
| CH₂CH(OCH₃)₂ | H | H | CH₃ | CH₃ | |
| CH₂CH(OCH₃)₂ | H | H | OCH₃ | CH₃ | |
| CH₂CH(OCH₃)₂ | H | CH₃ | SCH₃ | CH₃ | |
| CH₂CH(OCH₃)₂ | 6-CF₃ | H | CH₃ | CH₃ | |
| CH₂CH(OCH₂CH₃)₂ | H | H | OCH₃ | CH₃ | |
| CH(OCH₃)CH(OCH₃)₂ | H | H | CH₃ | CH₃ | |
| CH(OCH₃)CH(OCH₃)₂ | H | CH₃ | OCH₃ | CH₃ | |
| CH(OCH₃)CH(OCH₂CH₃)₂ | H | H | SCH₃ | CH₃ | |
| CH(Cl)CH(OCH₃)₂ | H | H | CH₃ | CH₃ | |
| CH(Cl)CH(OCH₃)₂ | H | H | OCH₃ | CH₃ | |
| CH(Cl)CH(OCH₂CH₃)₂ | H | H | SCH₃ | CH₃ | |
| 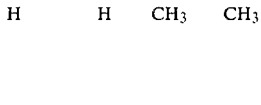 | H | H | CH₃ | CH₃ | |
| 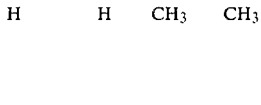 | H | H | OCH₃ | CH₃ | |
| 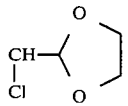 | H | H* | SCH₃ | CH₃ | |

TABLE XXXI-continued

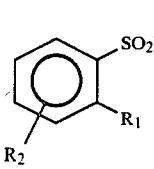

| R₁ | R₂ | R₃ | X₂ | Y₂ | m.p. (°C.) |
|---|---|---|---|---|---|
| 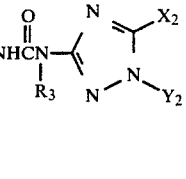 | H | H | CH₃ | CH₃ | |
|  | H | H | CH₃ | CH₃ | |
|  | H | H | OCH₃ | CH₃ | |
|  | H | H | CH₃ | CH₃ | |
|  | H | H | CH₃ | CH₃ | |
|  | H | H | CH₃ | CH₂CH₃ | |
|  | H | H | OCH₃ | CH₃ | |
| CHClCH₂Cl | H | H | SCH₃ | CH₃ | |
| CHClCH₂Cl | H | H | CH₃ | CH₃ | |
| CHClCHCl₂ | H | H | OCH₃ | CH₃ | |
| CHClCHCl₂ | H | H | OCH₃ | CH₂CH₃ | |
| CH=CBr₂ | H | H | SCH₃ | CH₂CH₃ | |
| CH=CF₂ | H | H | CH₃ | CH₃ | |
| CH=CH(OCH₃) | H | H | OCH₃ | CH₃ | |
| CH=CH(OCH₃) | H | H | OCH₃ | CH₃ | |
| CH=CH(OCH₂CH₃) | H | H | CH₃ | CH₃ | |
| CH=CHCO₂CH₃ | H | H | SCH₃ | CH₃ | |

TABLE XXXII

| R₁ | R₂ | R₃ | X₂ | Y₂ | m.p. (°C.) |
|---|---|---|---|---|---|
| CH₂CH₂CH₂F | H | H | CH₃ | CH₃ | |
| CH₂CH₂CH₂F | H | H | CH₃ | CH₂CH₃ | |

TABLE XXXII-continued $$\text{structure: } R_2\text{-phenyl(R}_1\text{)-SO}_2\text{NHC(O)N(R}_3\text{)-C(=N-N(Y}_2\text{)-)N=C(X}_2\text{)}$$

| $R_1$ | $R_2$ | $R_3$ | $X_2$ | $Y_2$ | m.p. (°C.) |
|---|---|---|---|---|---|
| CH₂CH₂CH₂F | H | H | CH₃ | CH₂CF₃ | |
| CH₂CH₂CH₂F | H | H | OCH₃ | CH₃ | |
| CH₂CH₂CH₂Br | H | H | OCH₃ | CH₂CH₃ | |
| CH₂CH₂CH₂Br | H | H | OCH₃ | CH₂CF₃ | |
| CH₂CH₂CH₂Cl | H | H | OCH₃ | CH₃ | |
| CH₂CH₂CH₂Cl | H | H | OCH₃ | CH₂CH₃ | |
| CH₂CH₂CH₂Cl | H | CH₃ | SCH₃ | CH₃ | |
| CH₂CH₂CH₂Cl | 6-Cl | H | SCH₃ | CH₂CH₃ | |
| CH₂CH₂CH₂Cl | 3-OCH₃ | CH₃ | SCH₃ | CH₂CF₃ | |
| CH₂CH₂CH₂OC(O)CH₃ | H | H | OCH₃ | CH₃ | |
| CH₂CH₂CH₂OC(O)CF₃ | H | H | SCH₃ | CH₃ | |
| CH₂CH₂CH₂OH | H | H | OCH₃ | CH₂CH₃ | |
| CH₂CH₂CH₂OH | H | H | OCH₃ | CH₂CF₃ | |
| CH₂CH₂CH₂OH | H | CH₃ | OCH₃ | CH₃ | |
| CH₂CH₂CH₂OH | 6-OCH₃ | H | CH₃ | CH₃ | |
| CH₂CH₂CH₂OCH₂C₆H₅ | H | H | CH₃ | CH₂CH₃ | |
| CH₂CH₂CH₂OSO₂CH₃ | H | CH₃ | CH₃ | CH₂CF₃ | |
| CH₂CH₂CH₂OSO₂—4-C₆H₄CH₃ | H | H | OCH₃ | CH₃ | |
| CH₂CH₂CH₂SCH₃ | H | H | SCH₃ | CH₃ | |
| CH₂CH₂CH₂S(O)₂CH₃ | H | H | CH₃ | CH₃ | |
| CH₂CH₂CH₂OSO₂N(CH₃)₂ | H | H | OCH₃ | CH₃ | |
| CH₂CH₂CH₂CO₂CH₃ | H | H | CH₃ | CH₃ | |
| CH₂CH₂CH₂OCH₃ | H | H | CH₃ | CH₃ | |
| CH₂CH₂CH₂OCH₃ | H | H | OCH₃ | CH₃ | |
| CH₂CH₂CH₂OCH₃ | H | CH₃ | SCH₃ | CH₃ | |
| CH₂CH₂CH₂OCH₃ | 6-Cl | H | CH₃ | CH₃ | |
| CH₂CH₂CH₂OCH₃ | 3-OCH₃ | CH₃ | OCH₃ | CH₃ | |
| CH₂CH₂CH₂OCH₂CH₃ | H | H | SCH₃ | CH₃ | |
| CH₂CH(OCH₃)CH₂(OCH₃) | H | H | CH₃ | CH₃ | |
| CH₂CH(OCH₃)CH₂(OCH₃) | H | H | OCH₃ | CH₃ | |
| CH₂CH(OCH₃)CH₂(OCH₃) | H | CH₃ | CH₃ | CH₂CF₃ | |
| CH₂CH(OCH₃)CH₂(OCH₃) | 6-OCH₃ | H | OCH₃ | CH₃ | |
| CH₂CH(OCH₂CH₃)CH₂(OCH₂CH₃) | H | H | SCH₃ | CH₂CH₃ | |
| CH₂CH(OCH₂CH₃)CH₂(OCH₂CH₃) | H | H | OCH₃ | CH₃ | |
| CH₂CH₂CH(OCH₃)₂ | H | H | CH₃ | CH₃ | |
| CH₂CH₂CH(OCH₃)₂ | H | H | OCH₃ | CH₃ | |
| CH₂CH₂CH(OCH₃)₂ | H | CH₃ | SCH₃ | CH₃ | |
| CH₂CH₂CH(OCH₃)₂ | 6-CF₃ | H | CH₃ | CH₃ | |
| CH₂CH₂CH(OCH₂CH₃)₂ | H | H | OCH₃ | CH₃ | |
| CH₂CH₂-(1,3-dioxolan-2-yl) | H | H | CH₃ | CH₃ | |
| CH₂CH₂-(1,3-dioxolan-2-yl) | H | H | OCH₃ | CH₃ | |
| CH₂CH₂-(4-methyl-1,3-dioxolan-2-yl) | H | H | CH₃ | CH₃ | |
| CH₂CH₂-(1,3-dioxan-2-yl) | H | H | CH₃ | CH₃ | |
| CHClCH₂Cl | H | H | SCH₃ | CH₃ | |
| CHClCH₂Cl | H | H | CH₃ | CH₃ | |
| CHClCHCl₂ | H | H | OCH₃ | CH₃ | |
| CHClCHCl₂ | H | H | OCH₃ | CH₂CH₃ | |

TABLE XXXIII

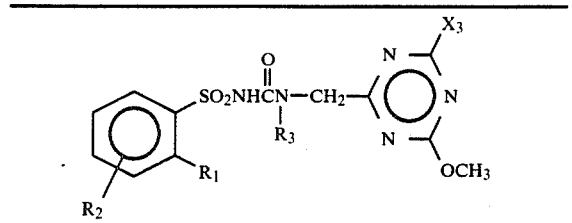

| R₁ | R₂ | R₃ | X₃ | m.p. (°C.) |
|---|---|---|---|---|
| CH₂CH₂F | H | H | CH₃ | |
| CH₂CH₂F | H | H | OCH₃ | |
| CH₂CH₂Br | H | H | CH₃ | |
| CH₂CH₂Cl | H | H | OCH₃ | |
| CH₂CH₂Cl | H | CH₃ | OCH₃ | |
| CH₂CH₂Cl | 6-Cl | H | CH₃ | |
| CH₂CH₂Cl | 3-OCH₃ | CH₃ | CH₃ | |
| CH₂CH₂OC(O)CH₃ | H | H | CH₃ | |
| CH₂CH₂OC(O)CF₃ | H | H | OCH₃ | |
| CH₂CH₂OH | H | H | CH₃ | |
| CH₂CH₂OH | H | H | OCH₃ | |
| CH₂CH₂OH | H | CH₃ | OCH₃ | |
| CH₂CH₂OH | 6-OCH₃ | H | OCH₃ | |
| CH₂CH₂OCH₂C₆H₅ | H | H | CH₃ | |
| CH₂CH₂OSO₂CH₃ | H | CH₃ | OCH₃ | |
| CH₂CH₂OSO₂—4-C₆H₄CH₃ | H | H | OCH₃ | |
| CH₂CH₂SCH₃ | H | H | CH₃ | |
| CH₂CH₂S(O)₂CH₃ | H | H | OCH₃ | |
| CH₂CH₂OSO₂N(CH₃)₂ | H | H | OCH₃ | |
| CH₂CH₂CO₂CH₃ | H | H | OCH₃ | |
| CH₂CH₂OCH₃ | H | H | OCH₃ | |
| CH₂CH₂OCH₃ | H | H | CH₃ | |
| CH₂CH₂OCH₃ | H | CH₃ | OCH₃ | |
| CH₂CH₂OCH₃ | 6-Cl | H | CH₃ | |
| CH₂CH₂OCH₃ | 3-OCH₃ | CH₃ | CH₃ | |
| CH₂CH₂OCH₂CH₃ | H | H | OCH₃ | |
| CH(OCH₃)CH₂(OCH₃) | H | H | OCH₃ | |
| CH(OCH₃)CH₂(OCH₃) | H | H | CH₃ | |
| CH(OCH₃)CH₂(OCH₃) | H | CH₃ | OCH₃ | |
| CH(OCH₃)CH₂(OCH₃) | 6-OCH₃ | H | CH₃ | |
| CH(OCH₂CH₃)CH₂(OCH₂CH₃) | H | H | CH₃ | |
| CH(OCH₂CH₃)CH₂(OCH₂CH₃) | H | H | OCH₃ | |
| CH₂CH(OCH₃)₂ | H | H | CH₃ | |
| CH₂CH(OCH₃)₂ | H | H | CH₃ | |
| CH₂CH(OCH₃)₂ | H | CH₃ | OCH₃ | |
| CH₂CH(OCH₃)₂ | 6-CF₃ | H | OCH₃ | |
| CH₂CH(OCH₂CH₃)₂ | H | H | CH₃ | |
| CH(OCH₃)CH(OCH₃)₂ | H | H | OCH₃ | |
| CH(OCH₃)CH(OCH₃)₂ | H | CH₃ | OCH₃ | |
| CH(OCH₃)CH(OCH₂CH₃)₂ | H | H | OCH₃ | |
| CH(Cl)CH(OCH₃)₂ | H | H | OCH₃ | |
| CH(Cl)CH(OCH₃)₂ | H | H | CH₃ | |
| CH(Cl)CH(OCH₂CH₃)₂ | H | H | OCH₃ | |

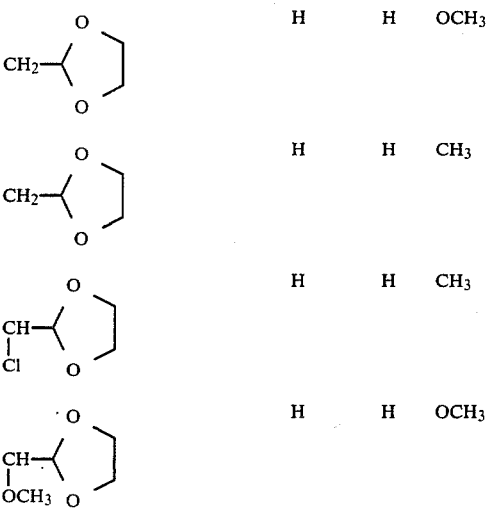

| R₁ | R₂ | R₃ | X₃ | m.p. (°C.) |
|---|---|---|---|---|
| (dioxolane-CH₂) | H | H | OCH₃ | |
| (dioxolane-CH₂) | H | H | CH₃ | |
| (dioxolane-CHCl) | H | H | CH₃ | |
| (dioxolane-CHOCH₃) | H | H | OCH₃ | |
| (methyldioxolane-CH₂) | H | H | OCH₃ | |
| (methyldioxolane-CHOCH₃) | H | H | CH₃ | |
| (methyldioxolane-CHCl) | H | H | OCH₃ | |
| (dioxane-CH₂) | H | H | OCH₃ | |
| (dioxane-CHCl) | H | H | CH₃ | |
| CHClCH₂Cl | H | H | OCH₃ | |
| CHClCH₂Cl | H | H | CH₃ | |
| CHClCHCl₂ | H | H | OCH₃ | |
| CHClCHCl₂ | H | H | CH₃ | |
| CH=CBr₂ | H | H | OCH₃ | |
| CH=CF₂ | H | H | CH₃ | |
| CH=CH(OCH₃) | H | H | OCH₃ | |
| CH=CH(OCH₃) | H | H | CH₃ | |
| CH=CH(OCH₂CH₃) | H | H | OCH₃ | |
| CH=CHCO₂CH₃ | H | H | OCH₃ | |

TABLE XXXIV

| R₁ | R₂ | R₃ | X₃ | m.p. (°C.) |
|---|---|---|---|---|
| CH₂CH₂CH₂F | H | H | CH₃ | |
| CH₂CH₂CH₂F | H | H | OCH₃ | |
| CH₂CH₂CH₂Br | H | H | CH₃ | |
| CH₂CH₂CH₂Cl | H | H | OCH₃ | |
| CH₂CH₂CH₂Cl | H | CH₃ | OCH₃ | |
| CH₂CH₂CH₂Cl | 6-Cl | H | CH₃ | |
| CH₂CH₂CH₂Cl | 3-OCH₃ | CH₃ | CH₃ | |
| CH₂CH₂CH₂OC(O)CH₃ | H | H | CH₃ | |
| CH₂CH₂CH₂OC(O)CF₃ | H | H | OCH₃ | |
| CH₂CH₂CH₂OH | H | H | CH₃ | |

TABLE XXXIV-continued

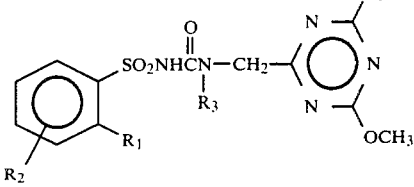

| R₁ | R₂ | R₃ | X₃ | m.p. (°C.) |
|---|---|---|---|---|
| CH₂CH₂CH₂OH | H | H | OCH₃ | |
| CH₂CH₂CH₂OH | H | CH₃ | OCH₃ | |
| CH₂CH₂CH₂OH | 6-OCH₃ | H | OCH₃ | |
| CH₂CH₂CH₂OCH₂C₆H₅ | H | H | CH₃ | |
| CH₂CH₂CH₂OSO₂CH₃ | H | CH₃ | OCH₃ | |
| CH₂CH₂CH₂OSO₂—4-C₆H₄CH₃ | H | H | OCH₃ | |
| CH₂CH₂CH₂SCH₃ | H | H | CH₃ | |
| CH₂CH₂CH₂S(O)₂CH₃ | H | H | OCH₃ | |
| CH₂CH₂CH₂OSO₂N(CH₃)₂ | H | H | CH₃ | |
| CH₂CH₂CH₂CO₂CH₃ | H | H | OCH₃ | |
| CH₂CH₂CH₂OCH₃ | H | H | OCH₃ | |
| CH₂CH₂CH₂OCH₃ | H | H | CH₃ | |
| CH₂CH₂CH₂OCH₃ | H | CH₃ | OCH₃ | |
| CH₂CH₂CH₂OCH₃ | 6-Cl | H | CH₃ | |
| CH₂CH₂CH₂OCH₃ | 3-OCH₃ | CH₃ | CH₃ | |
| CH₂CH₂CH₂OCH₂CH₃ | H | H | OCH₃ | |
| CH₂CH(OCH₃)CH₂(OCH₃) | H | H | OCH₃ | |
| CH₂CH(OCH₃)CH₂(OCH₃) | H | H | CH₃ | |
| CH₂CH(OCH₃)CH₂(OCH₃) | H | CH₃ | OCH₃ | |
| CH₂CH(OCH₃)CH₂(OCH₃) | 6-OCH₃ | H | CH₃ | |
| CH₂CH(OCH₂CH₃)CH₂(OCH₂CH₃) | H | H | CH₃ | |
| CH₂CH(OCH₃)CH₂(OCH₂CH₃) | H | H | OCH₃ | |
| CH₂CH₂CH(OCH₃)₂ | H | H | CH₃ | |
| CH₂CH₂CH(OCH₃)₂ | H | H | CH₃ | |
| CH₂CH₂CH(OCH₃)₂ | H | CH₃ | OCH₃ | |
| CH₂CH₂CH(OCH₃)₂ | 6-CF₃ | H | OCH₃ | |
| CH₂CH₂CH(OCH₂CH₃)₂ | H | H | CH₃ | |
| 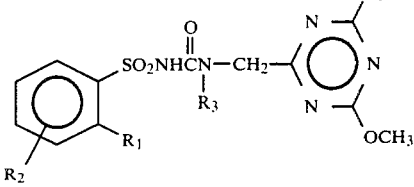 | H | H | OCH₃ | |
| 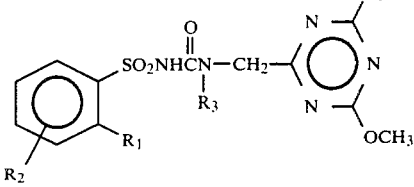 | H | H | CH₃ | |
| 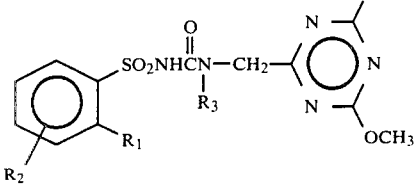 | H | H | OCH₃ | |
| 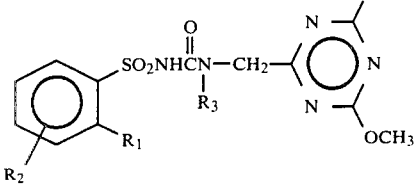 | H | H | OCH₃ | |

TABLE XXXV

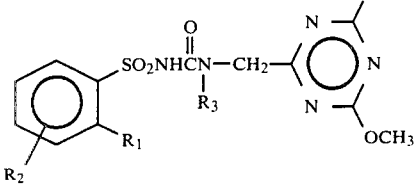

| R₁ | R₂ | R₃ | X | Y | m.p. (°C.) |
|---|---|---|---|---|---|
| CH₂CH₂Cl | H | H | CH₃ | H | |
| CH₂CH₂OCH₃ | H | H | CH₃ | NH₂ | |
| CH₂CH₂OH | H | H | CH₃ | NHCH₃ | |
| CH₂CH₂OC(O)CH₃ | 6-Cl | H | CH₃ | N(CH₃)₂ | |
| CH(OCH₃)CH₂(OCH₃) | H | CH₃ | CH₃ | CH₂CH₃ | |
| CH₂CH(OCH₃)₂ | H | H | CH₂CH₃ | CH₂CF₃ | |
| 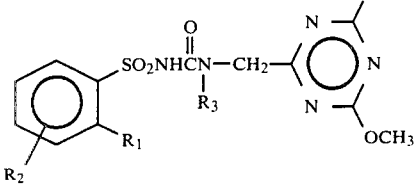 | H | H | CH₃ | CH₂OCH₃ | |
| CHClCH₂Cl | H | H | CH₃ | CH₂OCH₂CH₃ | |
| CH₂CH₂OCH₃ | 6-OCH₃ | H | CH₃ | OCH₃CH₃ | |
| CH₂CH₂OH | H | CH₃ | CH₃ | OCH₂CH₂CH₃ | |
| CH₂CH(OCH₃)₂ | H | H | CH₂CH₃ | OCH₂CH₂CH₂CH₃ | |
| CH(OCH₃)CH₂(OCH₃) | H | H | CH₃ | SCH₃ | |
| 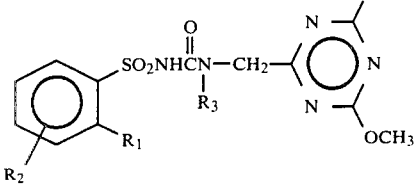 | H | H | CH₃ | SCH₂CH₃ | |
| CHClCH₂Cl | H | H | CH₃ | OCH₂CH=CH₂ | |

TABLE XXXV-continued

| $R_1$ | $R_2$ | $R_3$ | X | Y | m.p. (°C.) |
|---|---|---|---|---|---|
| $CH_2CH_2Cl$ | 3-Cl | H | $CH_3$ | $OCH_2CH=CHCH_3$ | |
| $CH_2CH_2OCH_3$ | H | H | $CH_3$ | $OCH_2C\equiv CH$ | |
| $CH_2CH_2OH$ | H | H | $CH_2CH_3$ | $OCH_2CH_2O\equiv CH$ | |
| $CH_2CH_2OC(O)CF_3$ | H | $CH_3$ | $CH_3$ | $OCH_2CH_2OCH_3$ | |
| $CH_2CH(OCH_3)_2$ | H | H | $CH_3$ | $CH(OCH_3)_2$ | |
| $CH_2CH_2Cl$ | H | H | $CH_2CH_3$ | ⟨O-CH-O⟩ (1,3-dioxolan-2-yl) | |
| $CH_2CH_2OCH_3$ | H | H | $CH_3$ | $OCH_2CF_3$ | |
| $CH_2CH(OCH_3)_2$ | H | H | $CH_3$ | $OCH_2CH_2F$ | |
| $CH_2CH_2Cl$ | H | H | $CH_3$ | $OCH_2CH_2Cl$ | |
| $CH_2CH_2OCH_3$ | H | H | $CH_3$ | $OCH_2CH_2Br$ | |
| $CH_2CH_2OC(O)CH_3$ | H | H | $CH_3$ | $OCF_2H$ | |
| $CH_2CH_2OH$ | 6-Cl | H | $CH_3$ | $OCF_2CHClF$ | |
| $CH_2$-⟨O-CH-O⟩ (1,3-dioxolan-2-ylmethyl) | H | H | $CH_3$ | $OCF_2CHBrF$ | |
| $CH_2CH_2Cl$ | H | H | $CH_3$ | $OCF_2CF_2H$ | |
| $CH_2CH(OCH_3)_2$ | H | H | $CH_3$ | $OCF_2CHFCF_3$ | |
| $CH(OCH_3)CH_2(OCH_3)$ | H | H | $CH_3$ | $SCF_2H$ | |
| $CH_2CH_2Cl$ | H | H | $CH_3$ | $SCF_2CHClF$ | |
| $CH_2CH_2OCH_3$ | H | H | $CH_3$ | $SCF_2CHBrF$ | |
| $CH_2CH_2OH$ | H | H | $CH_3$ | $SCF_2CF_2H$ | |
| $CH_2CH(OCH_3)_2$ | H | H | $CH_3$ | $SCF_2CF_2H$ | |
| $CH_2CH_2Cl$ | H | H | $OCH_3$ | $NHCH_3$ | |
| $CH_2CH_2OCH_3$ | H | H | $OCH_3$ | $N(CH_3)_2$ | |
| $CH_2$-⟨O-CH-O⟩ | H | H | $OCH_3$ | $CCH_2CF_3$ | |
| $CH_2CH_2Cl$ | H | $CH_3$ | $OCH_2CH_3$ | $CH_2OCH_3$ | |
| $CH_2CH_2OCH_3$ | 3-$OCH_3$ | H | $OCH_3$ | $CH_2OCH_2CH_3$ | |
| $CH_2CH_2OC(O)CF_3$ | H | H | $OCH_3$ | $OCH_2CH_3$ | |
| $CH_2CH(OCH_3)_2$ | H | H | $OCH_3$ | $SCH_3$ | |
| $CH_2CH_2Cl$ | H | H | $OCH_2CH_3$ | $SCH_2CH_3$ | |
| $CH_2CH_2Cl$ | H | H | $OCH_3$ | $OCH_2CH=CH_2$ | |
| $CH_2CH_2OCH_3$ | H | H | $OCH_3$ | $OCH_2CH_2OCH_3$ | |
| $CH_2CH_2OSO_2N(CH_3)_2$ | H | H | $OCH_3$ | $CH(OCH_3)_2$ | |
| $CH_2CH_2Cl$ | H | H | $OCH_3$ | ⟨O-CH-O⟩ (1,3-dioxolan-2-yl) | |
| $CH_2CH_2OCH_3$ | H | H | $OCH_3$ | $OCH_2CF_3$ | |
| $CH_2$-⟨O-CH-O⟩ | H | H | $OCH_3$ | $OCH_2CH_2F$ | |
| $CH_2CH_2Cl$ | H | H | $OCH_3$ | $OCH_2CH_2Cl$ | |
| $CH_2CH_2OCH_3$ | H | H | $OCH_3$ | $OCF_2H$ | |
| $CH_2CH_2OH$ | H | H | $OCH_3$ | $SCF_2H$ | |
| $CH(OCH_3)CH_2(OCH_3)$ | H | H | Cl | $NH_2$ | |
| $CH_2CH_2Cl$ | H | H | Cl | $NHCH_3$ | |

TABLE XXXV-continued

| R₁ | R₂ | R₃ | X | Y | m.p. (°C.) |
|---|---|---|---|---|---|
| CH₂CH₂OCH₃ | 6-OCH₃ | H | Cl | N(CH₃)₂ | |
| CH₂CH₂OSO₂N(CH₃)₂ | H | H | Cl | CH₃ | |
| CHClCH₂Cl | H | H | Cl | OCH₃ | |
| CH₂CH₂Cl | H | H | Cl | OCF₂H | |
| CH₂CH₂OCH₃ | H | H | CH₂CH₃ | NHCH₃ | |
| CH₂-(1,3-dioxolan-2-yl) | H | H | CH₂CH₃ | N(CH₃)₂ | |
| CH₂CH₂OH | H | CH₃ | CH₂CH₃ | CH₂OCH₃ | |
| CH₂CH₂Cl | H | H | CH₂CH₃ | SCH₃ | |
| CH₂CH₂OCH₃ | H | H | CH₂CH₃ | CH(OCH₃)₂ | |
| CH₂CH₂OH | H | H | CH₂CH₃ | 1,3-dioxolan-2-yl | |
| CH(OCH₃)CH₂(OCH₃) | H | H | CH₂CH₃ | OCH₂CF₃ | |
| CH₂CH₂Cl | H | H | CH₂CH₃ | OCF₂H | |
| CH₂CH₂OCH₃ | H | H | OCH₂CH₃ | NHCH₃ | |
| CH₂CH₂OH | H | H | OCH₂CH₃ | N(CH₃)₂ | |
| CH₂CH₂OC(O)CF₃ | H | H | OCH₂CH₃ | CH₂OCH₃ | |
| CH₂CH₂SCH₃ | H | H | OCH₂CH₃ | SCH₃ | |
| CH₂CH₂Cl | H | H | OCH₂CH₃ | CH(OCH₃)₂ | |
| CH₂CH₂OCH₃ | H | H | OCH₂CH₃ | OCH₂CF₃ | |
| CH(OCH₃)CH₂(OCH₃) | H | H | OCH₂CH₃ | 1,3-dioxolan-2-yl | |
| CH₂CH₂Cl | H | H | OCH₂CH₃ | OCF₂H | |
| CH₂CH₂OCH₃ | H | H | OCF₂H | N(CH₃)₂ | |
| CH₂CH₂OH | H | H | OCF₂H | CH₂OCH₃ | |
| CH₂-(1,3-dioxolan-2-yl) | H | H | OCF₂H | SCH₃ | |
| CH(OCH₃)CH₂(OCH₃) | H | H | OCF₂H | CH(OCH₃)₂ | |
| CHClCH₂Cl | H | H | OCF₂H | 1,3-dioxolan-2-yl | |
| CH₂CH₂SCH₃ | H | H | OCF₂H | OCH₂CF₃ | |
| CH₂CH₂Cl | H | H | OCF₂H | OCF₂H | |
| CH₂CH₂Cl | H | H | Br | NH₂ | |
| CH₂CH₂OCH₃ | H | H | Br | OCH₃ | |
| CH₂CH₂OCH₃ | H | H | Br | CH₃ | |
| CH₂CH₂Cl | H | H | Br | OCF₂H | |
| CH₂CH₂Cl | H | H | F | NH₂ | |
| CH₂CH₂Cl | H | H | F | OCH₃ | |
| CH₂CH₂OCH₃ | H | H | F | CH₃ | |

TABLE XXXVI

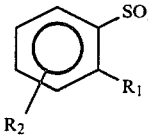

| R₁ | R₂ | R₃ | X | Y | m.p. (°C.) |
|---|---|---|---|---|---|
| CH₂CH₂Cl | H | H | CH₃ | H | |
| CH₂CH₂OCH₃ | H | H | CH₃ | NH₂ | |
| CH₂CH₂OH | H | H | CH₃ | NHCH₃ | |
| CH₂CH₂OC(O)CH₃ | 6-Cl | H | CH₃ | N(CH₃)₂ | |
| CH(OCH₃)CH₂(OCH₃) | H | CH₃ | CH₃ | CH₂CH₃ | |
| CH₂CH(OCH₃)₂ | H | H | CH₂CH₃ | CH₂CF₃ | |
| 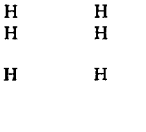 | H | H | CH₃ | CH₂OCH₃ | |
| CHClCH₂Cl | H | H | CH₃ | CH₂OCH₂CH₃ | |
| CH₂CH₂OCH₃ | 6-OCH₃ | H | CH₃ | OCH₂CH₃ | |
| CH₂CH₂OH | H | CH₃ | CH₃ | OCH₂CH₂CH₃ | |
| CH₂CH(OCH₃)₂ | H | H | CH₂CH₃ | OCH₂CH₂CH₂CH₃ | |
| CH(OCH₃)CH₂(OCH₃) | H | H | CH₃ | SCH₃ | |
| 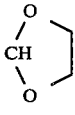 | H | H | CH₃ | SCH₂CH₃ | |
| CHClCH₂Cl | H | H | CH₃ | OCH₂CH=CH₂ | |
| CH₂CH₂Cl | 3-Cl | H | CH₃ | OCH₂CH=CHCH₃ | |
| CH₂CH₂OCH₃ | H | H | CH₃ | OCH₂C≡CH | |
| CH₂CH₂OH | H | H | CH₂CH₃ | OCH₂CH₂C≡CH | |
| CH₂CH₂OC(O)CF₃ | H | CH₃ | CH₃ | OCH₂CH₂OCH₃ | |
| CH₂CH(OCH₃)₂ | H | H | CH₃ | CH(OCH₃)₂ | |
| CH=CHCl | H | CH₃ | CH₃ | CH(OCH₂CH₃)₂ | |
| CH₂CH₂Cl | H | H | CH₂CH₃ |  | |
| CH₂CH₂OCH₃ | H | H | CH₃ | OCH₂CF₃ | |
| CH₂CH(OCH₃)₂ | H | H | CH₃ | OCH₂CH₂F | |
| CH₂CH₂Cl | H | H | CH₃ | OCH₂CH₂Cl | |
| CH₂CH₂OCH₃ | H | H | CH₃ | OCH₂CH₂Br | |
| CH₂CH₂OC(O)CH₃ | H | H | CH₃ | OCF₂H | |
| CH₂CH₂OH | 6-Cl | H | CH₃ | OCF₂CHClF | |
| 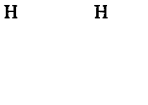 | H | H | CH₃ | OCF₂CHBrF | |
| CH₂CH₂Cl | H | H | CH₃ | OCF₂CF₂H | |
| CH₂CH(OCH₃)₂ | H | H | CH₃ | OCF₂CHFCF₃ | |
| CH(OCH₃)CH₂(OCH₃) | H | H | CH₃ | SCF₂H | |
| CH₂CH₂Cl | H | H | CH₃ | SCF₂CHClF | |
| CH₂CH₂OCH₃ | H | H | CH₃ | SCF₂CHBrF | |
| CH₂CH₂OH | H | H | CH₃ | SCF₂CF₂H | |
| CH₂CH(OCH₃)₂ | H | H | CH₃ | SCF₂CF₂H | |
| CH₂CH₂Cl | H | H | OCH₃ | NHCH₃ | |
| CH₂CH₂OCH₃ | H | H | OCH₃ | N(CH₃)₂ | |
| | H | H | OCH₃ | CCH₂CF₃ | |
| CH₂CH₂Cl | H | CH₃ | OCH₂CH₃ | CH₂OCH₃ | |

TABLE XXXVI-continued

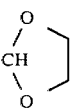

| R₁ | R₂ | R₃ | X | Y | m.p. (°C.) |
|---|---|---|---|---|---|
| CH₂CH₂OCH₃ | 3-OCH₃ | H | OCH₃ | CH₂OCH₂CH₃ | |
| CH₂CH₂OC(O)CF₃ | H | H | OCH₃ | OCH₂CH₃ | |
| CH₂CH(OCH₃)₂ | H | H | OCH₃ | SCH₃ | |
| CH₂CH₂Cl | H | H | OCH₂CH₃ | SCH₂CH₃ | |
| CH₂CH₂Cl | H | H | OCH₃ | OCH₂CH=CH₂ | |
| CH₂CH₂OCH₃ | H | H | OCH₃ | OCH₂CH₂OCH₃ | |
| CH₂CH₂OSO₂N(CH₃)₂ | H | H | OCH₃ | CH(OCH₃)₂ | |
| CH₂CH₂Cl | H | H | OCH₃ | 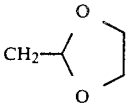 | |
| CH₂CH₂OCH₃ | H | H | OCH₃ | OCH₂CF₃ | |
| 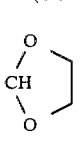 | H | H | OCH₃ | OCH₂CH₂F | |
| CH₂CH₂Cl | H | H | OCH₃ | OCH₂CH₂Cl | |
| CH₂CH₂OCH₃ | H | H | OCH₃ | OCF₂H | |
| CH₂CH₂OH | H | H | OCH₃ | SCF₂H | |
| CH₂CH₂OCH₃ | H | H | CH₂CH₃ | NHCH₃ | |
| 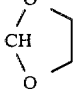 | H | H | CH₂CH₃ | N(CH₃)₂ | |
| CH₂CH₂OH | H | CH₃ | CH₂CH₃ | CH₂OCH₃ | |
| CH₂CH₂Cl | H | H | CH₂CH₃ | SCH₃ | |
| CH₂CH₂OCH₃ | H | H | CH₂CH₃ | CH(OCH₃)₂ | |
| CH₂CH₂OH | H | H | CH₂CH₃ | 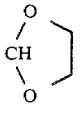 | |
| CH(OCH₃)CH₂(OCH₃) | H | H | CH₂CH₃ | OCH₂CF₃ | |
| CH₂CH₂Cl | H | H | CH₂CH₃ | OCF₂H | |
| CH₂CH₂OCH₃ | H | H | OCH₂CH₃ | NHCH₃ | |
| CH₂CH₂OH | H | H | OCH₂CH₃ | N(CH₃)₂ | |
| CH₂CH₂OC(O)CF₃ | H | H | OCH₂CH₃ | CH₂OCH₃ | |
| CH₂CH₂SCH₃ | H | H | OCH₂CH₃ | SCH₃ | |
| CH₂CH₂Cl | H | H | OCH₂CH₃ | CH(OCH₃)₂ | |
| CH₂CH₂OCH₃ | H | H | OCH₂CH₃ | OCH₂CF₃ | |
| CH(OCH₃)CH₂(OCH₃) | H | H | OCH₂CH₃ | 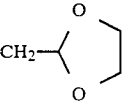 | |
| CH₂CH₂Cl | H | H | OCH₂CH₃ | OCF₂H | |
| CH₂CH₂OCH₃ | H | H | OCF₂H | N(CH₃)₂ | |
| CH₂CH₂OH | H | H | OCF₂H | CH₂OCH₃ | |
|  | H | H | OCF₂H | SCH₃ | |

TABLE XXXVI-continued

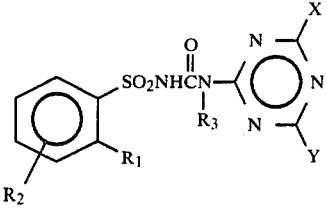

| $R_1$ | $R_2$ | $R_3$ | X | Y | m.p. (°C.) |
|---|---|---|---|---|---|
| $CH(OCH_3)CH_2(OCH_3)$ | H | H | $OCF_2H$ | $CH(OCH_3)_2$ | |
| $CHClCH_2Cl$ | H | H | $OCF_2H$ |  | |
| $CH_2CH_2SCH_3$ | H | H | $OCF_2H$ | $OCH_2CF_3$ | |
| $CH_2CH_2Cl$ | H | H | $OCF_2H$ | $OCF_2H$ | |

TABLE XXXVII

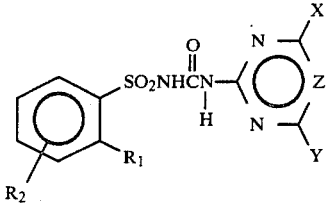

| $R_1$ | $R_2$ | X | Y | Z | m.p. (°C.) |
|---|---|---|---|---|---|
| $CH_2CH_2Cl$ | H | $OCH_3$ | $CH_3$ | $CCH_3$ | |
| $CH_2CH_2OCH_3$ | 6-$OCH_3$ | $OCH_3$ | $OCH_3$ | $CCH_3$ | |
| $CH_2CH_2Cl$ | H | $OCH_3$ | $CH_3$ | $CBr$ | |
| 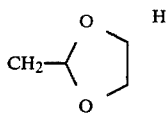 | H | $OCH_3$ | $OCH_3$ | $CBr$ | |
| $CH_2CH_2OCH_3$ | H | $Cl$ | $OCH_3$ | $CCl$ | |
| $CH_2CH_2Cl$ | 3-Cl | $CH_3$ | $CH_3$ | $CCl$ | |
| $CH_2CH_2OCH_3$ | H | $OCH_3$ | $CH_3$ | $CF$ | |
| 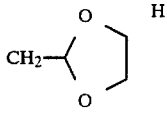 | H | $CH_3$ | $CH_3$ | $CF$ | |
| $CH_2CH_2Cl$ | H | $OCH_3$ | $CH_3$ | $CCH_2CH_3$ | |
| $CH_2CH_2OCH_3$ | H | $OCH_3$ | $OCH_3$ | $CCH_2CH_3$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XXXVIII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 18

Wettable Powder

| | |
|---|---|
| N—[(4,6-dimethoxy-1,3,5-triazin-2-yl)aminocarbonyl]-aminosulfonyl-2-(2-methoxyethyl)benzene-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 19

Wettable Powder

| | |
|---|---|
| N—[(4,6-dimethoxypyrimidin-2-yl)aminocarbonyl]amino-sulfonyl-2-(2-chloroethyl)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 20

Granule

| | |
|---|---|
| Wettable Powder of Example 19 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 21

Extruded Pellet

| | |
|---|---|
| N—[(4-methoxy-6-methylpyrimidin-2-yl)aminocarbonyl]-aminosulfonyl-2-(2-chloroethyl)benzenesulfonamide | 25% |
| anhydrous sodium sulfate | 10% |
| Crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 m diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 22

Oil Suspension

| | |
|---|---|
| N—[(4,6-dimethoxypyrimidin-2-yl)aminocarbonyl]amino-sulfonyl-2-(2-chloroethyl)benzenesulfonamide | 25% |
| polyoxyethylene soroitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 23

Wettable Powder

| | |
|---|---|
| N—[(4-methoxy-6-methylpyrimidin-2-yl)aminocarbonyl]-aminosulfonyl-2-(2-chloroethyl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 24

Low Strength Granule

| | |
|---|---|
| N—[(4-methoxy-6-methylpyrimidin-2-yl)aminocarbonyl]-aminosulfonyl-2-(2-methoxyethyl)benzene-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 25

Aqueous Suspension

| | |
|---|---|
| N—[(4-methoxy-6-methylpyrimidin-2-yl)aminocarbonyl]-aminosulfonyl-2-(2-p-toluenesulfonyloxyethyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 26

Solution

| | |
|---|---|
| N—[(4-methoxy-6-methyl-1,3,5-triazin-2-yl)aminocarbonyl]aminosulfonyl-2-(2-p-toluenesulfonyloxyethyl)benzenesulfonamide, sodium salt | 5% |
| water | 95% |

The salt is added directly to the water with stirring to produce the solution, which may then be packaged for use.

EXAMPLE 27

Low Strength Granule

| | |
|---|---|
| N—[(4-methoxy-6-methylpyrimidin-2-yl)aminocarbonyl]-aminosulfonyl-2-(2-methoxyethyl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 28

Granule

| | |
|---|---|
| N—[(4,6-dimethoxy-1,3,5-triazin-2-yl)aminocarbonyl]-aminosulfonyl-2-(2-chloroethyl)benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 29

High Strength Concentrate

| | |
|---|---|
| N—[(4,6-dimethoxy-1,3,5-triazin-2-yl)aminocarbonyl]-aminosulfonyl-2-(2-chloroethyl)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 30

Wettable Powder

| | |
|---|---|
| N—[(4-methoxy-6-methylpyrimidin-2-yl)aminocarbonyl]-aminosulfonyl-2-(2-p-toluenesulfonyloxyethyl)-benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 31

Oil Suspension

| | |
|---|---|
| N—[(4,6-dimethoxy-1,3,5-triazin-2-yl)aminocarbonyl]-aminosulfonyl-2-(2-methoxyethyl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 32

Dust

| | |
|---|---|
| N—[(4-methoxy-6-methyl-1,3,5-triazin-2-yl)aminocarbonyl]aminosulfonyl-2-(2-p-toluenesulfonyloxyethyl)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 33

Emulsifiable Concentrate

| | |
|---|---|
| N—[(4,6-dimethoxypyrimidin-2-yl)aminocarbonyl]aminosulfonyl-2-(2-p-toluenesulfonyloxyethyl)benzene- | 20% |

| | |
|---|---|
| -continued | |
| sulfonamide | |
| chlorobenzene | 74% |
| sorbitan monostearate and polyoxyethylene condensates thereof | 6% |

The ingredients are combined and stirred to produce a solution which can be emulsified in water for application.

UTILITY

The compounds of the present invention are active herbicides. They have utility for broad-spectrum pre- and/or post-emergence weed control in areas where complete control of all vegetation is desired, such as around fuel storage tanks, ammmunition depots, industrial storage areas, parking lots, drive-in theaters, around billboards, highway and railroad structures. Alternatively, the subject compounds are useful for the selective pre- or post-emergence weed control in crops, such as wheat, barley, rice, sorghum, and corn, or as plant growth modifiers.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.0005 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (*Xanthium pensylvanicum*), sorghum, corn, soybean, sugar beet, rice, wheat and purple nutsedge (*Cyperus rotundus*) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:
C=chlorosis/necrosis;
D=defoliation;
E=emergence inhibition;
G=growth retardation;
H=formative effect;
I=darker green color;
U=unusual pigmentation;
X=axially stimulation;
S=albinism; and
6Y=abscised buds or flowers.

The compounds also have plant growth modifying properties, e.g., they may retard the growth of various plant species, effect defoliation, etc.

Compounds

Compound 1
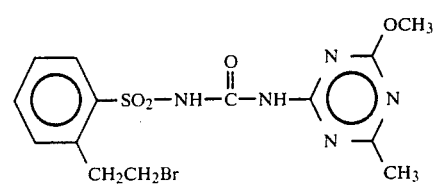

Compound 2
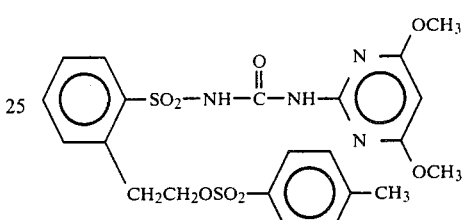

Compound 3
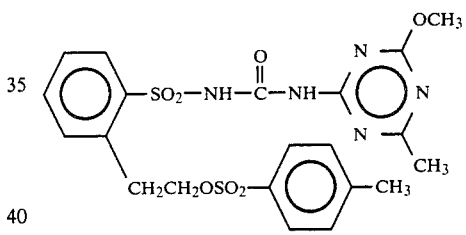

Compound 4
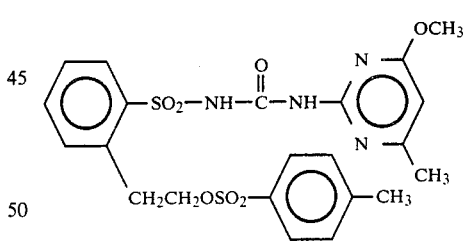

Compound 5
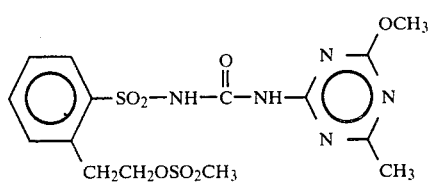

Compound 6
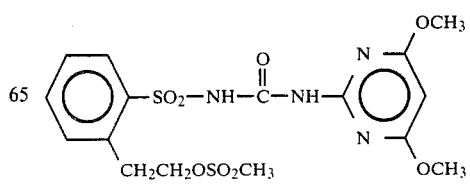

-continued
Compounds
Compound 7
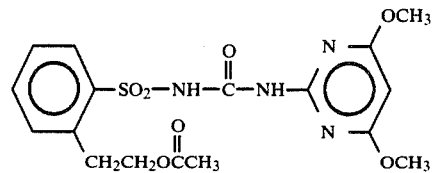
Compound 8
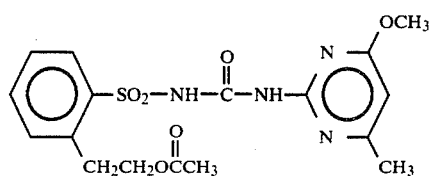
Compound 9
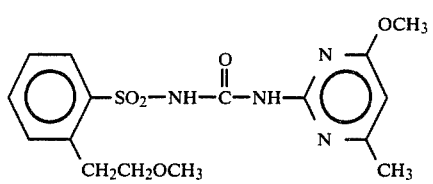
Compound 10
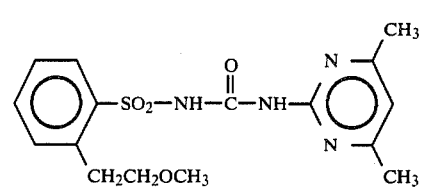
Compound 11
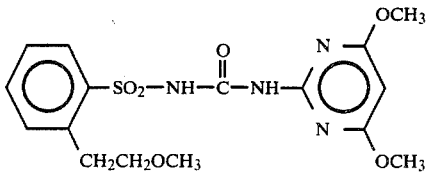
Compound 12
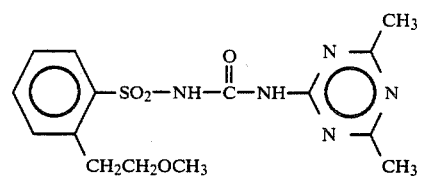
Compound 13
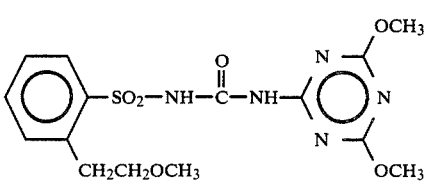
-continued
Compounds
Compound 14
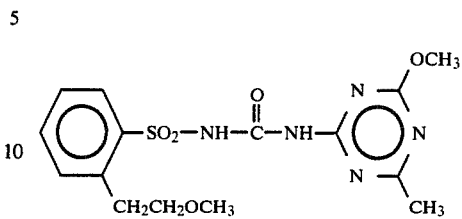
Compound 15
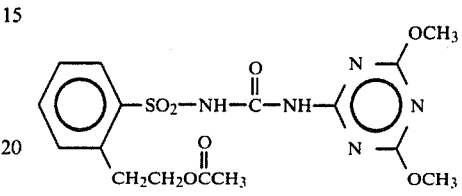
Compound 16
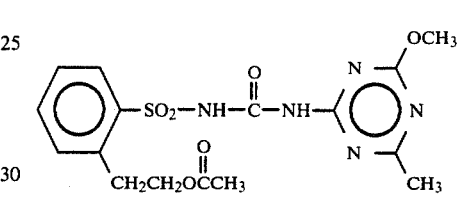
Compound 17
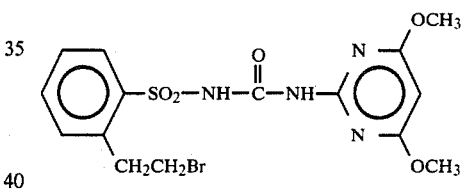
Compound 18
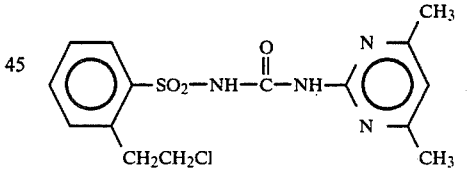
Compound 19
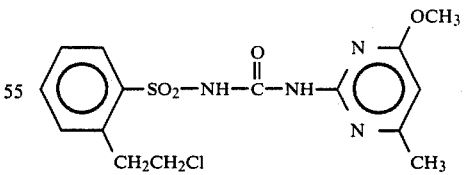
Compound 20
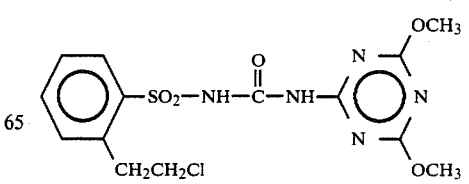

-continued
Compounds
Compound 21
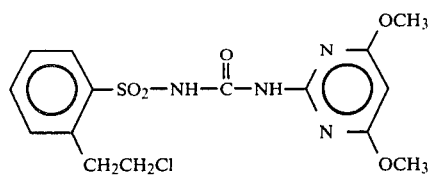
Compound 22
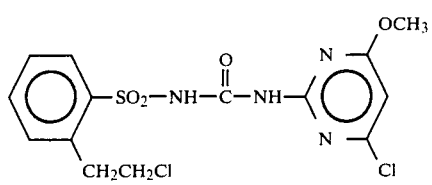
Compound 23
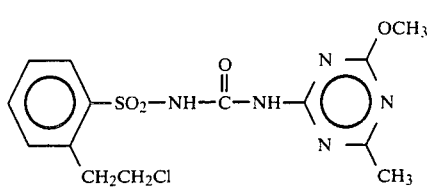
Compound 24
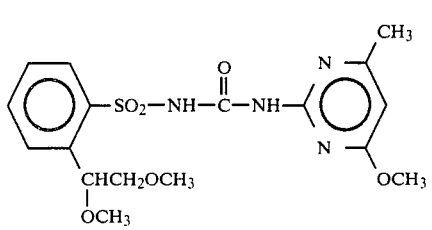
Compound 25
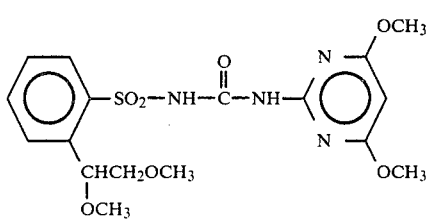
Compound 26
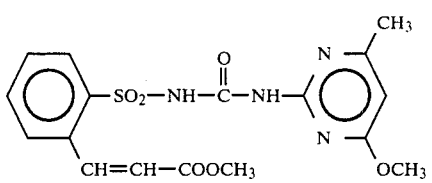
Compound 27
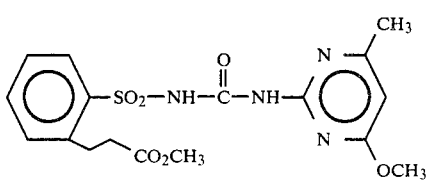
-continued
Compounds
Compound 28
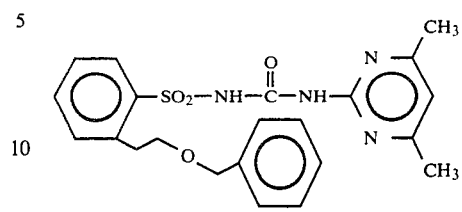
Compound 29
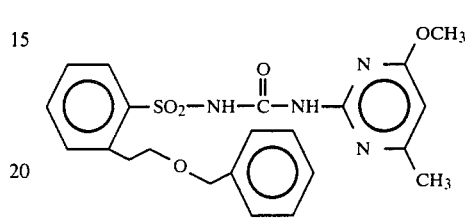
Compound 30
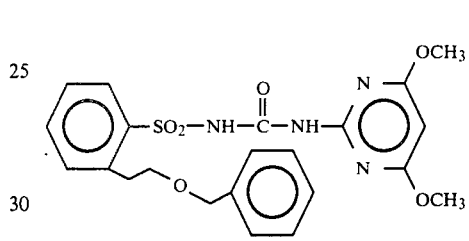
Compound 31
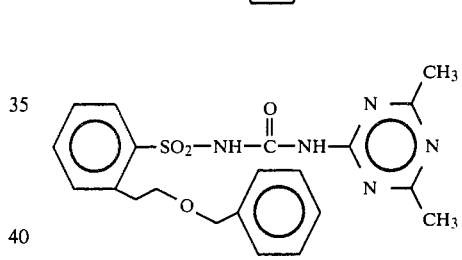
Compound 32
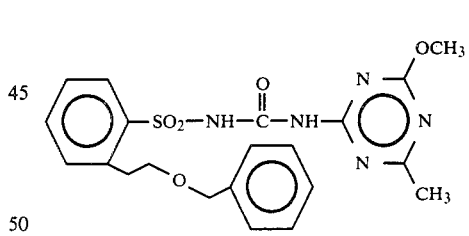
Compound 33
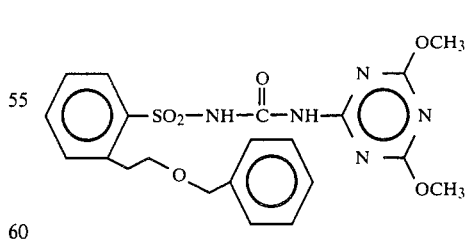
Compound 34
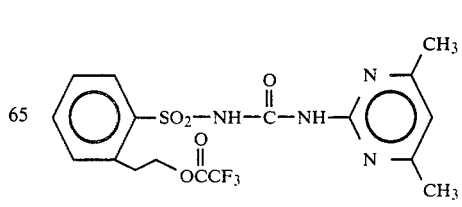

Compound 35
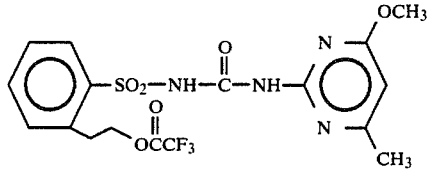
Compound 36
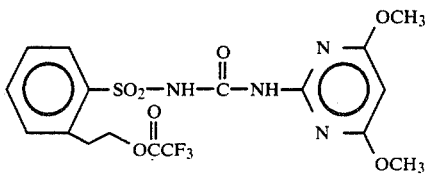
Compound 37
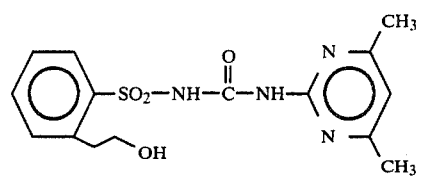
Compound 38
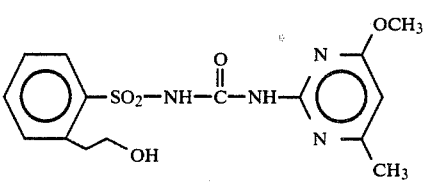
Compound 39
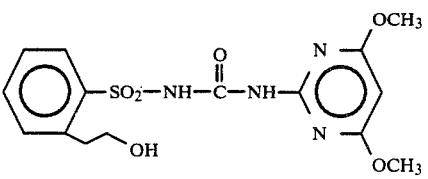
Compound 40
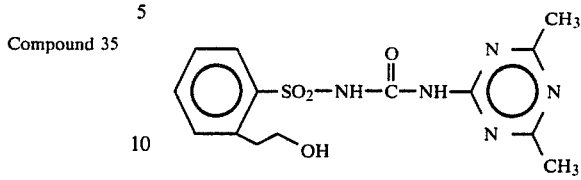
Compound 41
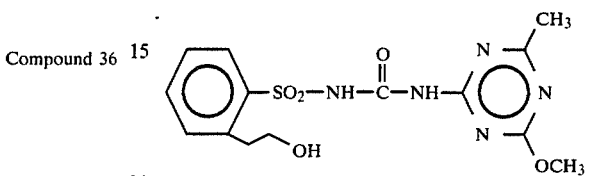
Compound 42
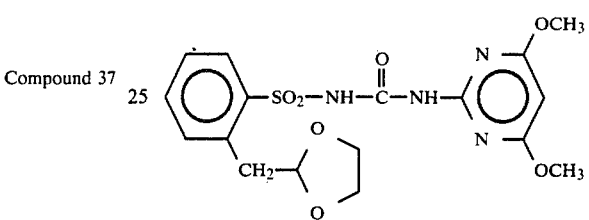
Compound 43
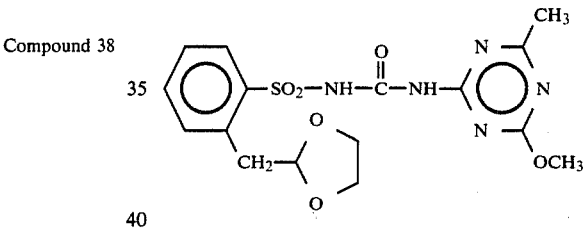
Compound 44
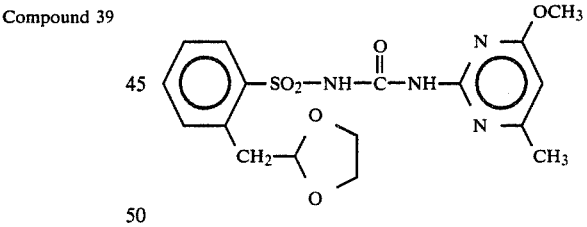

TABLE A

| Rate g/ha | Cmpd. 1 50 | Cmpd. 1 400 | Cmpd. 2 400 | Cmpd. 3 400 | Cmpd. 4 400 | Cmpd. 5 50 | Cmpd. 6 50 | Cmpd. 7 50 | Cmpd. 7 400 | Cmpd. 8 50 | Cmpd. 8 400 | Cmpd. 9 50 | Cmpd. 9 400 | Cmpd. 10 50 |
|---|---|---|---|---|---|---|---|---|---|---|---|---|---|---|
| | | | | | | POST-EMERGENCE | | | | | | | | |
| Bush bean | 5C,9G,6Y | 9C | 9D,9G,6Y | 6C,9G,6Y | 9C | 5C,9G,6Y | 4C,8G,6Y | 4C,9G,6Y | 9C | 6C,9G,6Y | 5C,9G,6Y | 9D,9G,6Y | 9C | 6C,9G,6Y |
| Cotton | 3C,7G | 5C,9G | 5C,9G | 6C,9G | 5C,9G | 5C,9G | 4C,5G | 2C,5G | 4C,9G | 5C,9G | 5C,9G | 5C,9G | 9C | — |
| Morningglory | 5C,9G | 5C,9G | 5C,9G | 9C | 9C | 2C | 0 | 3C,4H | 4C,9G | 6C,9G | 10C | 9C | 9C | 3C,9H |
| Cocklebur | 2C,9G | 9C | 9H | 9C | 9H | — | 0 | 4C,9G | 5C,9G | 4C,9G | 9C | 6C,9G | 9C | 3C,9G |
| Sicklepod | 3C,5H | 5C,9G | 5C,9G | 4C,8G | 5C,9G | 2C | 0 | 3C,8G | 2C,9G | 1C,5G | 4C,8G | 8G | 9C | 3C,5G |
| Nutsedge | 0 | 3G | 5C,9G | 4G | 9C | 2C | 0 | 3C,8G | 4C,9H | 2C,6G | 3C,7G | 8G | 3C,9G | 0 |
| Crabgrass | 0 | 3G | 1C,5G | 0 | 2C,5G | 2C | 2C | 2C,7G | 2C,9G | 5C,9H | 2C,9G | 2C,9G,5X | 5C,9H | 2C,5G |
| Barnyardgrass | 0 | 2C,3H | 3C,9H | 0 | 5C,9H | 0 | 1C,4H | 5C,9H | 2C,4G | 2C,4G | 2C,9G | 5C,9G | 4C,9G | 2C,9H |
| Wild Oats | 0 | 9C | 3G | 5C,9H | 3C,9G | 1H | 0 | 0 | 0 | 2C,6H | 9C | 9C | 4U,9G | 2C,9H |
| Wheat | 0 | 2G | 0 | 3G | 3C,9G | 5C,9G | 0 | 5C,9G | 1C | 3G | 8G | 5C,9G | 9C | 3G |
| Corn | 2G | 2C,7H | 3C,8H | 2C,6H | 2C,9G | 1H | 2C,6H | 5C,9G | 2C,9G | 4C,9G | 4C,9G | 5C,9G | 4U,9G | 1C,6H |
| Soybean | 4C,9G | 9C | 5C,9G | 5C,9G | 5C,9G | 5C,9G | 2C,8G | 5C,8G | 9C | 2C | 2C | 2C | 2C,5H | 2C,5H |
| Rice | 2G | 5G | 5C,9G | 5G | 5C,9G | 0 | 2G | 5C,9G | 6C,9G | 4C,9G | 5C,9G | 5C,9G | 9C | 3C,9G |
| Sorghum | 1C | 2C,8G | 2C,9H | 2C,5G | 9C | 0 | 1C | 1C,5G | 3C,9G | 2C,9G | 9G | 9G | 6C,9G | 2C,9G |
| Sugar beet | 5C,9G | 5C,9G | 9C | 5C,9G | 9C | 0 | 4C,8H | — | — | 2C,9G | 2C,9G | — | — | — |
| | | | | | | PRE-EMERGENCE | | | | | | | | |
| Morningglory | 9C | 9C | 9G | 9C | 9G | 7G | 3G | 9G | 9G | 5C,9G | 9G | 9G | 9G | 9G |
| Cocklebur | 9H | 9H | 9H | — | 9H | — | 8H | 8H | 9H | 9H | 9H | 9H | 9H | 9H |
| Sicklepod | 9G | 5C,9G | 9G | 9G | 9G | 4G | 7G | 9G | 9G | 9G | 9G | 9G | 9G | — |
| Nutsedge | 0 | 2C | 10E | 3G | 9H | 0 | 0 | 10E | 10E | 9G | 10E | 10E | 10E | 5G |
| Crabgrass | 1C | 2C | 5G | 0 | 2C,5G | 0 | 2G | 6G | 2C,9G | 4C,8H | 5C,8H | 4C,9G | 4C,9G | 2C,8G |
| Barnyardgrass | 1H | 2C,3H | 3C,8H | 6G | 4C,9H | 0 | 2C,6G | 4C,9H | 5C,8G | 9H | 5C,9G | 5C,9G | 4C,9G | 2C,7H |
| Wild Oats | 2H | 1C | 0 | 3G | 3C,9H | 1C | 0 | 1C,5G | 2C,6G | 4C,8H | 4C,8H | 4C,8H | 5C,9H | 2C,7H |
| Wheat | 5G | 2C,8G | 2C | 2C,8H | 9H | 0 | 5G | 5G | 1C,8G | 2C,9G | 4C,9G | 9G | 9H | 5G |
| Corn | 8H | 9H | 2C | 3C,8H | 9H | 1C | 9H | 9H | 9H | 9H | 10H | 9G | 10E | 2C,7G |
| Soybean | 0 | 6G | 3C,7G | 4G | 5C,9H | 0 | 4C,6H | 4C,6H | 9H | 10E | 9H | 8H | 9H | 0 |
| Rice | 2U,9G | 2C,8G | 5G | 2C,7H | 9H | 2C | 10E | 10E | 6C,9H | 10E | 10E | 5C,9H | 10E | 3C,7G |
| Sorghum | 5C,9G | 10E | 9G | 5C,9G | 10E | 2G | 3C,9H | 3C,9H | 10E | 5C,9H | 5C,9H | 5C,9H | 5C,9H | 3C,9H |
| Sugar beet | 3C,9G | — | — | — | — | — | 10E | 10E | — | — | — | — | — | 2C,9G |

| Rate g/ha | Cmpd. 11 50 | Cmpd. 11 400 | Cmpd. 12 400 | Cmpd. 13 400 | Cmpd. 14 400 | Cmpd. 15 50 | Cmpd. 15 400 | Cmpd. 16 50 | Cmpd. 16 400 | Cmpd. 17 50 | Cmpd. 17 400 | Cmpd. 18 50 | Cmpd. 19 50 | Cmpd. 20 50 |
|---|---|---|---|---|---|---|---|---|---|---|---|---|---|---|
| | | | | | | POST-EMERGENCE | | | | | | | | |
| Bush bean | 9C | 9C | | | | 4S,9G,6Y | 5C,9G,6Y | 4C,8G,6Y | 9C | 5C,9G,6Y | 9C | 6C,9G,6Y | 9C | 9C |
| Cotton | — | — | | | | 2C,2H | 4C,9G | 4C,4G | 4C,9G | 2C,7G | 4C,9G | 4C,9G | 5C,9G | 9C |
| Morningglory | 2C,8G | 10C | | | | 2C,4H | 4C,8G | 3C,7H | 5C,9G | 2C,4G | 5C,9G | 2C,7G | 2C,7G | 5C,9G |
| Cocklebur | 10C | 10C | | | | 2C | 4C,9G | 3C,7H | 9C | 1H,4G | 6C,9G | 4C,9G | 4C,9G | 9C |
| Sicklepod | 9C | 9C | | | | 4C,6G | 4C,7H | 4C,5H | 2C,9G | 2C,8G | 2C,9G | 3C,8G | 5C,9G | 9C |
| Nutsedge | 2C,8G | 2C,9G | | | | 3G | 3G | 0 | 1C,2G | 2C,9G | 1C,4G | 9G | 7G | 1C,5G |
| Crabgrass | 3C,5G | 2C,7G | | | | 3G | 3G | 2C | 1C,3G | 2C,9G | 5C,9H | 1C,5G | 3G | 3G |
| Barnyardgrass | 3C,9H | 9C | | | | 2C,4H | 2C,2H | 2C | 2C,6H | 2C,8H | 2C,8H | 2C,8H | 3C,9H | 0 |
| Wild Oats | 2G | 0 | | | | 1C | 0 | 0 | 0 | 5C,9H | 5C,9G | 2C,8G | 2C,5G | 0 |
| Wheat | 0 | 9C | | | | 0 | 0 | 0 | 0 | 0 | 0 | 0 | 1C,3G | 0 |
| Corn | 2U,9G | 9C | | | | 3C,7H | 2C,9H | 10E | 2C,9G | 1C,5H | 2C,8H | 1C,6H | 2C,9H | 5C,9G |
| Soybean | 5C,9G | 9C | | | | 3C,6G | 4C,9G | 3C,9H | 3C,9G | 5C,9G | 5C,9G | 2C,9G | 5C,9G | 0 |
| Rice | 5C,9G | 9C | | | | 1C | 4C,9H | 3C,9G | 2C,9G | 3G | 8G | 1C,8G | 6G | 0 |
| Sorghum | 3C,9G | 2C,9H | | | | 1C | 1C,3G | 2C,7G | 3C,9G | 1C | 3C,8H | 9G | 2C,9G | 9C |
| Sugar beet | — | — | | | | — | — | 2C,9G | — | 2C,9G | 4C,9G | 2C,9G | 5C,9G | — |
| | | | | | | PRE-EMERGENCE | | | | | | | | |

TABLE A-continued

| | | | | | | | | | | | | |
|---|---|---|---|---|---|---|---|---|---|---|---|---|
| Morningglory | 8H | 9H | 8H | 9G | 10C | 1C,2H | 9G | 8H | 9G | 8G | 9G | 9G |
| Cocklebur | 9H | 9H | 3H | 8H | 9H | — | 8H | 9H | 9H | 9H | 9H | 9H |
| Sickleped | 9H | 9G | 0 | 2C,9G | 5C,9G | 2C,4H | 8H | 9G | 9G | 9G | 9G | 9G |
| Nutsedge | 10E | 10E | 0 | 0 | 0 | 0 | 10E | 4G | 10E | 8G | 4G | 8G |
| Crabgrass | 2C | 2C,8G | 2C | 0 | 1C | 2C,4G | 1C | 0 | 1C | 0 | 0 | 4G |
| Barnyardgrass | 2C,8H | 3C,9H | 2C | 0 | 2G | 0 | 2C,7H | 2C,7G | 4C,9H | 3C,6G | 5C,9H | 5C,9G |
| Wild Oats | 4G | 2C,8H | 0 | 2C,2H | 3G | 0 | 0 | 0 | 4G | 2C,8G | 3C,8G | 3C,8G |
| Wheat | 2G | 7G | 2G | 1C | 0 | 0 | 0 | 0 | 2G | 0 | 7G | 7G |
| Corn | 2C,7G | 9H | 2G | 2C,8H | 2C,9H | 3C | 4C,6H | 2C,3G | 2U,9H | 2C,9G | 9H | 9H |
| Soybean | 7H | 9H | 2G | 3C,5H | 3C,7H | 1C | 3C,7H | 1C,2H | 9H | 9H | 6H | 3G |
| Rice | 9H | 10E | 3G | 2C | 2C | 0 | 2C,3G | 6G | 6H | 4C,8H | 3G | 3G |
| Sorghum | 3C,8H | 5C,9H | — | 2C | 1C,5G | 1H | 1C,4G | 3C,8H | 3C,8H | 2C,8G | 2C,8G | 2G |
| Sugar beet | — | — | — | 5C,9G | 10E | | 10E | 10E | 10E | 9G | 4C,9G | 9G |

| | Cmpd. 21 | Compound 22 | | Cmpd. 23 | Cmpd. 24 | Cmpd. 25 |
|---|---|---|---|---|---|---|
| Rate g/ha | 50 | 50 | 400 | 50 | 50 | 50 |
| | POST-EMERGENCE | | | | | |
| Bush bean | 9C | 2C,3G | 4C,8G,6Y | 9D,9G,6Y | 9C | 9C |
| Cotton | 5C,9G | 3C,7G | 4C,8G | 9C | 4C,9G | 5C,8G |
| Morningglory | 3C,7G | 3C,8G | 5C,9G | 5C,9G | 4C,9G | 4C,9G |
| Cocklebur | 9C | 3C,9G | 9C | 9C | 9C | 5C,9G |
| Sicklepod | 6C,9G | 2C,5G | 5C,9G | 5C,9G | 5C,9G | 5C,9G |
| Nutsedge | 5C,9G | 5C,9G | 9G | 3C,9G | 3C,9G | 10C |
| Crabgrass | 4G | 5G | 1C,5G | 2C | 3C,9H | 2C,8G |
| Barnyardgrass | 3C,9H | 2C,6H | 3C,9H | 2G | 5C,9H | 9C |
| Wild Oats | 0 | 0 | 1C,5G | 1H | 2C | 0 |
| Wheat | 1C,6G | 4G | 1C | 2G | 4G | 1C,2G |
| Corn | 5C,9G | 1C,7G | 2C,7H | 2C,6H | 2C,9G | 4U,9G |
| Soybean | 9C | 3H | 5C,9G | 9C | 5C,9G | 5C,9G |
| Rice | 3G | 2C,6H | 2C,7G | 1C,3G | 5C,9G | 5C,9G |
| Sorghum | 1C,5H | 4C,9H | 2C,9H | 2C,6H | 2C,9G | 3U,9G |
| Sugar beet | 5C,9G | 4C,9G | 5C,9G | 9C | 4C,9G | 9C |
| | PRE-EMERGENCE | | | | | |
| Morningglory | 9G | 9G | 9G | 5C,9G | 9G | 8G |
| Cocklebur | 9H | 9H | 9H | 9H | 9H | 9H |
| Sicklepod | 9G | 3C,6G | 9G | 9G | 5C,9G | 4C,9G |
| Nutsedge | 10E | 8G | 10E | 4G | 9G | 10E |
| Crabgrass | 2G | 1C | 1C,3G | 0 | 2C,4G | 1C,2G |
| Barnyardgrass | 2C,8H | 2C,7G | 3C,9H | 2C | 3C,9H | 3C,9H |
| Wild Oats | 2C,5G | 0 | 2C,5G | 0 | 2C,5G | 2C,5G |
| Wheat | 1C,3G | 0 | 1C,7G | 0 | 2C,7G | 1C,7G |
| Corn | 8G | 2C,6G | 2C,8G | 2C,8G | 5C,9H | 2C,9G |
| Soybean | 9H | 2C | 2C,6G | 9H | 9H | 9H |
| Rice | 2C,6G | 2C,3G | 2C,6H | 2C,3G | 4C,9H | 9H |
| Sorghum | 2C,8G | 3C,8H | 2C,9H | 2C,8H | 3C,9H | 2C,9H |
| Sugar beet | 5C,9G | 9G | 10E | 10E | 9C | 9C |

TEST B

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (*Xanthium pensylvanicum*), sorghum, corn, cotton, soybean, sugar beet, rice, wheat and purple nutsedge (*Cyperus rotundus*) tubers were planted and treated pre-emergence with the test chemicals dissolved in a non-phytotoxic solvent. At the same time, these crop and weed species were treated with a soil/foliage application. Treated plants and controls were maintained in a greenhouse for sixteen days, after which all species were compared to controls and visually rated for response to treatment. The ratings are based on a numerical scale extending from 0=no injury, to 10=complete kill. The accompanying descriptive symbols have the following meanings:

C=chlorosis/necrosis;
E=emergence inhibition;
G=growth retardation;
H=formative effects; and
U=unusual pigmentation.

The ratings for the compounds tested by this procedure are presented in Table B.

TABLE B

| | Cmpd. 26 | Compound 27 | | Compound 28 | | Compound 29 | | Compound 30 | | Cmpd. 31 |
|---|---|---|---|---|---|---|---|---|---|---|
| Rate g/ha | 50 | 50 | 400 | 50 | 400 | 50 | 400 | 50 | 400 | 50 |
| POST-EMERGENCE | | | | | | | | | | |
| Morningglory | 2C | 1C,2H | 2C | 8B | 8B | 4C,8G | 5C,9H | 2C,7G | 10C | 0 |
| Cocklebur | 4G | 0 | 2H | 4H | 5H | 2C,5H | 2C,8H | 3C,8H | 10C | 0 |
| Sicklepod | 2C | 0 | 2C | 3C,4H | 4C,5H | 5C,9G | 5C,9G | 5C,9G | 10C | 0 |
| Nutsedge | 0 | 0 | 0 | 2C,3G | 2C,5G | 5G | 2C,5G | 4C,8G | 9C | 0 |
| Crabgrass | 2G | 0 | 3G | 0 | 1C | 2G | 2C,5G | 2C,3G | 5C,9G | 0 |
| Barnyardgrass | 3H | 0 | 0 | 0 | 3C,3H | 2C,8H | 4C,9H | 9H | 10C | 0 |
| Wild Oats | 0 | 0 | 0 | 0 | 0 | 0 | 2G | 0 | 2C,6G | 0 |
| Wheat | 0 | 0 | 0 | 0 | 0 | 0 | 2G | 0 | 2C,4G | 0 |
| Corn | 2C,6G | 2H | 2C,5H | 0 | 2G | 3C,8H | 2C,8H | 2U,9G | 3U,9G | 0 |
| Soybean | 2C,8G | 2H | 4G | 1C,3H | 2C,8H | 3C,9G | 4C,9H | 5C,9G | 5C,9G | 0 |
| Rice | 2C,5G | 0 | 2C,4G | 2C,9G | 4C,9G | 2C,9G | 5C,9G | 5C,9G | 6C,9G | 0 |
| Sorghum | 2C,4G | 0 | 2C,3H | 2C | 4C,5G | 2C,6G | 3C,8H | 3C,5G | 2C,9H | 0 |
| Sugar beet | 3C,8G | 2C,5G | 2C,8G | 3C,6G | 4C,8G | 4C,8G | 4C,9G | 9C | 10C | 0 |
| Cotton | 2G | 3C,5G | 4C,8G | 5C,9H | 4C,9H | 4C,9G | 10C | 10C | 10C | 0 |
| PRE-EMERGENCE | | | | | | | | | | |
| Morningglory | 7G | 7G | 9G | 2C,2H | 7G | 9G | 9H | 8G | 10E | 0 |
| Cocklebur | 8H | 9H | 9H | 1H | 6H | 9H | 9H | 9H | 9H | 0 |
| Sicklepod | 8G | 1H | 7G | 0 | 3G | 6G | 2C,7G | 9G | 9G | 0 |
| Nutsedge | 0 | 0 | 0 | 0 | 2C,6G | 0 | 9G | 5G | 10E | 0 |
| Crabgrass | 0 | 0 | 2C | 0 | 0 | 0 | 2C,5G | 3G | 3C,8G | 0 |
| Barnyardgrass | 2C | 2C | 2C,6G | 2C,5G | 2C,8H | 2C,9H | 5C,9H | 4C,9H | 5C,9H | 0 |
| Wild Oats | 2C,3G | 0 | 2C,7G | 0 | 2C,5G | 2C,7G | 3C,8H | 3C,6G | 4C,8G | 0 |
| Wheat | 5G | 0 | 4G | 0 | 4G | 1C,7G | 2C,8G | 2G | 4C,8G | 0 |
| Corn | 2C,6G | 2C,7G | 3C,9H | 2C,6G | 9G | 3C,9G | 5C,9H | 2C,9G | 4C,9H | 0 |
| Soybean | 2C,4H | 2C,2H | 3C,7G | 2C | 3C,3H | 3C,8G | 4C,8H | 3C,8H | 9H | 0 |
| Rice | 3C,5G | 3G | 3C,8G | 3C,8H | 10E | 5C,9G | 10E | 5C,9H | 10E | 0 |
| Sorghum | 3C,7G | 2C,3H | 2C,8G | 3C,6G | 4C,9G | 3C,9G | 4C,9H | 4C,9H | 9C | 0 |
| Sugar beet | 2C,8G | 8G | 9G | 9G | 3C,9G | 5C,9G | 10E | 9C | 10E | 0 |
| Cotton | 5G | 8G | 9G | — | 5G | 2C,7H | 9G | 9G | 3C,9G | 0 |

| | Compound 32 | | Compound 33 | | Compound 34 | | Compound 35 | | Cmpd. 36 |
|---|---|---|---|---|---|---|---|---|---|
| Rate g/ha | 50 | 400 | 50 | 400 | 50 | 400 | 50 | 400 | 50 |
| POST-EMERGENCE | | | | | | | | | |
| Morningglory | 5C,9G | 5C,9G | 2C,5G | 5C,9H | 2C,3G | 9C | 6C,9G | 9C | 3C,5H |
| Cocklebur | 3C,8G | 4C,8G | 3G | 2C,8G | 2C | 4C,9G | 3C,7H | 5G | 3C,8H |
| Sickleod | 2C,4G | 3C,7G | 3C,6H | 3C,9G | 2C,3H | 4C,8H | 4C,9H | 5C,9G | 4C,9G |
| Nutsedge | 3G | 0 | 0 | 0 | 2C | 3C,8G | 3C,7G | 3C,9G | 6C,9G |
| Crabgrass | 2G | 3G | 0 | 3G | 2G | 1C | 2G | 5C,8G | 2G |
| Barnyardgrass | 0 | 3H | 0 | 1H | 2C,3H | 4C,9H | 3C,9H | 5C,9G | 2C,9H |
| Wild Oats | 0 | 0 | 0 | 0 | 0 | 1C,4G | 0 | 2C,7G | 0 |
| Wheat | 0 | 0 | 0 | 0 | 0 | 1C,2G | 0 | 5G | 0 |
| Corn | 2C,8H | 2C,8H | 2G | 2C,5G | 2C,7H | 2C,9H | 9G | 9C | 4C,9G |
| Soybean | 4C,9G | 5C,9G | 4C,9G | 5C,9G | 2C,5H | 2C,8H | 5C,9G | 5C,9G | 5C,9G |
| Rice | 5G | 4G | 0 | 4G | 3C,8H | 5C,9G | 4C,9G | 5C,9G | 4C,9G |
| Sorghum | 2C,3H | 2C,3H | 0 | 1C | 2C,6G | 4C,8H | 2C,7G | 2C,9G | 2C,7H |
| Sugar beet | 4C,8G | 9C | 4C,9G | 5C,9G | 2C,6G | 4C,8G | 9C | 9C | 2C,8G |
| Cotton | 4C,8G | 5C,9G | 3C,7G | 5C,9H | 4C,8G | 4C,9G | 9C | 9C | 9C |
| PRE-EMERGENCE | | | | | | | | | |
| Morningglory | 9G | 2C,9H | 8H | 9G | 2C | 9G | 9G | 2C,9G | 8G |
| Cocklebur | 2G | 9H | 6H | 8H | 0 | 8H | 9G | 9H | 9H |
| Sicklepod | 9G | 9G | 6G | 7G | 2C,4G | 7H | 9G | 9G | 2C,9G |
| Nutsedge | 0 | 0 | 0 | 0 | 0 | 0 | 5G | 4C,9G | 8G |
| Crabgrass | 0 | 2G | 0 | 1C | 0 | 4G | 2C | 2C,8G | 2G |
| Barnyardgrass | 3G | 3C,6H | 0 | 2C,2H | 2C,5G | 3C,8H | 5C,9H | 5C,9H | 2C,9H |
| Wild Oats | 1C | 2C | 0 | 0 | 2C,4G | 3C,7G | 4C,8G | 5C,9H | 5G |
| Wheat | 0 | 0 | 0 | 0 | 2C | 2C,5G | 2C,5G | 2C,9G | 2G |
| Corn | 2C | 9G | 3C,8G | 2C,9G | 2C,4G | 4C,9H | 5C,9H | 10H | 3C,9H |
| Soybean | 8H | 3C,8H | 2C,2H | 8H | 1C,1H | 4C,7H | 9H | 9H | 3C,9H |
| Rice | 2C | 3C,7G | 2G | 3G | 3C,7H | 4C,9H | 5C,9H | 10E | 2C,8H |
| Sorghum | 2C,4G | 3C,8H | 0 | 2G | 3C | 5C,9H | 5C,9H | 5C,9G | 2C,7G |
| Sugar beet | 2C,5G | 9G | 8G | 5C,9H | 2C,7G | 3C,9G | 10E | 10E | 9G |

TABLE B-continued

| | | | | | | | | | |
|---|---|---|---|---|---|---|---|---|---|
| Cotton | 6G | 9G | 7G | 8G | 6G | 9G | 5C,9G | 5C,9G | 9G |

| | Cmpd. 37 | Cmpd. 38 | Cmpd. 39 | Cmpd. 40 | Compound 41 | Cmpd. 42 | Cmpd. 43 | Cmpd. 44 |
|---|---|---|---|---|---|---|---|---|
| Rate g/ha | 50 | 50 | 50 | 400 | 50 | 400 | 400 | 400 |
| POST-EMERGENCE | | | | | | | | |
| Morningglory | 1C,2H | 5C,9G | 1C,2H | 2C | 2C,3H | 9C | 10C | 10C | 9C |
| Cocklebur | 5G | 2C,9G | 9C | 1C | 1H | 9C | 9C | 9C | 9C |
| Sicklepod | 2C,3H | 5C,9G | 5C,9G | 1C | 2C | 5C,9G | 5C,9G | 4C,9G | 4C,9G |
| Nutsedge | 4G | 2C,9G | 3C,9G | 0 | 0 | 7G | 9G | 5G | 5G |
| Crabgrass | 0 | 2C,8G | 5G | 0 | 2G | 2C,5G | 2C,9G | 2C,7G | 2C,8G |
| Barnyardgrass | 3C,5H | 3C,9H | 5C,9H | 0 | 0 | 2C,7H | 5C,9G | 2C,6H | 5C,9G |
| Wild Oats | 0 | 4G | 0 | 0 | 0 | 1C | 2C,8G | 3G | 3C,8G |
| Wheat | 0 | 0 | 0 | 0 | 0 | 0 | 7G | 0 | 3C,8G |
| Corn | 2C,7H | 2C,9G | 3C,9G | 1U,9G | 2C,8H | 2U,9G | 2U,9G | 2U,9G | 2C,9G |
| Soybean | 2C,8G | 5C,9G | 5C,9G | 2C,2H | 4C,9G | 5C,9G | 5C,9G | 4C,9G | 5C,9G |
| Rice | 9G | 6C,9G | 4C,9G | 2C,9G | 2G | 4C,9G | 4C,9G | 4C,8G | 4C,9G |
| Sorghum | 2C,6G | 4C,9H | 2C,9H | 2C,3G | 0 | 2C,9H | 2C,9G | 3C,8H | 2C,9G |
| Sugar beet | 6G | 5C,9G | 3C,9G | 3C,8G | 4C,9H | 9C | 5C,9G | 9C | 5C,9G |
| Cotton | 3C,6G | 5C,9G | 9H | 1C | 2C,8G | 10C | 9C | 10C | 10C |
| PRE-EMERGENCE | | | | | | | | |
| Morningglory | 2G | 9G | 8G | 8G | 7G | 9H | 9G | 9G | 9C |
| Cocklebur | 9H | 9H | 9H | 0 | 7H | 9H | 9H | 9H | 9H |
| Sicklepod | 5G | 9G | 9G | 0 | 2G | 9G | 9G | 9G | 8G |
| Nutsedge | 0 | 7G | 9G | 0 | 0 | 2C,5G | 10E | 5G | 10E |
| Crabgrass | 0 | 4G | 2G | 0 | 0 | 1C | 4G | 1C | 4C,8G |
| Barnyardgrass | 2G | 9H | 3C,9H | 0 | 2H | 7H | 3C,8H | 2C,3G | 4C,9H |
| Wild Oats | 6G | 2C,8H | 2C,6G | 0 | 2C | 2C,3H | 2C,7G | 2C,5G | 4C,8H |
| Wheat | 2G | 8G | 3G | 0 | 0 | 2G | 1C,8G | 0 | 9H |
| Corn | 3C,7H | 5C,9H | 2C,9G | 1C,3G | 2C,8G | 3C,9H | 2C,9H | 2C,9G | 9H |
| Soybean | 1C,1H | 9H | 8H | 1C,1H | 2C,4H | 9H | 8H | 3C,7H | 9H |
| Rice | 2C,7H | 10E | 3C,9H | 0 | 2C,3G | 5C,9H | 10E | 3C,8H | 10E |
| Sorghum | 2C,8H | 5C,9H | 3C,9H | 0 | 2C,5G | 5C,9H | 5C,9H | 3C,7H | 2C,9G |
| Sugar beet | 8G | 10E | 9G | 2C,3H | 4C,9G | 5C,9G | 5C,9G | 10E | 5C,9G |
| Cotton | 7G | 9H | 9G | 0 | 6G | 9G | 5C,9G | 9G | 9G |

TEST C

Twenty-five cm diameter plastic pots filled with Woodstown sandy loam soil were planted to soybeans, cotton, corn, rice, wheat, velvetleaf (*Abutilon theophrasti*), sicklepod (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*), johnsongrass (*Sorghum halepense*), and wild oats (*Avena fatua*). Additional plant species such as sunflower, rape, sugar beets, sorghum, bush bean, alfalfa, mustard (*Brassica kaber*), field bindweed (*Convolvulus arvensis*), teaweed (*Sida spinosa*), and sesbania (*Sesbania exaltata*) were sometimes added to this standard test in order to further evaluate selectivity. Approximately 2½ weeks after planting, the young plants and the soil around them were sprayed overall with the test chemicals dissolved in a non-phytotoxic solvent. Approximately fourteen days after treatment, all species were compared to untreated controls and visually rated for response to treatment. The rating system was as described previously for Test A. The data are presented in Table C.

Under greenhouse conditions, several of the test compounds controlled a number of weed species at rates of application which were non-injurious to corn and sorghum.

TABLE C

Over-the-Top Soil/Foliage Treatment

| | Compound 2 | | Compound 3 | | Compound 4 | | Compound 7 | | Compound 8 | | Compound 9 | | | Compound 10 | |
|---|---|---|---|---|---|---|---|---|---|---|---|---|---|---|---|
| Rate g/ha | 125 | 500 | 125 | 500 | 125 | 500 | 16 | 62 | 16 | 62 | 4 | 16 | 62 | 1 | 4 |
| Soybeans | 9G | 9G | 8G | 9G | 10C | 10C | 8G,6C | 10C | 7G,7C | 10C | 9G | 9G | 10C | 2G | 0 |
| Velvetleaf | 8G | 10C | 9C | 10C | 9G | 10C | 7G | 7G | 7G | 8G | 8G | 10C | 10C | 2G | 2G |
| Sesbania | 10C | 10C | 9G | 10C | 10C | 10C | 7G | 10C | 7G | 8G | 9G | 10C | 10C | 6G | 0 |
| Sicklepod | 8G | 10G | 2C | 6G | 10G | 10G | 8G | 9G | 5G | 8G | 2G | 6G | 10G | 3G | 0 |
| Cotton | 9G | 10C | 9C | 10C | 10G | 10G | 7G | 9G | 8G | — | 6G | 8G | 9G | — | 7G |
| Morningglory | 7G | 10G | 8G | 10G | 10G | 10G | 9G | 10C | 3G | 4G | 7G | 7G | 10G | 3G | 2C |
| Alfalfa | — | — | — | — | — | — | 6G | 7G | 7G | 10C | 7G | 6G | 9G | — | 0 |
| Jimsonweed | 0 | 0 | 0 | 2G | 0 | 5C | 8G | 9G | 7G | 8G | 6G | 8G | 9G | 9G | 0 |
| Cocklebur | 0 | 4G | 0 | 4G | 9G | 9G | 7G | 8G | 2G | 7G | 5G | 8G | 9G | 7G | 5G |
| Sunflower | 8G | 10C | 10C | 10C | 10C | 10C | 7G | 9G | 7G | 8G | 6G | 9G | 10C | 6G | 5G,2H |
| Rape | 10C | 10C | 10C | 10C | 10C | 10C | 9G | 10C | 3G | 7G | 7G | 9G | 9G | 6G | 9G |
| Sugar beets | 8G | 10G | 10G | 10G | 10G | 10G | — | — | | | | | | | |
| Corn | 0 | 8H | 0 | 0 | 6G | 8G | 4G | 7G,4C | 4G,3H | 6G,2C | 4G | 9G | 9G | 1G | 0 |
| Crabgrass | 0 | 0 | 0 | 0 | 0 | 0 | 0 | 3G | 0 | 2G | 0 | 6G | 8G | 0 | 0 |
| Rice | 0 | 4G | 0 | 0 | 2G | 5G | 2G | 6G,5C | 3G | 5G | 6G | 7G | 8G | 1G | 3G |
| Nutsedge | 6G | 8G | 0 | 0 | 5G | 7G | 1G | 5G | 0 | — | 7G | 8G | 8G | 0 | — |
| Barnyardgrass | 0 | 7G | 0 | 0 | 9G | 9G | 5G,5C | 7G,6C | 4G | 6G | 8G | 8G | 9G | 0 | 2G |
| Wheat | 0 | 1G | 0 | 0 | 0 | 0 | 8G,4C | 5G,3C | 4G | 4G | 2G | 8G | 8G | 0 | 0 |
| Giant Foxtail | 0 | 0 | 0 | 0 | 5G | 5G | — | — | 0 | 0 | 3G | 7G | 8G | 0 | 0 |
| Wild Oats | 0 | 0 | 0 | 0 | 3G | 4G | 2G,1C | 2G,3C | — | 2G,2C | 4G | 8G | 8G | 0 | 0 |
| Sorghum | 0 | 8G | 0 | 0 | 7G | 8G | 2G | 8G | 2G | 5G | 6G | 8G | 9G | 0 | 3G |

TABLE C-continued

Over-the-Top Soil/Foliage Treatment

| | | | | | | | | | | | | | | | |
|---|---|---|---|---|---|---|---|---|---|---|---|---|---|---|---|
| Johnsongrass | 0 | 0 | 0 | 0 | 0 | 4G | 2G | 4G | 0 | 0 | 6G | 8G | 9G | 0 | 7G |
| Field Bindweed | 0 | 0 | 0 | 0 | 6G | 8G | 1G | 5G | 0 | 0 | 0 | 3G | 9G | 0 | 0 |
| Bushbean | 6G | 8G | 8C | 9C | 9G | 10G | — | — | | | | | | | |
| Teaweed | | | | | | | | | | | | | | | |

| | Compound 10 | | Compound 11 | | | | Compound 14 | | Compound 18 | | Compound 19 | | | | |
|---|---|---|---|---|---|---|---|---|---|---|---|---|---|---|---|
| Rate g/ha | 16 | 62 | 1 | 4 | 16 | 62 | 4 | 16 | 16 | 62 | 1 | 4 | 4 | 16 | 16 |
| Soybeans | 5G | 7G | 2G | 4C,5G | 10C | 10C | 0 | 4G | 6G | 9G,9C | 6G | 8G | 9G,7C | 9G,8C | 10G |
| Velvetleaf | 7G | 9G | 4G | 4C | 9G | 10C | 7G | 9G | 5G | 4G | 6G | 10G | 9G,6C | 10C | 10G |
| Sesbania | 7G | 8C | 6G | 7C,8G | 9C | 10C | 7G | 10C | 10C | 10C | 8G | 10G | 10C | 10C | 10G |
| Sicklepod | 0 | 2G | 4G | — | 8G | 9G | 0 | 4G | 4G,3C | 9G | 6G | 10G | 10C | 10C | 10G |
| Cotton | 8G | 9G | 5G | 10C | 9C | 10C | 3G | 9G | — | 6G | 5G | 10G | 8G,4C | 10C | 10G |
| Morningglory | 8G | 3C,8G | 2G | 6G | 10C | 10C | 8G | 9G | 5G | 3G | 3G | 5G | 4G | 7G | 6G |
| Alfalfa | 0 | 0 | 3G | 4G | 10C | 10C | — | — | 3G | 4G | — | — | 7G | 8G,2C | — |
| Jimsonweed | 2G | 4G | 4G | 6G | 7G | 8G | 0 | 3G | 0 | 2G | 0 | 10G | 7G | — | 10G |
| Cocklebur | 7G | 7G | 3G | 4G | 9C | 10C | — | 10C | 2G | 3G | 2G | 10G | — | — | 9G |
| Sunflower | 9G | 10C | 3G | 10C | 10C | 10C | 7G | 9C | 6G | 5G | — | — | 7G | 10C | — |
| Rape | 10C | 10C | 4G | 10C | 10C | 10C | 8G | 9C | 8G | 9G | — | — | 10C | 10C | — |
| Sugar beets | | | | | | | 9G | 9G | — | — | 4G | 10G | — | — | 10G |
| Corn | 0 | 6G,2H | 0 | 2H,2G | 4G | 5G | 0 | 0 | 1G | 4G | 0 | 0 | 1G | 5G,3H | 7G |
| Crabgrass | 0 | 0 | 0 | 0 | 0 | 1G | 0 | 0 | 0 | 2G | 0 | 0 | 3G | 3G | 0 |
| Rice | 7G | 8G | 0 | 0 | 3G | 3C,5G | 0 | 0 | 0 | 0 | 0 | 0 | 2G | 3G | 3G |
| Nutsedge | 0 | 0 | 0 | 0 | 5C,3G | 4C,6G | 0 | 0 | 0 | 2G | 0 | 0 | 2G | 2G | 0 |
| Barnyardgrass | 3G | 8G | 0 | 2G | 3G | 4G | 0 | 0 | 1G | 4G | 0 | 0 | — | 9G | 0 |
| Wheat | 0 | 2G | 0 | 0 | 1G | 4G | 0 | 0 | 0 | 2G | 0 | 0 | 0 | 0 | 0 |
| Giant Foxtail | 0 | 0 | 0 | 2G | 3G | 8G | 0 | 0 | 0 | 1G | 0 | 0 | 0 | 0 | 0 |
| Wild Oats | 0 | 2G | 0 | 1G | 2G | 5G | 0 | 0 | 0 | 1G | 0 | 0 | 0 | 0 | 0 |
| Sorghum | 7G | 9G | 0 | 0 | 2G | 8G | 0 | 0 | 8G | 9G | — | — | 2G | 2G | — |
| Johnsongrass | 9G | 9G | 0 | 0 | 0 | 2G | 0 | 0 | 1G | 1G | 0 | 0 | 7G,2U | 3G | 0 |
| Field Bindweed | 0 | 9C | 0 | 4G | 3G | 10C | 0 | 0 | 0 | 0 | — | — | 0 | 0 | — |
| Bush bean | | | 0 | — | — | — | 7G | 8G | — | — | — | — | — | — | — |
| Teaweed | | | | | | | | | | | | | | | |

| | Compound 19 | | Compound 20 | | | | | Compound 21 | | | | Compound 22 | | |
|---|---|---|---|---|---|---|---|---|---|---|---|---|---|---|
| Rate g/ha | 62 | 62 | 4 | 4 | 4 | 16 | 62 | 1 | 4 | 16 | 16 | 62 | 62 | 16 | 62 |
| Soybeans | 10G | 10C | 10C | 10C | 9G,7C | 9G,7C | 9G,7C | 10C | 10C | 10C | 9G | 10C | 10C | 3G | 4G |
| Velvetleaf | 10G | 10C | 6G | 4G | 10C | 10C | 10C | 6G | 9G | 10G | 9C | 10C | 9C | 3G | 6G |
| Sesbania | 10G | 10C | 10C | 10C | 9G | 10C | 10C | 7G | 10C | 10C | 10C | 10C | 10C | 10C | 10C |
| Sicklepod | 10G | 9G,3C | 2C,7G | 6G | 8G | 10C | 10C | 2C | 7C | 10C | 8G | 10G | 8G | 2G | 3G |
| Cotton | 10G | 10C | 10C | 10C | 9G | 9G,3C | 10C | 3G | 7C | 9G | 10C | 9G | 9G | 9G | 10C |
| Morningglory | 8G | 10C | 8G | 7G | 7G,2C | 9G | 10C | 0 | 2G | 8G | 8G | 8C | 10C | 3G | 6G,4C |
| Alfalfa | — | 8G,2C | 7G | 5G | 4G | 8G | 9G | — | — | — | 5G | — | 7G | 1C,2G | 2C,7G |
| Jimsonweed | 10G | 8G,2C | 7G | 8G | 4G | 8G | 9G,4C | 4G | 3G | 6G | 2G | — | 9G | 3G | 6G |
| Cocklebur | 10G | 10C | 8G | 5G | — | 6G | 7G | — | 3G | 7G | 5G | 10C | 8G | 8G | 10C |
| Sunflower | — | 10C | 9G | 10C | 9G | 10C | 10C | — | — | — | 10C | — | 10C | 9G | 10C |
| Rape | — | 10C | 8C,9G | 10C | 9G | 10C | 10C | — | — | — | 7G | — | 8G | 8G | 8G |
| Sugar beets | 10G | — | — | — | — | — | — | 6G | 7C | 10C | — | 10C | — | — | — |
| Corn | 7G | 8G,3H | 0 | 0 | 0 | 0 | 0 | 2C | 3C | 3C | 6G,3H | 6G | 7G | 0 | 0 |
| Crabgrass | 0 | 0 | 0 | 0 | 0 | 0 | 0 | 0 | 0 | 0 | 3G | 0 | 5G | 0 | 0 |
| Rice | 2G | 5G | 8G | 0 | 0 | 0 | 0 | 2G | 0 | 0 | 2G | 0 | 4G | 0 | 0 |
| Nutsedge | 0 | 8G | 0 | 0 | 0 | 0 | 0 | 0 | 0 | 8G | 4C,7G | 8G | 7G | 0 | 0 |
| Barnyardgrass | 0 | 9G | 0 | 0 | 0 | 0 | 0 | 0 | 0 | 2G | 7G,4C | 8G | 8G | 0 | 0 |
| Wheat | 0 | 0 | 0 | 0 | 0 | 0 | 0 | 0 | 0 | 0 | 3G | 0 | 3G | 0 | 1G |
| Giant Foxtail | 0 | 0 | 0 | 0 | 0 | 0 | 0 | 2G | 0 | 0 | 4G | 0 | 10C | 0 | 0 |
| Wild Oats | 0 | 0 | 0 | 0 | 0 | 0 | 0 | 0 | 0 | 0 | 5G | 0 | 7G | 0 | 0 |
| Sorghum | — | 8G | 0 | 0 | 0 | 0 | 0 | — | — | — | 4G | — | 7G | 0 | 0 |
| Johnsongrass | 0 | 2G | 8G | 0 | 0 | 0 | 0 | 0 | 0 | 0 | 0 | 0 | 2G | 0 | 0 |
| Field Binweed | — | — | 0 | 0 | 0 | 0 | 0 | — | — | — | 0 | — | 3G | 2G | 4G,3C |
| Bush bean | — | — | — | — | — | — | — | — | — | — | — | — | — | — | — |
| Teaweed | | | | | | | | | | | | | | | |

| | Compound 23 | | Compound 24 | | Compound 42 | | | | Compound 43 | | | | Compound 44 | | | |
|---|---|---|---|---|---|---|---|---|---|---|---|---|---|---|---|---|
| Rate g/ha | 16 | 62 | 4 | 16 | 4 | 16 | 62 | 250 | 4 | 16 | 62 | 250 | 1 | 4 | 16 | 62 |
| Soybeans | 10C | 10C | 7G | 9G | 3G | 8G | 9G | 9C | 2G | 4G | 8G | 9G | 2G | 3G | 7G | 9G |
| Velvetleaf | 6G | 6G | 3G | 5G | 5G | 8C | 10C | 10C | 0 | 3G | 9G | 10C | 0 | 0 | 3G | 3G |
| Sesbania | 10C | 10C | 5G | 6G | — | — | — | — | — | — | — | — | — | — | — | — |
| Sicklepod | 7G | 8G | 5G | 8G | 0 | 7G | 9G | 9G | 0 | 3G | 4G | 8G | 0 | 0 | 0 | 3G |
| Cotton | 10C | — | 4G | 7G | 0 | 5G | 10C | 9G | 0 | 6G | 9G | 9G | 0 | 2G | 4G | 5G |
| Morningglory | 3G | 8G | 2G | 5G | 0 | 5G | 6G | 10C | 4G | 7G | 8G | 10C | 0 | 3G | 4G | 7G |
| Alfalfa | 5G | 8C,7G | — | — | | | | | | | | | | | | |
| Jimsonweed | 6G | 10C | 4G | 8G | 0 | 0 | 7G | 9G | 0 | 0 | 8G | 9G | 0 | 3G | 5G | 6G |
| Cocklebur | 7C,7G | 9G | 6G | 9G | 3G | 6G | 8G | 10C | 0 | 3G | 9G | 10C | 0 | 2G | 4G | 6G |
| Sunflower | 9G | 10C | — | — | — | — | — | — | — | — | — | — | — | — | — | — |
| Rape | 9G | 10C | — | — | — | — | — | — | — | — | — | — | — | — | — | — |
| Sugar beets | — | — | 7G | 9G | 4G | 8G | 10G | 10G | 10C | 10C | 10C | 10G | 0 | 4G | 8G | 9G |
| Corn | 0 | 0 | 3G | 7G | 0 | 6G | 9G | 9G | 0 | 0 | 5G | 8G | 0 | 2G | 6G | 7G |
| Crabgrass | 0 | 0 | 0 | 2G | 0 | 0 | 0 | 4G | 0 | 0 | 0 | 2G | 0 | 0 | 0 | 0 |

TABLE C-continued

| | | | | | | Over-the-Top Soil/Foliage Treatment | | | | | | | | | | |
|---|---|---|---|---|---|---|---|---|---|---|---|---|---|---|---|---|
| Rice | 1G | 4G | 0 | 4G | 0 | 0 | 6G | 9G | 0 | 0 | 0 | 0 | 0 | 0 | 4G | 8G |
| Nutsedge | 0 | 0 | 0 | 7G | 0 | 5G | 7G | 9G | 0 | 0 | 3G | 3G | 0 | 0 | 0 | 0 |
| Barnyardgrass | 0 | 0 | — | — | 0 | 0 | 9C | 9C | 0 | 0 | 0 | 0 | 0 | 0 | 3G | 7G |
| Wheat | 0 | 0 | 0 | 0 | 0 | 0 | 0 | 0 | 0 | 0 | 0 | 0 | 0 | 0 | 0 | 3G |
| Giant Foxtail | 0 | 0 | 0 | 0 | 0 | 0 | 4G | 6G | 0 | 0 | 3G | 3G | 0 | 0 | 0 | 3G |
| Wild Oats | 0 | 0 | 0 | 0 | 0 | 0 | 0 | 3G | 0 | 0 | 0 | 0 | 0 | 0 | 0 | 0 |
| Sorghum | 0 | 0 | — | — | — | — | — | — | — | — | — | — | — | — | — | — |
| Johnsongrass | 0 | 0 | 0 | 4G | 0 | 7G | 8G | 8G | 0 | 0 | 0 | 3G | 0 | 0 | 3G | 7G |
| Field Bindweed | 6G | 5G | — | — | — | — | — | — | — | — | — | — | — | — | — | — |
| Bush bean | — | — | — | — | — | — | — | — | — | — | — | — | — | — | — | — |
| Teaweed | | | | | 5G | 6G | 10C | 10C | 0 | 5G | 10C | 10C | 0 | 0 | 4G | 5G |

TEST D

Two plastic bulb pans were filled with fertilized and limed Woodstown sandy loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Approximately twenty-eight days after treatment, the plants were evaluated and visually rated for response to the chemical treatments utilizing the rating system described previously for Test A. The data are summarized in Table D.

TABLE D

PRE-EMERGENCE ON WOODSTOWN SANDY LOAM

| | Compound 1 | | Compound 2 | | Compound 3 | | Compound 4 | | Compound 7 | | Compound 8 | |
|---|---|---|---|---|---|---|---|---|---|---|---|---|
| Rate g/ha | 62 | 250 | 31 | 125 | 31 | 125 | 31 | 125 | 31 | 125 | 31 | 125 |
| Crabgrass | 0 | 0 | 2G | 3G | 0 | 0 | 2G | 5G | 0 | 3G | 0 | 5G |
| Barnyardgrass | 0 | 2G | 2G | 3G | 0 | 0 | 8G | 9G | 6G | 8G | 7G | 9G |
| Sorghum | 2G | 5G | 0 | 2G | 0 | 0 | 6G | 9G | 5G | 9G | 8G | 10C |
| Wild Oats | 0 | 2G | 0 | 2G | 0 | 0 | 4G | 6G | 2G | 3G | 2G | 4G |
| Johnsongrass | 0 | 0 | 0 | 0 | 0 | 0 | 2G | 6G | 0 | 0 | 0 | 2G |
| Dallisgrass | 0 | 0 | 0 | 2G | 0 | 0 | 3G | 4G | 0 | 0 | 0 | 2G |
| Giant foxtail | 0 | 0 | 0 | 2G | 0 | 0 | 5G | 7G | 2G | 6G | 0 | 2G |
| Ky. bluegrass | 0 | 2G | 0 | 3G | 0 | 0 | 7G | 9G | 0 | 3G | 0 | 2G |
| Cheatgrass | 0 | 0 | 0 | 2G | 0 | 0 | 8G | 9G | 0 | 0 | 0 | 3G |
| Sugar beets | 10C | 10C | 6G | 8G | 4G | 8G | 9G | 10C | 9G | 10C | 7G | 10C |
| Corn | 3G | 4G | 2C | 4G,3C | 0 | 3G | 6G,5H | 9G | 5G | 8G,7H | 6G,5H | 9G |
| Mustard | 10C | 10C | 9G | 10C | 8G | 9G | 9G | 10C | 9G | 10C | 9G | 10C |
| Cocklebur | 3G | 7G | 5G | 8G | — | 6G | 8G | 9G | 0 | 3G | 2G | 6G,3H |
| Nutsedge | 3G | 4G | 4G | 7G | 0 | 2G | 9G | 9G | 10C | 10C | 2G | 10C |
| Cotton | 5G | 7G | 2G | 2G | 3G | 6G | 7G | 8G | 0 | 3G | 0 | 8G |
| Morningglory | 4G | 6G | 0 | 0 | 0 | 2G | 8G | 9G | 4G | 4G | 4G | 5G |
| Sicklepod | 3G | 8G | 0 | 3G | 0 | 0 | 7G | 8G | 6G | 7G | 2G | — |
| Teaweed | 2G | 8G | 0 | 0 | 0 | 0 | 7G | 8G | 0 | 3G | 0 | 0 |
| Velvetleaf | 8G | 9G | 4G | 7G | 2G | 5G | 8G | 9G | 2G | 7G | 0 | 3G |
| Jimsonweed | 8G | 9G | 6G | 6G | 6G | 7G | 9G | 9G | 0 | 5G | 0 | 4G |
| Soybean | 6G,5H | 8G,7H | 0 | 3G,4H | 0 | 3G,5H | 8G,5H | 8G,7H | 7G,5H | 9G | 5G,2H | 9G |
| Rice | 0 | 3G | 0 | 2G | 0 | 0 | 7G | 9G | 7G | 10C | 7G | 10C |
| Wheat | 0 | 0 | 0 | 0 | 0 | 0 | 2G | 4G | 2G | 3G | 0 | 2G |

| | Compound 9 | | | Compound 10 | | Compound 11 | | Compound 13 | | Cmpd. 17 | |
|---|---|---|---|---|---|---|---|---|---|---|---|
| Rate g/ha | 16 | 31 | 125 | 31 | 125 | 31 | 125 | 8 | 31 | 62 | 250 |
| Crabgrass | 0 | 4G | 8G | 0 | 3G | 2G | 6G | 0 | 0 | 0 | 0 |
| Barnyardgrass | 7G | 8G | 9G | 3G | 6G,5H | 6G | 7G,5H | 0 | 2G | 4G | 6G |
| Sorghum | 8G | 9G | 10C | 8G,8H | 10C | 7G,5H | 9G,9C | 0 | 2G | 3G | 5G |
| Wild Oats | 5G | 6G | 8G | 3G | 6G,3H | 0 | 2G | 0 | 2G | 0 | 3G |
| Johnsongrass | 0 | 2G | 7G | 2G | 7G,5H | 5G | 5G | 0 | 3G | 0 | 0 |
| Dallisgrass | 0 | 0 | 8G | 2G | 2G | 0 | 3G | 0 | 0 | 0 | 0 |
| Giant foxtail | 0 | 2G | 7G | 0 | 0 | 3G | 6G,5C | 0 | 4G | 0 | 0 |
| Ky. bluegrass | 8G | 9G | 10C | 3G | 8G | 7G | 8G | 2G | 3G | 0 | 0 |
| Cheatgrass | 9G | 9G | 10C | 7G,5H | 8G,8C | 8G,8C | 9G,9C | 0 | 2G | 2G | 4G |
| Sugar beets | 10C | 10C | 10C | 6G | 9G | 10C | 10C | 8G | 10C | 2G | 9G |
| Corn | 3G | 8G,7H | 9G,9C | 2G | 7G,7H | 5G,7H | 9G,9C | 2G | 4G | 2G | 3G |
| Mustard | 9G | 10C | 10C | 9G | 10C | 9G,9C | 9G,9C | 8G | 9G | 9G | 10G |
| Cocklebur | 5G | 5G | 8G,5H | 2G | 6G,5H | 3G | 6G,5H | 0 | 5G | 2G | 2G |
| Mutsedge | 8G | 9G | 10C | 4G | 7G | 10C | 10C | 4G | 5G | 8G | 8G |
| Cotton | 5G | 6G | 9G | 0 | 6G | 2G,5H | 7G | 2G | 5G | 0 | 2G |
| Morningglory | 6G | 7G | 8G | 2G | 7G,3H | 0 | 3G | 3G,3C | 6G,5C | 2G | 4G |
| Sicklepod | 2G | 8G | 9G | 0 | 3G | 5G | 8G,5C | 0 | 8G | 0 | 3G |

TABLE D-continued
PRE-EMERGENCE ON WOODSTOWN SANDY LOAM

| | | | | | | | | | | | |
|---|---|---|---|---|---|---|---|---|---|---|---|
| Teaweed | 0 | 4G | 7G | 0 | 2G | 2G | 6G | 3G | 7G | 0 | 2G |
| Velvetleaf | 8G | 8G | 9G | 5G,3H | 7G,5C | 5G | 8G | 3G,3C | 8G,7H | 5G | 6G |
| Jimsonweed | 8G | 8G | 9G | 0 | 2G | 4G | 8G | 2G | 7G | 4G | 8G |
| Soybean | 6G,3C | 8G | 9G | 4G | 2G | 4G,5H | 6G,7H | 0 | 2G | 0 | 2G |
| Rice | 7G | 8G | 10C | 8G | 10C | 8G | 9G | 0 | 3G | 0 | 3G |
| Wheat | 2G | 3G | 7G | 3G | 4G | 0 | 2G | 0 | 3G | 0 | 3G |

| | Cmpd. 18 | | Compound 19 | | | Compound 20 | | Compound 21 | | | |
|---|---|---|---|---|---|---|---|---|---|---|---|
| Rate g/ha | 31 | 125 | 31 | 31 | 125 | 125 | 31 | 125 | 31 | 31 | 125 | 125 |
| Crabgrass | 0 | 3G | 0 | 5G | 0 | 6G | 0 | 0 | 0 | 5G | 3G | 6G |
| Barnyardgrass | 5G | 7G | 4G | 8G | 6G,3C | 9G | 0 | 0 | 6G | 5G | 8G | 9G |
| Sorghum | 6G | 8G | 3G | 8G | 5G,5H | 9G | 0 | 5G | 4G | 3G | 7G | 4G |
| Wild Oats | 2G | 5G | 2G | 5G | 4G | 7G | 0 | 0 | 4G | 0 | 4G | 2G |
| Johnsongrass | 7G | 8G | 9G | 5G | 4G | 7G | 0 | 0 | 4G | 4G | 4G | 5G |
| Dallisgrass | 2G | 3G | 0 | 6G | 2G | 8G | 0 | 0 | 0 | 5G | 2G | 6G |
| Giant foxtail | 0 | 2G | 0 | 5G | 0 | 7G | 0 | 0 | 2G | 4G | 6G | 6G |
| Ky. bluegrass | 6G | 9G | 5G | 8G | 8G | 9G | 0 | 0 | 0 | 5G | 4G | 8G |
| Cheatgrass | 5G | 9G | 6G | 9G | 7G | 9G | 0 | 0 | 6G | 5G | 8G | 7G |
| Sugar beets | 7G | 8G | 7G | 7G | 8G | 8G | 9G | 10C | 10C | 8G | 10C | 10C |
| Corn | 6G,5C | 8G,5H | 5G,5H | 7G | 5G,5H | 9G | 0 | 0 | 3G | 3C | 9G | 5G,5H |
| Mustard | — | — | 9G | 9G | 9G,9C | 9G | 9G | 10C | 9G,9C | 9G | 9G,9C | 10C |
| Cocklebur | — | — | 2G,2H | 3G | 3G,3H | 7G | 0 | 5G,2H | 7G | — | 8G | 7G |
| Nutsedge | — | — | 8G | 7G | 9G | 8G | 2G | 8G | 8G | 8G | 10C | 10C |
| Cotton | — | — | 0 | 6G | 3G | 8G | 7G | 9G | 7G | 2G | 9G | 4G |
| Morningglory | — | — | 0 | 5G | 0 | 7G | 3G | 7G | 6G | 3G | 9G | 4G |
| Sicklepod | — | — | 6G | 8G | 7G | 9G | 2G | 5G | 7G | 4G | 9G | 8G |
| Teaweed | — | — | 3G | 7G | 10C | 7G | 0 | 3G | 2G | 4G | 5G | 6G |
| Velvetleaf | — | — | 4G | 7G | 8G | 9G | 0 | 4G | 7G | 4G | 9G | 6G |
| Jimsonweed | — | — | 5G | 7G | 5G | 8G | 0 | 4G | 8G | 4G | 9G | 5G |
| Soybean | — | — | 4G,3H | 7G | 5G,5H | 8G,7H | 6G | 9G | 6G | 3G,3H | 8G | 6G,5H |
| Rice | — | — | 5G | 5G | 7G | 7G | 2G | 3G | 6G | 3G | 8G | 5G |
| Wheat | — | — | 0 | 2G | 2G | 4G | 0 | 0 | 0 | 0 | 2G | 0 |

| | Compound 22 | | Compound 24 | | Cmpd. 25 | | Compound 42 | | Conpound 43 | | | Compound 44 | | | |
|---|---|---|---|---|---|---|---|---|---|---|---|---|---|---|---|
| Rate g/ha | 31 | 125 | 2 | 16 | 2 | 16 | 16 | 62 | 250 | 4 | 16 | 62 | 250 | 4 | 16 | 62 | 250 |
| Crabgrass | 0 | 6G | 0 | 3G | 0 | 3G | 0 | 4G | 5G | 0 | 0 | 4G | 4G | 0 | 0 | 3G | 6G |
| Barnyardgrass | 2G | 4G | 0 | 6G | 2G | 4G | 3G | 6G | 6G | 0 | 0 | 0 | 0 | 3G | 6G | 9G | 3G |
| Sorghum | 2G | 3G | 0 | 9G | 5G | 7G | — | — | — | — | — | — | — | — | — | — | — |
| Wild Oats | 0 | 2G | 0 | 0 | 0 | 0 | 0 | 6G | 6G | 0 | 0 | 0 | 3G | 0 | 0 | 3G | 6G |
| Johnsongrass | 0 | 2G | 0 | 5G | 0 | 5G | 3G | 6G | 8G | 0 | 0 | 0 | 4G | 5G | 6G | 8G | 9G |
| Dallisgrass | 0 | 0 | 0 | 5G | 0 | 5G | — | — | — | — | — | — | — | — | — | — | — |
| Giant foxtail | 0 | 0 | 0 | 6G | 0 | 4G | 0 | 0 | 3G | 0 | 0 | 0 | 0 | 0 | — | — | 4G |
| Ky. bluegrass | 0 | 0 | — | — | — | — | — | — | — | — | — | — | — | — | — | — | — |
| Cheatgrass | 0 | 3G | 3G | 8G | 0 | 7G | — | — | — | — | — | — | — | — | — | — | — |
| Sugar beets | 6G | 7G | 2G | 6G | 3G | 7G | 5G | 8G | 9G | 3G | 8G | 9G | 9G | 3G | 8G | 9G | 9G |
| Corn | 2G,3C | 3G,3C | 0 | 0 | 0 | 4G | 2G | 8G | 9G | 0 | 0 | 3G | 7G | 0 | 4G | 9G | 9G |
| Mustard | — | — | 7G | 9G | 6G | 9G | — | — | — | — | — | — | — | — | — | — | — |
| Cocklebur | — | — | 0 | 8G | 6G | 8G | 0 | 7G | 8G | 0 | 0 | 6G | 8G | 0 | 6G | 7G | 9G |
| Nutsedge | — | — | 0 | 2G | 2G | 7G | 3G | 5G | 9G | 0 | 3G | 5G | 7G | 0 | 0 | 4G | 8G |
| Cotton | — | — | 0 | 4G | 3G | 7G | 0 | 3G | 8G | 0 | 0 | 8G | 9G | 0 | 3G | 5G | 9G |
| Morningglory | — | — | 0 | 6G | 0 | 6G | 3G | 8G | 8G | 0 | 6G | 7G | 8G | 0 | 0 | 2G | 8G |
| Sicklepod | — | — | 7G | 9G | 0 | 6G | 3G | 8G | 8G | 0 | 3G | 5G | 8G | 0 | 0 | 4G | 8G |
| Teaweed | — | — | 0 | 5G | 3G | 5G | 0 | 7G | 5G | 0 | 4G | 4G | 5G | 0 | 3G | 4G | 8G |
| Velvetleaf | — | — | 0 | 5G | 3G | 4G | 0 | 5G | 8G | 0 | 0 | 3G | 7G | 0 | 3G | 7G | 9G |
| Jimsonweed | — | — | 0 | 0 | 0 | 2G | 0 | 7G | 7G | 0 | 3G | 5G | 7G | 2G | 7G | 8G | 9G |
| Soybean | — | — | 4G | 6G,5H | 3G | 7G,5H | 4G | 7G | 8G | 0 | 0 | 5G | 8G | 2G | 4G | 7G | 9G |
| Rice | — | — | 5G | 8G | 3G | 7G | 0 | 8G | 8G | 0 | 0 | 5G | 8G | 0 | 6G | 9G | 10G |
| Wheat | — | — | 0 | 0 | 0 | 0 | 0 | 0 | 3G | 0 | 0 | 0 | 0 | 0 | 0 | 3G | 7G |

TEST E

Plastic pans lined with polyethylene liners were filled with prepared Woodstown sandy loam soil. Seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*), rapeseed (*Brassica napus*), downy brome (*Bromus tectorum*), ripgut brome (*Bromus rigidus*), Russian thistle (*Salsola kali*), Galium aparine, speedwell (*Veronica persica*), kochia (*Kochia scoparia*), shepherds's purse (*Capsella bursapastoria*), Matricaria inodora, black nightshade (*Solanum nigrum*), wild buckwheat (*Polygonum convolvulus*), tansy mustard (*Descurainia pinnata*), tumble mustard (*Sisymbrium altissium*), yellow rocket (*Barbarea vulgaris*) and sugar beets (*Beta vulgaris*) were planted. These pans were treated pre-emergence. At the same time pans in which these plant species were already growing wee treated post-emergence. Plant height at the time of treatment ranged from 1-20 cm, depending upon plant species.

The compounds applied were diluted with a non-phytotoxic solvent and sprayed over-the-top of the pans. An untreated control and a solvent alone control were included for comparison. All treatments were maintained in the greenhouse for 19-22 days, at which time the treatments were compared to the controls and the effects visually rated. The recorded data are presented in Table E.

Several of the compounds tested provided selective weed control in wheat and/or barley.

TABLE E

| | Compound 7 | | | Compound 8 | | Compound 10 | | Compound 11 | | | | Compound 13 | |
|---|---|---|---|---|---|---|---|---|---|---|---|---|---|
| Rate g/ha | 30 | 125 | 500 | 16 | 62 | 62 | 16 | 1 | 4 | 16 | 62 | 4 | 16 |
| | | | | | | Pre-Emergence | | | | | | | |
| wheat | 1G | 7G | 8G | 2G | 3G | 0 | 0 | 0 | 0 | 0 | 0 | 0 | 0 |
| barley | 3G | 6G | 7G | 3G | 5G | 0 | 0 | 0 | 0 | 2G | 2G | 0 | 0 |
| wild oats | 3G | 6G | 7G | 3G | 4G | 5G | 0 | 0 | 0 | 2G | 2G | 0 | 0 |
| downy brome | 3G | 9G | 9G | 5G | 8G | 8G | 6G | — | — | 6G | 6G | | |
| cheatgrass | 3G | 7G | 7G | 4G | 7G | 5G | 6G | — | 0 | 6G | 6G | 0 | 0 |
| blackgrass | 6G | 7G | 2C,8G | 5G | 8G | 1C,8G | 4G | 2G | 4G | 3C,9G | 3C,9G | 0 | 0 |
| annual bluegrass | 6G | 9G | 2C,9G | 5G | 7G | 8G | 5G | 3G | 2G | 8G | 2C,8G | 0 | 0 |
| green foxtail | 5G | 7G | 9C,9G | 5G | 7G | 1C | 0 | 0 | 2G | 6G | 1C,6G | 0 | 0 |
| quackgrass | 6G | 8G | 3C,9G | 4G | 8G | 8G | 7G | — | — | 7G | 9G | | |
| Italian ryegrass | 6G | 8G | 5C,9G | 4G | 8G | 2C,8G | 1C,4G | 0 | 3G | 1C,2G | 4G | 0 | 0 |
| ripgut brome | 5G | 8G | 5C,9G | 4G | 8G | 7G | 5G | — | — | 7G | 8G | | |
| Russian thistle | 0 | 3G | 2C,9G | 0 | 3G | 1C,2G | 2G | 0 | 0 | 1C,2G | 2C,6G | 0 | 6G |
| tansy mustard | — | — | — | — | — | 2C,9G | 8G | — | — | 7C,9G | 7C,9G | | |
| Galium aparina | 10C | 10C | 8G | 8G | 7G | 2C,6G | 3G | — | 6G | 2C,8G | 4C,8G | 4G | 7G |
| tumble mustard | 9G | 10C | 10C | 9G | 10C | 2C,9G | 8G | — | — | 9C,9G | 9C,9G | | |
| kochia | 4G | 3G | 10C | 0 | 0 | 5G | 0 | 2G | 8G | 5C,7G | 5G | 0 | 0 |
| shepherd's purse | 10C | 10C | 10C | 9G | 10C | 2C,9G | 8G | 10E | 10E | 8C,9G | 7C,9G | 7G | 10C |
| Matricaria inodora | 8G | 9G | 10C | 8G | 8G | 0 | 0 | 7G | 2C,9G | 8G | 9G | 2G | 7G |
| black nightshade | 0 | 6G | 6G | 0 | 0 | 2G | 0 | 0 | 4G | 7G | 7G | 0 | 3G |
| yellow rocket | 9G | 9G | 9G | 9G | 9G | 9G | 9G | — | — | 3C,9G | 3C,9G | | |
| rapeseed | 9G | 9G | 5C,9G | 9G | 9G | 2C,9G | 6G | 8G | 10C | 6C,9G | 5C,9G | 0 | 7G |
| wild buckwheat | 4G | 6G | 3C,9G | 2G | 4G | 5G | 1C | 2G | 7G | 3C,7G | 3C,6G | 1C,2G | 1C,9G |
| speedwell | | | | | | | | 3G | 3G | — | — | 0 | 2G |
| sugarbeets | | | | | | | | 6G | 8G | — | — | 4G | 2C,9G |
| | | | | | | Post-Emergence | | | | | | | |
| wheat | 2G | 2G | 3G | 3G | 2G | 4G | 1G | 0 | 0 | 4G | 5G | 0 | 0 |
| barley | 2G | 4G | 4G | 2G | 4G | 2G | 1G | 0 | 0 | 3G | 3G | 0 | 0 |
| wild oats | 0 | 3G | 4G | 5G | 5G | 5G | 4G | 0 | 0 | 4G | 3G | 0 | 0 |
| downy brome | 0 | 6G | 5G | 7G | 4G | 6G | 4G | — | — | 4G | 5G | | |
| cheatgrass | 0 | 5G | 3G | 5G | 5G | 5G | 2G | 0 | 0 | 3G | 3G | 0 | 0 |
| blackgrass | 3G | 0 | 5G | 4G | 4G | 2C,9G | 2C,8G | 0 | 4G | 2C,8G | 3C,9G | 0 | 0 |
| annual bluegrass | 5G | 0 | 5G | 6G | 6G | 8G | 5G | 0 | 0 | 2C,9G | 2C,8G | 0 | 0 |
| green foxtail | — | — | — | — | — | 5G | 4G | 0 | 0 | 8G | 7G | 0 | 0 |
| quackgrass | 0 | 0 | 4G | 8G | 5G | 7G | 6G | — | — | 7G | 6G | | |
| Italian ryegrass | 3G | 5G | 6G | 5G | 6G | 7G | 7G | 0 | 0 | 5G | 6G | 0 | 0 |
| ripgut brome | 2G | 3G | 6G | 4G | 5G | 7G | 6G | — | — | 5G | 5G | | |
| Russian thistle | — | — | 8C | — | — | 0 | 0 | — | — | 10C | 7C | — | — |
| tansy mustard | 10C | 10C | 10C | 10C | 10C | 8C,9G | 8C,9G | — | — | 10C | 10C | | |
| Galium aparine | 3C,7G | 10C | 3C,9G | 3C,7G | 10C | 2C,4G | 2C,4G | 0 | 3G | 2C,8G | 3C,7G | 0 | 5G |
| tumble mustard | 8C,8G | 10C | 10C | 7G | 10C | 10C | 9C,9G | — | — | 10C | 10C | | |
| kochia | 2G | 9C | 7G | 0 | 0 | 2G | 0 | 3G | 5G | 7C,8G | 3C,8G | 0 | 0 |
| shepherd's purse | 9C,9G | 10C | 9C,9G | 6G | 7C,8G | 10C | 10C | 10C | 10C | 10C | 10C | 5G | 8G |
| Matricaria inodora | 3C,5G | 3C,8G | 3C,8G | 5G | 3C,7G | 2C,6G | 2C,5G | 3G | 2C,7G | 8C,9G | 9C,9G | 0 | 5G |
| black nightshade | 4G | 7G | 4G | 0 | 5G | 5G | 5G | 0 | 0 | 8G | 5G | 0 | 0 |
| yellow rocket | 8G | 10C | 10C | 8C | 3C,8G | 10C | 2C,8G | — | — | 10C | 10C | | |
| rapeseed | 8G | 7C,9G | 7G | 5G | 8G | 8C,9G | 8G | 7G | 10C | 10C | 10C | 9G | 10C |
| wild buckwheat | 10C | 10C | 7G | 5G | 7G | 6G | 5G | | | | | 6G | 8G |
| Veronica persica | | | | 2G | 5G | — | — | 0 | 8G | 5C,8G | 3C,8G | | |
| speedwell | | | | | | | | 0 | 3G | — | — | 0 | 0 |
| sugar beets | | | | | | | | 8G | 9G | — | — | 7G | 9G |

| | Compound 18 | | Compound 19 | | Compound 20 | | | Compound 21 | | Compound 23 | | | |
|---|---|---|---|---|---|---|---|---|---|---|---|---|---|
| Rate g/ha | 16 | 62 | 16 | 62 | 4 | 16 | 62 | 16 | 62 | 16 | 62 | 1 | 4 |
| | | | | | Pre-Emergence | | | | | | | | |
| wheat | 0 | 5G | 0 | 2G | 0 | 0 | 2G | 0 | 0 | — | 0 | 0 | 0 |
| barley | 0 | 4G | 0 | 3G | 0 | 0 | 2G | 0 | 0 | — | 0 | 0 | 0 |
| wild oats | 3G | 6G | 0 | 4G | 0 | 0 | 1G | 0 | 0 | — | 0 | 0 | 0 |
| downy brome | | | | | | | | | | | | | |
| cheatgrass | 8G | 8G | 2G | 7G | 0 | 0 | 3G | 0 | 0 | — | 0 | 0 | 0 |
| blackgrass | 8G | 9G,9C | 3G | 6G | 0 | 2G | 6G | 0 | 2G | — | 9G,3C | 0 | 0 |
| annual bluegrass | 8G | 9G | 3G | 7G | 0 | 2G | 5G | 0 | 0 | — | 6G | 0 | 0 |
| green foxtail | 0 | 2G | 0 | 0 | 0 | 0 | 2G | 0 | 0 | — | 2G | 0 | 0 |
| quackgrass | | | | | | | | | | | | | |
| Italian ryegrass | 7G | 8G,8C | 0 | 8G | 0 | 3G | 5G | 0 | 0 | — | 8G | 0 | 0 |
| ripgut brome | | | | | | | | | | | | | |
| Russian thistle | 0 | 0 | 6G | 7G | 0 | 0 | 3C,5G | 5G | 9G | 8G | — | 4G | 9G |
| tansy mustard | | | | | | | | | | | | | |
| Galium aparina | 2G,3U | 2G,3U | 0 | 0 | 6G | 8G | 8C,9G | 0 | 4G | 8G | — | 0 | 3G |
| tumble mustard | | | | | | | | | | | | | |
| kochia | 6G | 6G | 5G | 6G | 0 | 4G | 8G | 3G | 8G | 9G | — | 0 | 7G |
| shepherd's purse | 8G | 9G,9C | 10C | 10C | 7G | 9G | 10C | 10C | 10C | 10C | — | 4G | 8G |
| Matricaria inodora | 7G | 9G | 10C | 10C | 3G | 9G | 10C | 8G | 9G | 10C | — | 4G | 7G |
| black nightshade | 2G | 6G | 0 | 4G | 6G | 5G | 6G | 0 | 5G | 7G | — | 0 | 7G |
| yellow rocket | | | | | | | | | | | | | |
| rapeseed | 9G | 9G | 10C | 10C | 2G | 8G | 10C | 10C | 10C | — | 10C | 3G | 9G |
| wild buckwheat | 2G | 2G | 0 | 5G,1C | 0 | 8G | 9G | 1G | 5G | 10C | — | 3G | 10C |
| speedwell | 8G | 7G | 9G | 9G | 4G | 5G | — | 0 | 0 | 10C | — | 0 | 6G,1C |
| sugarbeets | 7G | 9G | 9G,3C | 10C | 5G | 8G | 2C,9G | 6G | 10C | 10C | — | 4G | 7G |

TABLE E-continued

| | | | | | Post-Emergence | | | | | | | | |
|---|---|---|---|---|---|---|---|---|---|---|---|---|---|
| wheat | 0 | 0 | 1G | 2G | 0 | 0 | 0 | 0 | 1G | 0 | 0 | 0 | 0 |
| barley | 0 | 1G | 1G | 2G | 0 | 0 | 0 | 0 | 0 | 0 | 0 | 0 | 0 |
| wild oats | 0 | 1G | 1G | 1G | 0 | 0 | 3G | 0 | 0 | 0 | 0 | 0 | 0 |
| downy brome | | | | | | | | | | | | | |
| cheatgrass | 5G | 7G | 1G | 4G | 0 | 0 | 0 | 0 | 0 | 1G | 4G | 0 | 0 |
| blackgrass | 4G | 7G | 1G | 6G | 0 | 0 | 0 | 0 | 0 | 6G | 8G,7C | 0 | 0 |
| annual bluegrass | 4G | 6G | 1G | 5G | 0 | 0 | 3G | 0 | 0 | 6G | 7G | 0 | 0 |
| green foxtail | 3G | 4G | 0 | 0 | 0 | 0 | 0 | 0 | 0 | 0 | 6G | 0 | 0 |
| quackgrass | | | | | | | | | | | | | |
| Italian ryegrass | 5G | 7G,6C | 2G | 8G | 0 | 0 | 0 | 0 | 0 | 0 | 8G | 0 | 0 |
| ripgut brome | | | | | | | | | | | | | |
| Russian thistle | 3G | 8G | 2G | 5G | 0 | 0 | 8C | 4G | 10C | 10C | 10C | 10C | 10C |
| tansy mustard | | | | | | | | | | | | | |
| *Galium aparine* | 0 | 0 | 0 | 0 | — | — | — | 0 | 6G | 0 | 6G | 0 | 0 |
| tumble mustard | | | | | | | | | | | | | |
| kochia | 0 | 8G | 0 | 5G | — | 0 | 2G | 4G | 9G | 10C | 10C | 7G | 8G,7C |
| shepherd's purse | 10G | 10G | 1G | 5G | 0 | 9C | 10C | 8G | 10C | 10C | 10C | 8G,7C | 10C |
| *Matricaria inodora* | 4G | 9G | 3G,1C | 5G,7C | 4G | 7G | 8G | 4G | 9G | 8G,7C | 10C | 1G,1C | 8G,3C |
| black nightshade | 0 | 3G | 0 | 0 | 0 | 2G | 4G | 0 | 0 | 0 | 5G | 0 | 0 |
| yellow rocket | | | | | | | | | | | | | |
| rapeseed | 10G | 10G | 4G,1C | 10C | 8G | 9C,9G | 10C | 10C | 10C | 9G | 9G,9C | 0 | 0 |
| wild buckwheat | 10G | 10G | 5G,4C | 5G,4C | 0 | 5G | 8G | 9G,7C | 10C | 10C | 10C | 3G,1C | 5G |
| *Veronica persica* | | | | | | | | | | | | | |
| speedwell | 0 | 5G | 0 | 5G | 0 | 2G | 2G | 0 | 0 | 8G | 10C | 0 | 4G |
| sugar beets | 5G | 6G | 8G | 7G,7C | 0 | 3G | 7G | 10C | 10C | 9G | 10C | 4G,2C | 10C |

TEST F

This test was designed to evaluate the potential utility of compounds from within the scope of the invention for selective weed control in rice. The crop was transplanted into simulated paddies containing soil and propagules of barnyardgrass (Echinochloa sp.), water chestnut (Eleocharis sp.), and arrowhead (Sagittaria sp.). Direct seeded rice, *Scirpus mucronatus, Cyperus difformis,* water plantain (*Alisma trivale*), and *Monochloria vaginalis* were also treated with several of the test chemicals to further determine selectivity. Three days after transplanting, the test chemicals were applied to the paddy water in a non-phytotoxic solvent at the rates shown in Table F. The paddies were maintained in a greenhouse, and plant response ratings were taken several weeks after application utilizing either the rating system as described for Test A or a 0 to 100 rating system where 0 is no injury and 100 is plant death. It will be seen that several of the compounds tested provide control of troublesome weeds at rates which are non-injurious to rice.

TABLE F

| | Compound 2 | | | | | | Compound 7 | | | | Compound 9 | | Compound 11 | | | | Compound 17 | |
|---|---|---|---|---|---|---|---|---|---|---|---|---|---|---|---|---|---|---|
| Rate g/ha | 8 | 16 | 16 | 30 | 63 | 63 | .12 | .25 | 2.5 | 10 | 2.5 | 10 | .5 | 2 | 2.5 | 10 | 10 | 25 |
| Rice transplants | 0 | 0 | 0 | 0 | 0 | 0 | 0 | 0 | 0 | 0 | 0 | 4G | 0 | 40 | 4G | 2C,8G | 5G | 0 |
| Rice direct seeded | — | — | 0 | — | — | 0 | 0 | 0 | — | — | | | 90 | 90 | — | — | | |
| Barnyardgrass | 0 | 80 | 75 | 90 | 90 | 100 | 0 | 0 | 9C | 9C | 8G | 10C | 80 | 100 | 9G | 10C | 4G | 9C |
| Water chestnut | 60 | 100 | 80 | 90 | 100 | 95 | 0 | 100 | 4G | 9G | 3G | 8G | 100 | 100 | 9G | 2C,9G | 5G | — |
| Arrowhead | 70 | — | 90 | 90 | — | 95 | 0 | 0 | 3H | 5G,2H | 9G,6C | 9G,5C | 100 | 100 | 9G | — | 2G | 10E |
| Scirpus | 50 | 0 | 50 | 50 | 80 | 70 | 0 | 0 | — | — | | | 50 | 80 | — | — | | |
| Cypress | 20 | 90 | 50 | 95 | 90 | 100 | 0 | 0 | — | 0 | | | 100 | 100 | — | — | | |
| Water plantain | 80 | 70 | 100 | 90 | 90 | 100 | 0 | 70 | — | — | | | 100 | 100 | — | — | | |
| Monocnaria | 50 | — | 70 | 70 | — | 100 | | | | | | | | | | | | |

| | Compound 17 | | Compound 19 | | | | | | | | | | | | |
|---|---|---|---|---|---|---|---|---|---|---|---|---|---|---|---|
| Rate g/ha | 40 | 100 | 1 | 2.5 | 5 | 5 | 5 | 10 | 10 | 20 | 20 | 20 | 20 | 40 | 40 | 80 |
| Rice transplants | 3G | 5I | 0 | 0 | 0 | 0 | 4G | 2G | 0 | 2G,1C | 3G | 7G | 1G | 3G | 8G | 2C,8G |
| Rice direct seeded | | | | | | | | | | | | | | | | |
| Barnyardgrass | 8G | 9C | 3G | 5G | 6G | 9C | 10C | 9C | 10C | 9C | 10C | 8G | 10C | 10C | 10C | 10C |
| Water chestnut | 3C,9G | 9G | 10C | 10C | 10C | 9G | 2C,7G | 10C | 8G | 10C | 9G,2C | 9G | 9G,3C | 9G,2C | 9G,3C | 2C,9G |
| Arrowhead | 9G | 10E | 1H | 5G,2H | 8G,3H | 10E | — | 9G,3C | 10E | 9G,4C | 9G,5C | — | 9G,3C | 9G,5C | 9G,2C | — |
| Scirpus | | | | | | | | | | | | | | | | |
| Cypress | | | | | | | | | | | | | | | | |
| Water plantain | | | | | | | | | | | | | | | | |
| Monocnaria | | | | | | | | | | | | | | | | |

| | Compound 19 | | Compound 20 | | | | Compound 21 | | | | | | | | |
|---|---|---|---|---|---|---|---|---|---|---|---|---|---|---|---|
| Rate g/ha | 80 | 160 | 20 | 40 | 80 | 160 | 1 | 2.5 | 5 | 5 | 10 | 10 | 10 | 10 | 15 | 20 |
| Rice transplants | 7G | 8G,4C | 0 | — | 0 | 8G | 0 | 0 | 0 | 1G | 0 | 0 | 0 | 0 | 0 | 0 |
| Rice direct seeded | | | | | | | | | | | | | | | | |
| Barnyardgrass | 10C | 10C | 0 | — | — | 6G | 1G | 1G | 6G | 3C,8G | 9C | 9C | 9C | 9C | 9C | 10C |
| Water chestnut | 9G,4C | 10G,7C | 5G | 9G | 8G | 8G | 10C | 10C | 10C | 10C | 10C | 10C | 10C | 10C | 10C | 10C |
| Arrowhead | 9G,6C | 9G,3C | 0 | 0 | 0 | 0 | 0 | 2H | 2G,3H | — | 5G,2H | 4G,2H | 6G,3H | 5G,3H | 9G | 9G |
| Scirpus | | | | | | | | | | | | | | | | |
| Cypress | | | | | | | | | | | | | | | | |
| Water plantain | | | | | | | | | | | | | | | | |

TABLE F-continued

| Monocnaria | Compound 21 | | | | | | | | | | | | | | | Compound 22 | |
|---|---|---|---|---|---|---|---|---|---|---|---|---|---|---|---|---|---|
| Rate g/ha | 20 | 20 | 20 | 20 | 30 | 30 | 30 | 40 | 40 | 40 | 50 | 50 | 60 | 80 | 80 | 4 | 16 |
| Rice transplants | 4G | 0 | 0 | 0 | 0 | 0 | 0 | 0 | 0 | 0 | 0 | 0 | 7G | 7G | 3G | 0 | 0 |
| Rice direct seeded | | | | | | | | | | | | | | | | 20 | 20 |
| Barnyardgrass | 2C,9G | 9C | 10C | 10C | 10C | 9C | 10C | 10C | 9C | 10C | 9C | 10C | 10C | 10C | 10C | 70 | 90 |
| Water chestnut | 9G | 10C | 6G | 10G | 10C | 9G | 9G | 10C | 9G | 10C | 9G | 9G, 6C | 10C | 10C | 10C | 0 | 20 |
| Arrowhead | — | 5G | 4G,2H | 9G,3H | 9G | 10G | 9G | 10E | 10E | 10C | 8G | 9G | 10E | — | 10E | 100 | 100 |
| Scirpus | | | | | | | | | | | | | | | | 0 | 30 |
| Cypress | | | | | | | | | | | | | | | | — | — |
| Water plantain | | | | | | | | | | | | | | | | 70 | 70 |
| Monocnaria | | | | | | | | | | | | | | | | | |

What is claimed is:

1. A compound of the formula:

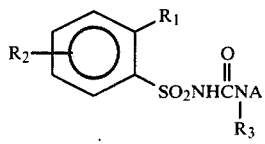

wherein $R_1$ is $(CH_2)_nCH_2CHR_4R_5$, $CHClCH_2Cl$, $CHClCHCl_2$, $CH=CBr_2$, $CH=CHR_9$, $CH=CHCO_2CH_3$ or $CH=CF_2$;

$R_2$ is H, F, Cl, $CH_3$, $OCH_3$ or $CF_3$;

$R_3$ is H or $CH_3$;

$R_4$ is H, F, Cl, Br or $CH_3$;

$R_5$ is F, Cl, Br, $OCH_2\phi$, $OSO_2R_6$, $OSO_2CF_3$, $OSO_2C_6H_4R_7$, $S(O)_mR_6$ or $OSO_2N(CH_3)_2$;

$R_6$ is $C_1-C_3$ alkyl;

$R_7$ is H, F, Cl, Br, $CH_3$, $OCH_3$ or $CF_3$;

$R_9$ is $OCH_3$ or $OCH_2CH_3$;

n is 0 or 1;

m is 0, 1 or 2;

A is

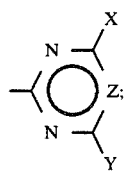 A-1

X is $CH_3$, $OCH_3$, F, Cl, F, Br, $CH_2CH_3$, $OCH_2CH_3$ or $OCF_2H$;

Y is H, $NH_2$, $NHCH_3$, $N(CH_3)_2$, $C_1-C_4$ alkyl, $C_1-C_4$ alkyl substituted with 1-3 atoms of (a) F, (b) Cl or (c) Br, $CH_2OCH_3$, $CH_2OCH_2CH_3$, $C_1-C_4$ alkoxy, $C_1-C_2$ alkylthio, $C_3-C_4$ alkenyloxy, $C_3-C_4$ alkynyloxy, $OCH_2CH_2OCH_3$, $CH(OCH_3)_2$, $CH(OCH_2CH_3)_2$,

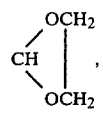

$OCH_2CF_3$, $OCH_2CH_2F$, $OCH_2CH_2Cl$, $OCH_2CH_2Br$ or $GCF_2T$: wherein G is O or S and T is H, CHClF, CHBrF, $CF_2H$ or $CHFCF_3$; and Z is CH; and their agriculturally suitable salts, provided that (a) when $R_4$ is halogen, then $R_5$ must be the same halogen;

(b) when $R_5$ is halogen, then $R_4$ is either hydrogen or the same halogen; and (c) when X is F, Cl or Br, then Y is $NH_2$, $NHCH_3$, $N(CH_3)_2$, $CH_3$, $OCH_3$ or $OCF_2H$.

2. A compound of claim 1 wherein $R_2$ is H, and $R_1$ is $(CH_2)_nCH_2CHR_4R_5$.

3. A compound of claim 2 wherein

X is $CH_3$, $OCH_3$, Cl or $OCF_2H$ and Y is $CH_3$, $CH_2CH_3$, $OCH_3$, $OCH_2CH_3$, $OCF_2H$, $SCF_2H$, $CH_2OCH_3$ or $CF_3$.

4. A compound of claim 3 wherein $R_1$ is $CH_2CH_2Cl$.

5. A compound of claim 4 wherein $R_3$ is H.

6. The compound of claim 1 which is N-[(4,6-dimethoxypyrimidin-2-yl)aminocarbonyl]aminosulfonyl-2-(2-p-toluenesulfonyloxyethyl)benzenesulfonamide.

7. The compound of claim 1 in which is N-[(4-methoxy-6-methylpyrimidin-2-yl)aminocarbonyl]aminosulfonyl-2-(2-p-toluenesulfonyloxyethyl)benzenesulfonamide.

8. The compound of claim 1 which is N-[(4-methoxy-6-methylpyrimidin-2-yl)aminocarbonyl]aminosulfonyl-2-(2-chloroethyl)benzenesulfonamide.

9. The compound of claim 1 which is N-[(4,6-dimethoxypyrimidin-2-yl)aminocarbonyl]aminosulfonyl-2-(2-chloroethyl)benzenesulfonamide.

10. A composition suitable for controlling the growth of undesired vegetation which comprises an effective amount of a compound of claim 1 and at least one of the following: surfactant, solid or liquid inert diluent.

11. A composition suitable for controlling the growth of undesired vegetation which comprises an effective amount of a compound of claim 2 and at least one of the following: surfactant, solid or liquid inert diluent.

12. A composition suitable for controlling the growth of undesired vegetation which comprises an effective amount of a compound of claim 3 and at least one of the following: surfactant, solid or liquid inert diluent.

13. A composition suitable for controlling the growth of undesired vegetation which comprises an effective amount of a compound of claim 4 and at least one of the following: surfactant, solid or liquid inert·diluent.

14. A composition suitable for controlling the growth of undesired vegetation which comprises an effective amount of a compound of claim 5 and at least one of the following: surfactant, solid or liquid inert diluent.

15. A composition suitable for controlling the growth of undesired vegetation which comprises an effective amount of the compound of claim 6 and at least one of the following: surfactant, solid or liquid inert diluent.

16. A composition suitable for controlling the growth of undesired vegetation which comprises an effective amount of the compound of claim 7 and at least one of the following: surfactant, solid or liquid inert diluent.

17. A composition suitable for controlling the growth of undesired vegetation which comprises an effective amount of the compound of claim 8 and at least one of the following: surfactant, solid or liquid inert diluent.

18. A composition suitable for controlling the growth of undesired vegetation which comprises an effective amount of the compound of claim 9 and at least one of the following: surfactant, solid or liquid inert diluent.

19. A method for controlling the growth of undesired vegetation which comprises applying to the locus to be protected an effective amount of a compound of claim 1.

20. A method for controlling the growth of undesired vegetation which comprises applying to the locus to be protected an effective amount of a compound of claim 2.

21. A method for controlling the growth of undesired vegetation which comprises applying to the locus to be protected an effective amount of a compound of claim 3.

22. A method for controlling the growth of undesired vegetation which comprises applying to the locus to be protected an effective amount of a compound of claim 4.

23. A method for controlling the growth of undesired vegetation which comprises applying to the locus to be protected an effective amount of a compound of claim 5.

24. A method for controlling the growth of undesired vegetation which comprises applying to the locus to be protected an effective amount of the compound of claim 6.

25. A method for controlling the growth of undesired vegetation which comprises applying to the locus to be protected an effective amount of the compound of claim 7.

26. A method for controlling the growth of undesired vegetation which comprises applying to the locus to be protected an effective amount of the compound of claim 8.

27. A method for controlling the growth of undesired vegetation which comprises applying to the locus to be protected an effective amount of the compound of claim 9.

* * * * *